US011435360B2

(12) United States Patent
Farokhzad et al.

(10) Patent No.: US 11,435,360 B2
(45) Date of Patent: *Sep. 6, 2022

(54) SYSTEM AND SENSOR ARRAY

(71) Applicant: THE BRIGHAM AND WOMEN'S HOSPITAL, INC., Boston, MA (US)

(72) Inventors: Omid Farokhzad, Waban, MA (US); Morteza Mahmoudi, Brookline, MA (US); Claudia Corbo, Milan (IT)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/215,923

(22) Filed: Mar. 29, 2021

(65) Prior Publication Data

US 2021/0311039 A1 Oct. 7, 2021

Related U.S. Application Data

(60) Division of application No. 17/099,331, filed on Nov. 16, 2020, which is a continuation-in-part of application No. 15/880,627, filed on Jan. 26, 2018, now Pat. No. 10,866,242, which is a continuation of application No. PCT/US2017/067013, filed on Dec. 18, 2017.

(60) Provisional application No. 62/435,409, filed on Dec. 16, 2016.

(51) Int. Cl.
*G01N 31/00* (2006.01)
*G01N 33/53* (2006.01)
*G01N 33/68* (2006.01)
*C01G 49/02* (2006.01)
*G06K 9/00* (2022.01)
*G06N 20/20* (2019.01)
*G06K 9/62* (2022.01)
*G01N 33/543* (2006.01)
*G16B 40/20* (2019.01)
*G01N 33/574* (2006.01)
*B82Y 35/00* (2011.01)

(52) U.S. Cl.
CPC ......... *G01N 33/6848* (2013.01); *C01G 49/02* (2013.01); *G01N 33/5432* (2013.01); *G01N 33/54326* (2013.01); *G01N 33/57488* (2013.01); *G01N 33/6842* (2013.01); *G06K 9/00563* (2013.01); *G06K 9/6267* (2013.01); *G06N 20/20* (2019.01); *G16B 40/20* (2019.02); *B82Y 35/00* (2013.01); *C01P 2004/64* (2013.01)

(58) Field of Classification Search
None
See application file for complete search history.

(56) References Cited

U.S. PATENT DOCUMENTS

| | | | |
|---|---|---|---|
| 5,498,545 A | 3/1996 | Vestal | |
| 5,928,952 A | 7/1999 | Hutchins et al. | |
| 5,952,653 A | 9/1999 | Covey et al. | |
| 6,291,183 B1 | 9/2001 | Pirrung | |
| 6,361,944 B1 | 3/2002 | Mirkin | |
| 6,413,780 B1 | 7/2002 | Bach et al. | |
| 6,649,419 B1 | 11/2003 | Anderson | |
| 6,730,517 B1 | 5/2004 | Koster et al. | |
| 6,759,010 B2 | 7/2004 | Lewis | |
| 6,969,615 B2 | 11/2005 | Knezevic | |
| 7,348,184 B2 | 3/2008 | Rich et al. | |
| 7,375,234 B2 | 5/2008 | Sharpless et al. | |
| 7,442,921 B2 | 10/2008 | Franzen | |
| 7,754,861 B2 | 7/2010 | Boschetti et al. | |
| 7,960,184 B2 | 6/2011 | Morozov et al. | |
| 8,021,891 B2 | 9/2011 | Bird | |
| 8,268,264 B2 | 9/2012 | Lenz | |
| 8,357,537 B2 | 1/2013 | Blecka et al. | |
| 8,906,608 B2 | 12/2014 | Boschetti et al. | |
| 9,005,994 B2 | 4/2015 | Huo | |
| 9,234,895 B2 | 1/2016 | Hood | |
| 9,689,039 B2 | 6/2017 | Wong | |
| 9,758,811 B2 | 9/2017 | Brown et al. | |
| 9,945,994 B2 | 4/2018 | Hebrink et al. | |
| 10,144,955 B2 | 12/2018 | Fernando | |
| 10,866,242 B2 * | 12/2020 | Farokhzad | G01N 33/6848 |
| 2002/0009394 A1 | 1/2002 | Koster et al. | |
| 2002/0127727 A1 | 9/2002 | Bach et al. | |
| 2004/0132122 A1 | 7/2004 | Banerjee et al. | |
| 2004/0147040 A1 | 7/2004 | Bluggel et al. | |
| 2004/0153249 A1 | 8/2004 | Zhang et al. | |
| 2005/0053999 A1 | 3/2005 | Gough et al. | |

(Continued)

FOREIGN PATENT DOCUMENTS

CN 103874770 6/2014
CN 103703143 12/2016

(Continued)

OTHER PUBLICATIONS

Hajipour et al. (Biomater. Sci., 2014, 2, 1210-1221) (Year: 2014).*
Walkey, et al. (ACS Nano, 2014, 8, 2439-2455) (Year: 2014).*
Hadjidemetriou et al. (vol. 9, No. 8, pp. 8142-8156, 2015). (Year: 2015).*
Micallef, J. et al. Applying mass spectrometry based proteomic technology to advance the understanding of multiple myeloma. Journal of hematology & oncology 3, 1 (2010).
Miller, A., Hoogstraten, B., Staquet, M. & Winkler, A. Reporting results of cancer treatment, cancer 47, 207-214 (1981).

(Continued)

Primary Examiner — Lisa V Cook
(74) Attorney, Agent, or Firm — Quarles & Brady LLP

(57) ABSTRACT

The present disclosure provides a system comprising a communication interface and computer for assigning a label to the biomolecule fingerprint, wherein the label corresponds to a biological state. The present disclosure also provides a sensor arrays for detecting biomolecules and methods of use. In some embodiments, the sensor arrays are capable of determining a disease state in a subject.

29 Claims, 121 Drawing Sheets

(56) References Cited

U.S. PATENT DOCUMENTS

| | | |
|---|---|---|
| 2005/0148101 A1 | 7/2005 | Bamdad et al. |
| 2005/0272049 A1 | 12/2005 | Banerjee et al. |
| 2006/0081539 A1 | 4/2006 | Safar et al. |
| 2007/0072250 A1 | 3/2007 | Kim et al. |
| 2007/0178504 A1 | 8/2007 | Colpitts et al. |
| 2008/0160546 A1 | 7/2008 | Colpitts et al. |
| 2008/0277578 A1 | 11/2008 | Ferrari et al. |
| 2009/0004687 A1 | 1/2009 | Mansfield et al. |
| 2009/0054222 A1 | 2/2009 | Zhang et al. |
| 2009/0090855 A1 | 4/2009 | Kobold et al. |
| 2009/0253181 A1 | 10/2009 | Vangbo et al. |
| 2009/0291454 A1 | 11/2009 | Sim et al. |
| 2009/0298710 A1 | 12/2009 | Farokhzad et al. |
| 2009/0305392 A1 | 12/2009 | Alfredsson et al. |
| 2009/0326614 A1 | 12/2009 | El-Sayed et al. |
| 2010/0285490 A1 | 11/2010 | Dees et al. |
| 2010/0291224 A1 | 11/2010 | Tong et al. |
| 2011/0027894 A1 | 2/2011 | Farias-Eisner et al. |
| 2011/0076735 A1 | 3/2011 | Jovanovich et al. |
| 2011/0111443 A1 | 5/2011 | Nishimura et al. |
| 2011/0111978 A1 | 5/2011 | Boschetti et al. |
| 2011/0306514 A1 | 12/2011 | Hewitt et al. |
| 2012/0043208 A1 | 2/2012 | Jin et al. |
| 2012/0046184 A1 | 2/2012 | Dawson et al. |
| 2012/0088249 A1 | 4/2012 | Jovanovich et al. |
| 2012/0156135 A1 | 6/2012 | Farokhzad et al. |
| 2012/0171291 A1 | 7/2012 | Rademacher et al. |
| 2012/0171694 A1 | 7/2012 | Mansfield et al. |
| 2012/0196304 A1 | 8/2012 | Dees et al. |
| 2012/0328594 A1 | 12/2012 | McKenna et al. |
| 2013/0045873 A1 | 2/2013 | Hood et al. |
| 2013/0052661 A1 | 2/2013 | Huo |
| 2013/0058923 A1 | 3/2013 | Huo |
| 2013/0084561 A1 | 4/2013 | Coull et al. |
| 2015/0376678 A1 | 12/2015 | Krizman et al. |
| 2016/0327554 A1 | 11/2016 | Hung et al. |
| 2017/0010283 A1 | 1/2017 | Karl et al. |
| 2017/0074869 A1 | 3/2017 | Krijgsveld et al. |
| 2017/0131276 A1 | 5/2017 | Johnston |
| 2017/0146527 A1 | 5/2017 | Kelly et al. |
| 2017/0216218 A1 | 8/2017 | Farokhzad et al. |
| 2018/0074049 A1 | 3/2018 | Loke et al. |
| 2018/0136231 A1 | 5/2018 | Borrebaeck et al. |
| 2018/0172694 A1 | 6/2018 | Farokhzad |
| 2018/0356414 A1 | 12/2018 | Strano |
| 2018/0361000 A1 | 12/2018 | Weissleder |
| 2019/0195903 A1 | 6/2019 | Leboudec |
| 2020/0033357 A1 | 1/2020 | Tavernier et al. |
| 2021/0072255 A1 | 3/2021 | Farokhzad et al. |
| 2021/0132071 A1 | 5/2021 | Kostarelos et al. |

FOREIGN PATENT DOCUMENTS

| | | |
|---|---|---|
| EP | 1308520 | 7/2003 |
| EP | 2209893 | 7/2010 |
| JP | 2009524828 | 7/2009 |
| WO | 2007010252 | 1/2007 |
| WO | 2007091077 | 8/2007 |
| WO | 2010097785 | 9/2010 |
| WO | 2010148365 | 5/2011 |
| WO | 2011088128 | 7/2011 |
| WO | 2012068226 | 8/2012 |
| WO | 2012106385 A2 | 8/2012 |
| WO | 2013/022995 | 2/2013 |
| WO | 2018046542 | 3/2018 |
| WO | 2018112460 | 6/2018 |

OTHER PUBLICATIONS

Millioni, R. et al. High abundance proteins depletion vs low abundance proteins enrichment: comparison of methods to reduce the plasma proteome complexity. PloS one 6, e19603 (2011).

Mirshafiee, V., Kim, R., Park, S., Mahmoudi, M. & Kraft, M.L. Impact of protein pre-coating on the protein corona composition and nanoparticle cellular uptake. Biomaterials 75, 295-304 (2016).

Mirshafiee, V.; Mahmoudi, M.; Lou, K.; Cheng, J.; Kraft, M. L., Protein corona significantly reduces active targeting yield. Chemical Communications 2013, 49 (25), 2557-2559.

Misek, D. E., Patwa, T. H., Lubman, D. M. & Simeone, D. M. Early detection and biomarkers in pancreatic cancer. Journal of the National Comprehensive Cancer Network 5, 1034-1041 (2007).

Monopoli, M. P., Åberg, C., Salvati, A. & Dawson, K. A. Biomolecular coronas provide the biological identity of nanosized materials. Nature nanotechnology 7, 779-786 (2012).

Monopoli, M.P. et al. Physical—chemical aspects of protein corona: relevance to in vitro and in vivo biological impacts of nanoparticles. J. Am. Chem. Soc 133, 2525-2534 (2011).

Mortensen, N. P.; Hurst, G. B.; Wang, W.; Foster, C. M.; Nallathamby, P. D.; Retterer, S. T., Dynamic development of the protein corona on silica nanoparticles: composition and role in toxicity. Nanoscale 2013, 5 (14), 6372-6380.

Mozaffarian, D., Benjamin, E. J., Go, A. S., et al. Executive Summary: Heart Disease and Stroke Statistics—2016 Update: A Report from the American Heart Association. Circulation 2016, 133, 447.

Muntoni, S. et al. Serum lipoproteins and cancer. Nutrition, Metabolism and Cardiovascular Diseases 19, 218-225 (2009).

Nel, A.E. et al. Understanding biophysicochemical interactions at the nano-bio interface. Nature materials 8, 543 (2009).

Nie, S. et al. Glycoprotein biomarker panel for pancreatic cancer discovered by quantitative proteomics analysis. Journal of proteome research 13, 1873-1884 (2014).

O'Rourke, N. & Edwards, R. Lung cancer treatment waiting times and tumour growth. Clinical Oncology 12, 141-144 (2000).

Ono, M. et al. Prolyl 4-hydroxylation of a-fibrinogen a novel protein modification revealed by plasma proteomics. Journal of Biological Chemistry 284, 29041-29049 (2009).

Orr, W. S., Sandoval, J. A., Malkas, L. H. & Hickey, R. J. Acute Phase Proteins as Cancer Biomarkers. (INTECH Open Access Publisher, 2011).

Ostrand-Rosenberg, S. Cancer and complement. Nature biotechnology 26, 1348 (2008).

Paez, J. G. et al. EGFR mutations in lung cancer: correlation with clinical response to gefitinib therapy. Science 304, 1497-1500 (2004).

Palchetti, S. et al. Nanoparticles-cell association predicted by protein corona fingerprints. Nanoscale 8, 12755-12763 (2016).

Palchetti, S.; Colapicchioni, V.; Digiacomo, L.; Caracciolo, G.; Pozzi, D.; Capriotti, A. L.; La Barbera, G.; Laganà, A., The protein corona of circulating PEGylated liposomes. Biochimica et Biophysica Acta (BBA)—Biomembranes 2016, 1858 (2), 189-196.

Palmieri, V. et al. Dynamic light scattering for the characterization and counting of extracellular vesicles: a powerful noninvasive tool. Journal of Nanoparticle Research 16, 1-8 (2014).

Pan, S. et al. Multiplex targeted proteomic assay for biomarker detection in plasma: a pancreatic cancer biomarker case study. Journal of proteome research 11, 1937-1948 (2012).

Pan, S. et al. Protein alterations associated with pancreatic cancer and chronic pancreatitis found in human plasma using global quantitative proteomics profiling. Journal of proteome research 10, 2359-2376 (2011).

Pan, S., Brentnall, T. A. & Chen, R. Proteomics analysis of bodily fluids in pancreatic cancer. Proteomics 15, 2705-2715 (2015).

Panda, et al. "Affinity Pulldown of Biotinylated RNA for Detection of Protein-RNA Complexes." Bio-protocol vol. 6,24 (2016): e2062. doi: 10.21769/BioProtoc.2062.

Pang, W. W., Abdul-Rahman, P. S., Izlina Wan-Ibrahim, W. & Haji Hashim, O. Can the acute-phase reactant proteins be used as cancer biomarkers? International Journal of Biological Markers 25, 1 (2010).

Pardo, et al. "Resolving Affinity Purified Protein Complexes by Blue Native PAGE and Protein Correlation Profiling." Journal of visualized experiments : JoVE ,122 55498. Apr. 1, 2017, doi: 10.3791/55498.

(56) References Cited

OTHER PUBLICATIONS

Patwa, T. H. et al. The identification of phosphoglycerate kinase-1 and histone H4 autoantibodies in pancreatic cancer patient serum using a natural protein microarray. Electrophoresis 30, 2215-2226 (2009).
PCT/US2017/067013 International Search Report, dated May 1, 2018 (4 pages).
PCT/US2017/067013 Written Opinion, dated May 1, 2018 (10 pages).
Peer, D. et al. Nanocarriers as an emerging platform for cancer therapy. Nature nanotechnology 2, 751-760 (2007).
Pepe, M. S. et al. Phases of biomarker development for early detection of cancer. Journal of the National Cancer Institute 93, 1054-1061 (2001).
Petricoin, E. F. & Liotta, L. A. SELDI-TOF-based serum proteomic pattern diagnostics for early detection of cancer. Current Opinion in Biotechnology 15, 24-30 (2004).
Pichler, M. et al. High plasma fibrinogen level represents an independent negative prognostic factor regarding cancer-specific, metastasis-free, as well as overall survival in a European cohort of non-metastatic renal cell carcinoma patients. British journal of cancer 109, 1123 (2013).
Pio, R., Ajona, D. & Lambris, J. D. Complement inhibition in cancer therapy. Seminars in Immunology 25, 54-64, doi http://dx.doi.org/10.1016/j.smim.2013.04.001 (2013).
Pio, R., Corrales, L. & Lambris, J. D. The Role of Complement in Tumor Growth, Adv Exp Med Biol., 229-262 (Springer, 2014).
Popescu, I. D. et al. Potential serum biomarkers for glioblastoma diagnostic assessed by proteomic approaches. Proteome science 12, 1 (2014).
Pourshams, A. et al. Cohort profile: the Golestan Cohort Study—a prospective study of oesophageal cancer in northern Iran. International journal of epidemiology 39, 52-59 (2010).
Qian, W.-J. et al. Enhanced detection of low abundance human plasma proteins using a tandem IgY12-SuperMix immunoaffinity separation strategy. Molecular & Cellular Proteomics 7, 1963-1973 (2008).
Rahimi, M. et al. Zeolite Nanoparticles for Selective Sorption of Plasma Proteins. Scientific reports 5, 17259-17259 (2015).
Rahman, M. & Mahmoudi, M., Disease specific protein corona in SPIE BiOS 93380V-93380V-93388 (International Society for Optics and Photonics, 2015).
Rahman, M., Laurent, S., Tawil, N., Yahia, L.H. & Mahmoudi, M., Nanoparticle and Protein Corona, p. 21-44 (Springer Science & Business Media, 2013).
Rakow, N. A., Suslick, K. S. A. Colorimetric Sensor Array for Odour Visualization. Nature 2000, 406, 710-713.
Ridker, P. M., Hennekens, C. H., Buring, J. E., Rifai, N. C-Reactive Protein and Other Markers of Inflammation in the Prediction of Cardiovascular Disease in Women. New England Journal of Medicine 2000, 342, 836-843.
Rubio-Perez, C. et al. In silico prescription of anticancer drugs to cohorts of 28 tumor types reveals targeting opportunities. Cancer cell 27, 382-396 (2015).
Safarik, et al. "Magnetic techniques for the isolation and purification of proteins and peptides." Biomagnetic research and technology vol. 2, 1 7. Nov. 26, 2004, doi:10.1186/1477-044X-2-7.
Saha, K. et al. Regulation of Macrophage Recognition through the Interplay of Nanoparticle Surface Functionality and Protein Corona. ACS nano 10, 4421-4430 (2016).
Sakulkhu, et al. Significance of surface charge and shell material of superparamagnetic iron oxide nanoparticle (SPION) based core/shell nanoparticles on the composition of the protein corona. Biomater. Sci., 2015,3, 265-278.
Sakulkhu, U. et al. Ex situ evaluation of the composition of protein corona of intravenously injected superparamagnetic nanoparticles in rats. Nanoscale 6, 11439-11450 (2014).
Monopoli, et al. Nanoparticle coronas take shape. Nature Nanotechnology. Jan. 2011. vol. 6.
Hadjidemetriou, et al. In Vivo Biomolecule Corona around Blood-Circulating, Clinically Used and Antibody-Targeted Lipid Bilayer Nanoscale Vesicles. ACSNANO. 2015. vol. 9. No. 8. 8142-8156.
Colapicchioni et al. Personalized liposome-protein corona in the blood of breast, gastric and pancreatic cancer patients. Intl. J. of Biochem & Cell Biology. 2016. 180-187.
Honda, K. et al. Plasma biomarker for detection of early stage pancreatic cancer and risk factors for pancreatic malignancy using antibodies for apolipoprotein—All isoforms. Scientific reports 5 (2015).
Howlader N et al. SEER Cancer Statistics Review, 1975-2014, National Cancer Institute. Bethesda, MD, https://seer.cancer.gov/csr/1975_2014/, based on Nov. 2016 SEER data submission, posted to the SEER web site, Apr. 2017. (2017).
Huang, et al. "Superparamagnetic iron oxide nanoparticles conjugated with folic acid for dual target-specific drug delivery and MRI in cancer theranostics" Mater Sci Eng C Mater Biol Appl. Jan. 1, 2017;70(Pt 1):763-771. doi: 10.1016/j.msec.2016.09.052.
Huggins, C., Miller, G. M. & Jensen, E. V. Thermal Coagulation of Serum Proteins II. Deficient Coagulation in Dancer and the Iodoacetate Index. Cancer Research 9, 177-182 (1949).
Hwang, T. L., Liang, Y., Chien, K. Y. & Yu, J. S. Overexpression and elevated serum levels of phosphoglycerate kinase 1 in pancreatic ductal adenocarcinoma. Proteomics 6, 2259-2272 (2006).
Jaffe, A. S., Babuin, L., Apple, F. S. Biomarkers in Acute Cardiac Disease. Journal of the American College of Cardiology 2006, 48, 1-11.
Jankovska, et al. Affinity depletion versus relative protein enrichment: a side-by-side comparison of two major strategies for increasing human cerebrospinal fluid proteome coverage. Clin Proteom 16, 9 (2019). https://doi.org/10.1186/s12014-019-9229-1.
Jayaram, S., Gupta, M. K., Polisetty, R. V., Cho, W. C. & Sirdeshmukh, R. Towards developing biomarkers for glioblastoma multiforme: a proteomics view Expert review of proteomics 11, 621-639 (2014).
Jemal, A., Siegel, R., Xu, J. & Ward, E. Cancer statistics, 2010. CA: a cancer journal for clinicians 60, 277-300 (2010).
Jerant, A. F., Johnson, J. T., Sheridan, C. & Caffrey, T. J. Early detection and treatment of skin cancer. American family physician 62, 357-386 (2000).
Jiang, L., et al. "Patterning of plasmonic nanoparticles into multiplexed one-dimensional arrays based on spatially modulated electrostatic potential." ACS nano 5.10 (2011): 8288-8294.
Jung, et al., Specific Colorimetric Detection of Proteins Using Bidentate Aptamer-Conjugated Polydiacetylene (PDA) Liposomes. Adv. Funct. Mater. 2010, 20, 3092-3097.
Karna, E. et al. Serum and tissue level of insulin-like growth factor-l (IGF-I) and IGF-I binding proteins as an index of pancreatitis and pancreatic cancer International journal of experimental pathology 83, 239-246 (2002).
Kawasaki, E. S. & Player, A. Nanotechnology, nanomedicine, and the development of new, effective therapies for cancer. Nanomedicine: Nanotechnology, Biology and Medicine 1, 101-109 (2005).
Keshishian, H. et al. Quantification of cardiovascular biomarkers in patient plasma by targeted mass spectrometry and stable isotope dilution. Molecular & cellular proteomics 8, 2339-2349 (2009).
Keshishian, H. et al. Quantitative, multiplexed workflow for deep analysis of human blood plasma and biomarker discovery by mass spectrometry. Nature protocols 12, 1683 (2017).
Keshishian, H., Addona, T., Burgess, M., Kuhn, E. & Carr, S.A. Quantitative, multiplexed assays for low abundance proteins in plasma by targeted mass spectrometry and stable isotope dilution. Molecular & Cellular Proteomics 6, 2212-2229 (2007).
Kharya, S., Dubey, D. & Soni, S. Predictive Machine Learning Techniques for Breast Cancer Detection. (IJCSIT) International Journal of Computer Science and Information Technologies 4, 1023-1028 (2013).
Kolda, T., and Bader, B., Tensor decompositions and applications. SIAM review 51, 455-500 (2009).
Konduru et al., "Protein Corona: Implications for Nanoparticle Interactions with Pulmonary Cells," Particle and Fibre Toxicology, 2017,14:42, pp. 1-12.

(56) References Cited

OTHER PUBLICATIONS

Korbelik, M. & Cooper, P. Potentiation of photodynamic therapy of cancer by complement: the effect of ?-inulin. British journal of cancer 96, 67-72 (2007).

Koscielny, G. et al. Open Targets: a platform for therapeutic target identification and validation. Nucleic acids research 45, D985-D994 (2016).

Kourou, K., Exarchos, T.P., Exarchos, K.P., Karamouzis, M.V. & Fotiadis, D.I. Machine learning applications in cancer prognosis and prediction. Computational and structural biotechnology journal 13, 8-17 (2015).

Kugler, K.G. et al. The impact of sample storage time on estimates of association in biomarker discovery studies. Journal of clinical bioinformatics 1, 1 (2011).

Lacerda, S.H.D.P. et al. Interaction of gold nanoparticles with common human blood proteins. ACS nano 4, 365-379 (2009).

Laurent, S. et al. Corona protein composition and cytotoxicity evaluation of ultra-small zeolites synthesized from template free precursor suspensions. Toxicology Research 2, 270-279 (2013).

Le, N. D., Yazdani, M., Rotello, V. M. Array-Based Sensing Using Nanoparticles: An Alternative Approach for Cancer Diagnostics. Nanomedicine 2014, 9, 1487-1498.

Lee, D.-S., Jung, J.-K., Lim, J.-W., Huh, J.-S., Lee, D.-D. Recognition of Volatile Organic Compounds Using Sno 2 Sensor Array and Pattern Recognition Analysis. Sensors and Actuators B: Chemical 2001, 77, 228-236.

Lee, G. Cancerous immunoglobulins in cancer immunology. Journal of Clinical & Cellular Immunology 2014.

Levin, B. et al. Screening and surveillance for the early detection of colorectal cancer and adenomatous polyps, 2008: a joint guideline from the American Cancer Society, the US Multi-Society Task Force on Colorectal Cancer, and the American College of Radiology*‡. CA: a cancer journal for clinicians 58, 130-160 (2008).

Liaw A., M. Wiener, Classification and regression by randomForest. R news 2, 18-22 (2002).

Lim, S. H., Feng, L., Kemling, J. W., Musto, C. J. & Suslick, K. S. An optoelectronic nose for the detection of toxic gases. Nature chemistry 1, 562-567 (2009).

Lin, et al. A chemically functionalized magnetic nanoplatform for rapid and specific biomolecular recognition and separation. Biomacromolecules 2013, 14, 1, 160-168.

Little, D.P. et al., Maldi on a Chip:? Analysis of Arrays of Low-Femtomole to Subfemtomole Quantities of Synthetic Oligonucleotides and DNA Diagnostic Products Dispensed by a Piezoelectric Pipet. Analytial Chemistry, 69 (22), 1540-4546 (1997).

Liu, J.Z. et al. Association analyses identify 38 susceptibility loci for inflammatory bowel disease and highlight shared genetic risk across populations. Nature genetics 47, 979-986 (2015).

Longo, C. et al. Core-shell hydrogel particles harvest, concentrale and preserve labile low abundance biomarkers. PLoS one 4, e4763 (2009).

Luchini, A. et al. Smart hydrogel particles: biomarker harvesting: one-step affinity purification, size exclusion, and protection against degradation. Nano letters 8, 350-361 (2008).

Ludwig, J. A. & Weinstein, J. N. Biomarkers in cancer staging, prognosis and treatment selection. Nature Reviews Cancer 5, 845-856 (2005).

Lundqvist, M. et al. Nanoparticle size and surface properties determine the protein corona with possible implications tor biological impacts. Proceedings of the National Academy of Sciences 105, 14265-14270 (2008).

Machado, R. F., Laskowski, D., Deffenderfer, O., et al. Detection of Lung Cancer by Sensor Array Analyses of Exhaled Breath. American journal of respiratory and critical care medicine 2005, 171, 1286-1291.

Maciel, C. M. et al. Differential proteomic serum pattern of low molecular weight proteins expressed by adenocarcinoma lung cancer patients. Journal of experimental therapeutics & oncology 5 (2005).

Mahmoudi, M. et al. Protein-nanoparticle interactions: opportunities and challenges. Chemical reviews 111, 5610-5637 (2011).

Mahmoudi, M. et al. Variation of protein corona composition of gold nanoparticles following plasmonic heating. Nano letters 14, 6-12 (2013).

Mahmoudi, M., Bertrand, N., Zope, H. & Farokhzad, O.C. Emerging understanding of the protein corona at the nano-bio interfaces. Nano Today 11, 817-832 (2016).

Mahmoudi, M., Lohse, S., Murphy, C. J. & Suslick, K. S. Identification of Nanoparticles with a Colorimetric Sensor Array. ACS Sensors 1, 17-21 (2016).

Mahmoudi, M., Saeedi-Eslami, S. N., Shokrgozar, M. A., et al. Cell "Vision": Complementary Factor of Protein Corona in Nanotoxicology. Nanoscale 2012, 4, 5461-5468.

Májek, P., Reicheltová, Z., Suttnar, J., et al. Plasma Proteome Changes in Cardiovascular Disease Patients: Novel Isoforms of Apolipoprotein A1. Journal of translational medicine 2011, 9, 84.

Malik, G. et al. Serum levels of an isoform of apolipoprotein A-II as a potential marker for prostate cancer. Clinical Cancer Research 11, 1073-1085 (2005).

Mani, et al. "Magnetic particles in ultrasensitive biomarker protein measurements for cancer detection and monitoring." Expert opinion on medical diagnostics vol. 5,5 (2011): 381-391. doi: 10.1517/17530059.2011.607161.

Matuszak, et al. "Drug delivery to atherosclerotic plaques using superparamagnetic iron oxide nanoparticles." International journal of nanomedicine vol. 13 8443-8460. Dec. 11, 2018, doi:10.2147/IJN.S179273.

Zakynthinos, E., Pappa, N. Inflammatory Biomarkers in Coronary Artery Disease. Journal of cardiology 2009, 53, 317-333.

Zhang, C. & Suslick, K. S. Colorimetric sensor array for soft drink analysis. Journal of agricultural and food chemistry 55, 237-242 (2007).

Zhang, et al. Quantitative proteomics analysis of adsorbed plasma proteins classifies nanoparticles with different surface properties and size. Proteomics. Dec. 2011; 11(23): 4569-4577.

Zhang, Y., Askim, J.R., Zhong, W., Orlean, P. & Suslick, K.S. Identification of pathogenic fungi with an optoelectronic nose Analyst 139, 1922-1928 (2014).

Zheng, G., Patolsky, F., Cui, Y., Wang, W. U. & Lieber, C. M. Multiplexed electrical detection of cancer markers with nanowire sensor arrays. Nature biotechnology 23, 1294-1301 (2005).

Zheng, T. et al. A Rapid Blood Test to Determine the Active Status and Duration of Acute Viral Infection. ACS Infectious Diseases (2017).

Zheng, T. et al. Gold nanoparticle-enabled blood test for eariy stage cancer detection and risk assessment. ACS applied materials & interfaces 7, 6819-6827 (2015).

Zupancic, K. et al. Identification of plasma biomarker candidates in glioblastoma using an antibody-array-based proteomic approach. Radiology and oncology 48, 257-266 (2014).

Zwicker, J. I., Furie, B. C. & Furie, B. Cancer-associated thrombosis. Critical reviews in oncology/hematology 62, 126-136 (2007).

Salvador-Morales, C., Zhang, L., Langer, R. & Farokhzad, O.C. Immunocompatibility properties of lipid-polymer hybrid nanoparticles with heterogeneous surface functional groups. Biomaterials 30, 2231-2240 (2009).

Salvati, A. et al. Transferrin-functionalized nanoparticles lose their targeting capabilities when a biomolecule corona adsorbs on the surface. Nature nanotechnology 8, 137-143 (2013).

Schindelin, J. et al. Fiji: an open-source platform for biological-image analysis. Nature methods 9, 676-682 (2012).

Semb, K. A., Aamdal, S. & Oian, P. Capillary protein leak syndrome appears to explain fluid retention in cancer patients who receive docetaxel treatment. Journal of Clinical Oncology 16, 3426-3432 (1998).

Senyo, S.E. et al. Mammalian heart renewal by pre-existing cardiomyocytes. Nature 493, 433-436 (2013).

Shakeri, R. et al. Multiplex H. pylori serology and risk of gastric cardia and noncardia adenocarcinomas. Cancer research 75, 4876-4883 (2015).

(56) References Cited

OTHER PUBLICATIONS

Sharma, S., Ray, S., Moiyadi, A., Sridhar, E. & Srivastava, S. Quantitative proteomic analysis of meningiomas for the identification of surrogate protein markers. Scientific reports 4, 7140 (2014).
Shi, J., Kantoff, P.W., Wooster, R. & Farokhzad, O.C. Cancer nanomedicine: progress, challenges and opportunities. Nature Reviews Cancer 17, 20-37 (2017).
Shi, T. et al. IgY14 and SuperMix immunoaffinity separations coupled with liquid chromatography-mass spectrometry for human plasma proteomics biomarker discovery. Methods 56, 246-253 (2012).
Shoji, M. et al. Activation of coagulation and angiogenesis in cancer: immunohistochemical localization in situ of clotting proteins and vascular endothelial growth factor in human cancer. The American journal of pathology 152, 399 (1998).
Siegel, R. L., Miller, K. D. & Jemal, A. Cancer statistics, 2015. CA: a cancer journal for clinicians 65, 5-29 (2015).
Siegel, R. L., Miller, K. D. & Jemal, A. Cancer statistics, 2016. CA: a cancer journal for clinicians 66, 7-30 (2016).
Simberg, et al. Differential proteomics analysis of the surface heterogeneity of dextran iron oxide nanoparticles and the implications for their in vivo clearance. Biomaterials Aug. 2009; 30(23-24): 3926-3933.
Smith, R. A. et al. American Cancer Society guidelines for the early detection of cancer. CA: a cancer journal for clinicians 52, 8-22 (2002).
Star, A., Joshi, V., Skarupo, S., Thomas, D., Gabriel, J.-C. P. Gas Sensor Array Based on Metal-Decorated Carbon Nanotubes. The Journal of Physical Chemistry B 2006, 110, 21014-21020.
Staton, C.A., Brown, N.J. & Lewis, C.E. The role of fibrinogen and related fragments in tumour angiogenesis and metastasis. Expert opinion on biological therapy 3, 1105-1120 (2003).
Strehlitz, et al., Protein Detection with Aptamer Biosensors. Sensors 2008, 8, 4296-4307.
Strojan, K. et al. Dispersion of nanoparticles in different media importantly determines the composition of their protein corona. PloS one 12, e0169552 (2017).
Sun, C., Rosendahl, A. H., Ansari, D. & Andersson, R. Proteome-based biomarkers in pancreatic cancer. World J Gastroenterol 17, 4845-4852 (2011).
Sun, Z.-L. et al. Serum proteomic-based analysis of pancreatic carcinoma for the identification of potential cancer biomarkers. Biochimica et Biophysica Acta (BBA)-Proteins and Proteomics 1774, 764-771 (2007).
Sung, H.-J. et al. Identification and validation of SAA as a potential lung cancer biomarker and its involvement in metastatic pathogenesis of lung cancer. Journal of proteome research 10, 1383-1395 (2011).
Suslick, B.A., Feng, L. & Suslick, K.S. Discrimination of complex mixtures by a colorimetric sensor array: coffee aromas. Analytical chemistry 82, 2067-2073 (2010).
Szala, A. et al. Ficolin-2 and ficolin-3 in women with malignant and benign ovarian tumours. Cancer Immunology, Immunotherapy 62, 1411-1419 (2013).
Tan, H. T., Low, J., Lim, S. G. & Chung, M. Serum autoantibodies as biomarkers for early cancer detection. FEBS journal 276, 6880-6904 (2009).
Tenzer, S. et al. Rapid formation of plasma protein corona critically affects nanoparticle pathophysiology. Nature nanotechnology 8, 772-781 (2013).
Tenzer, S., et al. "Nanoparticle size is a critical physicochemical determinant of the human blood plasma corona: a comprehensive quantitative proteomic analysis." ACS nano 5.9 (2011): 7155-7167.
Tirtaatmadja, N. et al. Nanoparticles-induced inflammatory cytokines in human plasma concentration manner: an ignored factor at the nanobio-interface Journal of the Iranian Chemical Society 12, 317-323 (2015).
Tousoulis, D., Charakida, M., Stefanadis, C. Endothelial Function and Inflammation in Coronary Artery Disease. Heart 2006, 92, 441-444.

Trinkle-Mulcahy, et al. "Identifying specific protein interaction partners using quantitative mass spectrometry and bead proteomes " The Journal of cell biology vol. 183,2 (2008): 223-39. doi:10.1083/jcb.200805092.
Turner, A. P., Chen, B., Piletsky, S. A. In Vitro Diagnostics in Diabetes: Meeting the Challenge. Clinical chemistry 1999, 45, 1596-1601.
Vollmers, H. P. & Brändlein, S. Natural human immunoglobulins in cancer immunotherapy. (2009).
Walkey, C. D., Chan, W. C. Understanding and Controlling the Interaction of Nanomaterials with Proteins in a Physiological Environment. Chemical Society Reviews 2012, 41, 2780-2799.
Wang, J. et al. Cancer-derived immunoglobulin G promotes tumor cell growth and proliferation through inducing production of reactive oxygen species. Cell death & disease 4, e945 (2013).
Wang, Y. et al. Proteomic differential display identifies upregulated vinculin as a possible biomarker of pancreatic cancer. Oncology reports 28, 1845-1850 (2012).
Ward, D. et al. Identification of serum biomarkers for colon cancer by proteomic analysis. British journal of cancer 94, 1898 (2006).
Welter, D. et al. The NHGRI GWAS Catalog, a curated resource of SNP-trait associations. Nucleic acids research 42, D1001-D1006 (2013).
Whelan, S.A. et al. Mass spectrometry (LC-MS/MS) identified proteomic biosignatures of breast cancer in proximal fluid. Journal of proteome research 11, 5034-5045 (2012).
Wildes, D. & Wells, J.A. Sampling the N-terminal proteome of human blood. Proceedings of the National Academy of Sciences 107, 4561-4566 (2010).
Wright, C.F. et al. Genetic diagnosis of developmental disorders in the DDD study: a scalable analysis of genome-wide research data. The Lancet 385, 1305-1314 (2015).
Wulfkuhle, J. D., Liotta, L. A. & Petricoin, E. F. Proteomic applications for the early detection of cancer. Nature reviews cancer 3, 267-275 (2003).
Yan, L. et al. Confounding effect of obstructive jaundice in the interpretation of proteomic plasma profiling data for pancreatic cancer. Journal of proteome research 8, 142-148 (2008).
Yates, J.R., Ruse, C.I. & Nakorchevsky, A. Proteomics by mass spectrometry: approaches, advances, and applications. Annual review of biomedical engineering 11, 49-79 (2009).
Yoneyama, T. et al. Identification of IGFBP2 and IGFBP3 as Compensatory Biomarkers for CA19-9 in Early-Stage Pancreatic Cancer Using a Combination of Antibody-Based and LC-MS/MS-Based Proteomics. PloS one 11, e0161009 (2016).
Yusuf, S., Reddy, S., Ôunpuu, S., Anand, S. Global Burden of Cardiovascular Diseases. Circulation 2001, 104, 2855-2864.
Cruz, J.A. & Wishart, D.S. Applications of machine learning in cancer prediction and prognosis. Cancer informatics 2, 59 (2006).
Cuenca, A. G. et al. Emerging implications of nanotechnology on cancer diagnostics and 4therapeutics. Cancer 107, 459-466 (2006).
Cuzick, J. et al. Prevention and early detection of prostate cancer. The Lancet Oncology 15, e484-e492, doi:10.1016/S1470-2045(2014)70211-6.
De Lathauwer, L., B. De Moor, J. Vandewalle, A multilinear singular value decomposition. SIAM journal on Matrix Analysis and Applications 21, 1253-1278 (2000).
Del Pino, et al. Protein corona formation around nanoparticles—from the past to the future. Mater Horiz, 2014, 1, 301.
Deng, Z.J., Liang, M., Monteiro, M., Toth, I. & Minchin, R.F. Nanoparticle-induced unfolding of fibrinogen promotes Mac-1 receptor activation and inflammation. Nature nanotechnology 6, 39-44 (2011).
Deng, Z.J., Liang, M., Toth, I., Monteiro, M.J. & Minchin, R.F. Molecular interaction of poly (acrylic acid) gold nanoparticles with human fibrinogen. ACS nano 6, 8962-8969 (2012).
Dicker, L., Lin, X. & Ivanov, A.R. Increased power for the analysis of label-free LC-MS/MS proteomics data by combining spectral counts and peptide peak attributes. Molecular & Cellular Proteomics 9, 2704-2718 (2010).
Docter, D.; Distler, U.; Storck, W.; Kuharev, J.; Wünsch, D.; Hahlbrock, A.; Knauer, S. K.; Tenzer, S.; Stauber, R. H., Quanti-

(56) References Cited

OTHER PUBLICATIONS tative profiling of the protein coronas that form around nanoparticles. nature protocols 2014, 9 (9), 2030-2044.
DYNABEADS Products & Technology. ThermoFisher Scientific.
Einav, S. et al. Early postoperative serum S100β levels predict ongoing brain damage after meningioma surgery: a prospective observational study. Critical Care 10, 1 (2006).
Enroth, S., Hallmans, G., Grankvist, K. & Gyllensten, U. Effects of long-term storage time and original sampling month on biobank plasma protein concentrations. EBioMedicine 12, 309-314 (2016).
Etzioni, R. et al. The case for early detection. Nature Reviews Cancer 3, 243-252 (2003).
Faca, V. M. et al. A mouse to human search for plasma proteome changes associated with pancreatic tumor development. PLoS Med 5, e123 (2008).
Farias, V., A. Li, Optimal Recovery of Tensor Slices. Artificial Intelligence and Statistics, 1394-1402 (2017).
Farokhzad, O. C. et al. Targeted nanoparticle-aptamer bioconjugates for cancer chemotherapy in vivo. Proceedings of the National Academy of Sciences 103, 6315-6320 (2006).
Farrah, T. et al. A high-confidence human plasma proteome reference set with estimated concentrations in PeptideAtlas. Molecular & cellular proteomics 10, M110. 006353 (2011).
Feldman, E. B. & Carter, A. C. Circulating lipids and lipoproteins in women with metastatic breast carcinoma. The Journal of Clinical Endocrinology & Metabolism 33, 8-13 (1971).
Ferguson, M. K. et al. Sex-associated differences in survival of patients undergoing resection for lung cancer. The Annals of thoracic surgery 69, 245-249 (2000).
Ferrari, M. Cancer nanotechnology: opportunities and challenges. Nature Reviews Cancer 5, 161-171 (2005).
Fodor, S.P. et al., Light-directed, spatially addressable parallel chemical synthesis. Science, 251(4995), 767-773 (1991).
Fontana, R. S. et al. Early Lung Cancer Detection: Results of the Initial (Prevalence) Radiologic and Cytologic Screening in the Mayo Clinic Study 1, 2. American Review of Respiratory Disease 130, 561-565 (1984).
Forbes, S.A. et al. COSMIC: exploring the world's knowledge of somatic mutations in human cancer. Nucleic acids research 43, D805-D811 (2014).
Fortunato, J. E., Bassiouny, H. S., Song, R. H., et al. Apolipoprotein (a) Fragments in Relation to Human Carotid Plaque Instability. Journal of vascular surgery 2000, 32, 555-563.
Gabizon, A. et al. Cancer nanomedicines: closing the translational gap. The Lancet 384, 2175-2176 (2014).
Gan, C.S., Chong, P.K., Pham, T.K. & Wright, P.C. Technical, experimental, and biological variations in isobaric tags for relative and absolute quantitation (iTRAQ). Journal of proteome research 6, 821-827 (2007).
Gao, W.-M. et al. Distinctive serum protein profiles involving abundant proteins in lung cancer patients based upon antibody microarray analysis. BMC cancer 5, 1 (2005).
Gautam, P. et al. Proteins with altered levels in plasma from glioblastoma patients as revealed by iTRAQ-based quantitative proteomic analysis. PloS one 7, e46153 (2012).
Ghasemi, F., Hormozi-Nezhad, M. R. & Mahmoudi, M. Identification of catecholamine neurotransmitters using fluorescence sensor array. Analytica Chimica Acta 917, 85-92 (2016).
Ghavami, M. et al. Plasma concentration gradient influences the protein corona decoration on nanoparticles. Rsc Advances 3, 1119-1126 (2013).
Gopal, K., Grossi, E., Paoletti, P. & Usardi, M. Lipid composition of human intracranial tumors: A biochemical study. Acta neurochirurgica 11, 333-347 (1963).
Guo, D. et al. An LXR agonist promotes glioblastoma cell death through inhibition of an EGFR/AKT/SREBP-1/LDLR-dependent pathway. Cancer discovery (2011).
Guo, D. et al. EGFR signaling through an Akt-SREBP-1-dependent, rapamycin-resistant pathway sensitizes glioblastomas to anti-lipogenic therapy. Science signaling 2, ra82 (2009).
Guo, D. et al. The AMPK agonist AICAR inhibits the growth of EGFRvIII-expressing glioblastomas by inhibiting lipogenesis. Proceedings of the National Academy of Sciences 106, 12932-12937 (2009).
Guo, Q. et al. Elevated levels of plasma fibrinogen in patients with pancreatic cancer: possible role of a distant metastasis predictor. Pancreas 38, e75-e79 (2009).
Gupta, A. et al. Synergistic antimicrobial therapy using nanoparticles and antibiotics for the treatment of multidrug-resistant bacterial infection. Nano Futures 1, 015004 (2017).
Hadjidemetriou et al. "In vivo biomolecule corona around blood-circulating, clinically used, antibody-targeted lipid bilayer nanoparticle vesicles", ACS Nano, 9(8):8142-8156 (2015).
Hadjidemetriou, et al., A novel scavenging tool for cancer biomarker discovery based on the blood-circulating nanoparticle protein corona. Biomatrials 2019; 188:118-129.
Hadjidemetriou, et al., The Human In Vivo Biomolecule Corona onto PEGylated Liposomes: A Proof-of-Concept Clinical Study. Adv Mater 2018.
Hadjidemetriou, M., Al-Ahmady, Z. & Kostarelos, K. Time-evolution of in vivo protein corona onto blood-circulating PEGylated liposomal doxorubicin (DOXIL) nanoparticles. Nanoscale 8, 6948-6957 (2016).
Hajipour et al. "Personalized disease-specific protein corona influences the therapeutic of graphene oxide", Nanoscale. 7(19):8978-8994 (2015).
Hajipour, M. J., Laurent, S., Aghaie, A., Rezaee, F. & Mahmoudi, M. Personalized protein coronas: a "key" factor at the nanobiointerface. Biomaterials Science 2, 1210-1221 (2014).
Hanash, S. M., Pitteri, S. J. & Faca, V. M. Mining the plasma proteome for cancer biomarkers. Nature 452, 571-579 (2008).
Hansson, G. K., Hermansson, A. The Immune System in Atherosclerosis. Nature immunology 2011, 12, 204-212.
Hasija, K. & Bagga, H. K. Alterations of serum cholesterol and serum lipoprotein in breast cancer of women. Indian Journal of Clinical Biochemistry 20, 61-66 (2005).
Hassanein, M. et al. The state of molecular biomarkers for the early detection of lung cancer. Cancer prevention research 5, 992-1006 (2012).
Heath, J. R. & Davis, M. E. Nanotechnology and cancer. Annual review of medicine 59, 251 (2008).
Henschke, C. I. et al. Early Lung Cancer Action Project: overall design and findings from baseline screening. The Lancet 354, 99-105 (1999).
Hirsch, F. R., Franklin, W. A., Gazdar, A. F. & Bunn, P. A. Early detection of lung cancer: clinical perspectives of recent advances in biology and radiology. Clinical Cancer Research 7, 5-22 (2001).
Aggarwal, P., Hall, J.B., McLeland, C.B., Dobrovolskaia, M.A. & McNeil, S.E. Nanoparticle interaction with plasma proteins as it relates to particle biodistribution, biocompatibility and therapeutic efficacy. Advanced drug delivery reviews 61, 428-437 (2009).
Ahn, J.-M. & Cho, J.-Y. Current serum lung cancer biomarkers. Journal of Molecular Biomarkers & Diagnosis 2013 (2013).
Alexopoulos, C., Blatsios, B. & Avgerinos, A. Serum lipids and lipoprotein disorders in cancer patients. Cancer 60, 3065-3070 (1987).
Alexopoulos, C., Pournaras, S., Vaslamatzis, M., Avgerinos, A. & Raptis, S. Changes in serum lipids and ipoproteins in cancer patients during chemotherapy. Cancer chemotherapy and pharmacology 30, 412-416 (1992).
Ali, et al. "Eriotinib-Conjugated Iron Oxide Nanoparticles as a Smart Cancer-Targeted Theranostic Probe for MRI." Scientific reports vol. 6 36650. Nov. 11, 2016, doi:10.1038/srep36650.
Amici, A. et al. In vivo protein corona patterns of lipid nanoparticles. RSC Advances 7, 1137-1145 (2017).
Andersen, J.D. et al. Identification of candidate biomarkers in ovarian cancer serum by depletion of highly abundant proteins and differential in-gel electrophoresis. Electrophoresis 31, 599-610 (2010).
Anderson, L. Candidate-Based Proteomics in the Search for Biomarkers of Cardiovascular Disease. The Journal of physiology 2005, 563, 23-60.

(56) References Cited

OTHER PUBLICATIONS

Angel, T.E. et al. Mass spectrometry-based proteomics: existing capabilities and future directions. Chemical Society Reviews 41, 3912-3928 (2012).
Askim, J. R., Mahmoudi, M. & Suslick, K. S. Optical sensor arrays for chemical sensing: the optoelectronic nose. Chemical Society Reviews 42, 8649-8682 (2013).
Bagalkot, V. et al. Quantum dot-aptamer conjugates for synchronous cancer imaging, therapy, and sensing of drug delivery based on bi-fluorescence resonance energy transfer. Nano letters 7, 3065-3070 (2007).
Bakhtiary, Z. et al. Targeted superparamagnetic iron oxide nanoparticles for early detection of cancer: Possibilities and challenges. Nanomedicine: Nanotechnology, Biology and Medicine 12, 287-307 (2016).
Bally, M., et al. "Liposome and lipid bilayer arrays towards biosensing applications." Small 6.22 (2010): 2481-2497.
Beck, H.C., Overgaard, M. & Rasmussen, L.M. Plasma proteomics to identify biomarkers-application to cardiovascular diseases. Translational Proteomics 7, 40-48 (2015).
Benjamin, E. J., Blaha, M. J., Chiuve, S. E., et al. Heart Disease and Stroke Statistics—2017 Update: A Report from the American Heart Association. Circulation 2017, 135, e146-e603.
Beri, J., Rosenblatt, M.M., Strauss, E., Urh, M. & Bereman, M.S. Reagent for Evaluating Liquid Chromatography—Tandem Mass Spectrometry (LC-MS/MS) Performance in Bottom-Up Proteomic Experiments. Analytical chemistry 87, 11635-11640 (2015).
Bertrand, N. et al. Mechanistic understanding of in vivo protein corona formation on polymeric nanoparticles and impact on pharmacokinetics. Nature Communications 8, 777 (2017).
Bigdeli, A. et al. Exploring Cellular Interactions of Liposomes Using Protein Corona Fingerprints and Physicochemical Properties. ACS nano 10, 3723-3737 (2016).
BIO-RAD, ProteoMiner Protein Enrichment Technology.
Bisker, et al. Protein-targeted corona phase molecular recognition. Nat Commun 7, 10241 (2016). https://doi.org/10.1038/ncomms10241.
Bloom, D., Cafiero, E., Jané-Llopis, E., et al. The Global Economic Burden of Noncommunicable Diseases. Program on the Global Demography of Aging;2012.
Bloomston, M. et al. Fibrinogen ? overexpression in pancreatic cancer identified by large-scale proteomic analysis of serum samples. Cancer research 66, 2592-2599 (2006).
Bodansky, O. & McInnes, G. F. Thermal coagulation of serum proteins in cancer, in the postoperative phase of surgery, and in the administration of adrenocorticotropic hormone. Cancer 3, 1-14 (1950).
Brede et al. Advances in Chronic Kidney Disease, vol. 20, Issue 6, Nov. 2013, pp. 454-465. 2013.
Breiman, L. Random forests. Machine learning 45, 5-32 (2001).
Brenner et al., Gene expression analysis by massively parallel signature sequencing (MPSS) on microbead arrays. Nature Biotechnology 18:630-634, 2000.
Byrne, J.C. et al. 2D-DIGE as a strategy to identify serum markers for the progression of prostate cancer. Journal of proteome research 8, 942-957 (2008).
Cao, Z., Tang, H.-Y., Wang, H., Liu, Q. & Speicher, D.W. Systematic comparison of fractionation methods for in-depth analysis of plasma proteomes. Journal of proteome research 11, 3090-3100 (2012).
Capriotti, A.L. et al. Label-free quantitative analysis for studying the interactions between nanoparticles and plasma proteins. Analytical and bioanalytical chemistry 405, 635-645 (2013).
Capriotti, A.L. et al. Shotgun proteomic analytical approach for studying proteins adsorbed onto liposome surface. Analytical and bioanalytical chemistry 401, 1195-1202 (2011).
Caputo, D. et al. A protein corona-enabled blood test for early cancer detection. Nanoscale 9, 349-354 (2017).
Caracciolo, G. et al. Lipid composition: a "key factor" for the rational manipulation of the liposome-protein corona by liposome design. RSC Advances 5, 5967-5975 (2015).

Caracciolo, G., Caputo, D., Pozzi, D., Colapicchioni, V. & Coppola, R. Size and charge of nanoparticles following incubation with human plasma of healthy and pancreatic cancer patients. Colloids and Surfaces B: Biointerfaces 123, 673-678 (2014).
Caracciolo, G., et al. "Disease-specific protein corona sensor arrays may have disease detection capacity." Nanoscale Horizons 4.5 (2019): 1063-1076.
Caracciolo, G., Farokhzad, O.C. & Mahmoudi, M. Biological Identity of Nanoparticles In Vivo: Clinical Implications of the Protein Corona. Trends in Biotechnology 35, 257-264 (2017).
Carey, J. R. et al. Rapid identification of bacteria with a disposable colorimetric sensing array. Journal of the American Chemical Society 133, 7571-7576 (2011).
Carter, A. M. Complement Activation: An Emerging Player in the Pathogenesis of Cardiovascular Disease. Scientifica 2012, 2012.
Carter, H. B. et al. Early detection of prostate cancer: AUA Guideline. The Journal of urology 190, 419-426 (2013).
Cedervall, T. et al. Understanding the nanoparticle-protein corona using methods to quantify exchange rates and affinities of proteins for nanoparticles. Proceedings of the National Academy of Sciences 104, 2050-2055 (2007).
Cerasoli, E. et al. MiS-MALDI: microgel-selected detection of protein biomarkers by MALDI-ToF mass spectrometry. Molecular BioSystems 6, 2214-2217 (2010).
Choi, Y.-E., Kwak, J.-W. & Park, J. W. Nanotechnology for early cancer detection. Sensors 10, 428-455 (2010).
Colapicchioni et al. "Personalized lipsoome-protein corona in the blood of breast, gastric and pancreatic cancer patients". The International Journal of Biochemistry & Cell Biology. S1357-2725. 30016-9 . . . 10.1016/j. biocel.2015.09.002.
Consortium, E.P. Europe PMC: a full-text literature database for the life sciences and platform for innovation. Nucleic acids research, gku1061 (2014).
Consortium, U. UniProt: a hub for protein information. Nucleic acids research, gku989 (2014).
Corbo, C. et al. Unveiling the in Vivo Protein Corona of Circulating Leukocyte-like Carriers. ACS Nano (2017).
Corbo, C., Molinaro, R., Parodi, A., Furman, N. E. T., Salvatore, F., Tasciotti, E. The Impact of Nanoparticle Protein Corona on Cytotoxicity, Immunotoxicity and Target Drug Delivery. Nanomedicine 2016, 11, 81-100.
Corbo, C., Molinaro, R., Tabatabaei, M., Farokhzad, O.C. & Mahmoudi, M. Personalized protein corona on nanoparticles and its clinical implications. Biomaterials Science 5, 378-387 (2017).
Corbo, C., Molinaro, R., Taraballi, F., et al. Effects of the Protein Corona on Liposome-Liposome and Liposome-Cell Interactions. International Journal of Nanomedicine 2016, 11, 3049.
Croft, D. et al. The Reactome pathway knowledgebase. Nucleic acids research 42, D472-D477 (2013).
Lundqvist, et al. The nanoparticle protein corona formed in human blood or human blood fractions. PloS one 12.4 (Apr. 17, 2017): e0175871. 15 Pages.
Lundqvist, M., et al. The evolution of the protein corona around nanoparticles: a test study. ACS Nano 5, 7503-7509 (2011).
McDonald, W.H. & Yates, J.R., 3rd. Shotgun proteomics and biomarker discovery. Dis Markers 18, 99-105 (2002).
Mirshafiee, V. et al., The importance of selecting a proper biological milieu for protein corona analysis in vitro: Human plasma versus human serum. Int J Biochem Cell Biol. Jun. 2016;75:188-95. doi: 10.1016/j.biocel.2015.11.019. Epub Nov. 28, 2015.
Mody, et al. Introduction to metallic nanoparticles. Journal of Pharmacy and Bioallied Sciences 2.4 (2010): 282-289.
Nanjappa, V., et al. Plasma Proteome Database as a resource for proteomics research: 2014 update. Nudeic Acids Res 42, D959-965 (2014).
Nanni et al.: Serum protein profiling in patients with inflammatory bowel diseases using selective solid-phase bulk extraction, matrix-assisted laser desorption/ionization time-of-flight mass spectrometry and chemometric data analysis. Rapid Commun Mass Spectrom. 21(24):4142-4148 doi:10.1002/rcm.3323 (2007).
Nesvizhskii, A.I. Proteogenomics: concepts, applications and computational strategies. Nat Methods 11, 1114-1125 (2014).

(56) References Cited

OTHER PUBLICATIONS

Nibbe, et al., Discovery and Scoring of Protein Interaction Subnetworks Discriminative of Late Stage Human Colon Cancer. Mol Cell Proteomics. Apr. 2009; 8(4): 827-845. doi: 10.1074/mcp.M800428-MCP200.

O'Connell, et al., Characterization of the bionano interface and mapping extrinsic interactions of the corona of nanomaterials. Nanoscale, Aug. 26, 2015; 37(7): 15268-15276.

Omenn, G.S., et al. Overview of the HUPO Plasma Proteome Project: results from the pilot phase with 35 collaborating laboratories and multiple analytical groups, generating a core dataset of 3020 proteins and a publidy-available database. Proteomics 5, 3226-3245 (2005).

Palchetti, et al. Exploitation of nanoparticle-protein corona for emerging therapeutic and diagnostic applications. Journal of Materials Chemistry B 4.25 (May 23, 2016): 4376-4381.

Patra, et al., Component-Specific Analysis of Plasma Protein Corona Formation on Gold Nanopartides Using Multiplexed Surface Plasmon Resonance. Small, 2016; 12(9): 1174-1182.

Polanski, et al., A list of candidate cancer biomarkers for targeted proteomics. Biomark Insights, 2006; 1:1-48.

Pozzi, et al., Surface chemistry and serum type both determine the nanopartide-protein corona. Journal of Proteomics, 2015, 119, 209-217.

Proteominer protein enrichment kits, Instruction manual. Bio-Rad. Available at: http://www.bio-rad.com/webroot/web/pdf/lsr/literature/10010636D.PDF [Accessed on Sep. 17, 2020].

ProteominerTM Protein Enrichment Technology. [Online] Available at: http://wolfson.huji.ac.il/purification/PDF/AlbuminRemoval/BIORAD_ProteoMiner.pdf. [Accessed Sep. 17, 2020].

Puri et al.: Lipid-based nanopartides as pharmaceutical drug carriers: from concepts to clinic. Critical Reviews™ in Therapeutic Drug Carrier Systems. 26(6):523-580 (2009).

Ritz, S. et al., Protein Corona of Nanopartides: Distinct Proteins Regulate the Cellular Uptake, Biomacromolecules 2015, 16, 1311-1321, with 11 pages of supporting information.

RNA (ribonucleic acid), 1988. Illustrated Dictionary of Science, Andromeda. Retrieved online on Feb. 8, 2012 http://www.credoreference.com/etry/andidsci/ma_ribonucleic_acid.

Schottler, S., et al. Protein adsorption is required for stealth effect of poly(ethylene glycol)- and poly(phosphoester)-coated nanocamers. Nat Nanotechnol 11, 372-377 (2016).

Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.

Singh, et al. Drug delivery: advancements and challenges. Nanostructures for Drug Delivery. Elsevier, 2017. 865-886.

Smith, R., Mathis, A.D., Ventura, D. & Prince, J.T. Proteomics, lipidomics, metabolomics: a mass spectrometry tutorial from a computer scientist's point of view. BMC Bioinformatics 15, S9 (2014).

Song et al. Ascertaining effects of nanoscale polymeric interfaces on competitive protein adsorption at the individual protein level. Nanoscale, 2016; 8:3496-3509.

Tan et al.: Multi-dimensional on-particle detection technology for multi-category disease classification. Chem Commun (Camb). 52(17):3490-3493 doi:10.1039/c5cc09419d (2016).

Teng, Z.G., et al. Superparamagnetic high-magnetization composite spheres with highly aminated ordered mesoporous silica shell for biomedical applications. J Mater Chem B 1, 4684-4691 (2013).

Terracciano et al.: Peptidome profiling of induced sputum by mesoporous silica beads and MALDI-TOF MS for non-invasive biomarker discovery of chronic inflammatory lung diseases. Proteomics 11(16):3402-3414 doi:10.1002/pmic.201000828 (2011).

Thermo Fisher Scientific "Orbitrap Velos Pro Hardware Manual, Revision A—1288290", Jun. 2011, 202 pages.

Tiss et al.: Serum peptide profiling using MALDI mass spectrometry: avoiding the pitfalls of coated magnetic beads using well-established ZipTip technology. Proteomics 7 Suppl 1:77-89 doi:10.1002/pmic.200700746 (2007).

Troiano et al., A Quality by Design Approach to Developing and Manufacturing Polymeric Nanoparticle Drug Products, The AAPS Journal, 2016, 18, 6, 1354-1365.

U.S. Appl. No. 17/215,952 Office Action dated Jun. 10, 2021.
U.S. Appl. No. 17/215,952 Office Action dated Sep. 17, 2021.
U.S. Appl. No. 17/215,978 Final Office Action dated Feb. 22, 2022.
U.S. Appl. No. 17/099,331 Office Action dated Aug. 17, 2021.
U.S. Appl. No. 15/880,627 Notice of Allowance dated Sep. 18, 2020.
U.S. Appl. No. 15/880,627 Office Action dated Dec. 18, 2018.
U.S. Appl. No. 15/880,627 Office Action dated Jan. 30, 2020.
U.S. Appl. No. 15/880,627 Office Action dated Jun. 18, 2019.
U.S. Appl. No. 15/880,627 Office Action dated Jun. 20, 2018.
U.S. Appl. No. 17/099,331 Office Action dated Apr. 20, 2021.
U.S. Appl. No. 17/215,966 Office Action dated Sep. 23, 2021.
U.S. Appl. No. 17/215,978 Office Action dated Jun. 10, 2021.
U.S. Appl. No. 17/215,978 Office Action dated Oct. 8, 2021.

Ueda, K., et al. A comprehensive peptidome profiling technology for the identification of early detection biomarkers for lung adenocarcinoma. PLoS One 6, e18567 (2011).

Van Hong Nguyen, et al. Protein corona: a new approach for nanomedicine design. International journal of nanomedicine 12 (Apr. 18, 2017): 3137-3151.

Velstra et al.: Improved classification of breast cancer peptide and protein profiles by combining two serum workup procedures. J Cancer Res Clin Oncol. 138(12):1983-1992 doi:10.1007/s00432-012-1273-4 (2012).

Vilanova, O., et al. Understanding the Kinetics of Protein-Nanoparticle Corona Formation. ACS Nano 10, 10842-10850 (2016).

Villanueva et al.: Automated serum peptide profiling. Nat Protoc. 1(2):880-891 doi:10.1038/nprot.2006.128 (2006).

Villanueva et al.: Differential exoprotease activities confer tumor-specific serum peptidome patterns. J Clin Invest. 116(1):271-284 doi:10.1172/JCI26022 (2006).

Agasti et al. Adv Drug Deliv Rev. Mar. 8, 2010; 62(3): 316-328. 2010.

Andriole, G. L., et al. "Mortality results from a randomized prostate-cancer screening trial." New England Journal of Medicine 360.13 (2009): 1310-1319.

Bally, M., et al. "Ally, M., et al. Liposome and lipid bilayer arrays towards biosensing applications." Small 6.22 (2010): 2481-2497.

Bigbee W, et al. Tumor markers and immunodiagnosis. Chapter 13 In: Bast RC Jr., Kufe DW, Pollock RE, et al., editors. Cancer Medicine. 6th ed. Hamilton, Ontario, Canada: BC Decker Inc., 2003.

Buys SS, et al. Effect of screening on ovarian cancer mortality: the Prostate, Lung, Colorectal and Ovarian (PLCO) Cancer Screening Randomized Controlled Trial. JAMA 2011; 305(22):2295-2303.

Chintamaneni, M. et al. "Biomarkers in Alzheimer's disease: a review." ISRN pharmacology 2012 (2012): 984786.

Cramer, D. W., et al. "Ovarian cancer biomarker performance in prostate, lung, colorectal, and ovarian cancer screening trial specimens." Cancer prevention research 4.3 (2011): 365-374.

European Patent Office. Partial Supplementary European Search Report for application 17881767.2, dated Apr. 21, 2020.

Fengming, Y. et al. "Biomarkers of inflammatory bowel disease." Disease markers 2014 (2014).

Mahmoudi et al. "Emerging understanding of the protein corona at the nano-bio interfaces" Nanotoday 11(6) Dec. 2016, pp. 817-832.

Mahmoudi et al. "Protein-Nanoparticle Interactions: Opportunities and Challenges" Chem. Rev., 2011, 111(9), pp. 5610-5637.

Milani et al. "Reversible versus Irreversible Binding of Transferring to Polystyrene Nanopartides: Soft and Hard Corona" ACS Nano, 2012, 6(3), pp. 2532-2541.

Miotto et al. "Protein corona as a proteome fingerprint: The example of hidden biomarkers for cow mastitis", Colloids and Surface, 140(19): 40-49 (2015).

Mirshafiee et al. "Impact of protein pre-coating on the protein corona composition and nanoparticle cellular uptake" Biomaterials vol. 75, Jan. 2016 pp. 295-304.

Rahman, M. et al. Protein-Nanoparticle Interactions, Spring Series in Biophysics 15, 2013.

(56) References Cited

OTHER PUBLICATIONS

Sacanna, S. et al. "Thermodynamically stable pickering emulsions." Physical review letters 98.15 (2007): 158301.
Schrittwieser et al., "Direct protein quantification in complex sample solutions by surface-engineered nanorod probes", Scientific Reports, vol. 7, No. 1, Jul. 6, 2017.
Schröder FH, et al. Screening and prostate-cancer mortality in a randomized European study. New England Journal of Medicine 2009; 360(13):1320-1328.
Simberg, et al. Differential proteomics analysis of the surface heterogeneity of dextran iron oxide nanopartides and he implications for their in vivo clearance. Biomaterials. Aug. 2009; 30(23-24): 3926-3933.
Snider, et al. "Fundamentals of protein interaction network mapping." Molecular systems biology vol. 11, 12 848. Dec. 17, 2015, doi: 10.15252/msb.20156351.
Sparano JA, et al. Prospective validation of a 21-gene expression assay in breast cancer. New England Journal of Medicine 2015; First published online Sep. 28, 2015. doi: 10.1056/NEJMoa1510764.
Strehlilz, et al., Protein Detection with Aplamer Biosensors. Sensors 2008, 8, 4296-4307.
Tenzer, S., et al. "Nanopartide size is a critical physicochemical determinant of the human blood plasma corona: a comprehensive quantitative proteomic analysis." ACS nano 5.9 (2011 ): 7155-7167.
Trinkle-Mulcahy, et al. "Identifying specific protein interaction partners using quantitative mass spectrometry and bead proteomes." The Journal of ceii biology vol. 183,2 (2008): 223-39. doi:10.1083/jcb.200805092.
Van Holten et al. "Ciculating Biomarkers for Predicting Cardiovascular Disease Risk; a Systemic Review and Comprehensive Overview of Meta-Analyses" PLoS One, 2013 8(4): e62080.
Walkey, et al. ACS Nano, 2014, 8, 2439-2455. 2014.
Xia, X.-R., Monteiro-Riviere, N.A. & Riviere, J.E. An index for characterization of nanomaterials in biological systems. Nature nanotechnology 5, 671-675 (2010).
Xu, et al. "Streptavidin Bead Pulldown Assay to Determine Protein Homooligomerization." Bio-protocol vol. 7,22 (2017): e2901. doi: 10.21769/BioProtoc.2901.
Xue, Y., et al. "Quantifying thiol-gold interactions towards the efficient strength control." Nature communications 5.1 (2014): 1-9.
Yigitbas, T., "Multiplex immunoassay and bead based multiplex." Trends in Immunolabelled and Related Techniques. (2012): 351.
Altomare, et al., An in depth proteomic analysis based on ProteoMiner, affinity chromatography and nano-HPLC-MS/MS to explain the potential health benefits of bovine colostrum. Journal of pharmaceutical and biomedical analysis, Mar. 2016; 121:297-306.
Anderson, N.L. The clinical plasma proteome: a survey of clinical assays for proteins in plasma and serum. Clin Chem 56, 177-185 (2010).
Arvizo et al.: Identifying new therapeutic targets via modulation of protein corona formation by engineered nanoparticles. PLoS One 7(3):e33650, pp. 1-8 doi:10.1371/journal.pone.0033650 (2012).
Ashby et al., Size and surface functionalization of iron oxide nanoparticles influence the composition and dynamic nature of their protein corona. ACS Appl. Mater. Interfaces 2014, 6, p. 15412-15419.
Barkman et al.: Fabricated micro-nano devices for in vivo and in vitro biomedical applications. Wiley Interdisdp Rev Nanomed Nanobiotechnol 5(6):544-568 doi:10.1002/wnan.1236 (2013).
Barran-Berdon, et al., Time Evolution of Nanoparticle-Protein corona in Human Plasma: Relevance for targeted drug delivery. Langmuir, 2013, 29, 6485-6494.
Baumann et al.: Standardized approach to proteome profiling of human serum based on magnetic bead separation and matrix-assisted laser desorption/ionization time-of-flight mass spectrometry. Clin Chem. 51(6):973-980 doi:10.1373/clinchem.2004.047308 (2005).
Beeckmans: Chromatographic methods to study protein-protein interactions. Methods, Oct. 1999; 19(2):278-305.
Bolstad, et al. A comparison of normalization methods for high density oligonucleotide array data based on variance and bias. Bioinformatics. Jan. 22, 2003;19(2):185-93.
Boschetti, et al., Hexapeptide combinatorial ligand libraries: the march for the detection of the low-abundance proteome continues. BioTechniques, 2008; 44(5): 663-665.
Boschetti, et al., The ProteoMiner in the proteomic arena: a non-depleting tool for discovering low-abundance species. J Proteomics, Aug. 2008. 71(3): 255-264.
Calvo et al.: Clinical proteomics: from biomarker discovery and cell signaling profiles to individualized personal therapy. Biosci Rep. 25(1-2): 107-125 doi:10.1007/s10540-005-2851-3 (2005).
Canini, S. et al., Association between birth weight and first-trimester free beta-human chorionic gonadotropin and pregnancy-associated plasma protein A. Fertility and Sterility. Jan. 2008, vol. 89 No. 1. pp. 174-178.
Canovi et al.: Applications of surface plasmon resonance (SPR) for the characterization of nanoparticles developed or biomedical purposes. ensors (Basel). 12(12):16420-16432 doi:10.3390/s121216420 (2012).
Capriotti et al.: Analytical methods for characterizing the nanopartide-protein corona. Chromatographia 77 (11-12):755-769 DOI:10.1007/s10337-014-2677-x (2014).
Caracciolo, et al., Evolution of the protein corona of lipid gene vectors as a function of plasma concentration. Langmuir, 2011, 27, 15048-15053.
Casals et al. Time evolution of the nanopartide protein corona. ACS Nano. 4(7):3623-32. doi:10.1021/nn901372t (2010).
Clemments, A. M. et al., Protein Adsorption From Biofluids on Silica Nanopartides: Corona Analysis as a Function of Particle Diameter and Porosity, ACS Applied Materials & Interfaces 2015, 7, 21682-21689, with 5 pages of supporting Information.
Corbo, C. et al., Biomarker discovery by proteomics-based approaches for early detection and personalized medicine in colorectal cancer, Proteomics—Clinical Applications, 2017, 11, 5-6, paper 1600072, 19 pages.
Crutchfield, C.A., Thomas, S.N., Sokoll, L.J. & Chan, D.W. Advances in mass spectrometry-based clinical biomarker discovery. Clin Proteomics 13, 1 (2016).
De Las Rivas, et al., Protein-Protein Interactions Essentials: Key Concepts to Building and Analyzing Interactome Networks. Plos computational biology, Jun. 2010; 6(6): e1000807, 1-8 Pages.
Deng, Y., Qi, D., Deng, C., Zhang, X. & Zhao, D. Superparamagnetic high-magnetization microspheres with an Fe3O4@SiO2 core and perpendicularly aligned mesoporous SiO2 shell for removal of microcystins. J Am Chem Soc 130, 28-29 (2008).
Di Silvio, D. et al., Technical tip: high-resolution isolation of nanopartide-protein corona complexes from physiological fluids, Nanoscale, 2015, 7, 11980-11990, with 7 pages of supplementary information.
Dobrovolskaia et al., Protein corona composition does not accurately predict hematocompatibility of colloidal gold nanoparticles, Nanomedicine: Nanotechnology, Biology, and Medicine, 2014, 10:1453-1463.
Docter, et al. The nanoparticle biomolecule corona: lessons learned—challenge accepted?.Chemical Society Reviews44.17 (2015): 6094-6121.
Enten, A. et al., A Liquid-Handling Robot for Automated Attachment of Biomolecules to Microbeads, Journal of Laboratory Automation 2016, 21, 526-532.
Faunce et al.: Integrated research into the nanoparticle-protein corona: a new focus for safe, sustainable and equitable development of nanomedicines. Nanomedicine (Lond). 3(6):859-866 doi:10.2217/17435889.3.6.859 (2008).
Findeisen et al.: Preanalytical impact of sample handling on proteome profiling experiments with matrix-assisted laser desorption/ionization time-of-flight mass spectrometry. Clin Chem. 51(12):2409-2411 doi:10.1373/clinchem.2005.054585 (2005).
Foroozandeh et al.: Merging worlds of nanomaterials and biological environment: factors governing protein corona formation on nanopartides and its biological consequences. Nanoscale Res Lett. 10(221):1-12 doi:10.1186/s11671-015-0922-3 (2015).

(56) References Cited

OTHER PUBLICATIONS

Geyer et al.: Proteomics reveals the effects of sustained weight loss on the human plasma proteome. Mol Syst Biol. 12(12):901, pp. 1-16 doi:10.15252/msb.20167357 (2016).

Geyer, P.E., et al., Plasma proteome profiling to assess human health and disease. Cell systems, 2016;2: 185-195.

Geyer, P.E., Holdt, L.M., Teupser, D. & Mann, M. Revisiting biomarker discovery by plasma proteomics. Mol Syst Biol 13, 942 (2017).

Gocheva, V., et al. Quantitative proteomics identify Tenascin-C as a promoter of lung cancer progression and contributor to a signature prognostic of patient survival. Proc Natl Acad Sci U S A 114, E5625-E5634 (2017).

Gossmann, R. et al, Comparative examination of adsorption of serum proteins on HSA- and PLGA-based nanoparticles using SDS-PAGE and LC-MS, European Journal of Pharmaceutics and Biopharmaceutics 2015, 93, 80-87.

Hajipour, M. J. et al., Sensing of Alzheimer's Disease and Multiple Sclerosis Using Nano-Bio Interfaces, Journal of Alzheimer's Disease 2017, 59, 1187-1202.

Huo et al.: Developing a nanoparticle test for prostate cancer scoring. J Transl Med. 10(44):1-8 doi:10.1186/1479-5876-10-44 (2012).

Huo, Q. et al., A facile nanoparticle immunoassay for cancer biomarker discovery. Journal of Nanobiotechnology 2011, 9, paper 20, 12 pages.

Jager et al., Investigation of Arsenic-Stressed Yeast (*Saccharomyces cerevisiae*) as a Bioassay in Homeopathic Basic Research, Scientific World Journal; 2011; vol. 11, pp. 568-583,Published online Mar. 7, 2011.

Kashiwagi, K., et al. Differences of molecular expression mechanisms among neural cell adhesion molecule 1, synaptophysin, and chromogranin A in lung cancer cells. Pathol Int 62, 232-245 (2012).

Koene et al.: Serum protein profiles as potential biomarkers for infectious disease status in pigs. BMC Vet Res. 8 (32):1-14 doi:10.1186/1746-6148-8-32 (2012).

Koo et al.: Liquid flow in microchannels: experimental observations and computational analyses of microfluidics effects. Journal of Micromechanics and Microengineering 13(5):568-579 (2003).

Laurent, S. et al., Superparamagnetic iron oxide nanoparticles: promises for diagnosis and treatment of cancer. Int J Mol Epidemiol Genet. 2011; 2(4): 367-390. Published online Nov. 25, 2011.

Li et al. A review on phospholipids and their main applications in drug delivery systems. Asian Journal of Pharmaceutical Sciences 10:81-98 (2015).

Li, et al., Digging More Missing Proteins Using an Enrichment Approach with ProteoMiner. J. Proteome Res. Sep. 2017; 16(12): 4330-4339.

Li, J. et al. Block copolymer conjugated Au-coated Fe3O4 nanoparticles as vectors for enhancing colloidal stability and cellularuptake. Journal of Nanobiotechnology, 15(56) 1-11 (Year: 2017).

Li, Lei., Dynamic range compression with ProteoMiner™: principles and examples. Methods Mol Biol, 2015;1295:99-107.

Life Science Group: Reducing dynamic range with proteominer. Bio-Rad. Available at: http://icim.marseille.inserm.fr/IMG/pdf/jp08j1-5-BIORAD-PROTEOMINER.pdf [Accessed on Sep. 17, 2020].

Lilien et al.: Probabilistic disease classification of expression-dependent proteomic data from mass spectrometry of human serum. J Comput Biol. 10(6):925-946 doi:10.1089/106652703322756159 (2003).

Liu, J., et al. Highly water-dispersible biocompatible magnetite particles with low cytotoxicity stabilized by citrate groups. Angew Chem Int Ed Engl 48, 5875-5879 (2009).

Liu, Y. et al., Theranostic near-infrared fluorescent nanoplatform for imaging and systemic siRNA delivery to metastatic anaplastic thyroid cancer, Proceedings of the National Academy of Sciences of the United States of America Jul. 12, 2016, 113, 7750-7755.

Villanueva, Josep et al., "Serum peptide profiling by magnetic particle-assisted, automated sample processing and MALDI-TOF mass spectrometry". Anal. Chem. (Mar. 15, 2004), 76(6): 1560-1570.

Vroman, L., Adams, A.L., Fischer, G.C. & Munoz, P.C. Interaction of high molecular weight kininogen, factor XII, and fibrinogen in plasma at interfaces. Blood 55, 156-159 (1980).

Wang, et al., A magnetic nanoparticles relaxation sensor for protein-protein interaction detection at ultra-low magnetic field. Biosens Bioelectron. Jun. 15, 2016. 80:661-665. doi: 10.1016/j.bios.2016.02.037.

Wang, H., Li, L., Ding, L., Zhang, Z. & Pu, C. Association of genetic polymorphisms in the paraoxonase 1 gene with the risk and prognosis of non-small cell lung cancer in Chinese Han population. J Investig Med 60, 592-597 (2012).

Westmeier et al.: The bio-corona and its impact on nanomaterial toxicity. European Journal of Nanomedicine 7 (3):153-168 https://doi.org/10.1515/ejnm-2015-0018 (2015).

Williams, et al., Proteominer facilitates high-throughput proteomic analysis of low abundance proteins in the cartilage secretome (LB39). The Faseb journal, Apr. 2014; 28(S1), Abstract. https://doi.org/10.1096/fasebj.28.1_supplement.lb39 (2014).

Xu, S., et al. Toward designer magnetite/polystyrene colloidal composite microspheres with controllable nanostructure and desirable surface functionalities. Langmuir 28, 3271-3278 (2012).

Zaccaria, et al. Accessing to the minor proteome of red blood cells through the influence of the nanoparticle surface properties on the corona composition. International journal of nanomedicine 10 (Mar. 9, 2015): 1869-1883.

Zanganeh, et al. Protein corona: opportunities and challenges. The international journal of biochemistry & cell biology 75 (Jun. 2016): 143-147.

Zhang et al.: Evaluation of a novel, integrated approach using functionalized magnetic beads, bench-top MALDI-TOF-MS with prestructured sample supports, and pattern recognition software for profiling potential biomarkers in human plasma. J Biomol Tech 15(3):167-175 (2004).

Zhang et al.: Integrated Proteogenomic Characterization of Human High-Grade Serous Ovarian Cancer. Cell 166 (3):755-765 doi:10.1016/j.cell.2016.05.069 (2016).

Zhang, X. et al., Preparation and characterization of superparamagnetic Fe3O4/CNTs nanocomposites Dual-drug carrier, Journal of Wuhan University of Technology-Mater. Sci. Ed., 32(1), 42-46. (Year 2017).

Zou et al.: Synthesis and evaluation of superparamagnetic silica particles for extraction of glycopeptides in the microtiter plate format. Anal Chem. 80(4):1228-1234 doi:10.1021/ac701950h (2008).

\* cited by examiner

FIG. 2B

| Bare Liposomes | | | | |
|---|---|---|---|---|
| | Size Intensity (nm) | Pdi | Zeta-potential (mV) | TEM diameter (nm) |
| Cationic | 153.50±11.40 | 0.17±0.04 | 46.50±2.30 | 145.2±6.8 |
| Anionic | 146±3.25 | 0.113±0.076 | -69.1±4.54 | 141.3±3.8 |
| Neutral | 172.9±2.8 | 0.05±0.001 | -3.5±1.2 | 164.9±5.8 |
| Corona Coated Liposomes | | | | |
| Cationic | | | | |
| | Size Intensity (nm) | Pdi | Zeta-potential (mV) | Protein Assay (μg) |
| Healthy | 232.97±3.44 | 0.33±0.09 | -38.13±1.09 | 5.88±0.33 |
| Pancreas | 240.37±4.20 | 0.35±0.02 | -28.30±1.32 | 6.84±0.65 |
| Lung | 200.47±8.52 | 0.36±0.03 | -23.27±1.03 | 6.03±0.70 |
| Glioblastoma | 235.30±7.87 | 0.38±0.05 | -30.70±1.44 | 6.81±0.68 |
| Meningioma | 233.27±4.22 | 0.34±0.06 | -27.37±0.45 | 6.49±0.78 |
| Myeloma | 248.43±8.50 | 0.43±0.09 | -9.39±0.37 | 8.03±0.77 |
| Anionic | | | | |
| Healthy | 178.70±2.82 | 0.406±0.052 | -42.70±1.31 | 7.49±0.86 |
| Pancreas | 205.23±4.27 | 0.262±0.066 | -35.60±0.72 | 6.66±0.46 |
| Lung | 192.27±4.87 | 0.280±0.028 | -34.43±0.73 | 6.87±0.51 |
| Glioblastoma | 203.50±6.70 | 0.475±0.047 | -38.50±0.82 | 6.46±0.95 |
| Meningioma | 198.60±4.30 | 0.353±0.031 | -32.83±3.00 | 6.25±0.69 |
| Myeloma | 169.50±4.80 | 0.265±0.040 | -22.80±3.29 | 8.57±0.36 |
| Neutral | | | | |
| Healthy | 251.40±7.60 | 0.378±0.038 | -28.4±2.34 | 3.36±0.16 |
| Pancreas | 268.50±3.07 | 0.270±0.068 | -31.3±2.09 | 4.18±0.23 |
| Lung | 228.63±2.15 | 0.276±0.074 | -30.8±1.26 | 4.38±0.40 |
| Glioblastoma | 229.47±1.87 | 0.297±0.040 | -36.0±0.94 | 3.07±0.28 |
| Meningioma | 228.97±3.63 | 0.413±0.074 | -32.5±3.03 | 2.99±0.32 |
| Myeloma | 263.27±1.82 | 0.327±0.024 | -6.8±0.41 | 5.56±1.37 |

FIG. 7A

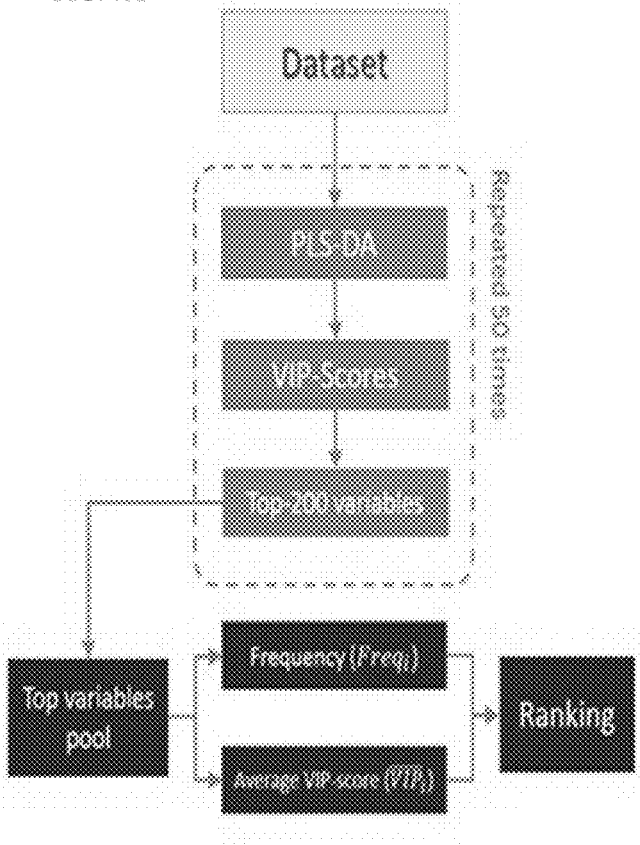

FIG. 7B

| Variable ID. (PLS model) | Protein name | Variable ID. (PLS model) | Protein name |
|---|---|---|---|
| 1 | PLMN | 33 | TRFE |
| 2, 19, 81 | FCN3 | 34 | APOE |
| 3 | BIN2 | 35 | IGHG1 |
| 4 | VTNC | 36 | FINC |
| 5 | ITIH1 | 37 | C4BPA |
| 6 | KNG1 | 38 | IGKC |
| 7 | CO9 | 39 | GELS |
| 8 | C1S | 40 | VTDB |
| 9 | RET4 | 41 | K1C16 |
| 10, 47 | C1R | 42 | IGHG3 |
| 11 | CO6 | 43 | LAC2 |
| 12 | IC1 | 44 | HORN |
| 13 | APOH | 45 | IGHG2 |
| 14 | CO7 | 46 | HRG |
| 15 | CO8A | 48 | SAA4 |
| 16, 49 | PROP | 50 | K1C14 |
| 17 | GRP78 | 52 | HPTR |
| 18, 61 | PHLD | 53 | KV118 |
| 20 | FHR5 | 54 | CO4A |
| 21 | CO8G | 55 | ZPI |
| 22 | COF1 | 56 | CXCL7 |
| 23, 62 | CBPN | 57 | CRP |
| 24 | FGL1 | 58 | IGHG4 |
| 25 | CBPB2 | 59 | SBSN |
| 26 | COL10 | 60 | ITAM |
| 27 | KRT86 | 63 | ITB2 |
| 28, 67 | CD59 | 64 | PGK1 |
| 29 | KAIN | 65 | COL11 |
| 30 | ALBU | 66 | EMIL1 |
| 31 | CO4B | 68 | QCR2 |
| 32 | A2MG | 69 | HV209 |

FIG. 7C

| Cancer type | Protein name |
|---|---|
| Glioblastoma | PLMN, VTNC, ITIH1, CO7, FHR5, CBPN ALBU, C4BPA, CO4A, CRP, APOE, CXCL7 |
| Meningioma | FCN3, RET4, CBPN |
| Pancreas | KNG1, IC1, CBPB2, TRFE, APOE, GELS, HPTR, CXCL7, PGK1 |
| Lung | CO9, SAA4, CRP, GELS |
| Myeloma | ALBU |

Weight map #i

Assignation map

FIG. 13

Sensor Array Elements

Various types of NPs (organic, inorganic, and or polymeric) with different physicochemical properties Examples Liposomes
Different Surface Charges/Functionalities | Different Sizes | Different Lipid Compositions and conjugates
e.g., cholesterol Superparamagnetic iron oxide nanoparticles
Different Surface Charges/Functionalities | Different Sizes | Different Shapes Gold Nanoparticles
Different Surface Charges/Functionalities | Different Sizes | Different Shapes

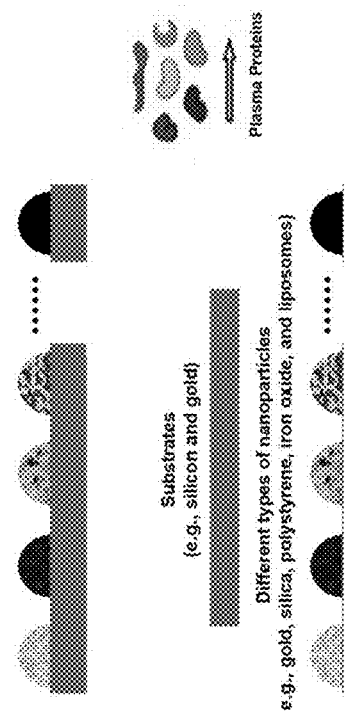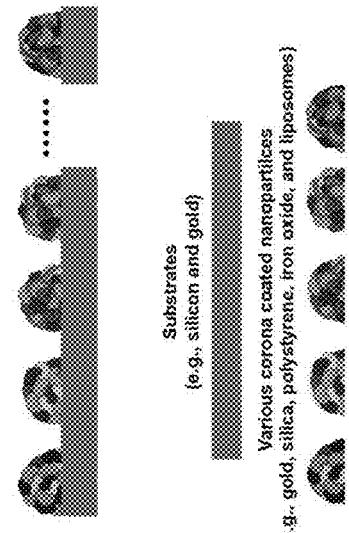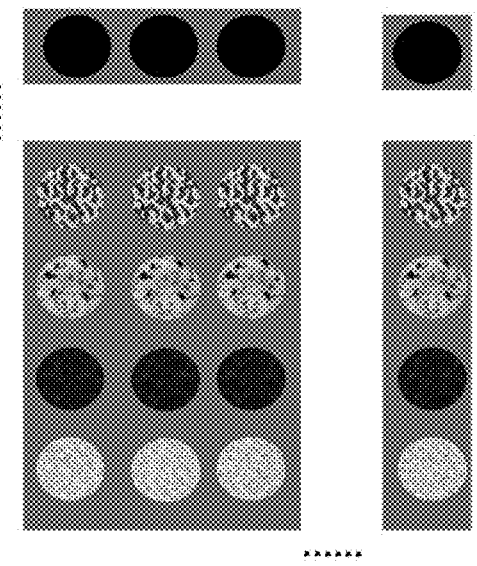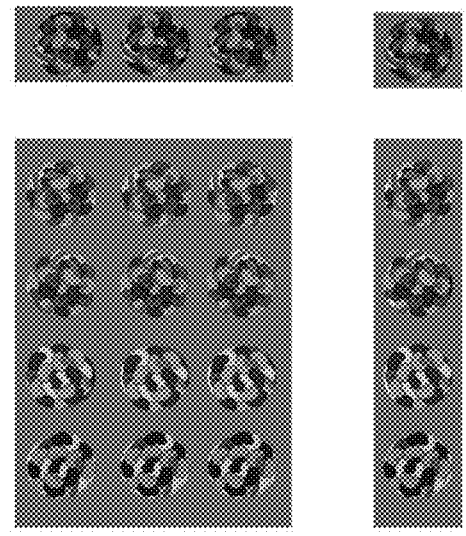
FIG. 16A
FIG. 16B

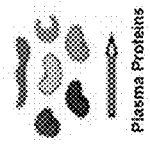
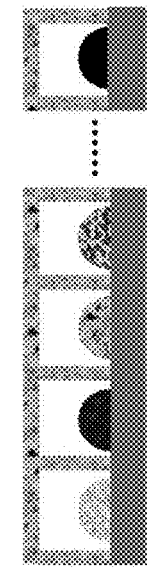
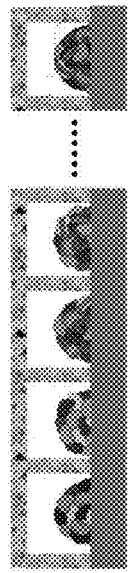
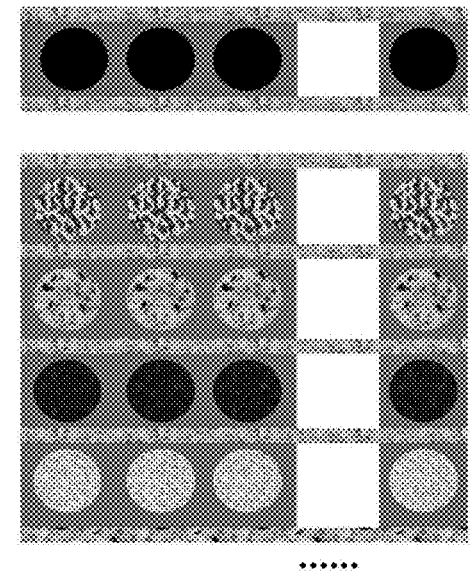
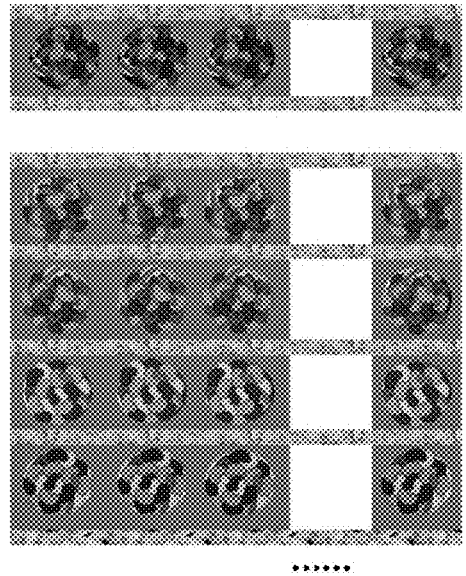
FIG. 18A
FIG. 18B

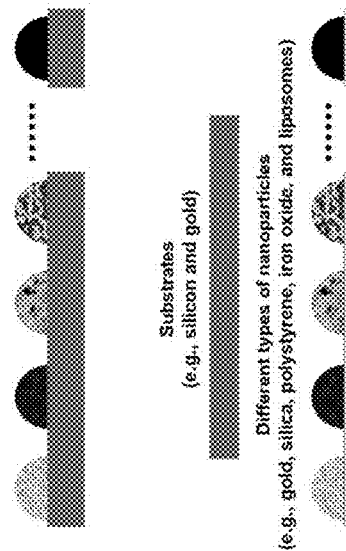
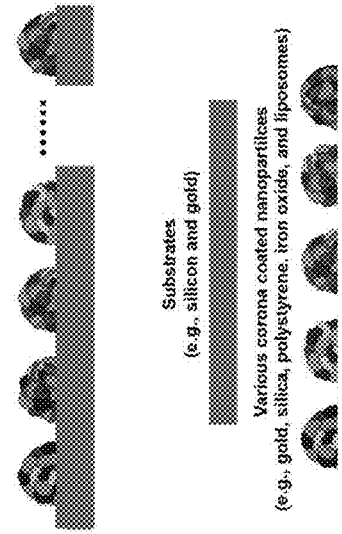
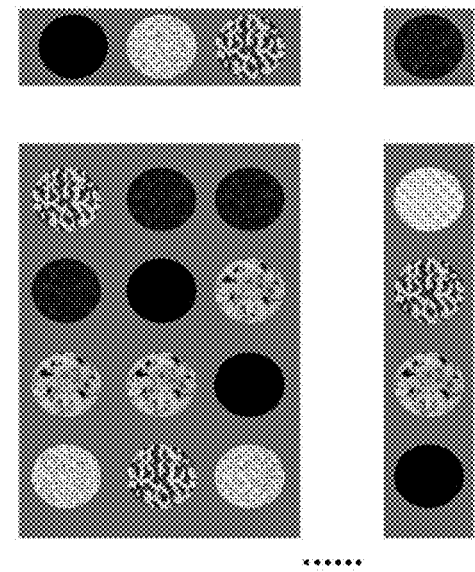
FIG. 20A
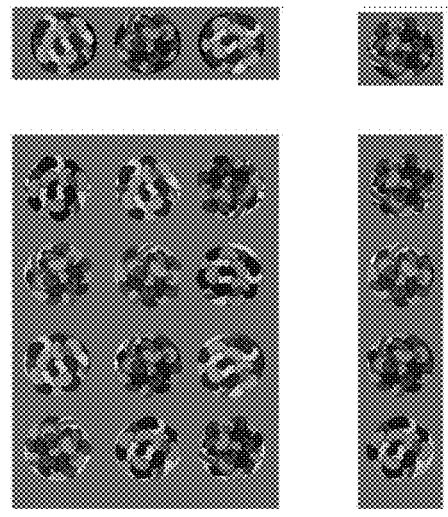
FIG. 20B

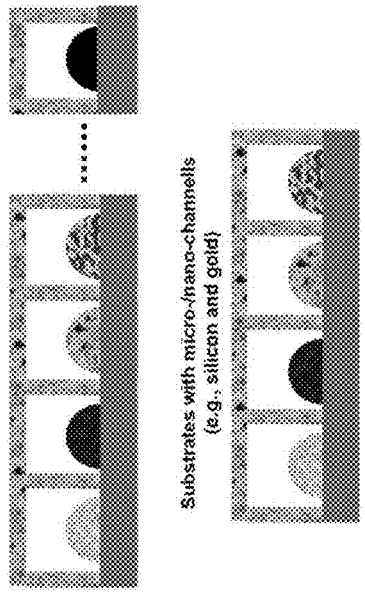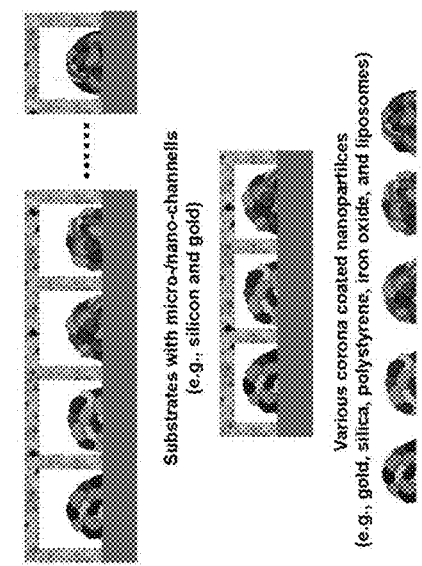
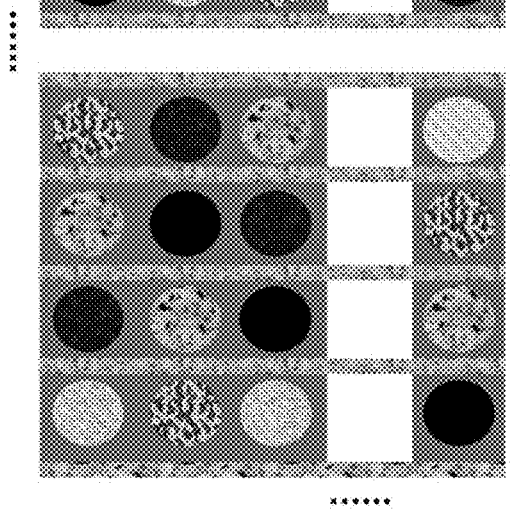
FIG. 22A
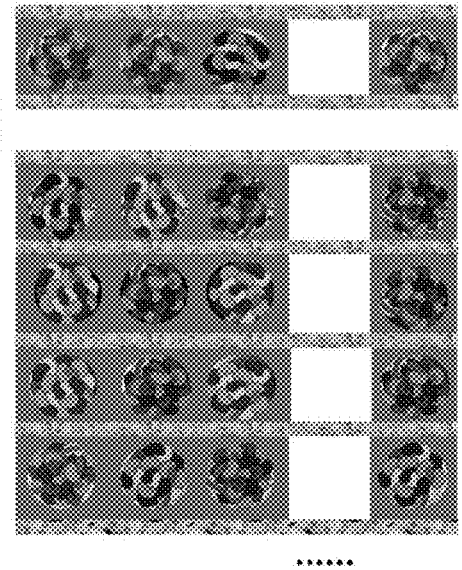
FIG. 22B

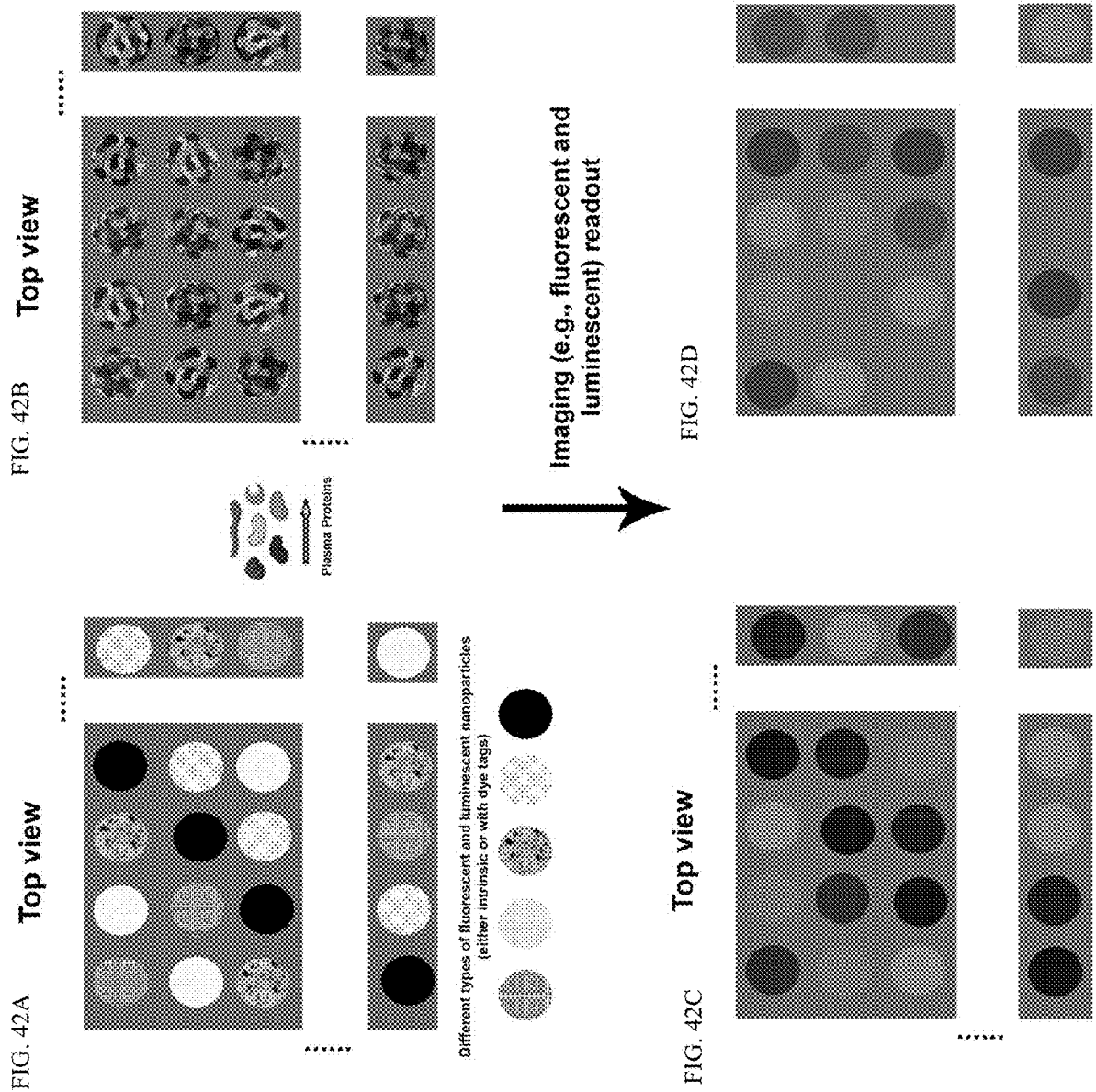

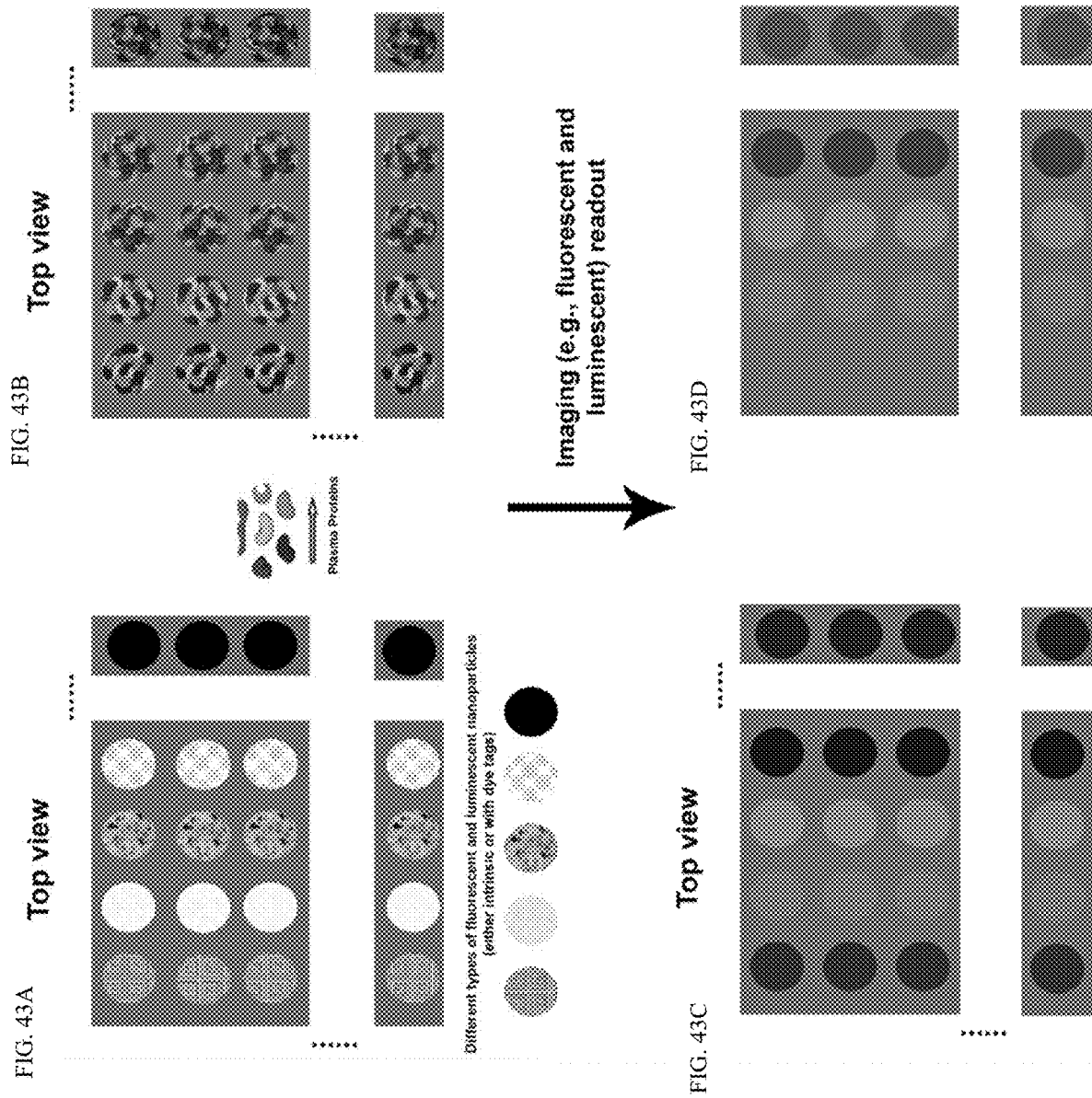

FIG. 44A

Polystyrene NPs

| | Size (nm) | Zeta potential (mV) | PDI |
|---|---|---|---|
| ○ | 98.6 ± 1.1 | -42.27 ± 1.35 | 0.09 |
| NH2 | 110.5 ± 0.9 | -27.57 ± 0.89 | 0.05 |
| COOH | 106.6 ± 0.5 | -49.38 ± 1.27 | 0.067 |

FIG. 44B

Silica NPs

| | Size (nm) | Zeta potential (mV) | PDI |
|---|---|---|---|
| ○ | 100.5 ± 1.6 | -53.72 ± 1.35 | 0.005 |
| NH2 | 93.9 ± 0.9 | -46.44 ± 0.92 | 0.055 |
| COOH | 120 ± 0.7 | -56.77 ± 1.4 | 0.02 |

Plain | -NH2 | -COOH
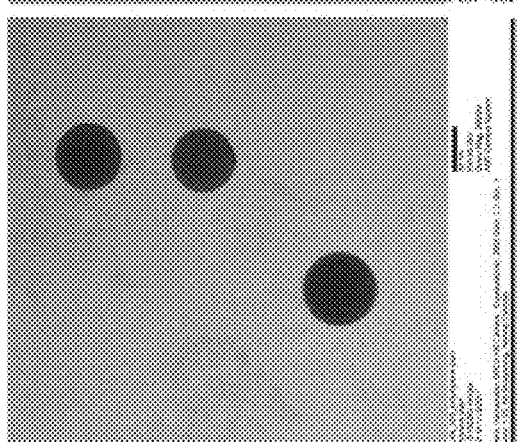 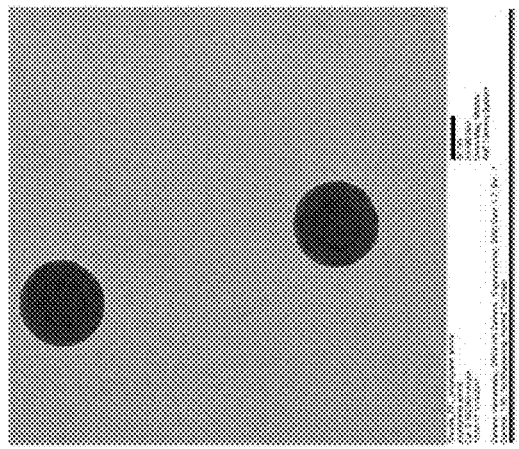 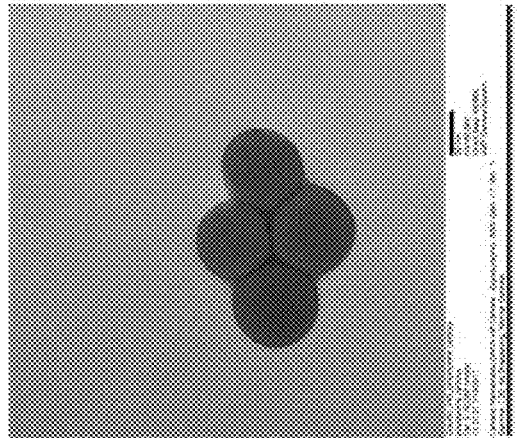
FIG. 44C
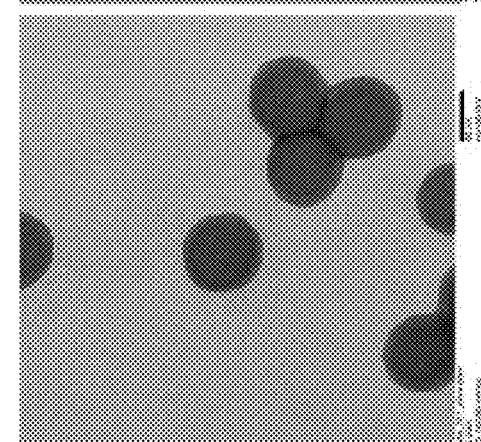 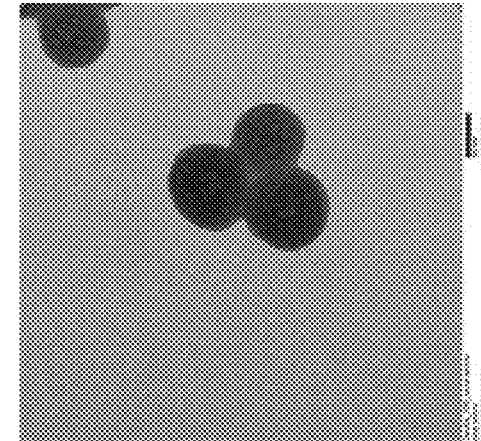 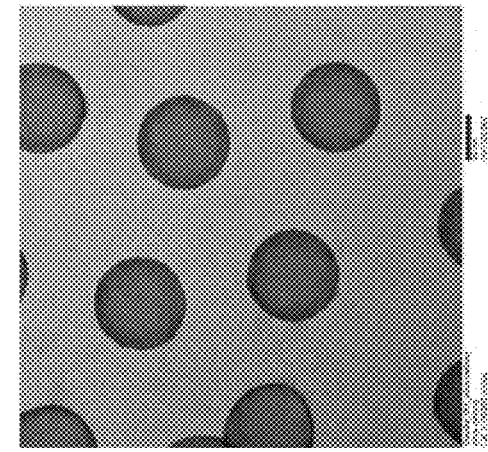
FIG. 44D
TEM imaging. Morphological and structural characterization of bare NPs stained using uranyl acetate. In this example, human healthy plasma was employed.

FIG. 45A

Polystyrene NPs

| | Size (nm) | Zeta potential (mV) | PDI |
|---|---|---|---|
| ○ | 146.4 ± 1.4 | -15.9 ± 0.32 | 0.029 |
| NH2 | 148.9 ± 4 | -26.25 ± 1.59 | 0.005 |
| COOH | 125.7 ± 1.8 | -21.6 ± 1.19 | 0.064 |

FIG. 45B

Silica NPs

| | Size (nm) | Zeta potential (mV) | PDI |
|---|---|---|---|
| ○ | 225.6 ± 2.3 | -23.4 ± 1.68 | 0.283 |
| NH2 | 198.2 ± 1.7 | -17.04 ± 0.71 | 0.179 |
| COOH | 175.1 ± 3.4 | -19.03 ± 0.71 | 0.179 |

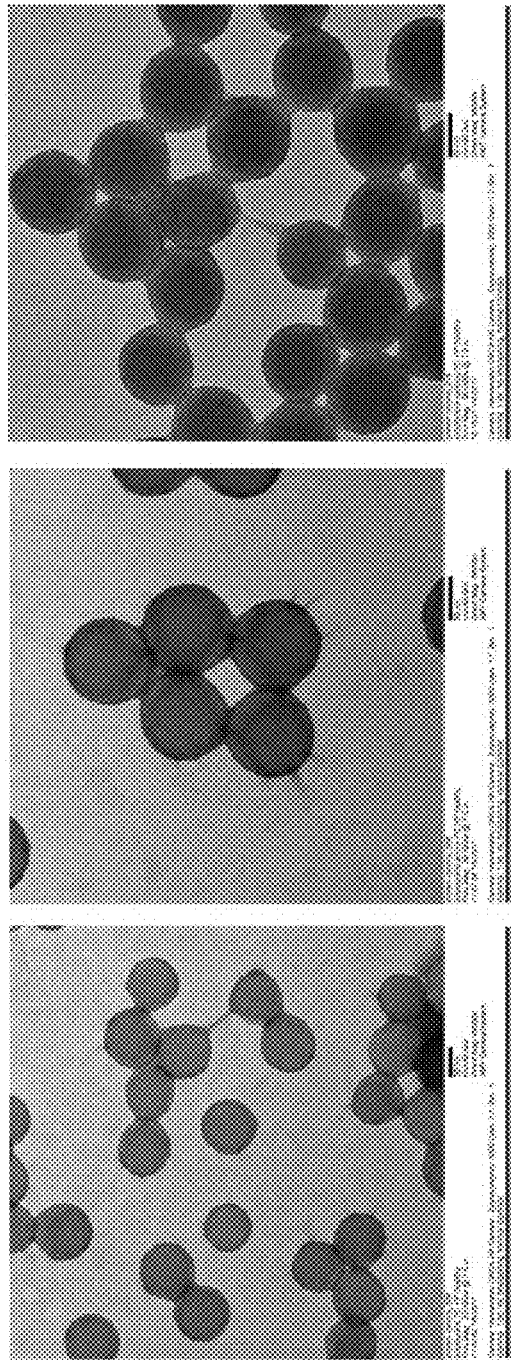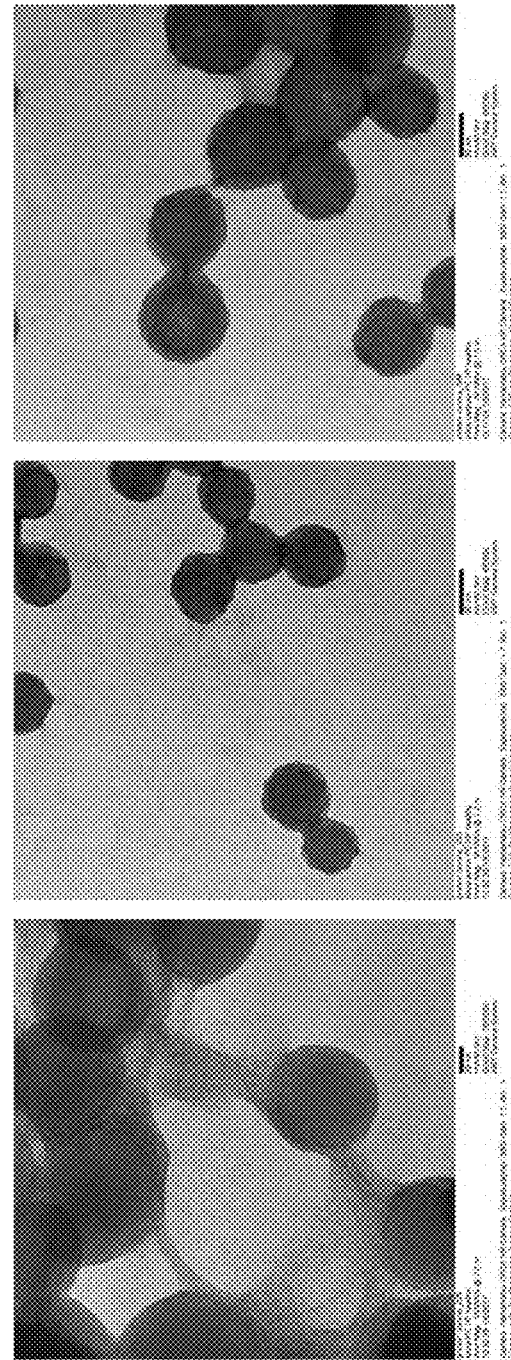
FIG. 45C
FIG. 45D
TEM imaging. Morphological and structural characterization of bare NPs stained using uranyl acetate. In this example, human healthy plasma was employed.

| NPs | BARE | | | CAD | | | NO CAD | | | CONTROL | | |
|---|---|---|---|---|---|---|---|---|---|---|---|---|
| | Size (nm) | SD | PDI | Size (nm) | SD | PDI | Size (nm) | SD | PDI | Size (nm) | SD | PDI |
| P | 98.6 | 1.1 | 0.09 | 153.6 | 3.2 | 0.24 | 187.5 | 10.7 | 0.15 | 146.4 | 1.4 | 0.288 |
| P-NH2 | 110.5 | 0.9 | 0.05 | 149.5 | 1.6 | 0.302 | 145.3 | 6.3 | 0.086 | 148.9 | 4 | 0.129 |
| P-COOH | 106.6 | 0.5 | 0.067 | 140.8 | 1.2 | 0.216 | 138.1 | 7.3 | 0.327 | 125.7 | 1.8 | 0.268 |
| S | 100.5 | 1.6 | 0.005 | 148.8 | 3.9 | 0.137 | 183.7 | 1.3 | 0.236 | 138.6 | 2.1 | 0.005 |
| S-NH2 | 93.9 | 0.9 | 0.055 | 175.7 | 3.3 | 0.238 | 114.7 | 14.5 | 0.444 | 140.9 | 6.8 | 0.007 |
| S-COOH | 120 | 0.7 | 0.02 | 171.4 | 2.1 | 0.294 | 171.3 | 13.7 | 0.198 | 175.1 | 3.4 | 0.17 |

Protein corona-coated NPs -AD plasma-

FIG. 67

| Biomarker ID | CC(1) Control | CC(2) Glioblastoma | CC(3) Meningioma | CC(4) Myeloma | CC(5) Pancreas | CC(6) Lung |
|---|---|---|---|---|---|---|
| 1323 | -0.16 | 0.04 | 0.80 | -0.41 | 0.16 | -0.51 |
| 1282 | -0.47 | -0.04 | 0.11 | 0.90 | -0.03 | -0.37 |
| 1518 | -0.22 | 0.76 | -0.12 | -0.12 | -0.15 | 0.05 |
| 742 | 0.38 | -0.06 | -0.21 | -0.72 | -0.03 | 0.58 |
| 1462 | -0.14 | -0.25 | -0.17 | -0.20 | -0.12 | 0.89 |
| 1373 | -0.30 | -0.13 | -0.10 | 0.98 | -0.21 | -0.16 |
| 1466 | -0.37 | 0.03 | 0.84 | -0.31 | 0.14 | -0.37 |
| 1313 | -0.28 | 0.03 | 0.59 | -0.05 | 0.37 | -0.68 |
| 1630 | 0.97 | -0.23 | -0.31 | -0.26 | -0.19 | -0.19 |
| 815 | -0.33 | -0.15 | -0.24 | 0.65 | -0.45 | 0.61 |
| 882 | -0.16 | -0.16 | -0.25 | -0.13 | -0.16 | 0.91 |
| 1284 | -0.47 | -0.01 | 0.42 | 0.74 | -0.34 | -0.28 |
| 891 | -0.37 | -0.05 | -0.33 | 0.55 | -0.34 | 0.68 |
| 954 | -0.19 | -0.10 | -0.25 | -0.20 | 0.99 | -0.20 |
| 782 | -0.37 | -0.32 | -0.39 | 0.66 | 0.02 | 0.50 |
| 820 | -0.34 | -0.24 | -0.43 | 0.36 | 0.02 | 0.72 |
| 1556 | -0.18 | -0.09 | -0.25 | -0.19 | 0.98 | -0.20 |
| 1286 | 0.41 | -0.35 | 0.18 | -0.31 | -0.51 | 0.40 |
| 868 | 0.15 | -0.28 | -0.44 | 0.16 | -0.32 | 0.72 |
| 1308 | 0.42 | 0.26 | -0.38 | -0.45 | -0.31 | 0.46 |
| 881 | -0.12 | -0.09 | -0.30 | -0.18 | 0.98 | -0.24 |
| 848 | -0.47 | -0.04 | -0.07 | 0.72 | -0.49 | 0.47 |
| 1267 | 0.56 | -0.01 | -0.01 | -0.61 | -0.44 | 0.39 |
| 950 | -0.18 | -0.13 | -0.26 | -0.14 | 0.96 | -0.20 |
| 1561 | 0.95 | -0.24 | -0.35 | -0.28 | -0.10 | -0.17 |
| 856 | -0.33 | -0.18 | -0.21 | 0.64 | -0.43 | 0.60 |
| 895 | -0.03 | -0.16 | -0.32 | -0.20 | -0.13 | 0.87 |
| 1270 | -0.60 | 0.65 | 0.57 | -0.08 | -0.02 | -0.37 |
| 1476 | 0.42 | -0.11 | -0.39 | -0.32 | -0.32 | 0.65 |
| 1416 | 0.59 | -0.05 | -0.10 | -0.61 | -0.36 | 0.40 |
| 786 | -0.15 | -0.19 | -0.32 | 0.02 | 0.94 | -0.25 |
| 751 | -0.38 | -0.23 | -0.36 | 0.33 | 0.05 | 0.70 |
| 1316 | 0.81 | -0.04 | -0.43 | -0.35 | -0.22 | 0.11 |
| 1351 | 0.87 | -0.35 | -0.21 | -0.05 | -0.36 | -0.12 |
| 992 | 0.90 | -0.24 | -0.29 | -0.21 | -0.17 | -0.18 |
| 1272 | -0.45 | 0.37 | 0.74 | -0.17 | 0.07 | -0.51 |
| 1363 | -0.63 | 0.12 | 0.81 | -0.12 | 0.05 | -0.19 |
| 1486 | -0.33 | 0.66 | 0.07 | -0.18 | -0.26 | 0.22 |
| 1496 | -0.18 | -0.08 | -0.24 | -0.18 | 0.93 | -0.19 |
| 96 | -0.23 | -0.13 | -0.22 | -0.18 | 0.92 | -0.11 |
| 1294 | -0.23 | -0.08 | 0.01 | 0.78 | -0.08 | -0.37 |
| 1027 | -0.18 | 0.69 | -0.02 | -0.26 | -0.05 | -0.02 |
| 1007 | -0.29 | -0.11 | 0.86 | -0.08 | -0.23 | -0.23 |
| 1362 | -0.21 | -0.11 | -0.05 | -0.23 | 0.87 | -0.25 |

FIG. 67 CONTINUED

| | | | | | | |
|---|---|---|---|---|---|---|
| 1302 | 0.29 | -0.32 | -0.37 | 0.75 | -0.20 | -0.19 |
| 802 | -0.51 | -0.22 | -0.15 | 0.55 | 0.57 | -0.13 |
| 1265 | -0.37 | 0.33 | 0.67 | -0.17 | 0.16 | -0.59 |
| 1489 | -0.45 | 0.10 | 0.78 | -0.20 | 0.03 | -0.26 |
| 878 | -0.09 | -0.26 | -0.32 | 0.85 | -0.06 | -0.08 |
| 1338 | -0.45 | 0.82 | 0.12 | -0.07 | -0.05 | -0.16 |
| 826 | 0.18 | 0.40 | 0.38 | -0.55 | 0.02 | -0.47 |
| 1424 | -0.19 | -0.21 | -0.32 | -0.09 | 0.09 | 0.77 |
| 335 | -0.20 | -0.10 | -0.27 | -0.15 | 0.93 | -0.16 |
| 879 | -0.20 | -0.03 | -0.19 | -0.21 | 0.89 | -0.20 |
| 1305 | -0.57 | 0.14 | 0.78 | 0.14 | -0.03 | -0.43 |
| 978 | -0.12 | -0.15 | -0.25 | -0.09 | -0.17 | 0.82 |
| 769 | -0.01 | -0.36 | -0.58 | 0.42 | 0.01 | 0.56 |
| 1567 | -0.16 | 0.58 | -0.15 | -0.16 | 0.18 | -0.14 |
| 35 | 0.60 | -0.31 | -0.39 | -0.37 | -0.13 | 0.46 |
| 1632 | -0.15 | -0.12 | 0.64 | -0.10 | -0.16 | -0.19 |
| 1431 | 0.53 | -0.35 | 0.42 | -0.44 | -0.24 | -0.16 |
| 788 | -0.45 | 0.11 | -0.13 | 0.87 | -0.22 | -0.03 |
| 1333 | -0.40 | -0.10 | -0.32 | 0.03 | 0.69 | 0.22 |
| 1357 | 0.47 | 0.01 | -0.56 | -0.14 | -0.30 | 0.50 |
| 997 | -0.16 | -0.13 | -0.22 | -0.12 | -0.16 | 0.83 |
| 1325 | 0.68 | -0.19 | 0.04 | -0.41 | -0.44 | 0.13 |
| 1275 | -0.45 | 0.50 | -0.08 | 0.52 | 0.05 | -0.34 |
| 1315 | -0.15 | 0.34 | 0.66 | -0.62 | 0.08 | -0.33 |
| 1545 | -0.12 | -0.05 | -0.26 | -0.15 | -0.21 | 0.85 |

FIG. 68

Table 9: Information of the atients in which their plasmas were used in this example.

| Label | Patient n. | Case ID | Age At Excision | Sex | Height (cm) | Weight (kg) | BMI | Excision Year | Clinical Diagnosis (Patient) |
|---|---|---|---|---|---|---|---|---|---|
| A | 1 | 104668 | 90+ | F | 157 | 70 | 28.4 | 2016 | Hysterectomy (1960), Alzheimer's disease (2015) |
| B | 2 | 104663 | 87 | M | 165 | 49 | 18 | 2016 | Alzheimer's disease (2016) |
| C | 3 | 104664 | 79 | F | 160 | 60 | 23.44 | 2016 | Alzheimer's disease (2016) |
| D | 4 | 104662 | 87 | F | | | | 2016 | Alzheimer's disease (2014) |
| E | 5 | 104666 | 83 | M | 180 | 92 | 28.4 | 2016 | Alzheimer's disease (2016) |
| F | 6 | 104659 | 89 | F | 160 | 72 | 28.13 | 2016 | Alzheimer's disease (2015) |
| G | 7 | 104667 | 77 | M | 173 | 72 | 24.06 | 2016 | Alzheimer's disease (2016) |
| H | 8 | 104658 | 70 | M | 173 | 70 | 23.39 | 2016 | Alzheimer's disease (2016) |
| I | 9 | 104660 | 85 | M | 188 | 72 | 20.37 | 2016 | Alzheimer's disease, Alzheimer's dementia (2016) |
| K | 10 | 104657 | 73 | M | 152 | 84 | 36.36 | 2016 | Alzheimer's disease (2009), Radiculopathy, Carotid artery stenosis |
| L | 11 | 56393 | 83 | F | 170 | 69 | 23.88 | 2009 | Atrial fibrillation (1999), Hypothyroidism, Viral encephalitis (1934), Fracture of the left foot (1991), Pelvic ring fracture (1978), Hysterectomy (1999), Cataract (1999), Alzheimer's disease (2009) |

SYSTEM AND SENSOR ARRAY

CROSS-REFERENCE TO RELATED APPLICATIONS

This application is a division of U.S. application Ser. No. 17/099,331 filed Nov. 16, 2020; which is a continuation-in-part of U.S. application Ser. No. 15/880,627 filed Jan. 26, 2018 now patented as U.S. Pat. No. 10,866,242; which is a continuation of PCT Application PCT/US2017/067013 filed on Dec. 18, 2017 which claims priority to U.S. Provisional Application 62/435,409 filed Dec. 16, 2016, the contents of which are incorporated by reference in its entirety.

STATEMENT REGARDING FEDERALLY SPONSORED RESEARCH N/A

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

The field of the invention is related to sensor arrays for the detection and diagnosis of different disease states, particularly, the invention relates to the ability to diagnose or prognose diseases or disorders.

The earlier a disease is diagnosed, the more likely that the disease can be cured or successfully managed leading to a better prognosis for the patient. When you treat a disease early, you may be able to prevent or delay problems from the disease and may improve the outcomes for the patient, including extending the patient's life and/or quality of life.

Early diagnosis of cancer is crucial, as many types of cancers can be successfully treated in their early stages. For example, five-year survival after early diagnosis and treatment of breast, ovarian, and lung cancers is 90%, 90%, and 70%, respectively, compared to 15%, 5%, and 10% for patients diagnosed at the most advanced stage of disease. Once cancer cells leave their tissue of origin, successful treatment using available established therapeutics becomes very unlikely. Although recognizing the warning signs of cancers and taking prompt action may lead to early diagnosis, the majority of cancers (e.g., lung) show symptoms only after cancer cells have already invaded the surrounding tissues and metastasized throughout the body. For example, more than 60% of patients with breast, lung, colon, and ovarian cancer have concealed or even metastatic colonies by the time their cancers are detected. Therefore, there is an urgent need for development of an effective approach for early detection of cancer. Such an approach should have the sensitivity to identify a cancer at various stages and the specificity to give a negative result when the person being tested is free of the cancer. There have been extensive efforts to develop methods for early detection of cancers; although huge numbers of risk factors and biomarkers have been introduced, a broadly relevant platform for early detection of a wide range of cancers remains elusive.

As various types of cancers can change the composition of blood plasma—even in their early stages—one promising approach for early detection is molecular blood analysis for biomarkers. Although this strategy has already worked for a few cancers (like PSA for prostate cancer), there are not yet specific biomarkers for early detection of the majority of cancers. For such cancers (e.g., lung), none of the defined candidate circulating biomarkers has been clinically validated, and very few have reached late-stage clinical development. Therefore, there is an urgent need for novel approaches to improve our ability to detect cancer at very early stages.

SUMMARY OF THE INVENTION

The present invention provides a sensitive versatile sensor array for detection of a wide range of diseases and disorders and determination of disease states in a subject. The uniqueness of the present invention is the combination of this recognition of a biomolecular fingerprint from a sample from a subject and the ability to determine a disease state for that subject on a continuum of health.

In some aspect, the invention provides a sensor array comprising a plurality of sensor elements, wherein the plurality of sensor elements differ from each other in at least one physiocochemical property and the plurality of sensor elements comprises at least two sensor elements. In some aspects, each sensor element is able to bind a plurality of biomolecules in a sample to produce a biomolecule corona signature, wherein each sensor element has a distinct biomolecule corona signature from the other. In some aspects, the sensor element is a nanoscale sensor element.

In some aspects, the plurality of sensor elements produces a plurality of biomolecule corona signatures when contacted by the sample, wherein the combination of the plurality of biomolecule corona signatures produces a biomolecule fingerprint for the sample.

In some aspects, the sensor elements are linked to the substrate.

In some aspects, the sensor elements are discrete elements (regions) on a substrate, plate or chip having topological and functional differences where each distinct element (region) produces a distinct biomolecule corona signature. Together, the substrate, chip or array itself forms the sensor array and provide the biomolecule fingerprint for the sample.

In some aspects, the invention provides methods of detecting a disease state in a subject comprising: obtaining a sample from the subject; contacting the sample with a sensor array, wherein the sensor array comprises a plurality of sensor elements, wherein the plurality of sensor elements differ from each other in at least one physiocochemical property and the plurality of sensor elements comprises at least two sensor elements, and determining a biomolecule fingerprint associated with the sample, wherein the biomolecule fingerprint may differentiate the disease state of the subject. In some aspects, the method further comprises comparing the biomolecule fingerprint of the sample to a panel of biomolecule fingerprints associated with a plurality of disease states to determine which disease state is associated with the sample.

In another aspect, the invention provides a method of determining a biomolecule fingerprint associated with at least disease state or at least one disease or a disorder, the method comprising the steps of: (a) obtaining a samples from at least two subjects diagnosed with the disease state or the at least one disease or disorder; (b) contacting each sample with a sensor array described herein, and (c) determining a biomolecule fingerprint for the sensor array that is associated with the disease state or at least one disease or disorder. In some aspects, step (c) further comprises detecting the composition of the biomolecule corona of each sensor element, wherein the combination of the composition of each biomolecule corona between the different sensor elements produce the biomolecule fingerprint associated with the sample. In other aspects, step (c) comprises dissociating the biomolecule corona from each sensor element and assaying the plurality of biomolecules of each biomolecule corona, wherein the combination of biomolecules assayed produced the biomolecule fingerprint.

In yet another aspect, the invention provides a method of diagnosing or prognosing a disease or disorder in a subject, comprising obtaining a sample from a subject; contacting the sample with a sensor array described herein to produce a biomolecule fingerprint, comparing the biomolecule fingerprint to a panel of biomolecule fingerprints associated with a plurality of diseases or disorders; and diagnosing or prognosing the disease or disorder.

In yet another aspect, the invention provides a method of identifying a pattern of biomarkers associated with a disease or disorder, the method comprising: (a) obtaining a samples from at least two subjects diagnosed with the disease or disorder and at least two control subjects; (b) contacting each sample with a sensor array to produce a plurality of biomolecule corona for each subject, and (c) comparing the composition of the plurality of biomolecule corona of the subjects with the disease or disorder to the composition of the plurality of biomolecule corona of the control subjects to determine a pattern of biomarkers associated with the disease or disorder.

In some aspects, the disease or disorder is cancer, endocrine disorder, cardiovascular disease, inflammatory disease or a neurological disease.

In one aspect, the disease or disorder is cancer.

In another aspect, the disease or disorder is cardiovascular disease. In one aspect, the cardiovascular disease is coronary artery disease (CAD).

In a further aspect, the disease or disorder is a neurological disorder. In one aspect, the neurological disorder is Alzheimer's disease.

In some aspects, the invention provides a kit for diagnosing or prognosing a disease or disorder, the kit comprising: a sensor array comprising a plurality of nanoscale sensor elements, wherein the plurality of sensor elements differ from each other in at least one physiocochemical property and the plurality of sensor elements comprises at least two sensor elements.

In other aspects, the invention provides kit for determining and/or detecting at least one biomarker associated with a disease or disorder, comprising at least one sensor array comprising a plurality of sensor elements, wherein the plurality of sensor elements differ from each other in at least one physiocochemical property and the plurality of sensor elements comprises at least two sensor elements.

In yet another aspect, the invention provides a method of distinguishing states of a complex biological sample of a subject using a plurality of particles having surfaces with different physicochemical properties, wherein the method comprises: exposing the complex biological sample to the plurality of particles to permit binding of proteins of the complex biological sample to the plurality of particles, wherein a pattern of binding of proteins amongst the plurality of particles differs based on the physicochemical properties of the surfaces of the particles; defining a biomolecule fingerprint representative of proteins that bind to the plurality of particles; and associating the biomolecule fingerprint with a biological state of the subject.

In another aspect, the invention provides a sensor array comprising a plurality of particles having surfaces with different physicochemical properties, wherein proteins of a complex biological sample bind to the plurality of particles upon exposure of the complex biological sample to the plurality of particles, wherein a pattern of binding of the proteins amongst the plurality of particles depends on the physicochemical property of a surface of the particle.

In yet a further aspect, the invention provides a sensor array comprising a plurality of liposomes, wherein the plurality of liposomes differ in at least one protein-binding property defined by a lipid-based surface of each liposome; wherein the lipid-based surface of each liposome contacts a subset of proteins of a sample at a lipid-protein interface, thereby binding the subset of proteins to produce a pattern of protein binding; wherein the pattern of protein binding of a first liposome is different than the pattern of protein binding of a second liposome differing from the first liposome in said at least one protein-binding property.

In another aspect, the invention provides a method of identifying a biological state of a subject using a plurality of liposomes differing in at least one protein-binding property defined by a lipid-based surface of each liposome, wherein the method comprises: exposing the sample to the plurality of liposomes to permit binding of proteins of the sample to the plurality of liposomes, wherein a pattern of binding of the proteins differs amongst liposomes with different protein-binding properties; separating the proteins from the liposomes; defining a biomolecule fingerprint of the proteins separated from the liposomes; and associating the biomolecule fingerprint with a state of the complex biological sample of the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2B. Physicochemical properties of different liposomes before and after interactions with human plasma from patients with different diseases. DLS and Zeta-Potential data on various liposomes before interactions with human plasma and corona complexes free from excess plasma, obtained following incubation with plasma from healthy and cancer patients (Pdi: Polydispersity index from cumulant fitting).

FIG. 7A. Schematic representation of study outline. Informative variable selection and classification model building.

FIG. 7B. The protein name and ID of 69 selected variables are listed. Some of the proteins were present in the protein corona of more than one liposome (DOPG, DOTAP and CHOL are denoted by fonts: Italic and underline font, bold font, and Plain font, respectively).

FIG. 7C. The disease-specific biomarkers covered as significant variables by the proposed models.

FIG. 13. Examples of the types of nanoscale sensor elements that can be used for some embodiments of the sensor arrays. Different types of nanoparticles (e.g., organic, inorganic, and polymeric nanoparticles) with various physicochemical properties (e.g., different, surface properties, sizes, and shapes) can be used as sensor elements. Sensor array can be created by minimum two elements to an unlimited number of elements.

FIG. 16A. Examples of protein corona sensor array chip with nano-curvatures (produced by wide variety of available approaches like lithography and mold casting), with different physicochemical properties, before interactions with protein source (e.g., human plasma of various disease). The specific protein corona will form on the surface of nano-objects, with different physicochemical properties. The substrates may also get coated by several types of proteins, which have negligible effects on the detection efficacy of the chip.

FIG. 16B. Examples of protein corona sensor array chip with nano-curvatures (produced by wide variety of available approaches like lithography and mold casting), with different physicochemical properties after interactions with protein source (e.g., human plasma of various disease). The specific protein corona will form on the surface of nano-objects, with different physicochemical properties. The substrates may also get coated by several types of proteins, which have negligible effects on the detection efficacy of the chip.

FIG. 18A. Examples of protein corona sensor array micro/nano fluidic chip with nano-curvatures (produced by wide variety of available approaches like lithography and mold casting), with different physicochemical properties, before interactions with protein source (e.g., human plasma of various disease).

FIG. 18B. Examples of protein corona sensor array micro/nano fluidic chip with nano-curvatures (produced by wide variety of available approaches like lithography and mold casting), with different physicochemical properties, after interactions with protein source (e.g., human plasma of various disease).

FIG. 20A. Examples of protein corona sensor array chip with random-ordered nano-curvatures (produced by wide variety of available approaches like lithography and mold casting), with different physicochemical properties, before interactions with protein source (e.g., human plasma of various disease).

FIG. 20B. Examples of protein corona sensor array chip with random-ordered nano-curvatures with different physicochemical properties after interactions with protein source (e.g., human plasma of various disease).

FIG. 22A. Examples of protein corona sensor array micro/nano fluidic chip with random-ordered nano-curvatures (produced by wide variety of available approaches like lithography and mold casting), with different physicochemical properties, before interactions with protein source (e.g., human plasma of various disease).

FIG. 22B. Examples of protein corona sensor array micro/nano fluidic chip with random-ordered nano-curvatures with different physicochemical properties after interactions with protein source (e.g., human plasma of various disease).

FIG. 42A. Example of sensor array with random order nanoscale sensor elements for fluorescence or luminescence readout.

FIG. 42B. Example of sensor array with random order nanoscale sensor elements for fluorescence or luminescence readout.

FIG. 42C. Example of sensor array with random order nanoscale sensor elements for fluorescence or luminescence readout.

FIG. 42D. Example of sensor array with random order nanoscale sensor elements for fluorescence or luminescence readout.

FIG. 43A. Example of sensor array with order nanoscale sensor elements for fluorescence or luminescence readout.

FIG. 43B. Example of sensor array with order nanoscale sensor elements for fluorescence or luminescence readout.

FIG. 43C. Example of sensor array with order nanoscale sensor elements for fluorescence or luminescence readout.

FIG. 43D. Example of sensor array with order nanoscale sensor elements for fluorescence or luminescence readout.

FIG. 44A. Characterization of bare polystyrene and silica nanoparticles with different functionalization (none, amine modification ($NH_2$) and carboxyl modification (COOH)), showing the three different polystyrene nanoparticles (non-functionalized, P—$NH_2$ and P—COOH) used, their sizes, DLS and zeta potential of the bare particles.

FIG. 44B. Characterization of bare polystyrene and silica nanoparticles with different functionalization (none, amine modification (NH2) and carboxyl modification (COOH)), showing the three different silica nanoparticles (non-functionalized, S—NH2 and S—COOH) used, their sizes, DLS and zeta potential.

FIG. 44C. Characterization of bare polystyrene and silica nanoparticles with different functionalization (none, amine modification (NH2) and carboxyl modification (COOH)), showing TEM of bare polystyrene nanoparticle.

FIG. 44D. Characterization of bare polystyrene and silica nanoparticles with different functionalization (none, amine modification (NH2) and carboxyl modification (COOH)), showing TEM of bare silica nanoparticles.

FIG. 45A. Characterization of protein corona-coated polystyrene and silica nanoparticles with different functionalization (none, amine modification (NH2) and carboxyl modification (COOH)), showing the sizes, DLS and zeta potential of the protein-corona loaded polystyrene nanoparticles.

FIG. 45B. Characterization of protein corona-coated polystyrene and silica nanoparticles with different functionalization (none, amine modification (NH2) and carboxyl modification (COOH)), showing the sizes, DLS and zeta potential of the protein-corona loaded silica nanoparticles.

FIG. 45C. Characterization of protein corona-coated polystyrene and silica nanoparticles with different functionalization (none, amine modification (NH2) and carboxyl modification (COOH)), showing TEM of protein-corona loaded polystyrene nanoparticles.

FIG. 45D. Characterization of protein corona-coated polystyrene and silica nanoparticles with different functionalization (none, amine modification (NH2) and carboxyl modification (COOH)), showing TEM of protein-corona loaded silica nanoparticles.

Figure 62:
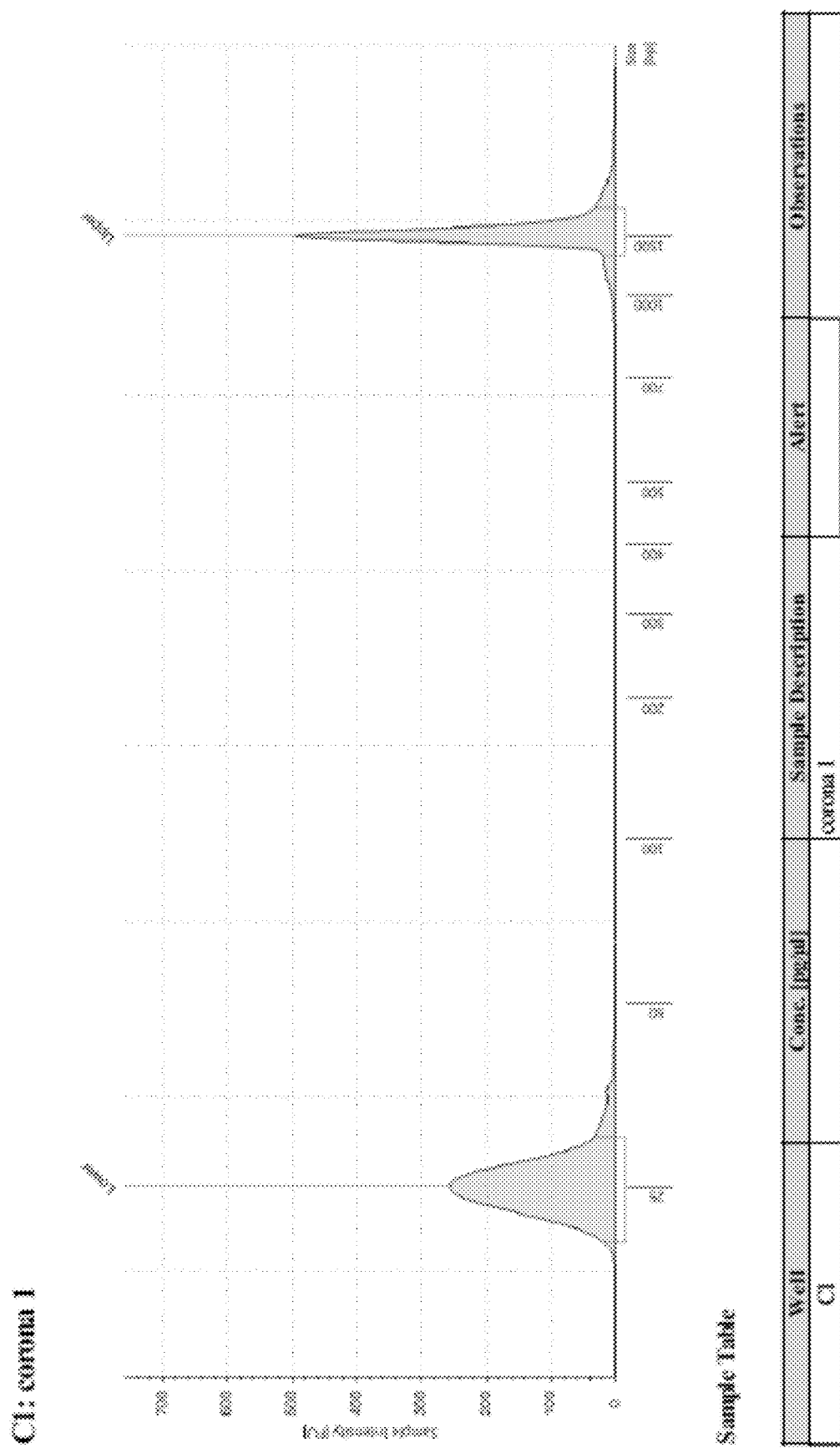
Figure 62:
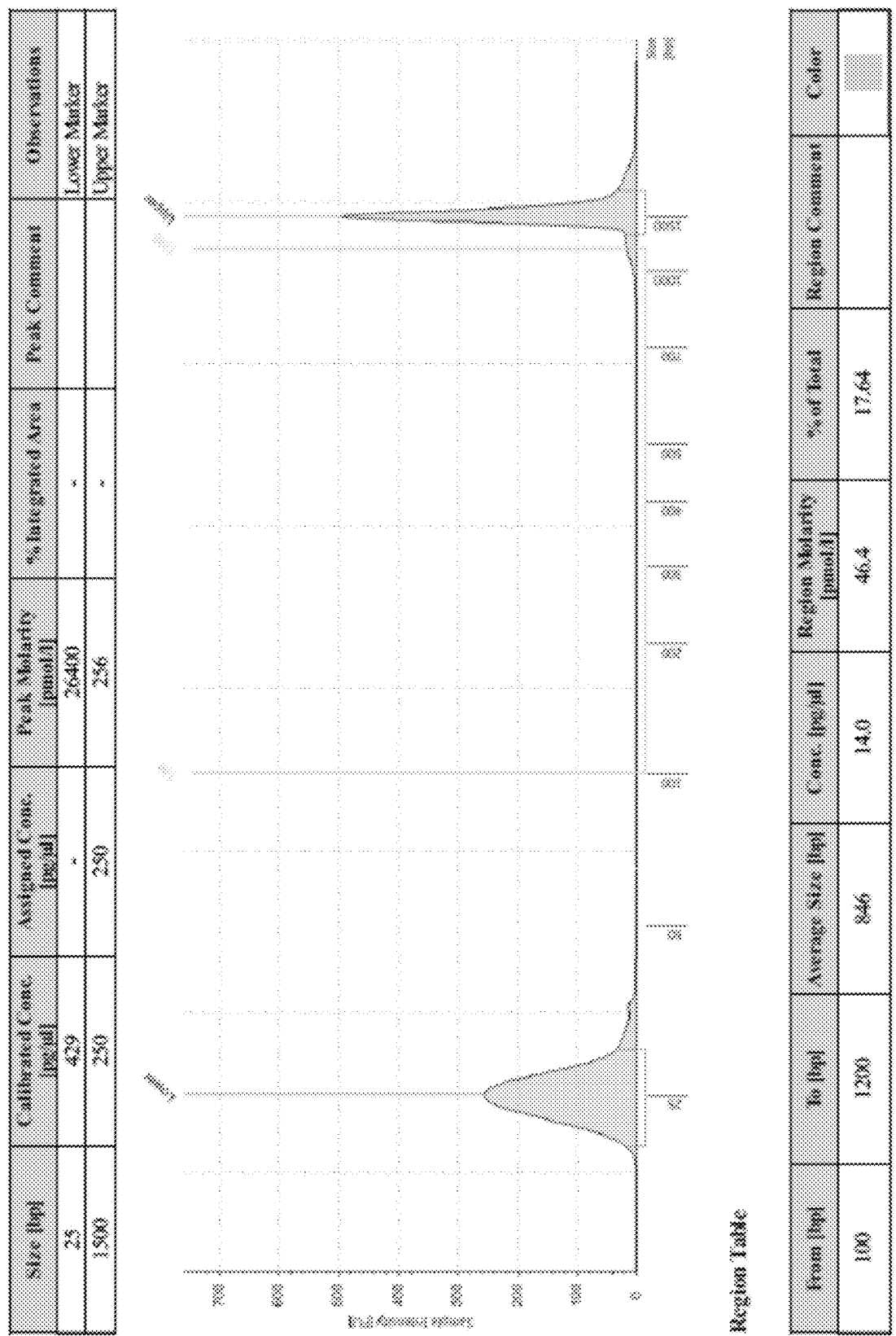

FIG. 62. Analysis of nucleic acid amounts associated with biomolecule corona of a nanoparticle when protein was dissociated from the corona by urea.

Figure 63:
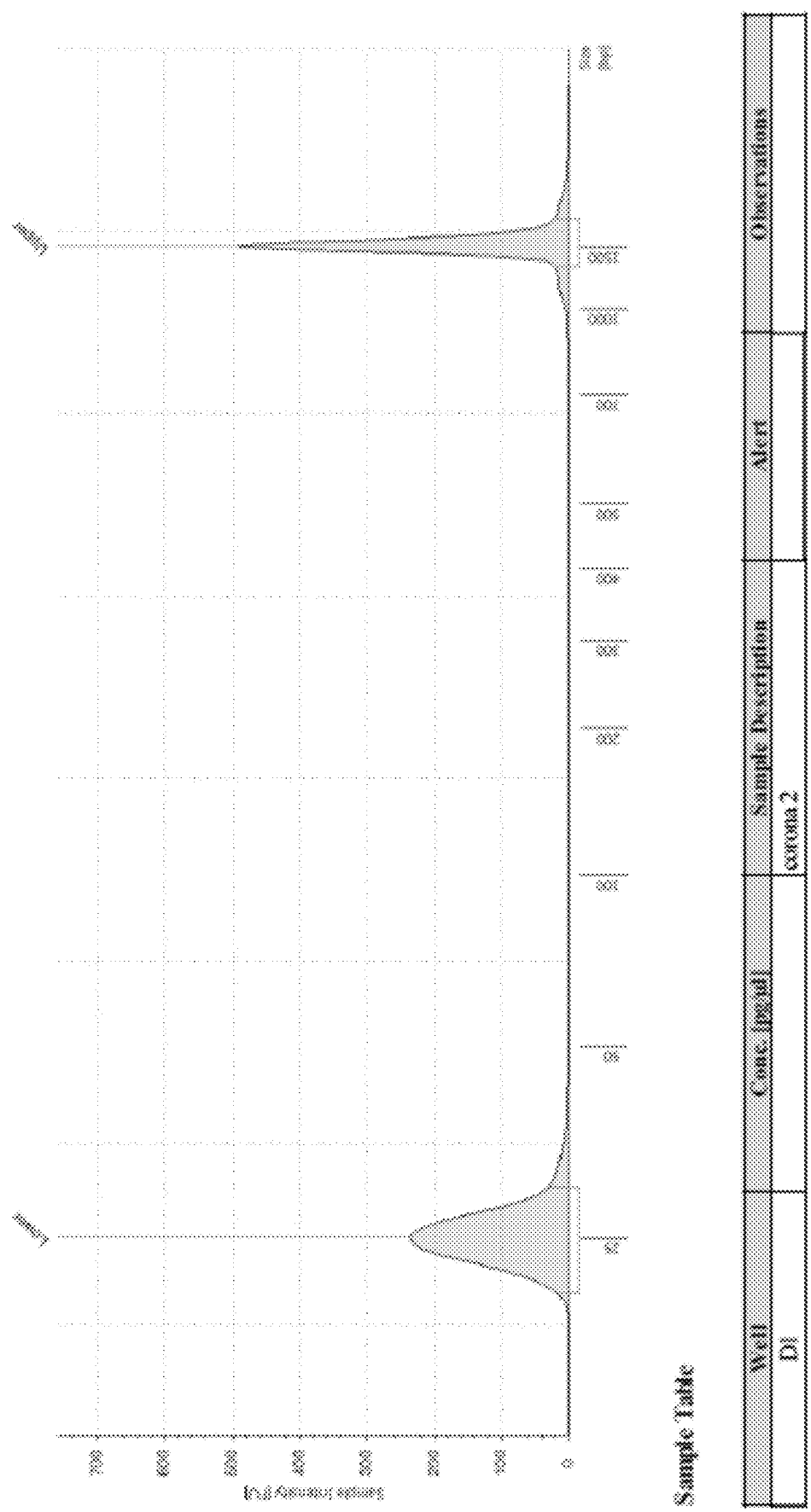
Figure 63:
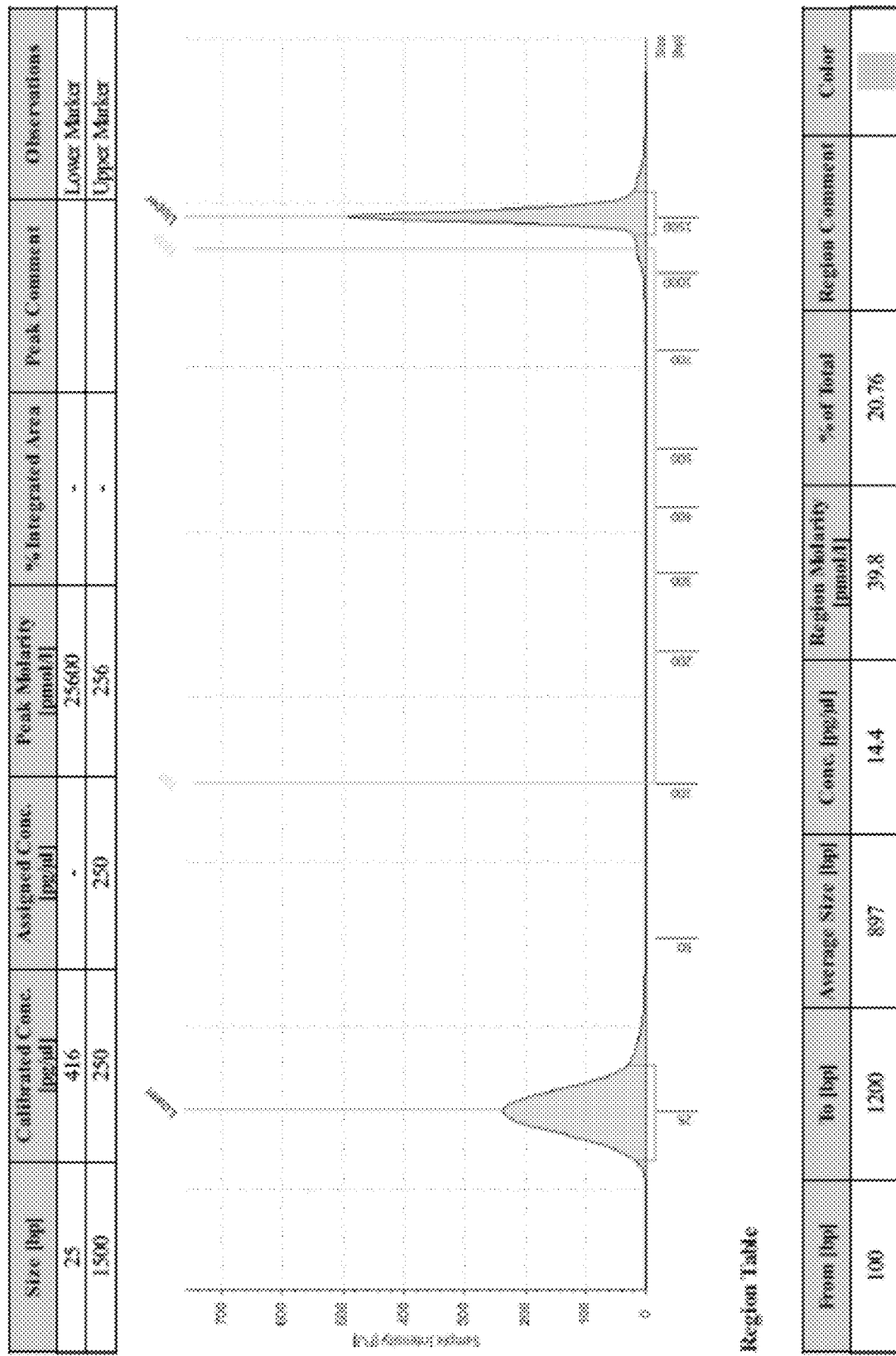

FIG. 63. Analysis of nucleic acid amounts associated with biomolecule corona of a nanoparticle when corona proteins were not dissociated from the surface of the particles.

Figure 64:
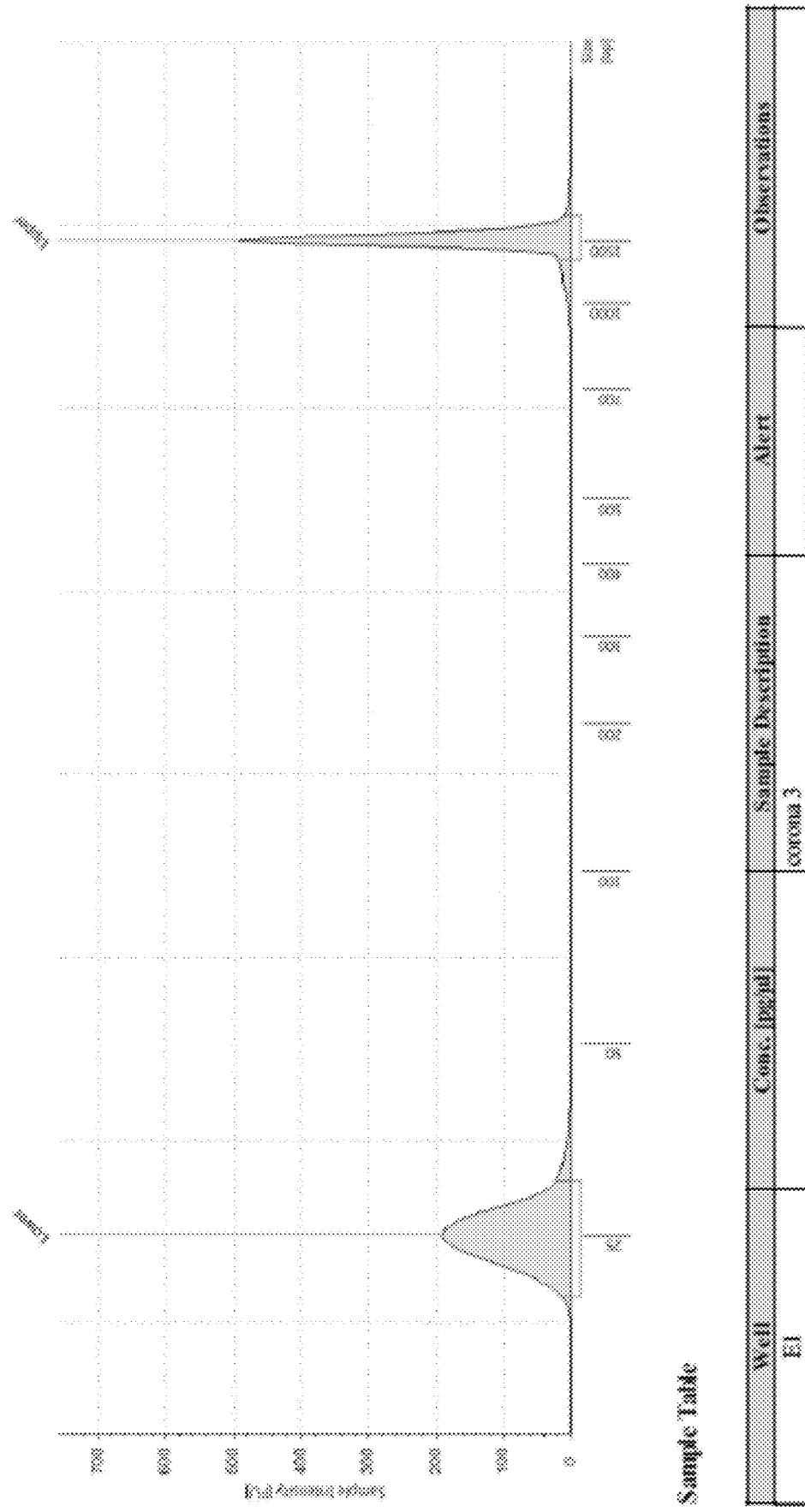
Figure 64:
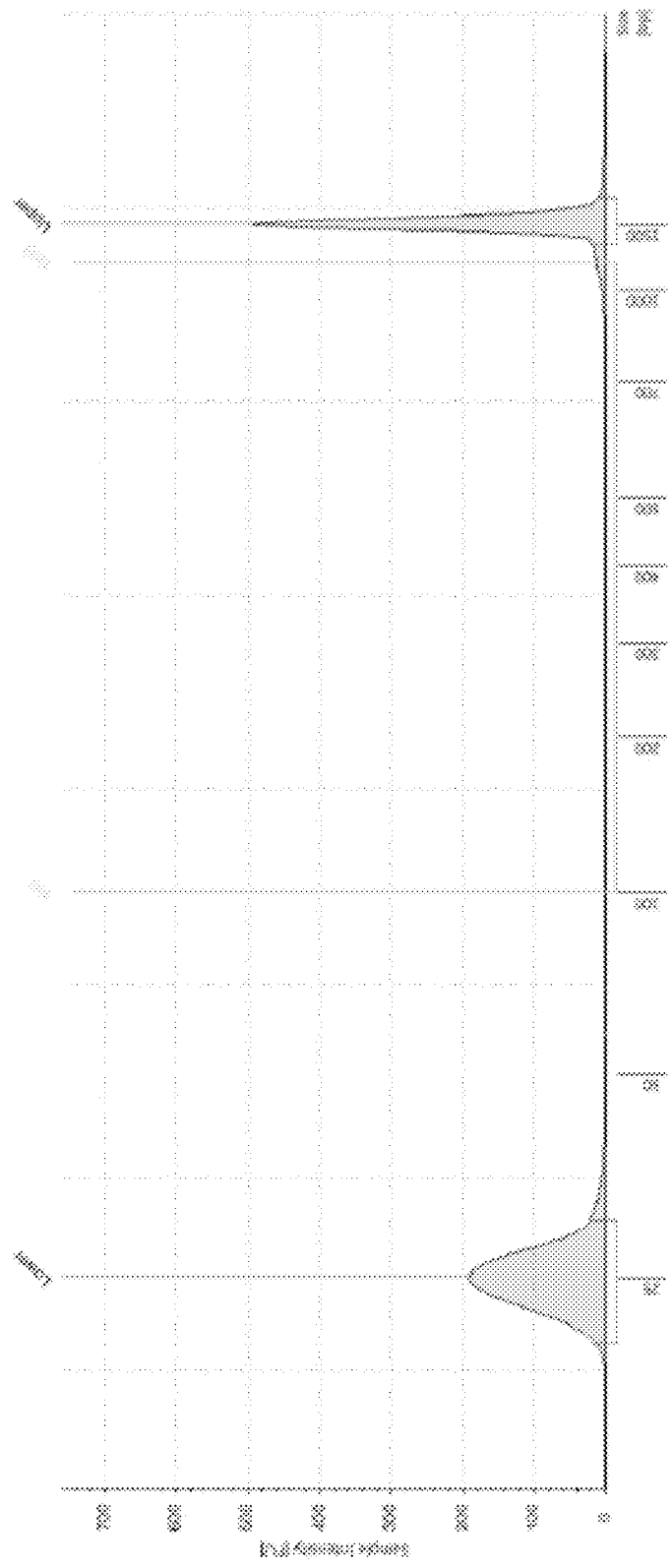

FIG. 64. Analysis of nucleic acid amounts associated with biomolecule corona of a nanoparticle when nucleic acids first purified from plasma with purification kit and then incubated with nanoparticles.

Figure 65:
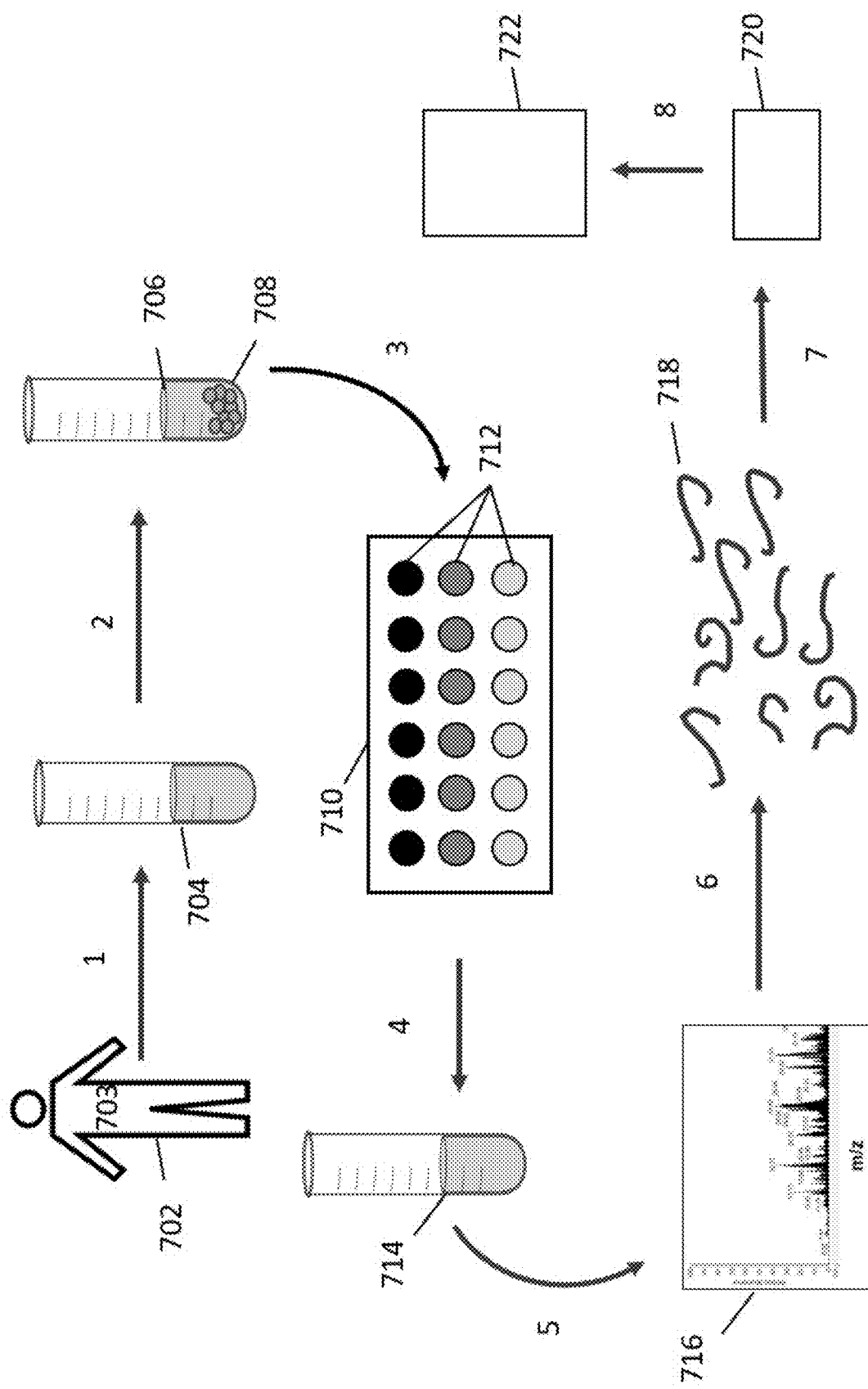

FIG. 65. Schematic diagram of a method of distinguishing states of a complex biological sample.

Figure 66:
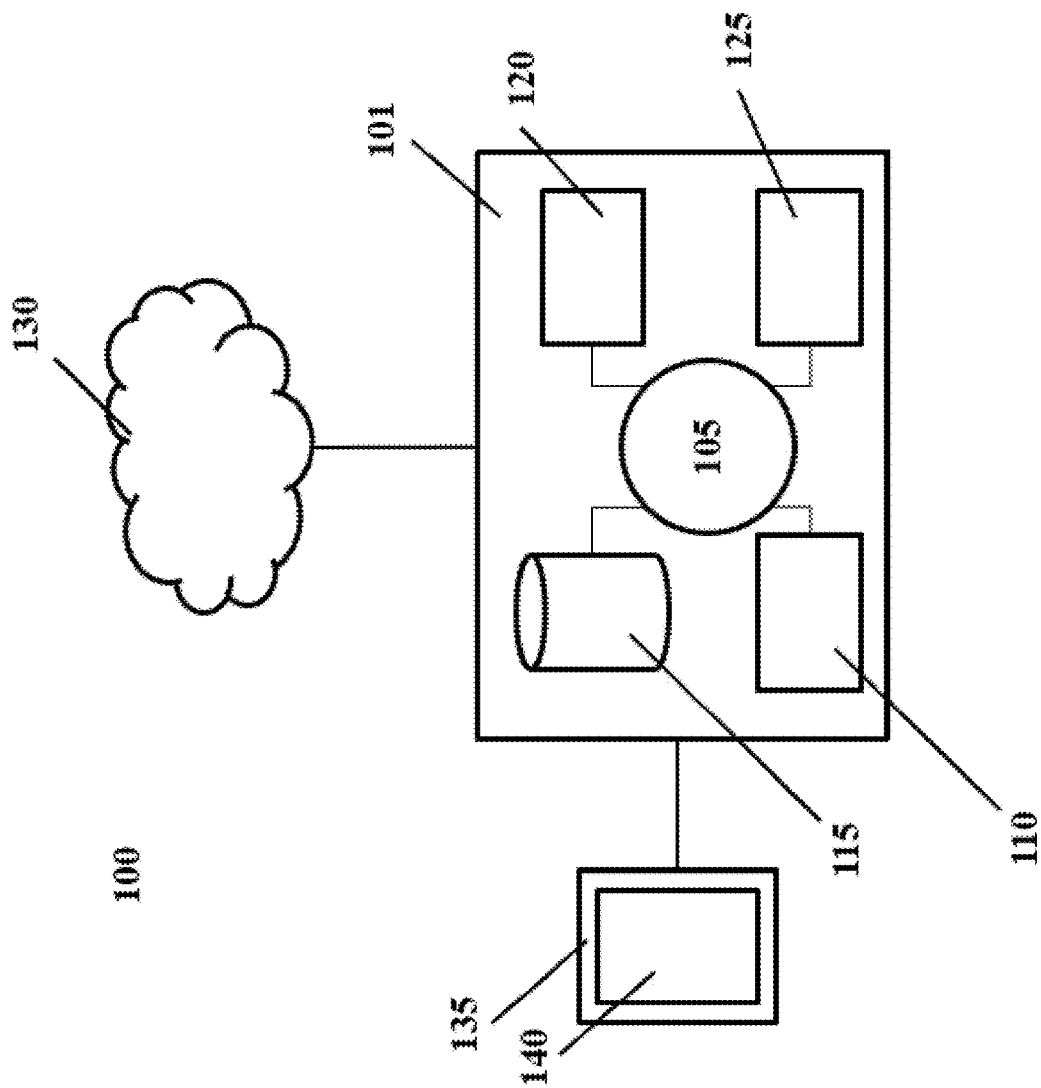

FIG. 66. Schematic diagram of a computer system.

FIG. 67. Table 3. Correlation coefficient of CPANN weight map for each variable in the six classes.

FIG. 68. Table 9: Information of the patients in which their plasmas were used in Example 6.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

The present invention provides sensor arrays and methods of use for the prognosis, diagnosis and detection of a disease state in a subject. The sensor array of the present invention differs from known sensor arrays that involve individual sensors that detect specific biomolecules. In the present sensor array, the biomolecules do not have to be known, as the system does not rely on the presence or absence of a specific biomolecules or amounts of specific disease markers. This new sensor array is able to detect changes in the compositions of the biomolecule corona associated with the different sensor elements. This ability to detect relative changes or patterns (either the actual biomolecules associated with the different sensor elements or in the amounts and/or conformations of each biomolecule associated with each sensor element) allows for determining a unique biomolecule fingerprint for each array. This biomolecule fingerprint can stratify different health and disease states of subjects. In some embodiments, the biomolecular fingerprint is not only able to differentiate between healthy subjects and subjects in various different stages of a disease or disorder but also to determine a pre-disease state in a subject where the subject will develop the disease or disorder at a later time. This is significantly different and novel over systems in the art that measure or detect specific biomarkers associated with a disease or disorder to provide a predisposition (e.g. a chance or likelihood) of developing the disease. The present sensor and methods is able to detect a disease before any signs or symptoms, in other words, can pre-diagnose the disease before any specific signs or symptoms appear.

The uniqueness of the present invention is the combination of this recognition of a biomolecular fingerprint from a sample from a subject and the ability to determine a disease state for that subject on a continuum of health.

The present invention is based on work by the inventors that have shown that the surface of sensor elements, e.g. nanoparticles, is rapidly covered with a layer of different biomolecules, including proteins, to form a "biomolecule corona" when contacted with a biological sample They type, amount, and categories of the biomolecules that make up these biomolecule corona are strongly related to the physicochemical properties of the sensor elements themselves and the complex interactions between the different biomolecules themselves and the sensor elements. These interactions lead to the production of a unique biomolecule corona signature for each sensor element. In other words, depending on which biomolecules interact with the sensor element not only influences the makeup of the biomolecule corona but also can alter which other different biomolecules can also interact with that specific sensor element.

Different sensor elements each with their own biomolecule corona signature can be contacted with a sample to produce a unique biomolecule fingerprint for that sample. This fingerprint can then be used to determine a disease state of a subject. Embodiments of the invention will be discussed in more detail below.

The present invention provides sensor arrays comprising, consisting essentially of or consists of a plurality of sensor elements wherein the plurality of sensor elements differ from each other in at least one physicochemical property. In some embodiments, each sensor element is able to bind a plurality of biomolecules in a sample to produce a biomolecule corona signature. In some embodiments, each sensor elements has a distinct biomolecule corona signature.

The plurality of sensor elements when contacted with a sample produces a plurality of biomolecule corona signatures which together form a biomolecule fingerprint. The "biomolecule fingerprint" is the combined composition or pattern of biomolecules of at least two biomolecule corona signatures for the plurality of sensor elements.

As used herein, the term "sensor element" refer to elements that are able to bind to a plurality of biomolecules when in contact with a sample and encompasses the term "nanoscale sensor element". In one embodiment, the sensor element is an element from about 5 nanometer to about 50000 nanometer in at least one direction. Suitable sensor elements include, for example, but not limited to a sensor element from about 5 nm to about 50,000 μm in at least one direction, including, about 5 μm to about 40000 nm, alternatively about 5 μm to about 30000 μm, alternatively about 5 μm to about 20,000 μm, alternatively about 5 μm to about 10,000 μm, alternatively about 5 nm to about 5000 μm, alternatively about 5 μm to about 1000 μm, alternatively about 5 μm to about 500 μm, alternatively about 5 μm to 50 μm, alternatively about 10 μm to 100 μm, alternatively about 20 μm to 200 μm, alternatively about 30 μm to 300 μm, alternatively about 40 μm to 400 μm, alternatively about 50 μm to 500 μm, alternatively about 60 μm to 600 μm, alternatively about 70 μm to 700 μm, alternatively about 80 μm to 800 μm, alternatively about 90 μm to 900 μm, alternatively about 100 μm to 1000 μm, alternatively about 1000 μm to 10000 μm, alternatively about 10000 μm to 50000 μm and any combination or amount inbetween (e.g. 5 nm, 10 μm, 15 μm, 20 μm, 25 μm, 30 μm, 35 μm, 40 μm, 45 μm, 50 μm, 55 μm, 60 μm, 65 μm, 70 μm, 80 μm, 90 μm, 100 μm, 125 μm, 150 μm, 175 μm, 200 μm, 225 μm, 250 μm, 275 μm, 300 μm, 350 μm, 400 μm, 450 μm, 500 μm, 550 μm, 600 μm, 650 μm, 700 μm, 750 μm, 800 μm, 850 μm, 900 μm, 1000 μm, 1200 μm, 1300 μm, 1400 μm, 1500 μm, 1600 μm, 1700 μm, 1800 μm, 1900 nm, 2000 μm, 2500 μm, 3000 μm, 3500 μm, 4000 μm, 4500 μm, 5000 μm, 5500 μm, 6000 nm, 6500 μm, 7000 μm, 7500 μm, 8000 μm, 8500 μm, 9000 μm, 10000 μm, 11000 μm, 12000 μm, 13000 μm, 14000 μm, 15000 μm, 16000 μm, 17000 μm, 18000 μm, 19000 μm, 20000 μm, 25000 μm, 30000 μm, 35000 μm, 40000 μm, 45000 μm, 50000 μm and any number inbetween). A nanoscale sensor element refers to a sensor element that is less than 1 micron in at least one direction. Suitable examples of ranges of nanoscale sensor elements include, but are not limited to, for example, elements from about 5 μm to about 1000 μm in one direction, including, from example, about 5 μm to about 500 μm, alternatively about 5 μm to about 400 μm, alternatively about 5 μm to about 300 μm, alternatively about 5 μm to about 200 μm, alternatively about 5 μm to about 100 μm, alternatively about 5 μm to about 50 μm, alternatively about 10 μm to about 1000 μm, alternatively about 10 μm to about 750 μm, alternatively about 10 μm to about 500 μm, alternatively about 10 μm to about 250 μm, alternatively about 10 μm to about 200 μm, alternatively about 10 μm to about 100 μm, alternatively about 50 μm to about 1000 μm, alternatively about 50 μm to about 500 μm, alternatively about 50 μm to about 250 μm, alternatively about 50 μm to about 200 μm, alternatively about 50 μm to about 100 μm, and any combinations, ranges or amount in-between (e.g. 5 nm, 10 μm, 15 μm, 20 μm, 25 nm, 30 μm, 35 μm, 40 μm, 45 μm, 50 μm, 55 μm, 60 μm, 65 μm, 70 μm, 80 μm, 90 μm, 100 nm, 125 μm, 150 μm, 175 μm, 200 μm, 225 μm, 250 μm, 275 μm, 300 μm, 350 μm, 400 nm, 450 μm, 500 μm, 550 μm, 600 μm, 650 μm, 700 μm, 750 μm, 800 μm, 850 μm, 900 nm, 1000 μm, etc.). In reference to the sensor arrays described herein, the use of the term sensor element includes the use of a nanoscale sensor element for the sensor and associated methods.

The term "plurality of sensor elements" refers to more than one, for example, at least two sensor elements. In some embodiments, the plurality of sensor elements includes at least two sensor elements to at least 1000 sensor elements, preferably about two sensor elements to about 100 sensor elements. In suitable embodiments, the array comprises at least two to at least 100 sensor elements, alternatively at least two to at least 50 sensor elements, alternatively at least 2 to 30 sensor elements, alternatively at least 2 to 20 sensor elements, alternatively at least 2 to 10 sensor elements, alternatively at least 3 to at least 50 sensor elements, alternatively at least 3 to at least 30 sensor elements, alternatively at least 3 to at least 20 sensor elements, alternatively at least 3 to at least 10 sensor elements, alternatively at least 4 to at least 50 sensor elements, alternatively at least 4 to at least 30 sensor elements, alternatively at least 4 to at least 20 sensor elements, alternatively at least 4 to at least 10 sensor elements, and including any number of sensor elements contemplated in between (e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 225, 250, 300, 350, 400, 450, 500, 550, 600, 650, 700, 750, 800, etc.). In some embodiments, the sensor array comprises at least 6 sensor elements to at least 20 sensor elements, alternatively at least 6 sensor elements to at least 10 sensor elements.

The term "plurality of nanoscale sensor elements" refers to more than one, for example, at least two nanoscale sensor elements. In some embodiments, the plurality of nanoscale sensor elements includes at least two nanoscale sensor elements to at least 1000 nanoscale sensor elements, preferably about two nanoscale sensor elements to about 100 nanoscale sensor elements. In suitable embodiments, the array comprises at least two to at least 100 nanoscale sensor elements, alternatively at least two to at least 50 nanoscale sensor elements, alternatively at least 2 to 30 nanoscale sensor elements, alternatively at least 2 to 20 nanoscale sensor elements, alternatively at least 2 to 10 nanoscale sensor elements, alternatively at least 3 to at least 50 nanoscale sensor elements, alternatively at least 3 to at least 30 nanoscale sensor elements, alternatively at least 3 to at least 20 nanoscale sensor elements, alternatively at least 3 to at least 10 nanoscale sensor elements, alternatively at least 4 to at least 50 nanoscale sensor elements, alternatively at least 4 to at least 30 nanoscale sensor elements, alternatively at least 4 to at least 20 nanoscale sensor elements, alternatively at least 4 to at least 10 nanoscale sensor elements, and including any number of nanoscale sensor elements contemplated in between (e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 225, 250, 300, 350, 400, 450, 500, 550, 600, 650, 700, 750, 800, etc.).

As used herein, the term "biomolecule corona" refers to the plurality of different biomolecules that are able to bind to a sensor element. The term "biomolecule corona" encompasses "protein corona" which is a term used in the art to refer to the proteins, lipids and other plasma components that bind nanoparticles when they come into contact with biological samples or biological system. For use herein, the term "biomolecule corona" also encompasses both the soft and hard protein corona as referred to in the art, see, e.g., Milani et al. "Reversible versus Irreversible Binding of Transferring to Polystyrene Nanoparticles: Soft and Hard Corona" ACS NANO, 2012, 6(3), pp. 2532-2541; Mirshafiee et al. "Impact of protein pre-coating on the protein corona composition and nanoparticle cellular uptake" Biomaterials vol. 75, January 2016 pp. 295-304, Mahmoudi et al. "Emerging understanding of the protein corona at the nano-bio interfaces" Nanotoday 11(6) December 2016, pp. 817-832, and Mahmoudi et al. "Protein-Nanoparticle Interactions: Opportunities and Challenges" Chem. Rev., 2011, 111(9), pp. 5610-5637, the contents of which are incorporated by reference in their entireties. As described in the art, adsorption curve shows the build-up of a strongly bound monolayer up to the point of monolayer saturation (at a geometrically defined protein-to-NP ratio), beyond which a secondary, weakly bound layer is formed. While the first layer is irreversibly bound (hard corona), the secondary layer (soft corona) exhibits dynamic exchange. Proteins that adsorb with high affinity form what is known as the "hard" corona, consisting of tightly bound proteins that do not readily desorb, and proteins that adsorb with low affinity form the "soft" corona, consisting of loosely bound proteins. Soft and hard corona can also be defined based on their exchange times. Hard corona usually shows much larger exchange times in the order of several hours. See, e.g., M. Rahman et al. Protein-Nanoparticle Interactions, Spring Series in Biophysics 15, 2013, incorporated by reference in its entirety.

The term "biomolecule corona signature" refers to the composition, signature or pattern of different biomolecules that are bound to each separate sensor element. The signature not only refers to the different biomolecules but also the differences in the amount, level or quantity of the biomolecule bound to the sensor element, or differences in the conformational state of the biomolecule that is bound to the sensor element. It is contemplated that the biomolecule corona signatures of each sensor elements may contain some of the same biomolecules, may contain distinct biomolecules with regard to the other sensor elements, and/or may differ in level or quantity, type or confirmation of the biomolecule. The biomolecule corona signature may depend on not only the physiocochemical properties of the sensor element, but also the nature of the sample and the duration of exposure. In some cases, the biomolecule corona signature is a protein corona signature. In another case, the biomolecule corona signature is a polysaccharide corona signature. In yet another case, the biomolecule corona signature is a metabolite corona signature. In some cases, the biomolecule corona signature is a lipidomic corona signature.

In some embodiments, the biomolecule corona signature comprises the biomolecules found in a soft corona and a hard corona. In some embodiments, the soft corona is a soft protein corona. In some embodiments, the hard corona is a hard protein corona.

The term "biomolecule" refers to biological components that may be involved in corona formation, including, but not limited to, for example, proteins, polypeptides, polysaccharides, a sugar, a lipid, a lipoprotein, a metabolite, an oligonucleotide, metabolome or combination thereof. It is contemplated that the biomolecule corona signatures of each sensor elements may contain some of the same biomolecules, may contain distinct biomolecules with regard to the other sensor elements, and/or may differ in level or quantity, type or confirmation of the biomolecule that binds to each sensor element. In one embodiment, the biomolecule is selected from the group of proteins, nucleic acids, lipids, and metabolomes.

In some embodiments, the sensor array comprises, consists essentially of or consists of a first sensor element that produces a first biomolecule corona signature and at least one second sensor element that produces at least one second biomolecule corona signature when the sensor array is contacted with a biological sample. A biomolecule fingerprint is the combination of the first biomolecule signature and the at least one second biomolecule signature. It is contemplated that the biomolecule signature can be made from at least two biomolecule corona signatures to as many different biomolecule signatures are assayed, e.g. at least 1000 different biomolecule corona signatures. The biomolecule corona may be assayed separately for each sensor element to determine the biomolecule corona signature for each element and combined to determine the biomolecule fingerprint or the two or more biomolecule corona can be assayed at the same time to develop the biomolecule fingerprint at once.

In some embodiments, the biomolecule fingerprint includes at least two biomolecule corona signatures. In some embodiments, the biomolecule fingerprint includes at two biomolecule corona signatures to at least 1000 biomolecule corona signatures, preferably about two biomolecule corona signatures to about 100 biomolecule corona signatures. In suitable embodiments, the biomolecule fingerprint comprises at least two to at least 100 biomolecule corona signatures, alternatively at least two to at least 50 biomolecule corona signatures, alternatively at least 2 to 30 biomolecule corona signatures, alternatively at least 2 to 20 biomolecule corona signatures, alternatively at least 2 to 10 biomolecule corona signatures, alternatively at least 3 to at least 50 biomolecule corona signatures, alternatively at least 3 to at least 30 biomolecule corona signatures, alternatively at least 3 to at least 20 biomolecule corona signatures, alternatively at least 3 to at least 10 biomolecule corona signatures, alternatively at least 4 to at least 50 biomolecule corona signatures, alternatively at least 4 to at least 30 biomolecule corona signatures, alternatively at least 4 to at least 20 biomolecule corona signatures, alternatively at least 4 to at least 10 biomolecule corona signatures, and including any number of biomolecule corona signatures contemplated in between (e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 225, 250, 300, 350, 400, 450, 500, 550, 600, 650, 700, 750, 800, etc.).

Advances in proteomic analyses using mass spectrometry have offered new insights into the changes that take place across the spectrum of health and disease including early-stage cancer. Yet the sensitivity and specificity of mass spectrometry approaches have not been adequate for robust early detection of cancers in part due to the high noise created by the 10000 of proteins comprising the human proteome, with estimated concentrations spanning 35-50 mg/ml for albumin to 1-10 pg/ml for some cytokines. The existing technologies have required a trade-off between the depth of coverage and the throughput of processing of plasma proteins. Several attempts have been made to substantially increase the current low levels of protein detection, including depletions of highly abundant proteins, isobaric labeling at the peptide level for multiplexed relative quantification, post-depletion plasma fractionation strategies, biomarker harvesting techniques, mathematical approaches for analyzing high-quality data sets, and multiplexed workflow (i.e., a combination of approaches). Despite such efforts, mass-spectrometry approaches to plasma proteomics have not met with robust success in the early detection of cancers. In fact no prior study, proteomic or otherwise, has reported accurate prediction and classification of a range of cancers, including the earliest pre-symptomatic stages. The present sensor array has provided the first detection system that accurately predicts and classifies a disease state, including pre-symptomatic disease state for a number of different diseases.

Prior attempts have tried to use the "disease-specific protein corona" to identify one cancer type using gel electrophoresis and changes in aggregation size of nanoparticles. However, as we show in the Examples below, the subtle differences in the protein corona at the surface of one type of nanoparticle were not sufficient for robust and accurate identification and discrimination of cancers with acceptable prediction accuracy, mainly due to the persistent issue of inadequate proteomic coverage. The sensory array described herein is able to accurately classify disease states. Not only it is able to predict the disease state, but it is also able to classify patients who are pre-symptomatic of the disease (e.g. Alzheimer's) or classify patients according to the type of disease (e.g. type of cancer).

To materially enhance the capacity of the protein corona for robust and accurate cancer detection with excellent prediction capacity, the inventors developed a sensor array (sometimes referred to herein as a Protein Corona Nanosystem or sensor array nanosystem). Compared with previous approaches limited to the surface of a single nanoparticle, it provides significantly more comprehensive proteomics data over a wider dynamic range of plasma protein concentrations. The sensor array allows for the sampling a complex biological sample (e.g., human plasma sample) using multi-nanoparticles with different physicochemical properties to significantly increase the number and range of both low- and high-abundance proteins identified without protein depletion. This effectively reduces the noise in the vast proteomic information available, yielding more-accurate early differentiation of the proteomic signature that is characteristic of a disease. In addition, because of the combination of protein-nanoparticle and protein-protein interaction that is uniquely derived using the sensor array, each type of protein may be present in different concentrations on the surface of different nanoparticles, providing additional proteomic information. The use of multi-nanoparticles with different physicochemical properties is mainly driven by our recent findings that even small alterations to the physicochemical properties of nanoparticles can elicit dramatic but reproducible changes in the protein corona composition.

The present sensor array has a sensitivity and dynamic range of ten (10) orders of magnitude in terms of protein detection using mass-spectroscopy approaches. The present assay is able to detect proteins that are found in the sub-ng range within a sample. This assay or approach has a much greater dynamic range than current assays for measuring proteins within a sample. For example, mass spectrometry only has a dynamic range 4-6 order of magnitude. This novel sensor array has the ability to sample a greater dynamic range than has previously been achievable. The present sensor array allows for detection and determination of low abundant and rare proteins that we not previously able to be detected.

The term "sample" refers to a biological sample or a complex biological sample obtained from a subject. Suitable biological samples include, but are not limited to, biological fluids, including, but not limited to, systemic blood, plasma, serum, lung lavage, cell lysates, menstrual blood, urine, processed tissue samples, amniotic fluid, cerebrospinal fluid, tears, saliva, semen and the like. In a preferred embodiment, the sample is a blood or serum sample. Blood plasma contains several thousands of different proteins with twelve orders of magnitude differences in the concentrations of these proteins. The present sensor array is able to detect changes within these blood samples over time or over disease states of the subject.

In some embodiments, the biological fluids or complex biological samples are prepared by methods and kits known in the art. For example, some biological samples (e.g. menstrual blood, blood samples, semen, etc.) may first be centrifuged at low speed to remove cell debris, blood clots and other cellular components that may interfere with the array. In other embodiments, for example, tissue specimens may be processed, e.g. tissue samples may be minced or homogenized, treated with enzymes to break up the tissue and/or centrifuged to remove cellular debris allowing for the assaying and extraction of the biomolecules within the tissue samples. Suitable methods of isolating and/or properly preparing and storing blood samples are known in the art, and may include, but are not limited to, the addition of an anti-coagulant agent.

Suitable sensor elements include, but are not limited to, for example, particles, such as organic particles, non-organic particles or combinations thereof. In some embodiments the particles are, for example, nanoparticles, microparticles, micelles, liposomes, iron oxide, graphene, silica, protein-based particles, polystyrene, silver, and gold particles, quantum dots, palladium, platinum, titanium, and combinations thereof. In some embodiments, nanoparticles are liposomes. One skilled in the art would be able to select and prepare suitable particles. In some preferred embodiments, the sensor elements are nanoscale sensor elements. Suitable nanoscale sensor elements are less than 1 micron in at least one direction. In some aspects, the nanoscale sensor elements are less than about 100 μm in at least one direction.

Overview

The present disclosure provides a method of detecting a disease state using a biomolecule corona nanosystem. In one embodiment, the method comprises detecting a disease-specific protein corona.

Sensor Arrays

FIG. 65 shows an exemplary scheme of the presently disclosed array system. As shown at step 1 of FIG. 65, a complex biological sample (e.g., blood 704) can be collected from a subject 702 expressing a biological state 703 (e.g., a disease state, for example before any physical symptoms of the disease and/or during early and intermediate stages of a disease). Suitable biological samples 704 include, but are not limited to, biological fluids, including, but not limited to, systemic blood, plasma, serum, lung lavage, cell lysates, menstrual blood, urine, processed tissue samples, amniotic fluid, cerebrospinal fluid, tears, saliva, semen and the like. In a preferred embodiment, the sample is a blood or serum sample. In some embodiments, plasma 706 of can be separated from blood cells 708 of subjects expressing a biological state 703 (e.g. healthy people (non-disease state) and cancer patients (disease state), as shown at step 2 of FIG. 65.

Next, as shown at step 3 of FIG. 65, a complex biological sample (e.g., plasma 706) can be incubated with a sensor array 710 comprising a plurality of particles 712 with different physicochemical properties. The plurality of particles 712 can be incubated with the plasma 706 to allow biomolecules in the plasma 706 (e.g., proteins in the plasma 706) to bind to one or more of the particles 712. Subsequently, as shown at step 4 of FIG. 65, the biomolecules (e.g. proteins) bound to the particles 712 can be isolated in a protein solution 714 for further analysis, for example to determine the compositions of the proteins bound to each type of particle 712 (e.g., anionic, neutral and cationic particles 712).

The protein solution 714 can be characterized by, for example as shown at step 5 of FIG. 65, liquid chromatography-tandem mass spectrometry (LC-MS/MS) 716. Proteins identified using LC-MS/MS 716 can then be analyzed at step 6 of FIG. 65 to determine a biomolecule fingerprint 718 (e.g. representative of proteins, nucleic acids, lipids and polysaccharides that bind to one or more of particles 712) associated with the biological state 703.

At step 7 of FIG. 65, a computer 720 (e.g., computer system 101 in FIG. 66) can be used to associate a biomolecule fingerprint 718 (e.g., protein fingerprint) with a biological state 703 (e.g. health state, disease state). For example, analysis of a biomolecule fingerprint 718 (e.g. protein fingerprint) of at least two samples (e.g. complex biological samples such as plasma 706) can be conducted with a computer system 720 to generate an association 722 between the biological state 703 and the biomolecule fingerprint 718 (at step 8 of FIG. 65). The generation of association 722 can be by an association analysis or statistical classification using methods known in the art, including, but not limited to, a wide variety of supervised and unsupervised data analysis and clustering approaches such as hierarchical cluster analysis (HCA), principal component analysis (PCA), Partial least squares Discriminant Analysis (PLS-DA), machine learning (also known as random forest), logistic regression, decision trees, support vector machine (SVM), k-nearest neighbors, naive bayes, linear regression, polynomial regression, SVM for regression, K-means clustering, and hidden Markov models, among others. In other words, the biomolecule fingerprint 718 of each sample (e.g. plasma 706) are compared/analyzed (e.g. using a computer 720) with each other to determine with statistical significance what patterns are common between the individual fingerprints to determine a biological state that is associated with the biomolecule (e.g. protein) fingerprint 718.

The association 722 can link the biomolecule fingerprint 718 (e.g., protein fingerprint) to a wide variety of biological states 703. For example, comparison of biomolecule fingerprints 718 between a subject 702 diagnosed with a disease (i.e., biological state 703 is a disease state) and a subject 702 not diagnosed with the disease (i.e., biological state 703 is a non-disease state) can give rise to an association 722 between the biomolecule fingerprint 718 of the subject 702 with the disease and the disease state. Such an association 722 between the biomarker fingerprint 718 and the disease state (i.e., biological state 703) can in some embodiments be determined very early during the progression of a disease (i.e., before any physical symptoms of the disease manifest and/or before diagnosis of the disease) or at later times during disease progression.

Other examples of biological states 703 that can be associated with a biomolecule fingerprint 718 include responsiveness or non-responsiveness to a drug or pharmaceutical, level of activation of the immune system (e.g., due to exposure of a subject to an exogenous antigen), susceptibility of a subject to adverse effects associated with administration of a drug, and identification of a subject's potential to exhibit an allergic reaction to administration of a particular composition or substance.

Computer Control Systems

The present disclosure provides computer control systems that are programmed to implement methods of the disclosure. FIG. 66 shows a computer system 100 that is programmed or otherwise configured to associate a biomolecule fingerprint 718 with a biological state 703. This determination, analysis or statistical classification is done by methods known in the art, including, but not limited to, for example, a wide variety of supervised and unsupervised data analysis and clustering approaches such as hierarchical cluster analysis (HCA), principal component analysis (PCA), Partial least squares Discriminant Analysis (PLS-DA), machine learning (also known as random forest), logistic regression, decision trees, support vector machine (SVM), k-nearest neighbors, naive bayes, linear regression, polynomial regression, SVM for regression, K-means clustering, and hidden Markov models, among others. The computer system 100 can perform various aspects of analyzing the biomolecule fingerprints 718 of the present disclosure, such as, for example, comparing/analyzing the biomolecule corona of several samples to determine with statistical significance what patterns are common between the individual biomolecule coronas to determine a biomolecule fingerprint 718 that is associated with the biological state 703. The computer system can be used to develop classifiers to detect and discriminate different biomolecule fingerprints 718 (e.g., characteristic of the composition of a protein corona). Data collected from the presently disclosed sensor array can be used to train a machine learning algorithm, specifically an algorithm that receives array measurements from a patient and outputs specific biomolecule corona compositions from each patient. Before training the algorithm, raw data from the array can be first denoised to reduce variability in individual variables.

Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ, SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FP-growth algorithm; Hierarchical clustering, such as Single-linkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The computer system 100 depicted in FIG. 66 is adapted to implement a method described herein. The system 100 includes a central computer server 101 that is programmed to implement exemplary methods described herein. The server 101 includes a central processing unit (CPU, also "processor") 105 which can be a single core processor, a multi core processor, or plurality of processors for parallel processing. The server 101 also includes memory 110 (e.g., random access memory, read-only memory, flash memory); electronic storage unit 115 (e.g. hard disk); communications interface 120 (e.g., network adaptor) for communicating with one or more other systems; and peripheral devices 125 which may include cache, other memory, data storage, and/or electronic display adaptors. The memory 110, storage unit 115, interface 120, and peripheral devices 125 are in communication with the processor 105 through a communications bus (solid lines), such as a motherboard. The storage unit 115 can be a data storage unit for storing data. The server 101 is operatively coupled to a computer network ("network") 130 with the aid of the communications interface 120. The network 130 can be the Internet, an intranet and/or an extranet, an intranet and/or extranet that is in communication with the Internet, a telecommunication or data network. The network 130 in some cases, with the aid of the server 101, can implement a peer-to-peer network, which may enable devices coupled to the server 101 to behave as a client or a server.

The storage unit 115 can store files, such as subject reports, and/or communications with the data about individuals, or any aspect of data associated with the present disclosure.

The computer server 101 can communicate with one or more remote computer systems through the network 130. The one or more remote computer systems may be, for example, personal computers, laptops, tablets, telephones, Smart phones, or personal digital assistants.

In some applications the computer system 100 includes a single server 101. In other situations, the system includes multiple servers in communication with one another through an intranet, extranet and/or the internet.

The server 101 can be adapted to store measurement data or a database as provided herein, patient information from the subject, such as, for example, medical history, family history, demographic data and/or other clinical or personal information of potential relevance to a particular application. Such information can be stored on the storage unit 115 or the server 101 and such data can be transmitted through a network.

Methods as described herein can be implemented by way of machine (or computer processor) executable code (or software) stored on an electronic storage location of the server 101, such as, for example, on the memory 110, or electronic storage unit 115. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110. Alternatively, the code can be executed on a second computer system 140.

Aspects of the systems and methods provided herein, such as the server 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

The computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

Aspects of the systems and methods provided herein, such as the computer system 101 in FIG. 66 can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Physicochemical Properties

In some embodiments, the plurality of sensor elements comprises, consists essentially of, or consists of a plurality of particles, wherein each particle is differentiated for each other by at least one physiochemical property such that each sensor element has a unique biomolecule corona signature when placed in contact with the same sample.

The physicochemical property of the sensor element found in an array refer to, for example, the composition, size, surface charge, hydrophobicity, hydrophilicity, surface functionality (surface functional groups), surface topography, surface curvature and shape. The term composition encompasses the use of different types of materials and differences in the chemical and/or physical properties of materials, for example, conductivity of the material chosen between the sensor elements.

Surface curvature is generally determined by the nanoparticle size. Thus, at a nanometer scale, as the size of the nanoparticles changes, the surface curvature of the particle changes, and this change of the surface curvature affects the binding selectivity of the surface. For example, at certain curvature, the surface of the particle may have a binding affinity for a specific type of biomolecule where a different curvature will have a different binding affinity and/or a binding affinity for a different biomolecule. The curvature can be adjusted to create a plurality of sensor elements with altered affinity for different biomolecules. A sensor array can be created including a plurality of sensor elements having different curvatures (e.g. different sizes) which results in a plurality of sensor elements each with a different biomolecule corona signature.

Surface morphology may also be modified by methods such as patterning the surface to provide different affinities, engineering surface curvatures on multiple length scales and the like. Patterning the surface is provided by, for example, forming the sensor elements by block polymerization in which the at least two blocks have different chemistries, forming the nanoparticles using mixtures of at least two different polymers and phase separating the polymers during polymerization, and/or cross-linking the separate polymers following phase separation. Engineered surface curvature on multiple length scales is provided, for example, by employing Pickering emulsions (Sacanna et al. 2007) stabilized by finely divided particles for the synthesis of nanoparticles. In some embodiments, finely dividend particles are selected from, for example, silicates, aluminates, titanates, metal oxides such as aluminum, silicon, titanium, nickel, cobalt, iron, manganese, chromium, or vanadium oxides, carbo blacks, and nitrides or carbides, e.g., boron nitride, boron carbide, silicon nitride, or silicon carbide, among others.

For example, the sensor elements including nanoscale sensor elements may each be functionalized to have different physicochemical properties. Suitable methods of functionalizing the sensor elements are known in the art and depend on composition of the sensor element (e.g. gold, iron oxide, silica, silver, etc.), and include, but not limited to, for example aminopropyl functionalized, amine functionalized, boronic acid functionalized, carboxylic acid functionalized, methyl functionalized, N-succinimidyl ester functionalized, PEG functionalized, streptavidin functionalized, methyl ether functionalized, triethoxylpropylaminosilane functionalized, thiol functionalized, PCP functionalized, citrate functionalized, lipoic acid functionalized, BPEI functionalized, carboxyl functionalized, hydroxyl functionalized, and the like. In one embodiment, the nanoparticles may be functionalized with an amine group (—$NH_2$ or a carboxyl group (COOH). In some embodiments, the nanoscale sensor elements are functionalized with a polar functional group. Non-limiting examples of the polar functional group comprise carboxyl group, a hydroxyl group, a thiol group, a cyano group, a nitro group, an ammonium group, an imidazolium group, a sulfonium group, a pyridinium group, a pyrrolidinium group, a phosphonium group or any combination thereof. In some embodiments, the functional group is an acidic functional group (e.g., sulfonic acid group, carboxyl group, and the like), a basic functional group (e.g., amino group, cyclic secondary amino group (such as pyrrolidyl group and piperidyl group), pyridyl group, imidazole group, guanidine group, etc.), a carbamoyl group, a hydroxyl group, an aldehyde group and the like. In some embodiments, the polar functional group is an ionic functional group. Non-limiting examples of the ionic function group comprise an ammonium group, an imidazolium group, a sulfonium group, a pyridinium group, a pyrrolidinium group, a phosphonium group. In some embodiments, the sensor elements are functionalized with a polymerizable functional group. Non-limiting examples of the polymerizable functional group include a vinyl group and a (meth) acrylic group. In some embodiments, the functional group is pyrrolidyl acrylate, acrylic acid, methacrylic acid, acrylamide, 2-(dimethylamino)ethyl methacrylate, hydroxyethyl methacrylate and the like.

In other embodiments, the physicochemical properties of the sensor elements may be modified by modification of the surface charge. For example, the surface can be modified to provide a net neutral charge, a net positive surface charge, a net negative surface charge, or a zwitterionic charge. The charge of the surface can be controlled either during synthesis of the element or by post-synthesis modification of the charge through surface functionalization. For polymeric nanoparticles, differences in charge can be obtained during synthesis by using different synthesis procedures, different charged comonomers, and in inorganic substances by having mixed oxidation states.

Nanoparticles

In some embodiments, the particles are nanoparticles. In some embodiments, the particles are liposomes. The liposomes may comprise any lipid capable of forming a particle. The term "lipid" refers to a group of organic compounds that are esters of fatty acids and are characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the liposome comprises one or more cationic lipids or anionic lipids, and one or more stabilizing lipids. Suitable liposomes are known in the art and include, but are not limited to, for example, DOPG (1,2-dioleoyl-sn-glycero-3-phospho-(1'-rac-glycerol), DOTAP (1,2-Dioleiyl-3 trimethylammonium-propane)-DOPE (dioleoylphosphatidylethanolamine), CHOL (DOPC-Cholesterol), and combinations thereof.

The lipid-based surface of a liposome can contact a subset of biomolecules (e.g., proteins) of a complex biological sample (e.g., plasma, or any sample having a complex mix of biomolecules such as proteins and nucleic acid and at least one of a polysaccharide and lipid) at a lipid-biomolecule (e.g. protein) interface, thereby binding the subset of proteins to produce a pattern of biomolecule (e.g. protein) binding.

In one embodiment, the liposome comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK the lipid is then able to associate with negatively charged nucleic acids. In certain embodiments, the cationic lipid comprises a zwitterionic lipid that assumes a positive charge on pH decrease. In certain embodiments, the liposomes comprise cationic lipid. In some embodiments, cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl) cholesterol (DC-Chol), N-(1-(2,3-dioleoyloxy)propyl)-N-2-(sperminecarboxamido)ethyl)-N,N-dimethy-lammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), N-(1,2-dimyristyloxyprop-3-yl)-N,N-dimethyl-N-hydroxyethyl ammonium bromide (DMRIE), 1,2-dioleoyl-sn-3-phosphoethanolamine (DOPE), N-(1-(2, 3-dioleyloxy)propyl)-N-(2-(sperminecarboxamido)ethyl)-N,N-dimethy-lammonium trifluoroacetate (DOSPA), dioctadecylamidoglycyl carboxyspermine (DOGS), and 1,2-ditetradecanoyl-sn-glycero-3-phosphocholine (DMPC). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA). In some embodiment, the lipid is an amino lipid.

In certain embodiments, the liposome comprises one or more additional lipids which stabilize the formation of particles during their formation. Suitable stabilizing lipids include neutral lipids and anionic lipids. The term "neutral lipid" refers to any one of a number of lipid species that exist in either an uncharged or neutral zwitterionic form at physiological pH. Representative neutral lipids include diaclphosphatidylcholines, diacylphosphatidylethanolamines, ceramides, sphingomyelins, dihydro sphingomyelins, cephalins, and cerebrosides. Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

The lipid nanoparticles may comprise liposomes that include phospholipids. The liposomes may include phosphatidylcholine. Components of the liposomes may also include variants of polyethylene glycol (PEG). For example, the PEG may be branched. The PEG may be unbranched. The PEG may comprise a chemical structure of the following formula: H—(O—$CH_2$—$CH_2$)$_n$-OH, where n is an integer from 2-200.

The term "anionic lipid" refers to any lipid that is negatively charged at physiological pH. These lipids include phosphatidylglycerol, cardiolipin diacylphosphatidylserine, diacylphosphatidic acid, N-dodecanoylphosphatidylethanolamines, N-succinylphosphatidylethanolamines, N-glutarylphosphatidylethanolamines, lysylphosphatidyiglycerols, palmitoyloleyolphosphatidylglycerol (POPG), and other anionic modifying groups joined to neutral lipids. In certain embodiments, the liposome comprises glycolipids (e.g., monosialoganglioside GM.sub.1). In certain embodiments, the liposome comprises a sterol, such as cholesterol. In certain embodiments, the liposome comprises an additional, stabilizing-lipid which is a polyethylene glycol-lipid. Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol).sub.2000) carbamyl]-1,2-dimyristyloxlpropyl-3-amine (PEG-c-DMA). In one embodiment, the polyethylene glycol-lipid is PEG-c-DOMG.

Suitable liposomes may be solid lipid nanoparticles (SLN) which can be made of solid lipid, emulsifier and/or water/solvent. SLN may include, but are not limited to, a combination of the following ingredients: triglycerides (tristearin), partial glycerides (Imwitor), fatty acids (stearic acid, palmitic acid), and steroids (cholesterol) and waxes (cetyl palmitate). Various emulsifiers and their combination (Pluronic F 68, F 127) have been used to stabilize the lipid dispersion. Suitable ingredients for the use in preparing SNL sensor elements include, but are not limited to, e.g., phospholipids, glycerol, poloxamer 188, soy phosphatidyl choline, compritol, cetyl palmitate, PEG 2000, PEG 4500, Tween® 85, ethyl oleate, Na alginate, ethanol/butanol, tristearin glyceride, PEG 400, isopropyl myristate, Pluronic F68, Tween® 80, trimyristin, tristearin, trilaurin, stearic acid, glyceryl caprate as Capmul® MCM C10, *Theobroma* oil, triglyceride coconut oil, 1-octadecanol, glycerol behenate as Compritol® 888 ATO, glycerol palmitostearate as Precirol® ATO 5, and cetyl palmitate wax and the like.

In some embodiments, the plurality of sensor elements comprise, consist essentially of, or consist of a plurality of half particles of different geometric shapes which can be made by molding technology, 3D printing or 4D printing. Suitable half particles are known in the art, and include, but are not limited to half and partial particles in any geometric shape, for example, spheres, rods, triangles, cubes and combinations thereof. Suitably, in one embodiment, the plurality of half particles have different physicochemical properties made by 3-D printing.

In some embodiments, the sensor elements, including nanoscale sensor elements, are made by 3D or 4 D printing. Suitable methods of 3D and 4D printing of sensor elements, including nanoscale sensor elements are known in the art. Suitable material for 3D and 4D printing include, but is not limited to, e.g., plastics and synthetic polymers (e.g., polyethylene glycol-diacrylate (PEG-DA), poly (e-caprolactone) (PCL), poly(propylene oxide) (PPO), poly(ethylene oxide) (PEO) etc.), metals, powders, glass, ceramics, and hydrogels. Suitable shapes made by 3D or 4D printing include, but are not limited to, for example, full or partial spheres (e.g. ¾ or half spheres), rods, cubes, triangles or other geometrical or non-geometrical shapes.

3D printing techniques include, but are not limited to, microextrusion printing, inkjet bioprinting, laser-assisted bioprinting, stereolithography, omnidirectional printing, and stamp printing.

In some embodiments, the nanoscale sensor elements are nanoparticles. Suitable nanoparticles are known in the art and include, but are not limited to, for example, natural or synthetic polymers, copolymers, terpolymers (with the cores being composed of metals or inorganic oxides, including magnetic cores). Suitable polymeric nanoparticles include, but are not limited to, e.g., polystyrene; poly(lysine), chitosan, dextran, poly(acrylamide) and its derivatives such as N-isopropylacrylamide, N-tertbutylacrylamide, N,N-dimethylacrylamide, polyethylene glycol, poly(vinyl alcohol), gelatin, starch, degradable (bio)polymers, silica and the like.

In various embodiments, the core of the nanoparticles can include an organic particle, an inorganic particle, or a particle including both organic and inorganic materials. For example, the particles can have a core structure that is or includes a metal particle, a quantum dot particle, a metal oxide particle, or a core-shell particle. For example, the core structure can be or include a polymeric particle or a lipid-based particle, and the linkers can include a lipid, a surfactant, a polymer, a hydrocarbon chain, or an amphiphilic polymer. For example, the linkers can include polyethylene glycol or polyalkylene glycol, e.g., the first ends of the linkers can include a lipid bound to polyethelene glycol (PEG) and the second ends can include functional groups bound to the PEG. In these methods, the first or second functional groups can include an amine group, a maleimide group, a hydroxyl group, a carboxyl group, a pyridylthiol group, or an azide group.

In certain embodiments, the nanoparticles can comprise polymers that include, for example, a sodium polystyrene sulfonate (PSS), polyethylene oxide (PEO), polyoxyethylene glycol, polyethylene glycol (PEG), polyethylene imine (PEI), polylactic acid, polycaprolactone, polyglycolic acid, poly(lactide-co-glycolide polymer (PLGA), cellulose ether polymer, polyvinylpyrrolidone, vinyl acetate, polyvinylpyrrolidone-vinyl acetate copolymer, polyvinyl alcohol (PVA), acrylate, polyacrylic acid (PAA), vinyl acetate, crotonic acid copolymers, polyacrylamide, polyethylene phosphonate, polybutene phosphonate, polystyrene, polyvinylphosphonate, polyalkylene, carboxy vinyl polymer, sodium alginate, carrageenan, xanthan gum, gum acacia, Arabic gum, guar gum, pullulan, agar, chitin, chitosan, pectin, karaya gum, locust bean gum, maltodextrin, amylose, corn starch, potato starch, rice starch, tapioca starch, pea starch, sweet potato starch, barley starch, wheat starch, hydroxypropylated high amylose starch, dextrin, levan, elsinan, gluten, collagen, whey protein isolate, casein, milk protein, soy protein, keratin, or a gelatin, or a copolymer, derivative, or mixture thereof.

In other embodiments, the polymer can be or include a polyethylene, polycarbonate, polyanhydride, polyhydroxyacid, polypropylfumerate, polycaprolactone, polyamide, polyacetal, polyether, polyester, poly(orthoester), polycyanoacrylate, polyvinyl alcohol, polyurethane, polyphosphazene, polyacrylate, polymethacrylate, polycyanoacrylate, polyurea, polystyrene, or a polyamine, or a copolymer, derivative, or mixture thereof.

In some embodiments, the present disclosure provides nanoparticles comprising biodegradable polymers. The non-limiting exemplary biodegradable polymers can be poly-β-amino-esters (PBAEs), poly(amido amines), polyesters including poly lactic-co-glycolic acid (PLGA), polyanhydrides, bioreducible polymers, and other biodegradable polymers. In some embodiments, the biodegradable polymer comprises 2-(3-aminopropylamino)ethanol end-modified poly(1,4-butanediol diacrylate-co-4-amino-1-butanol), (1-(3-aminopropyl)-4-methylpiperazine end-modified poly(1,4-butanediol diacrylate-co-4-amino-1-butanol), 2-(3-aminopropylamino)ethanol end-modified poly(1,4-butanediol diacrylate-co-5-amino-1-pentanol), (1-(3-aminopropyl)-4-methylpiperazine end-modified poly(1,4-butanediol diacrylate-co-5-amino-1-pentanol), 2-(3-aminopropylamino) ethanol end-modified poly(1,5 pentanediol diacrylate-co-3-amino-1-propanol), and (1-(3-aminopropyl)-4-methylpiperazine-end-modified poly(1,5 pentanediol diacrylate-co-3-amino-1-propanol).

Array Substrates

In some embodiments, the sensor array comprises a substrate. Regardless of the identity of the sensor element, this invention can be embodied by a matrix of sensor elements immobilized on, connected with and/or coupled to a solid substrate. The substrate may comprise, consist essentially of or consist of polydimethylsiloxane (PDMS), silica, gold or gold coated substrate, silver or silver coated substrate, platinum or platinum coated substrate, zinc or zinc coated substrate, carbon coated substrate and the like. One skilled in the art would be able to select an appropriate substrate for the sensor array. In some embodiments, the sensor elements and the substrate are made of the same element, for example, gold. In some embodiments, the substrate and sensor elements (e.g. nanoparticles) form a chip.

In some embodiments, the plurality of sensor elements comprises a single surface, plate or chip containing two or more discrete sensor elements (regions) with topological differences that allows for discrete biomolecule corona formation at each discrete element (region). The surface plate or chip may be fabricated to include the two or more discrete elements (regions) by the methods described herein. The discrete regions may be raised surfaces of differing geometric shapes, differing sizes or differing charges or other topological differences that result in discrete sensor elements with ability to form discrete biomolecule coronas.

In some embodiments, the sensor elements are non-covalently attached to the substrate. Suitable methods of non-covalent attachment are known in the art and include, but are not limited to, for example, metal coordination, charge interaction, hydrophobic-hydrophobic interaction, chelation and the like. In other embodiments, the sensor elements are covalently attached to the substrate. Suitable methods of covalently linking the sensor elements and the substrates include, but are not limited to, for example, click chemistry, irradiation, and the like.

Figure 23:
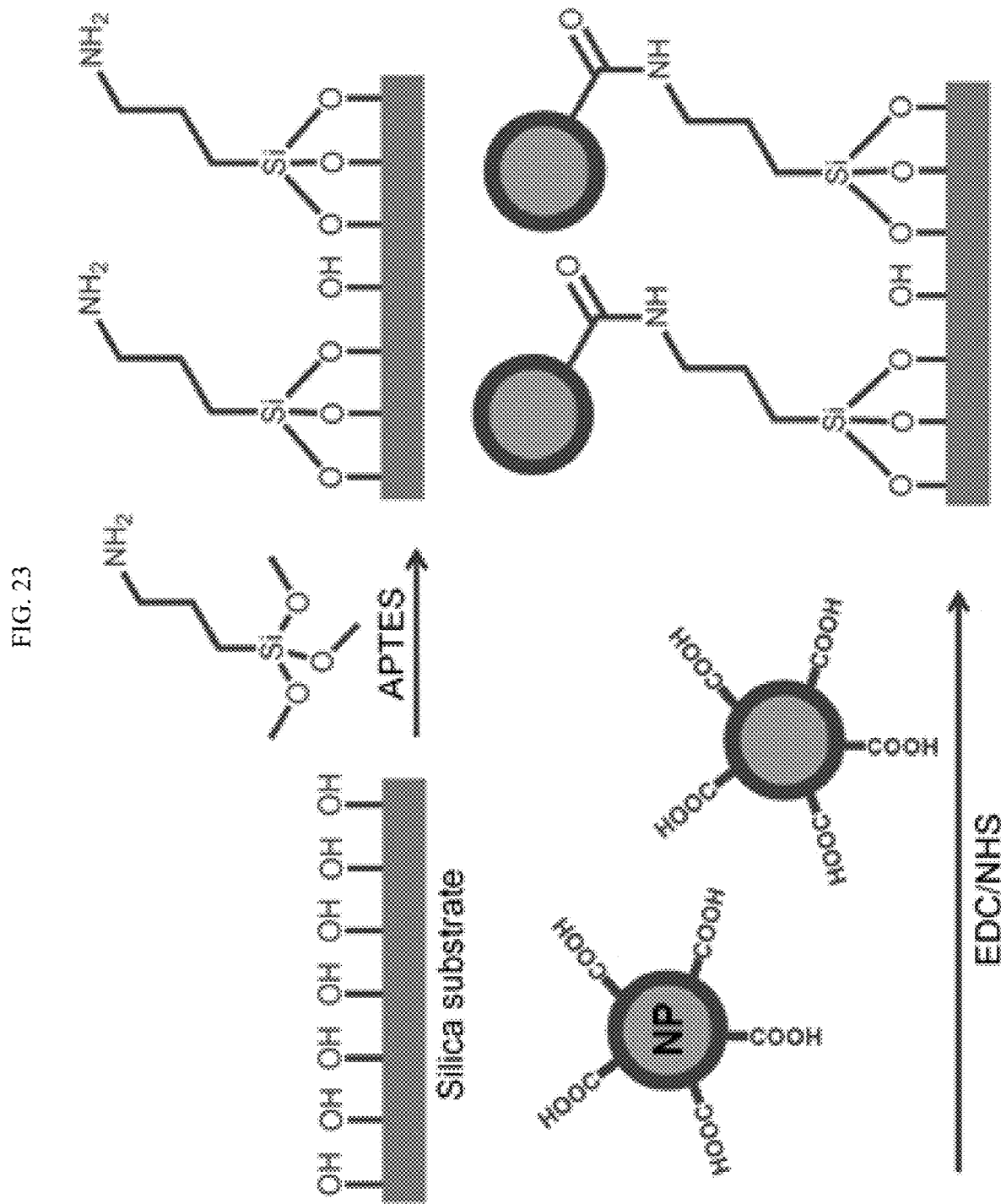
FIG. 23. Example of conjugation of nanoparticles to the silica substrate surface (as representative substrate) via the amidation reaction between the amino groups on silica substrate surface and carboxylic acid groups on nanoparticle surface.
Figure 24:
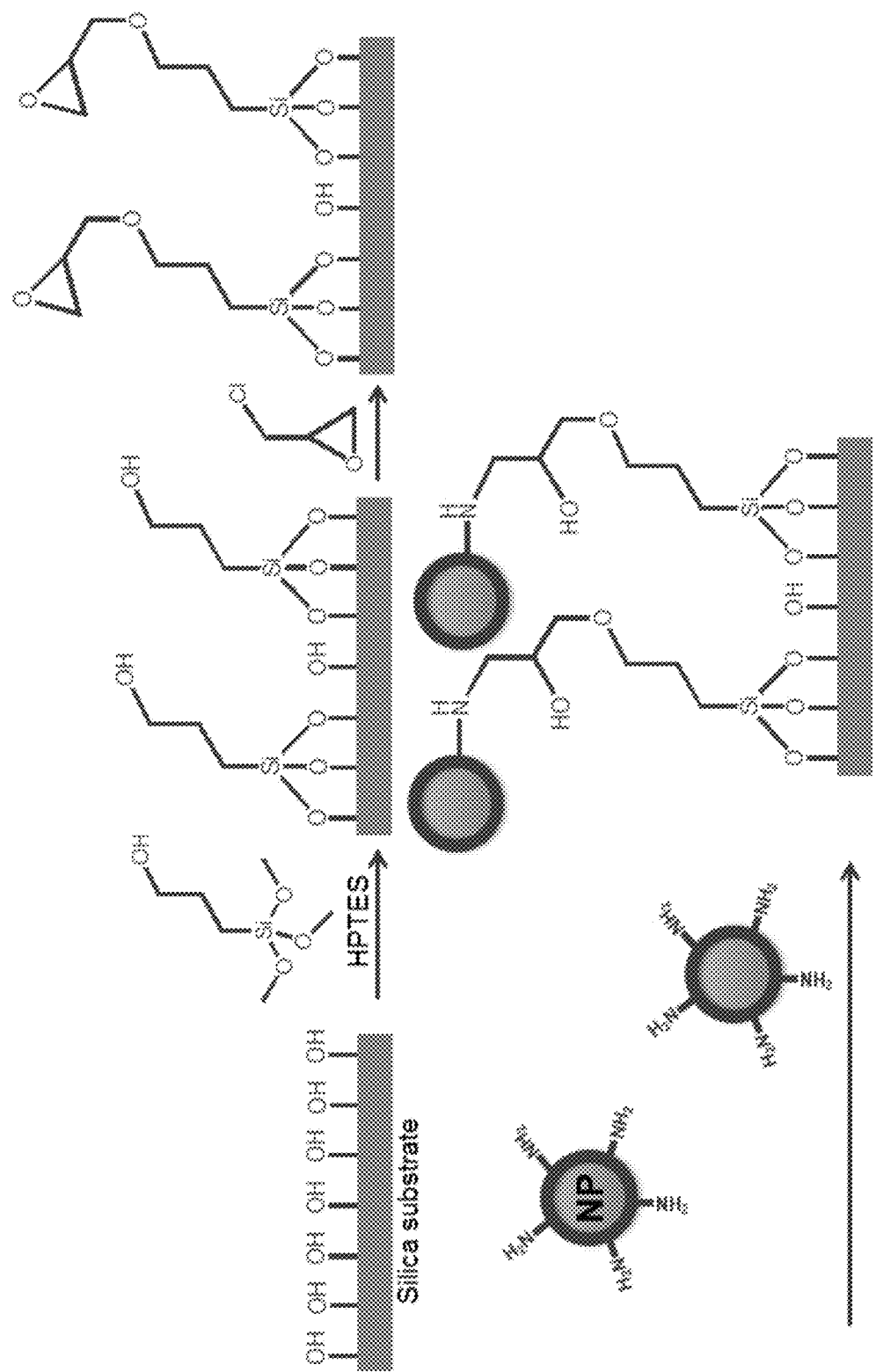
FIG. 24. Example of conjugation of nanoparticles to the silica substrate surface (as representative substrate) via the ring-opening reaction between the epoxy groups on silica substrate surface and amino groups on nanoparticle surface.
Figure 25:
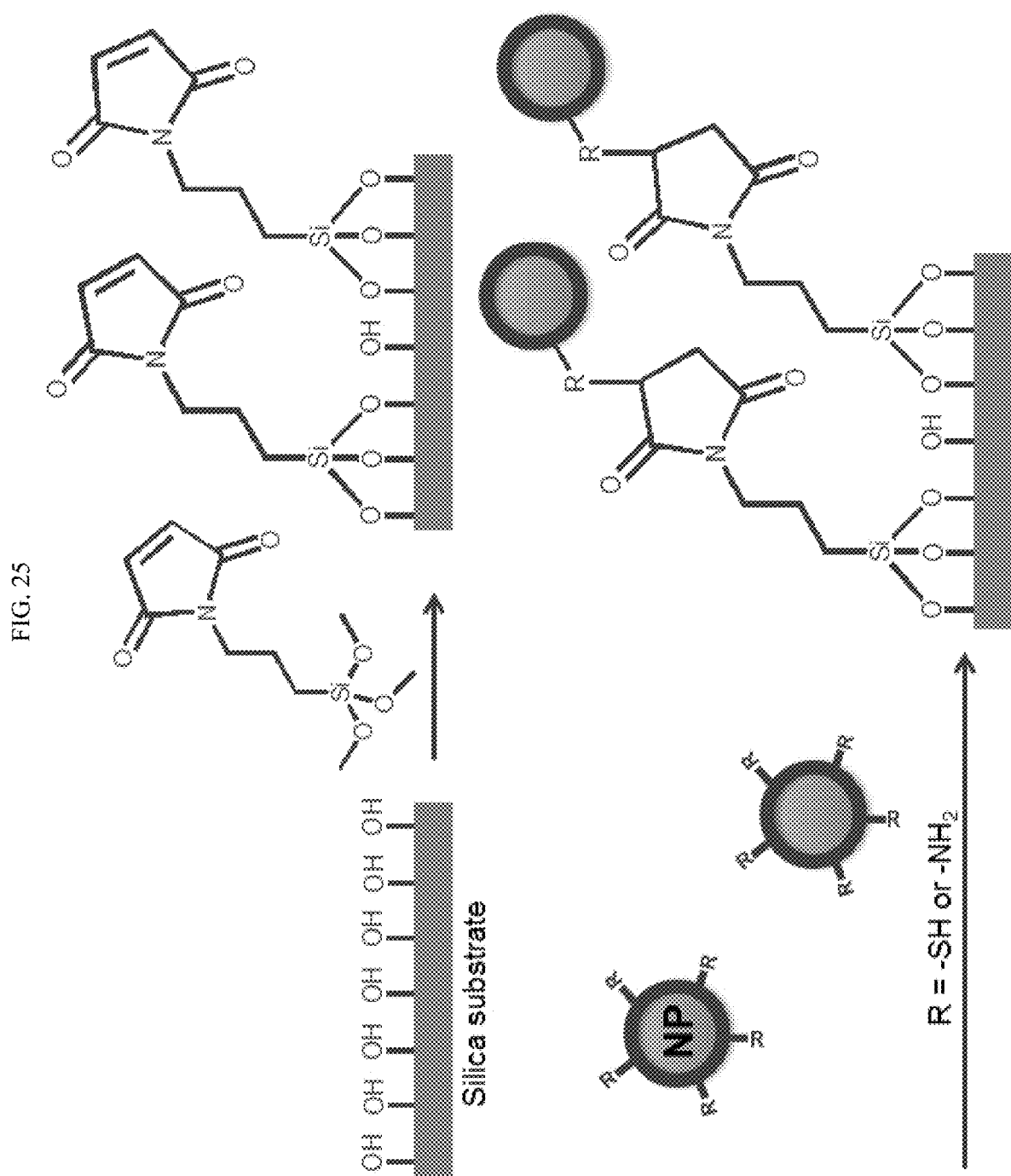
FIG. 25. Example of conjugation of nanoparticles to the silica substrate surface (as representative substrate) via the Michael Addition reaction between the maleimide groups on silica substrate surface and thiol or amino groups on nanoparticle surface.
Figure 26:
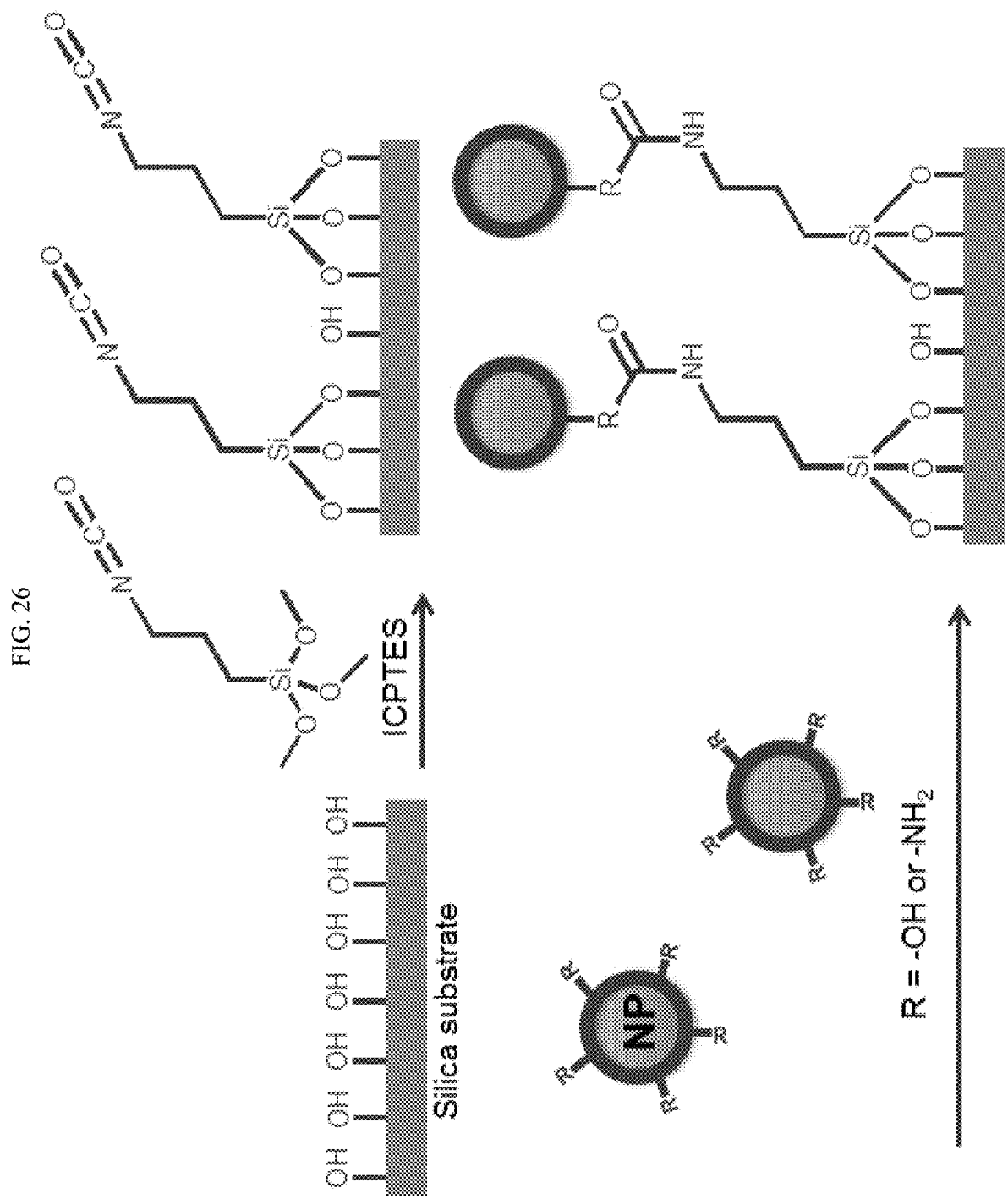
FIG. 26. Example of conjugation of nanoparticles to the silica substrate surface (as representative substrate) via the urethane reaction between the isocyanate groups on silica substrate surface and hydroxyl or amino groups on nanoparticle surface.
Figure 27:
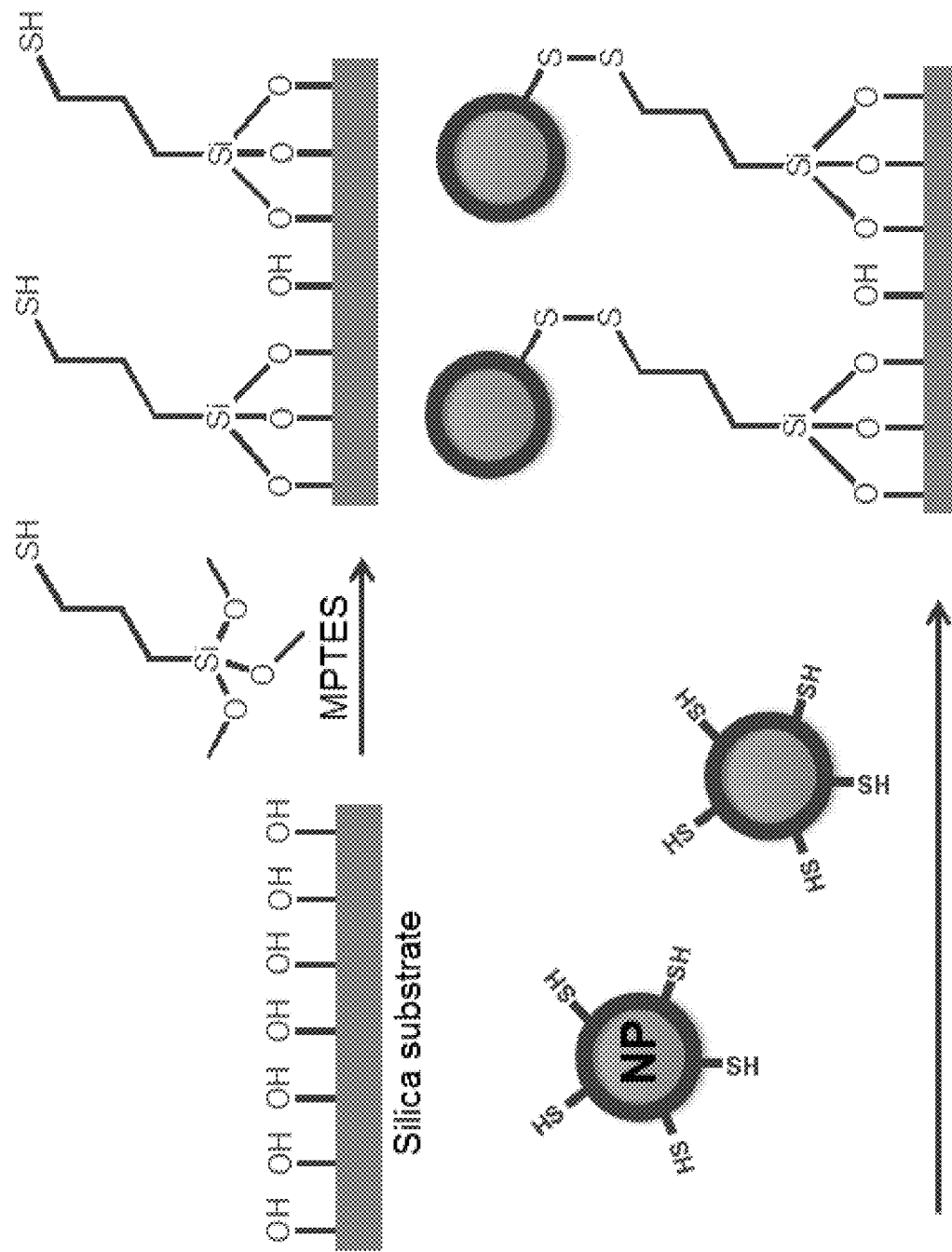
FIG. 27. Example of conjugation of nanoparticles to the silica substrate surface (as representative substrate) via the oxidation reaction between the thiol groups on silica substrate surface and the ones on nanoparticle surface.
Figure 28:
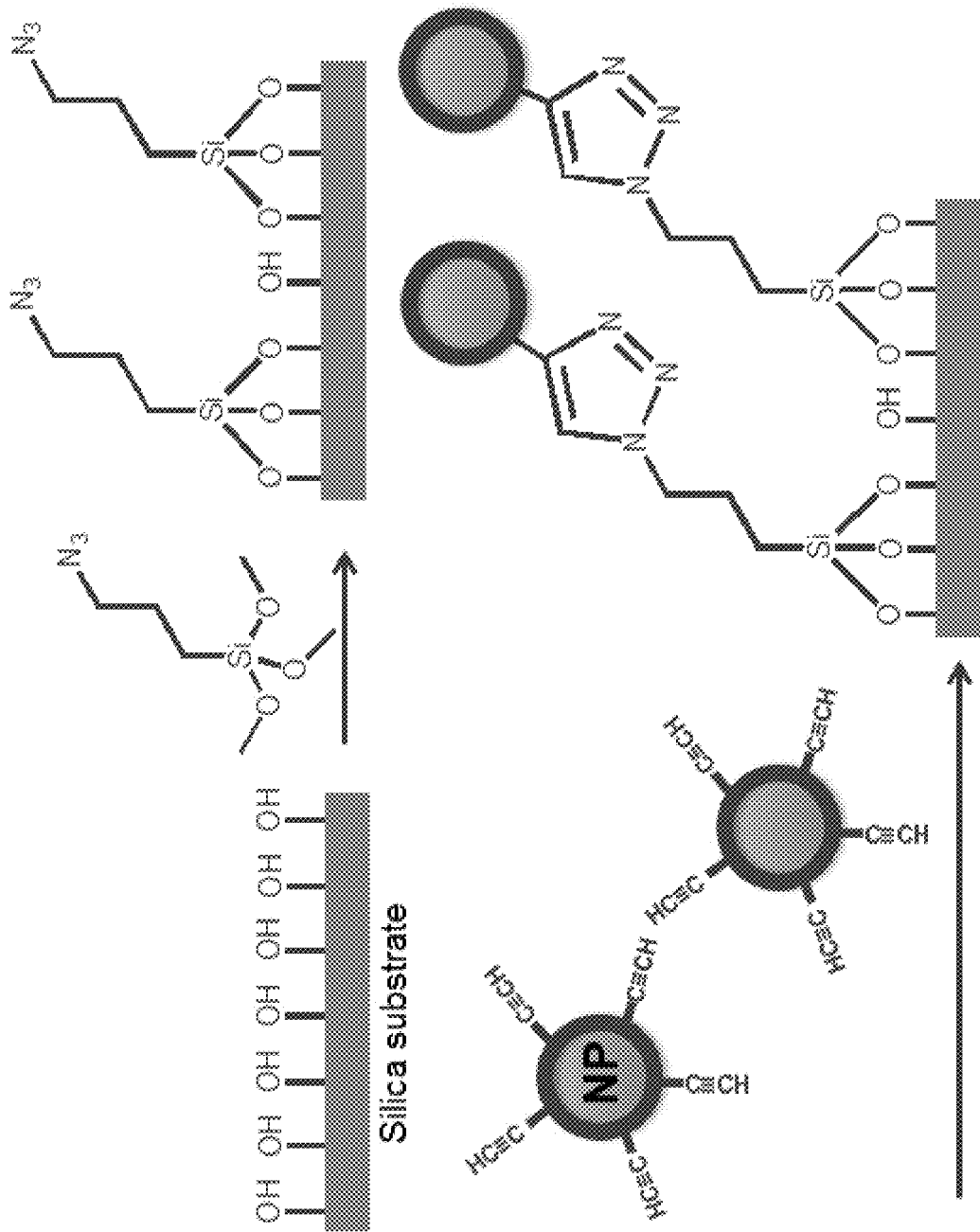
FIG. 28. Example of conjugation of nanoparticles to the silica substrate surface (as representative substrate) via the "Click" chemistry between azide groups on silica substrate surface and alkyne groups on nanoparticle surface.
Figure 29:
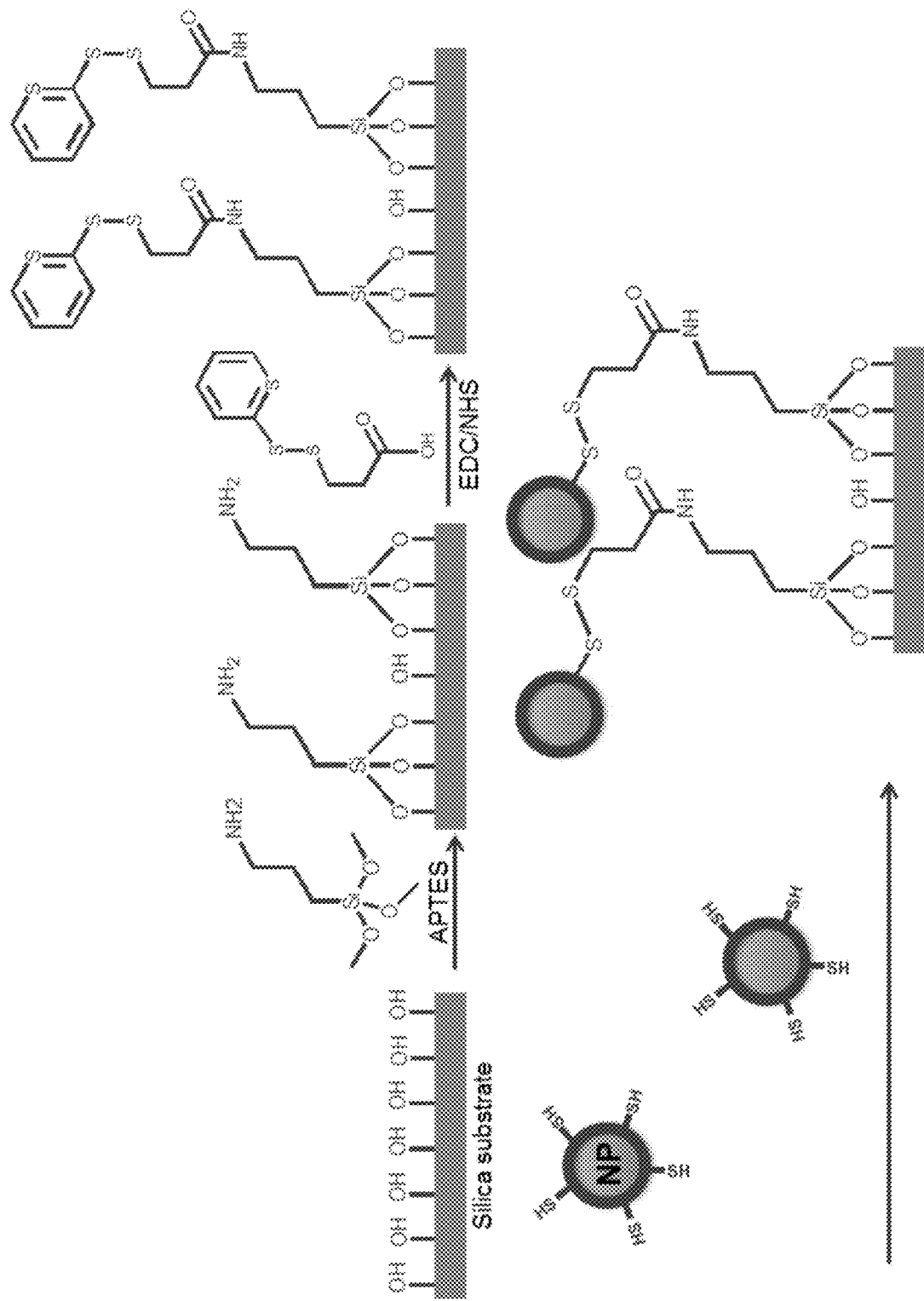
FIG. 29. Example of conjugation of nanoparticles to the silica substrate surface (as representative substrate) via the thiol exchange reaction between 2-pyridyldithiol groups on silica substrate surface and thiol groups on nanoparticle surface.
Figure 30:
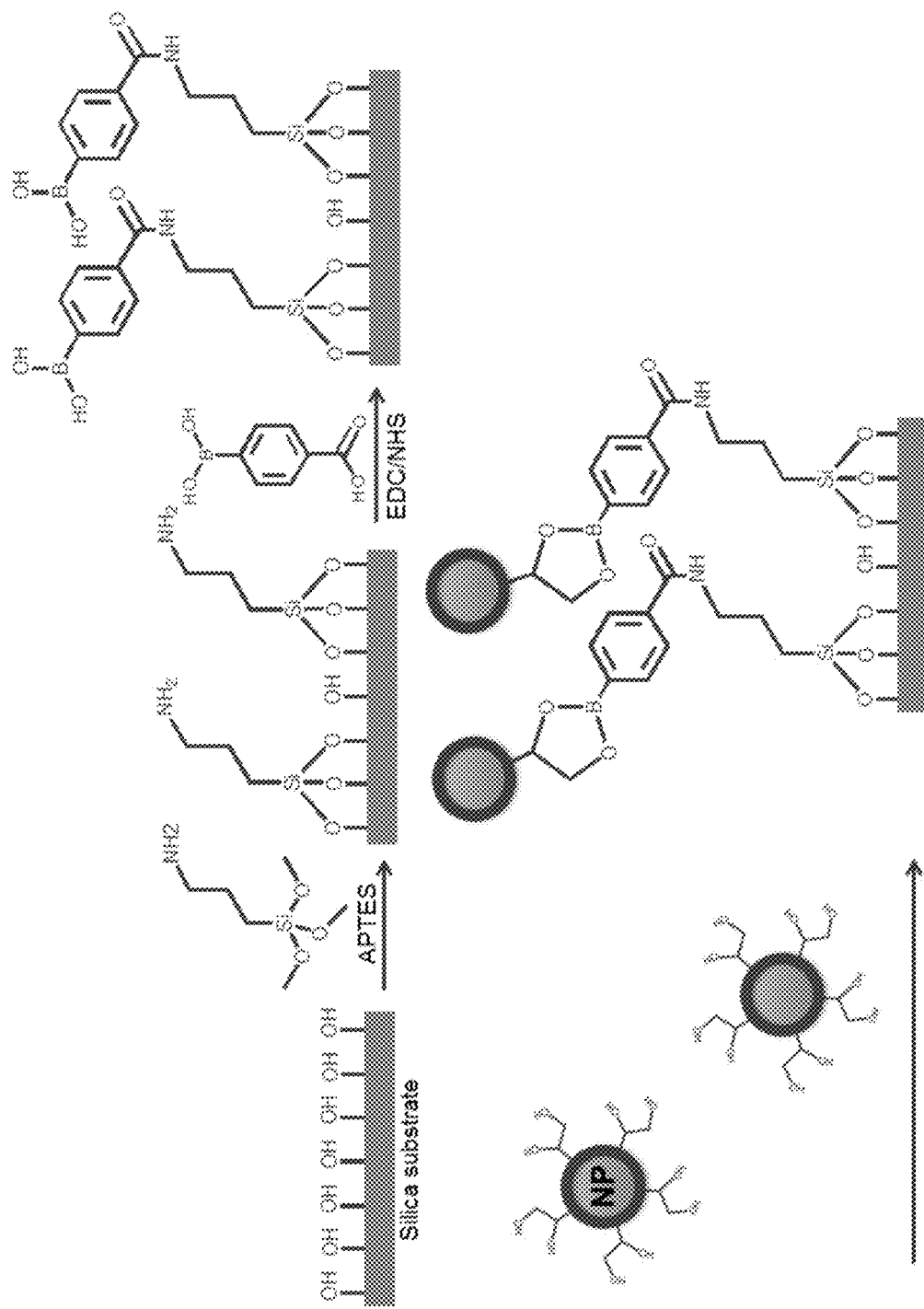
FIG. 30. Example of conjugation of nanoparticles to the silica substrate surface (as representative substrate) via the coordination reaction between boronic acid groups on silica substrate surface and diol groups on nanoparticle surface.
Figure 31:
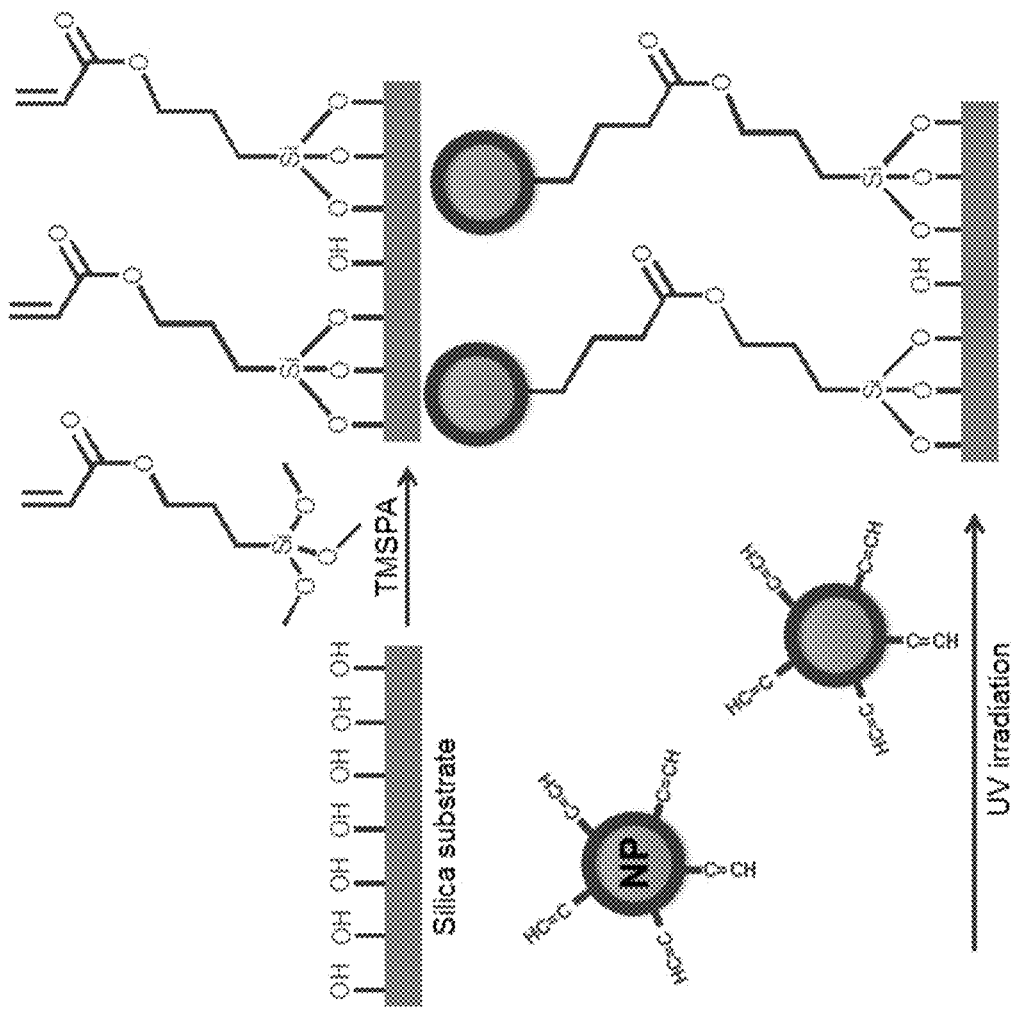
FIG. 31. Example of conjugation of nanoparticles to the silica substrate surface (as representative substrate) via the UV light-irradiated addition reaction between C=C bonds on silica substrate surface and C=C bonds on nanoparticle surface.
Figure 32:
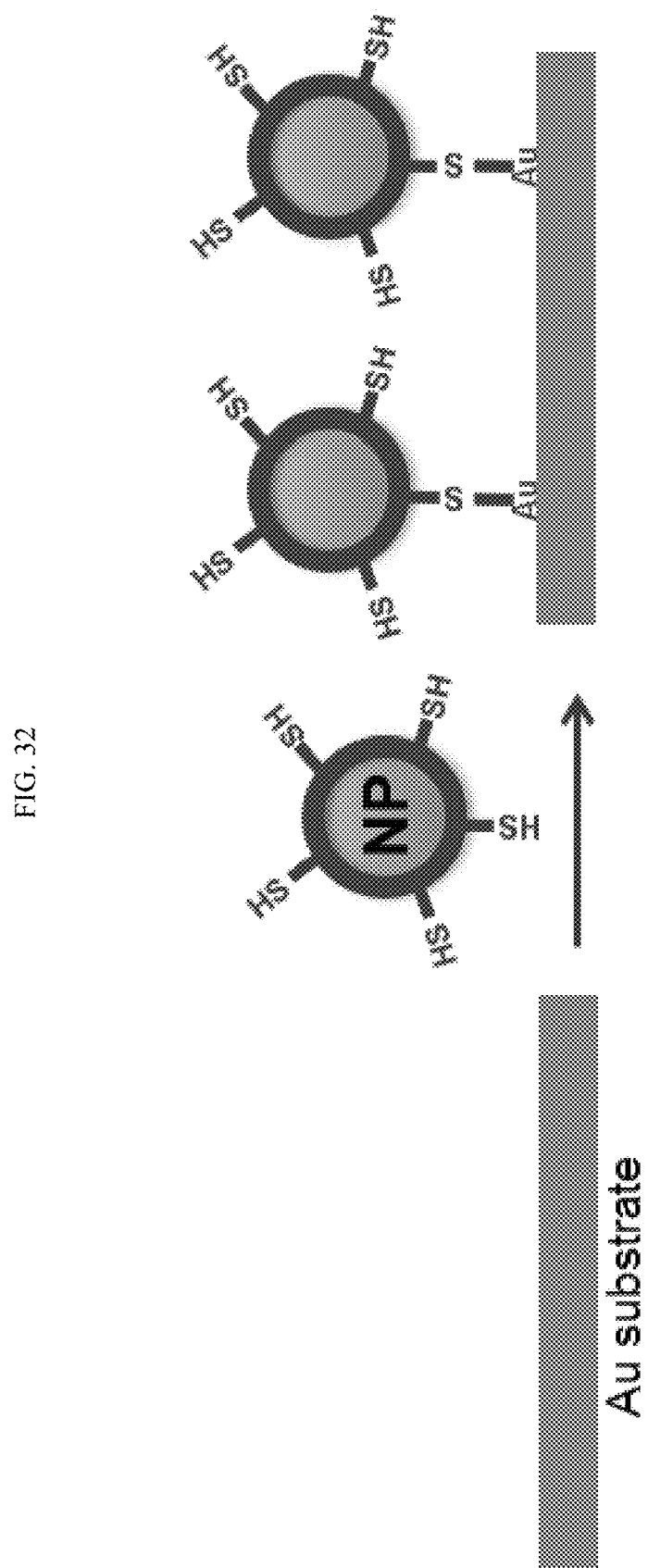
FIG. 32. Example of conjugation of nanoparticles to the gold substrate surface (as representative substrate) via Au-thiol bonds.
Figure 33:
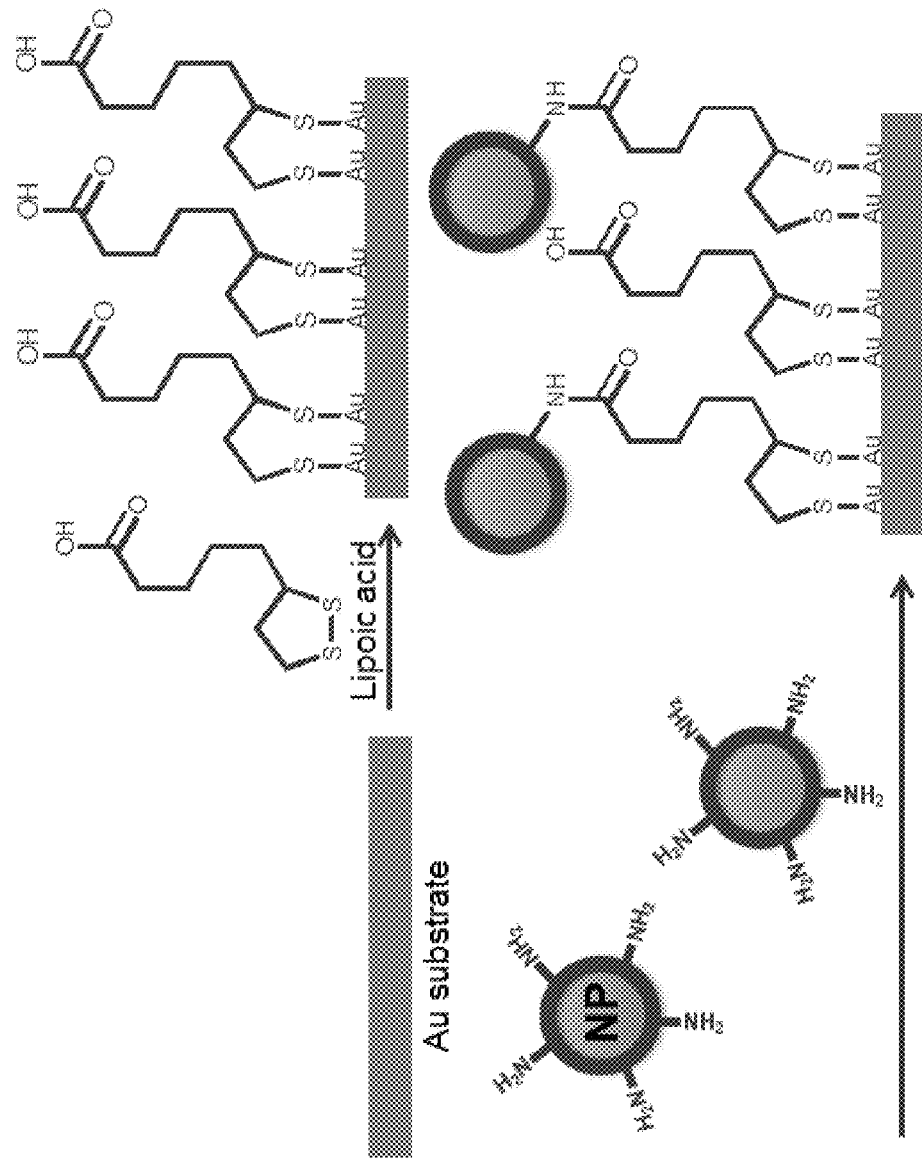
FIG. 33 Example of conjugation of nanoparticles to the gold substrate surface (as representative substrate) via the amidation reaction between the carboxylic acid groups on gold substrate surface and the amino groups on nanoparticle surface.
Figure 34:
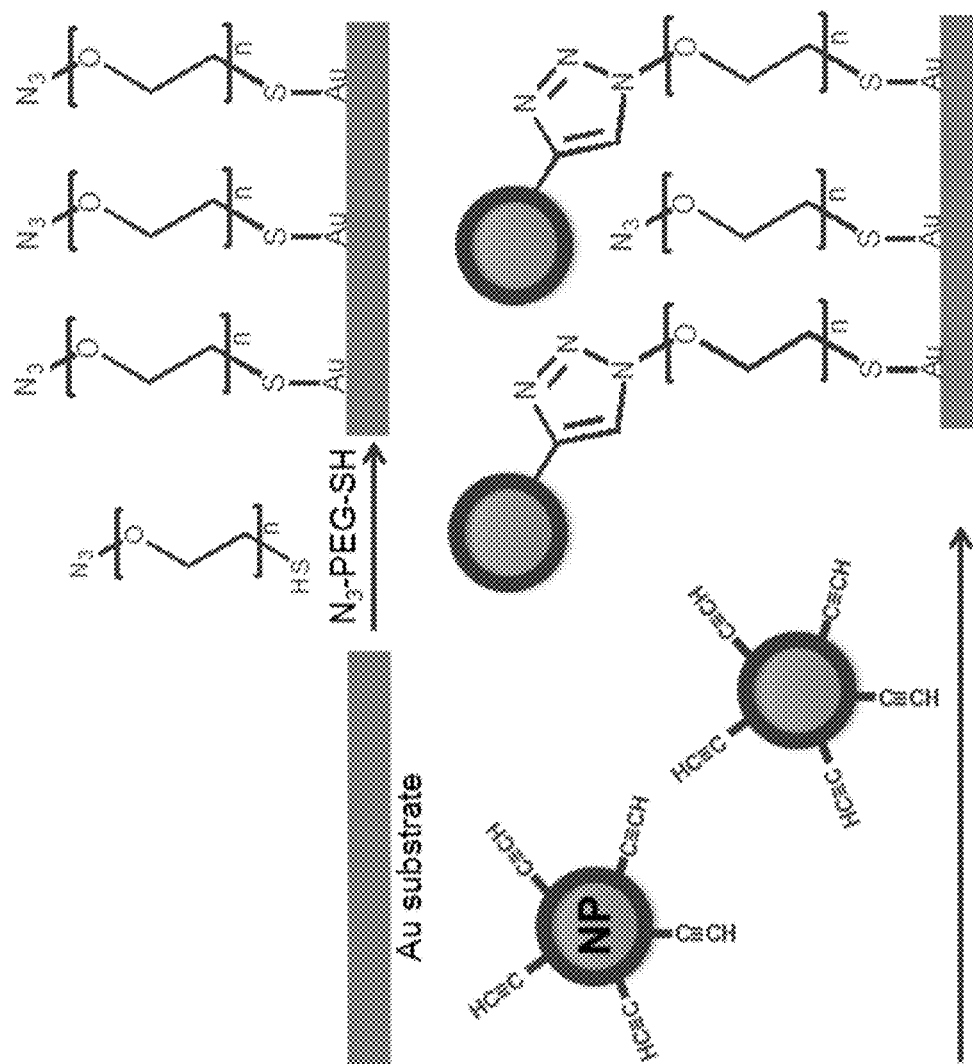
FIG. 34. Example of conjugation of nanoparticles to the gold substrate surface (as representative substrate) via "Click" chemistry between the azide groups on gold substrate surface and the alkyne groups on nanoparticle surface.
Figure 35:
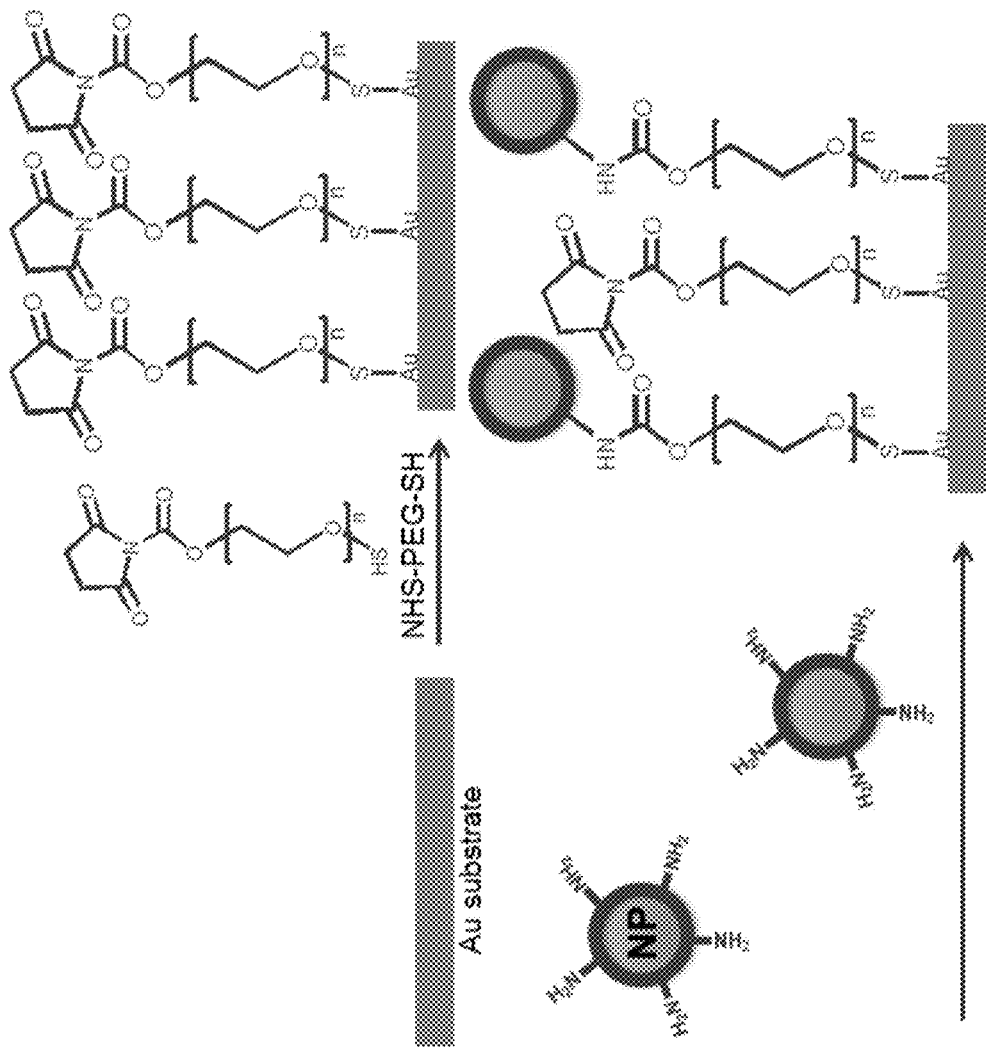
FIG. 35. Example of conjugation of nanoparticles to the gold substrate surface (as representative substrate) via urethane reaction between the NHS groups on gold substrate surface and the amino groups on nanoparticle surface.
Figure 36:
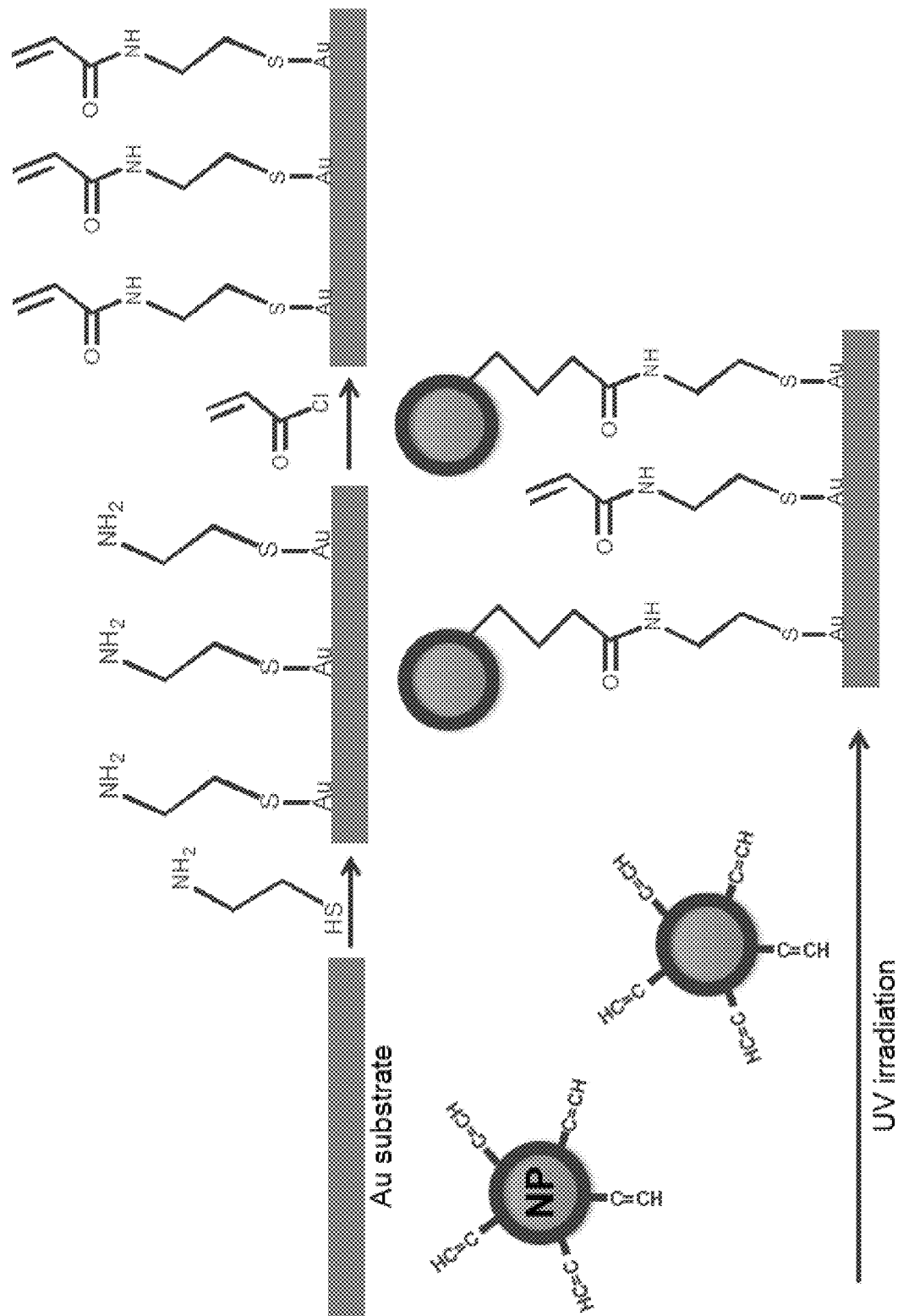
FIG. 36. Example of conjugation of nanoparticles to the silica substrate surface (as representative substrate) via the ring-opening reaction between the epoxy groups on gold substrate surface and amino groups on nanoparticle surface.
Figure 37:
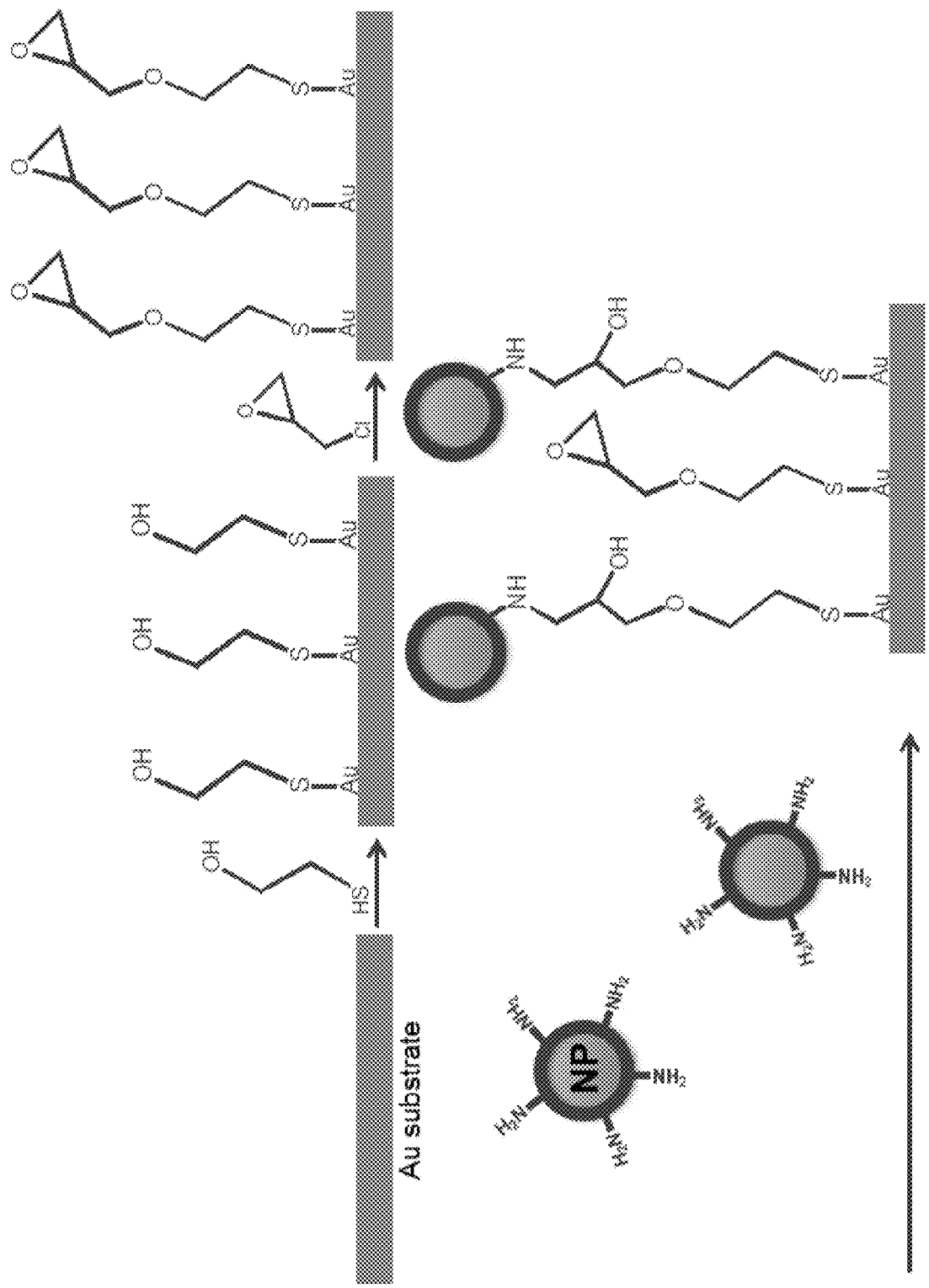
FIG. 37. Example of conjugation of nanoparticles to the gold substrate surface (as representative substrate) via the coordination reaction between boronic acid groups on silica substrate surface and diol groups on nanoparticle surface.
Figure 38:
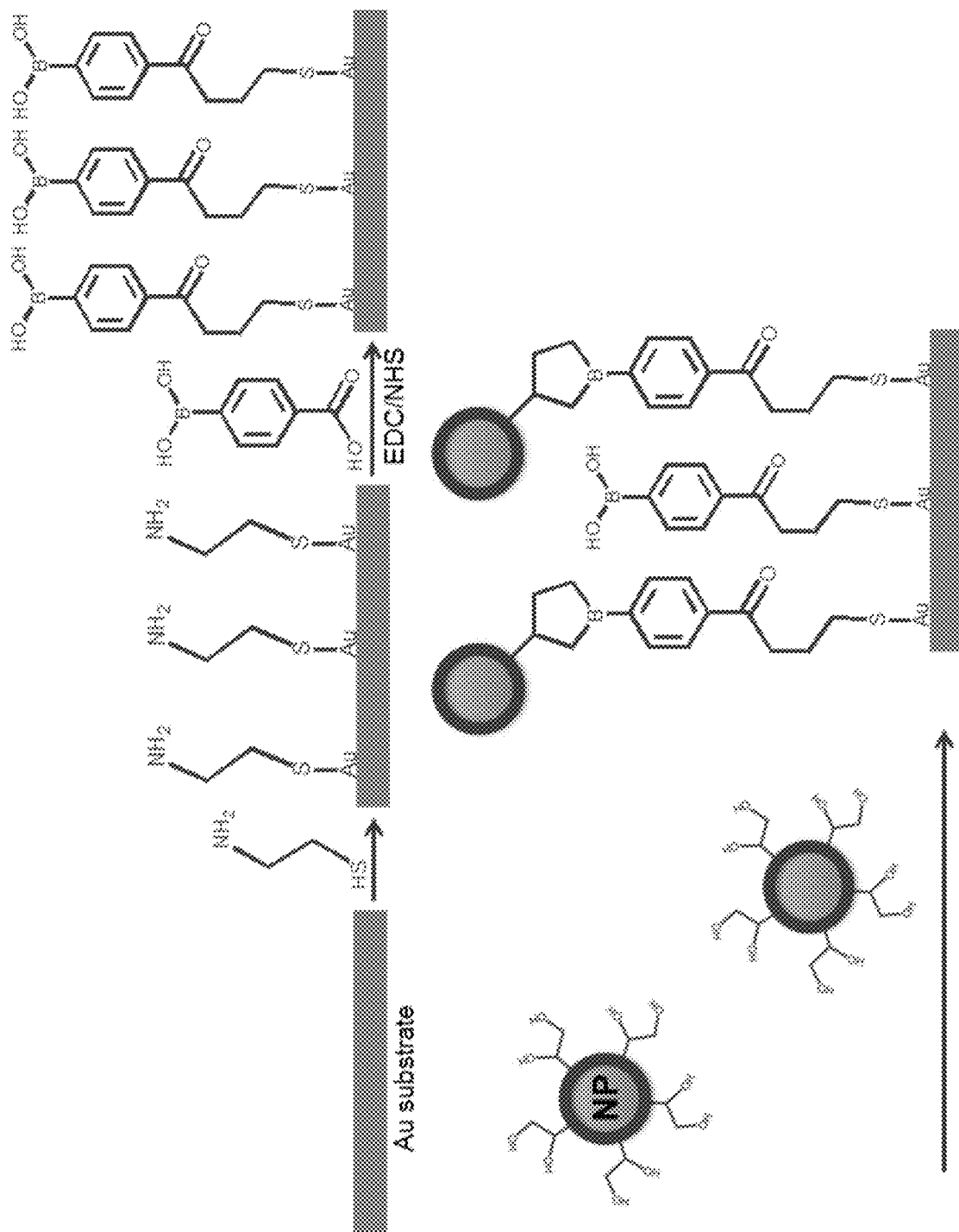
FIG. 38. Example of conjugation of nanoparticles to the gold substrate surface (as representative substrate) via the UV light-irradiated addition reaction between C=C bonds on gold substrate surface and C=C bonds on nanoparticle surface.
Figure 39:
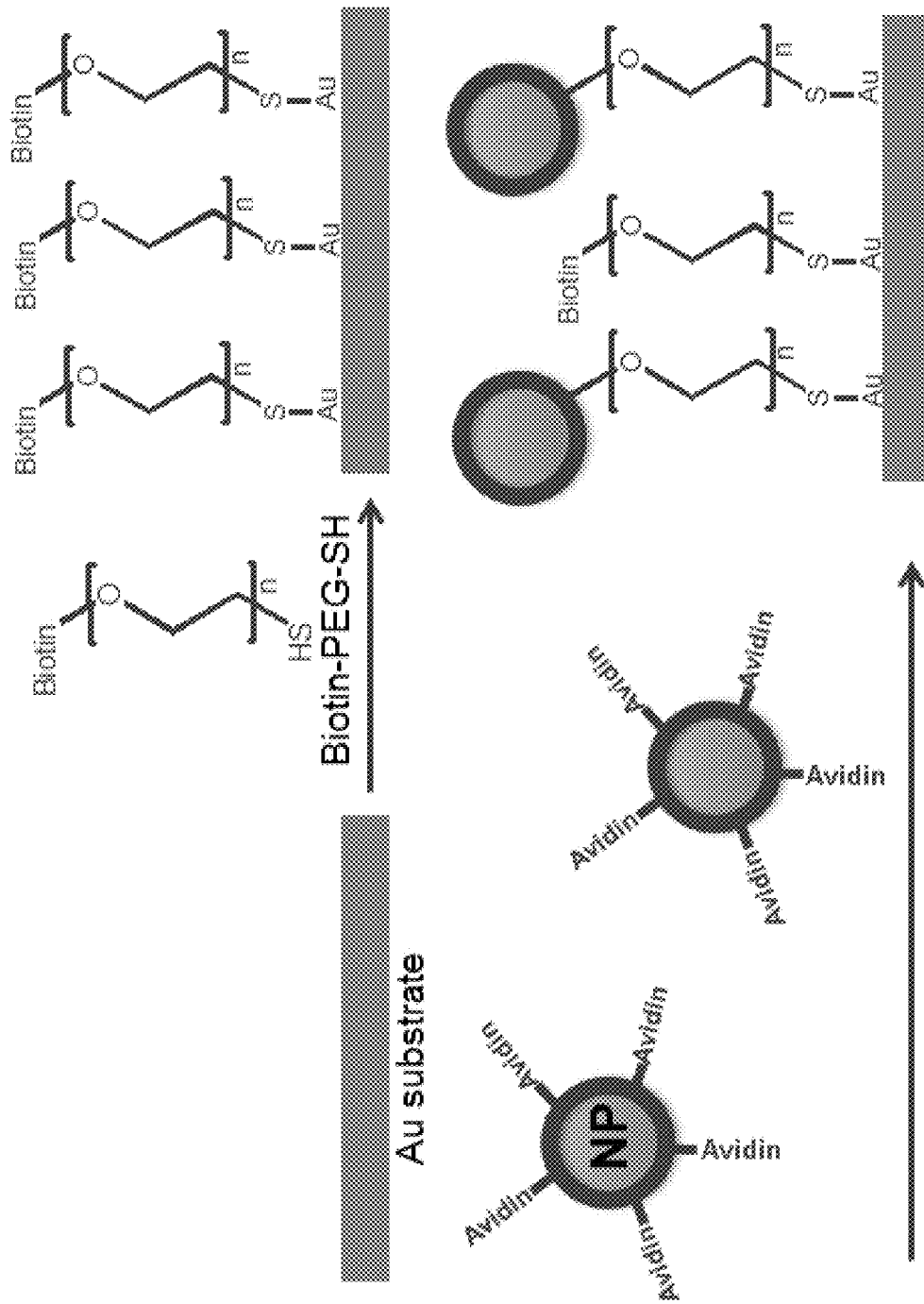
FIG. 39. Example of conjugation of nanoparticles to the gold substrate surface (as representative substrate) via the "Ligand-Receptor" interaction between biotin on gold substrate surface and avidin on nanoparticle surface.
Figure 40:
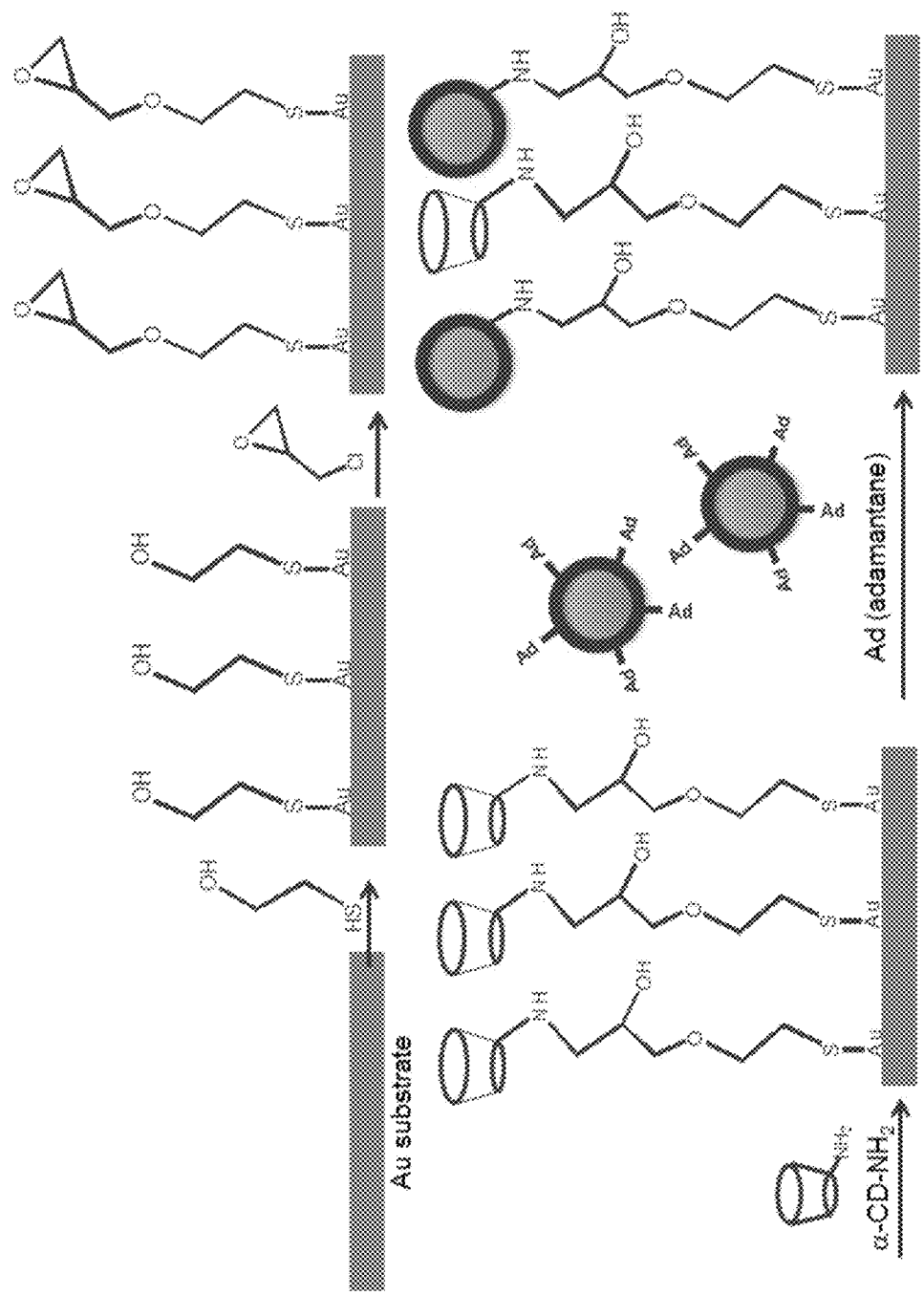
FIG. 40. Example of conjugation of nanoparticles to the gold substrate surface (as representative substrate) via the "Host-Guest" interaction between a-cyclodextrin (a-CD) on gold substrate surface and adamantine (Ad) on nanoparticle surface.
Figure 41:
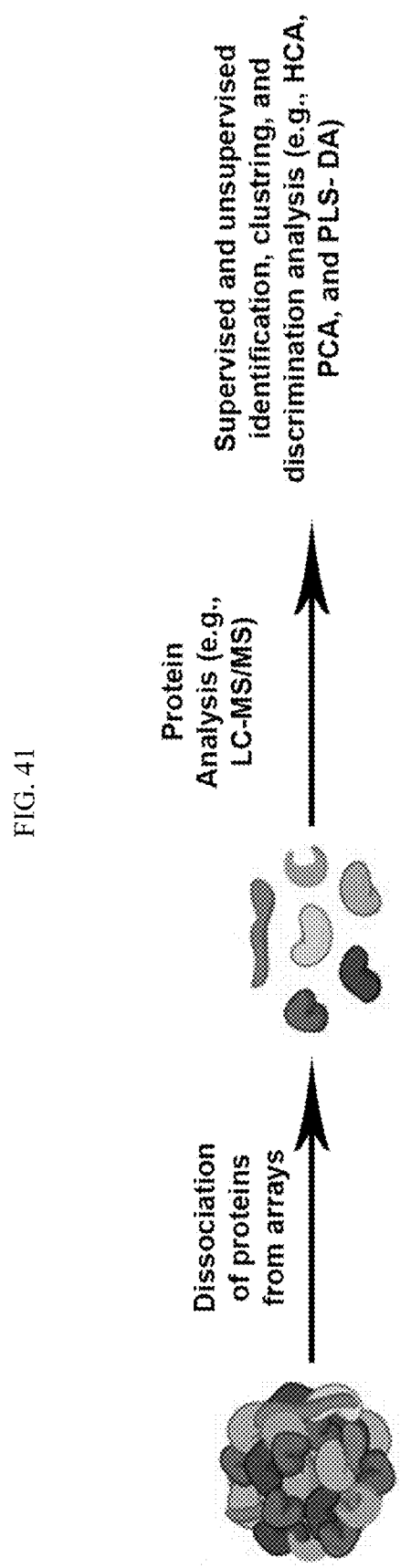
FIG. 41. Dissociation of proteins from the surface of nanoparticles and their corona composition analysis. Analysis of the protein corona sensor array data with supervised and unsupervised approaches to identify and discriminate diseases.

For purposes of illustration only, methods of attaching the sensor elements, e.g. nanoscale sensor elements, to substrates is demonstrated in FIGS. 23-40. For example, sensor elements may be conjugated to a substrate (e.g. silica substrate) via the amidation reaction between the amino groups on silica substrate surface and carboxylic acid groups on nanoparticle surface (FIG. 23), via the ring-opening reaction between the epoxy groups on silica substrate surface and amino groups on nanoparticle surface (FIG. 24), via the Michael Addition reaction between the maleimide groups on silica substrate surface and thiol or amino groups on nanoparticle surface (FIG. 25), via the urethane reaction between the isocyanate groups on silica substrate surface and hydroxyl or amino groups on nanoparticle surface (FIG. 26), via the oxidation reaction between the thiol groups on silica substrate surface and the ones on nanoparticle surface (FIG. 27), via the "Click" chemistry between azide groups on silica substrate surface and alkyne groups on nanoparticle surface (FIG. 28), via the thiol exchange reaction between 2-pyridyldithiol groups on silica substrate surface and thiol groups on nanoparticle surface (FIG. 29), via the coordination reaction between boronic acid groups on silica substrate surface and diol groups on nanoparticle surface (FIG. 30), via the UV light-irradiated addition reaction between C=C bonds on substrate surface and C=C bonds on nanoparticle surface (FIG. 31) and the like. Suitable methods of conjugating sensor elements to gold substrate are known in the art and include, for example, conjugation via Au-thiol bonds (FIG. 32), via the amidation reaction between the carboxylic acid groups on gold substrate surface and the amino groups on nanoparticle surface (FIG. 33), via "Click" chemistry between the azide groups on gold substrate surface and the alkyne groups on nanoparticle surface (FIG. 34), via urethane reaction between the NHS groups on gold substrate surface and the amino groups on nanoparticle surface (FIG. 35), via the ring-opening reaction between the epoxy groups on gold substrate surface and amino groups on nanoparticle surface (FIG. 36), via the coordination reaction between boronic acid groups on silica substrate surface and diol groups on nanoparticle surface (FIG. 37), via the UV light-irradiated addition reaction between C=C bonds on gold substrate surface and C=C bonds on nanoparticle surface (FIG. 38), via the "Ligand-Receptor" interaction between biotin on gold substrate surface and avidin on nanoparticle surface (FIG. 39), via the "Host-Guest" interaction between a-cyclodextrin (a-CD) on gold substrate surface and adamantine (Ad) on nanoparticle surface (FIG. 40), and the like.

In another example, so-called "click chemistry" can be used to attach the functional surface groups to the core structures of the nanoparticles (see, e.g., the Sigma Aldrich catalog and U.S. Pat. No. 7,375,234, which are both incorporated herein by reference in their entireties). Of the reactions comprising the click chemistry field, one example is the Huisgen 1,3-dipolar cycloaddition of alkynes to azides to form 1,4-disubstituted-1,2,3-triazoles. The copper (I)-catalyzed reaction is mild and very efficient, requiring no protecting groups, and requiring no purification in many cases. The azide and alkyne functional groups are generally inert to biological molecules and aqueous environments. The triazole has similarities to the ubiquitous amide moiety found in nature, but unlike amides, is not susceptible to cleavage. Additionally, they are nearly impossible to oxidize or reduce.

The plurality of sensor elements may be attached to the substrate randomly or in a distinct pattern. The sensor elements may be substantially uniformly positioned. The pattern of the arranged sensor elements may vary according to the pattern in which the sensor elements are attached to the substrate. Each sensor element is separated by a distance. The distance between the sensor elements (e.g. nanoparticles) arranged on the substrate may vary depending on the length of the linker used to attach or other fabrication conditions. According to various embodiments, the plurality of sensor elements on the array can be fabricated having a desired inter-element distance and pattern. Suitable distinct patterns are known in the art, including, but not limited to, parallel lines, squares, circles, triangles and the like. Further, the sensor elements may be arranged in rows, or columns. In some embodiments, the substrate is a flat substrate, in other embodiments, the substrate is in the form of microchannels or nanochannels. For illustrative purposes only, suitable embodiments are described in FIG. 15-22. The sensor elements may be contained within microchannels or nanochannels that restrict or control the flow of the sample through the sensor array. Suitable microchannels can range from 10 μm to about 100 μm in size.

In some embodiments, non-limiting examples of the plurality of sensor elements include, but are not limited to, (a) a plurality of sensor elements made of the same material but differing in physiochemical properties, (b) a plurality of sensor elements where one or more sensor element is made of a different material with the same or differing physiochemical properties, (c) a plurality of sensor elements made of the same material differing in size, (d) a plurality of sensor elements made of different material with relatively the same size; (e) a plurality of sensor elements made of different material and made of different sizes, (f) a plurality of sensor elements in which each element is made of a different material, (g) a plurality of sensor elements having different charges, among others. The plurality of sensor elements can be in any suitable combination of two or more sensor elements in which each sensor element provides a unique biomolecule corona signature. For example, the plurality of sensor elements may include one or more liposome and one or more nanoparticle described herein. In one embodiment, the plurality of sensor elements can be a plurality of liposomes with varying lipid content and/or varying charges (cationic/anionic/neutral). In another embodiment, the plurality of sensors may contain one or more nanoparticle made of the same material but of varying sizes and physiochemical properties. In another embodiment, the plurality of sensors may contain one or more nanoparticle made of differing materials (e.g. silica and polystyrene) with similar or varying sizes and/or physiochemical properties (e.g. modifications, for example, $-NH_2$, $-COOH$ functionalization). These combinations are purely provided as examples and are non-limiting to the scope of the invention.

Figure 58:
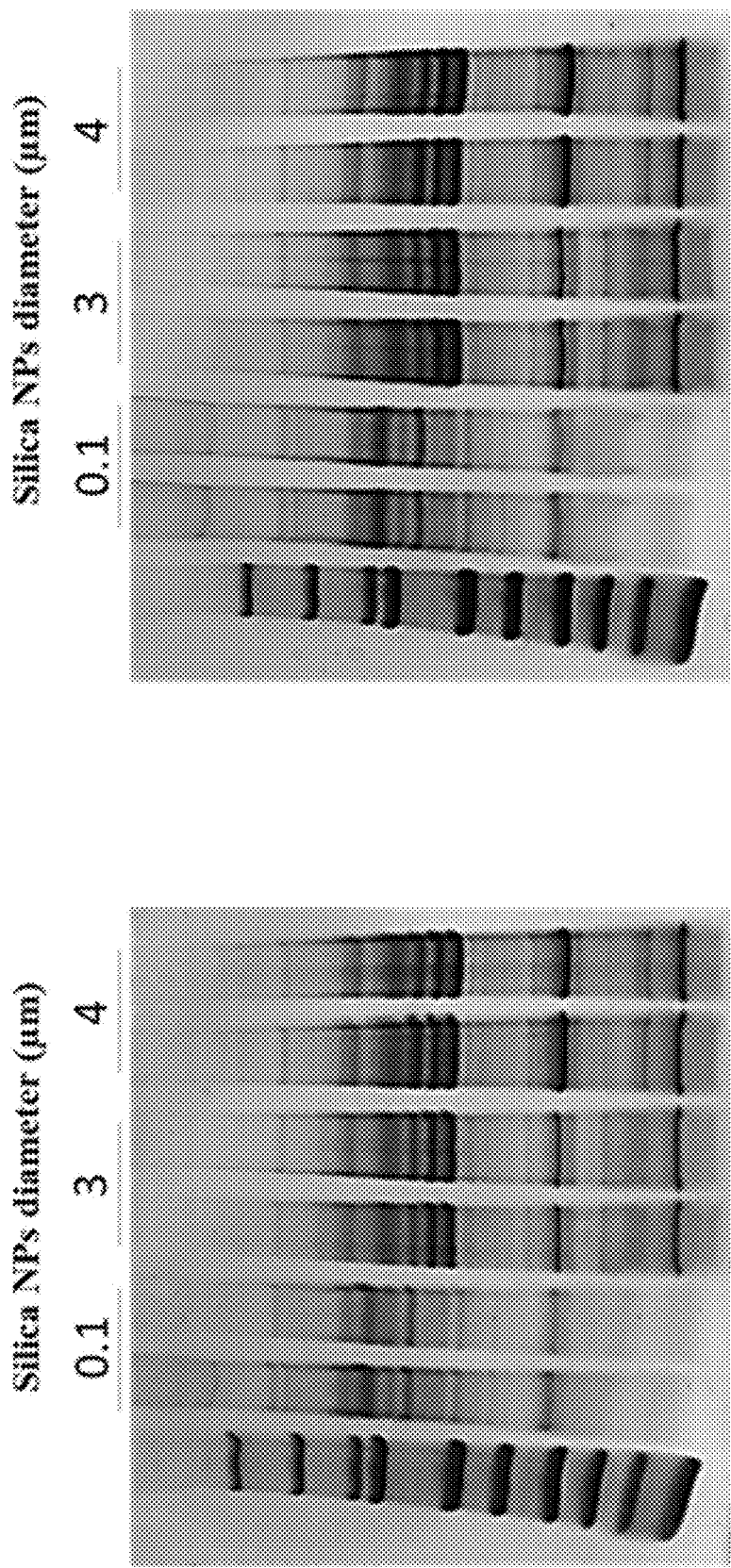
FIG. 58. SDS-Page gel analysis of silica nanoparticle of different diameters using the same volume loaded (10 ul, left) or same amount (10 ug, right).

The angle of curvature on the surface of the particles can change depending on the size of the particles. This change in angle of curvature in turn changes the surface area to which proteins may attach and interact with each other on the particles. As shown in FIG. 58, increasing the size of the particle results in a change in the amount of protein bound and also in the pattern of proteins attached to the different sized nanoparticles (in this example, the SDS-PAGE analysis of proteins on nanoparticles of diameters of 0.1 μm, 3 μm and 4 μm are shown).

Figure 12:
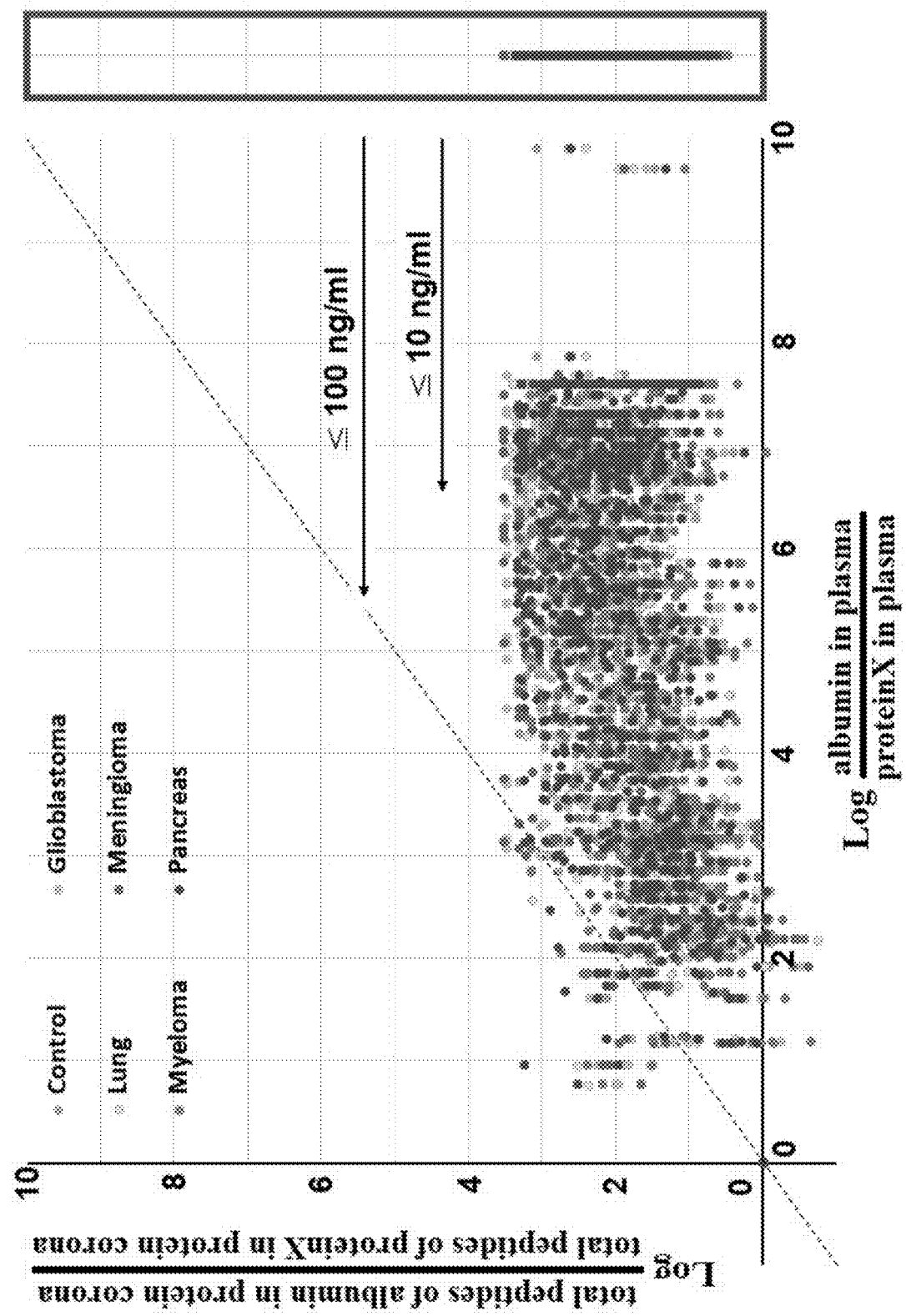
FIG. 12. Multi-liposomes concentrate low-abundance and rare proteins. Protein corona contribution vs. known plasma concentration, plotted on log-log scale. Each point represents a single protein and liposome, with corona contribution for each disease and healthy individuals, and both corona contribution and plasma concentration are normalized with respect to albumin. Plasma concentrations vary over 10 orders of magnitude, while the liposome array detects these same proteins over 4-5 orders of magnitude. Corona contributions of proteins whose plasma concentration is unknown/unreported are plotted in the red area to the right.
Figure 14:
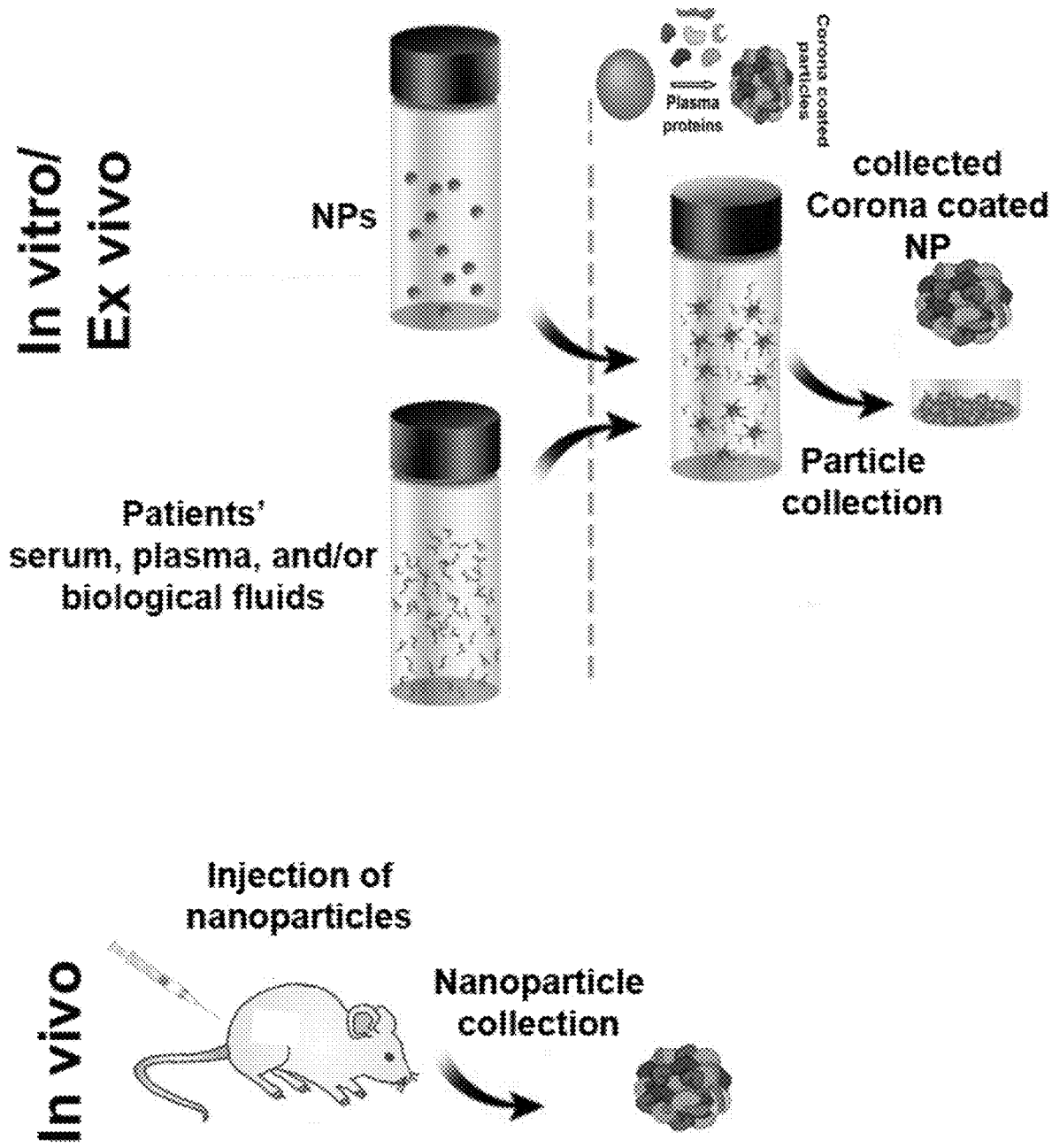
FIG. 14. Example of one method of collection of corona coated particles in in vitro, ex vivo, and in vivo conditions. The particles get incubated with biological fluids (e.g., plasma of patients with different type of disease) and the corona coated particles get collected and stored for analysis.
Figure 15A:
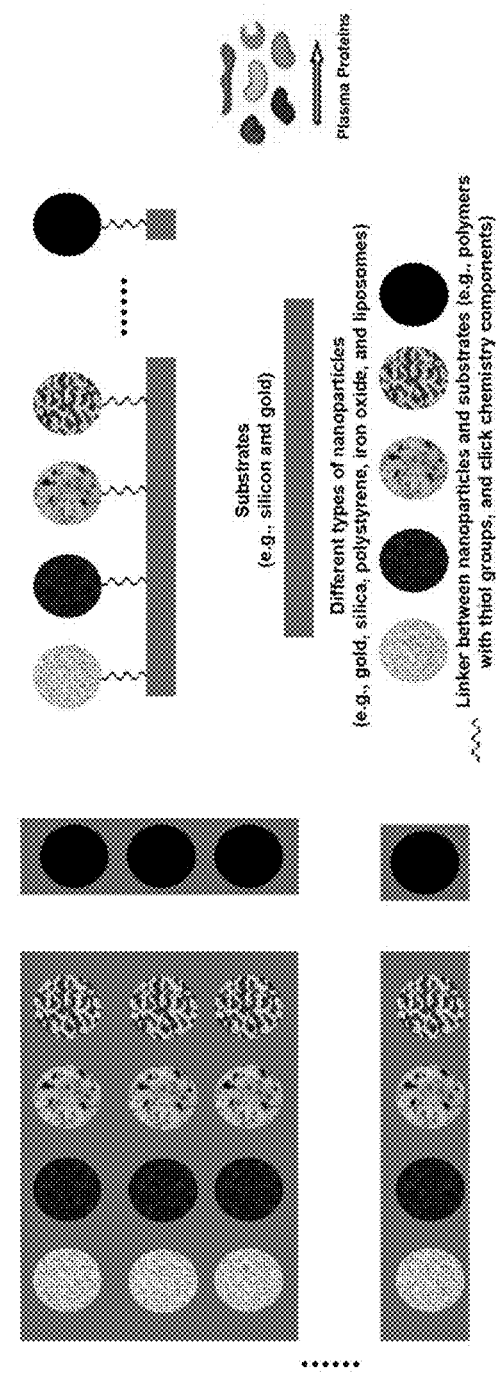
FIG. 15A. Examples of conjugation of nano-object materials (with different physicochemical properties) to substrates (with different physicochemical properties) to make a protein corona sensor array chip (A) before interactions with protein source (e.g., human plasma of various disease). The specific protein corona will form on the surface of nano-objects, with different physicochemical properties. The substrates may also get coated by several types of proteins, which have negligible effects on the detection efficacy of the chip.
Figure 15B:
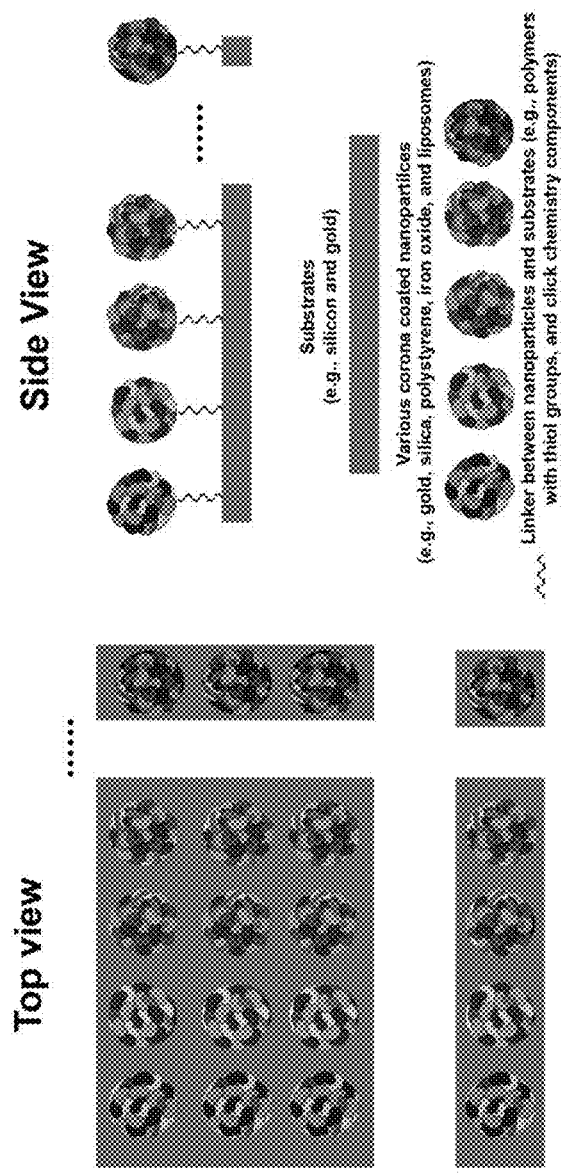
FIG. 15B. Examples of conjugation of nano-object materials (with different physicochemical properties) to substrates (with different physicochemical properties) to make a protein corona sensor array chip after interactions with protein source (e.g., human plasma of various disease).
Figure 17A:
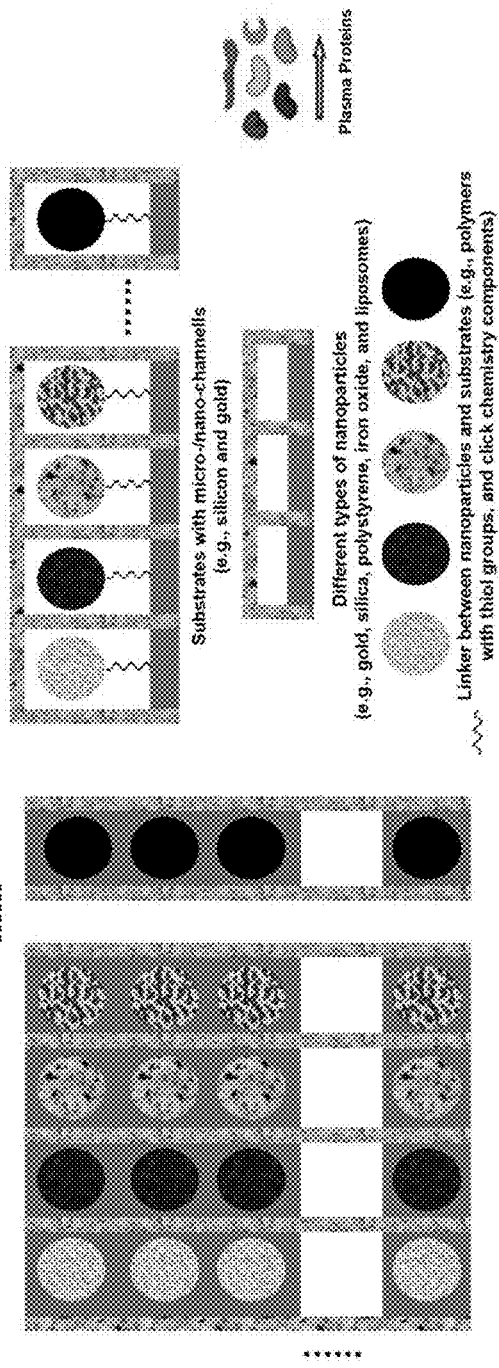
FIG. 17A. Examples of conjugation of nano-object materials (with different physicochemical properties) to substrates (with different physicochemical properties) to make a protein corona sensor array micro/nano fluidic chip before and (b) after interactions with protein source (e.g., human plasma of various disease). The specific protein corona will form on the surface of nano-objects, with different physicochemical properties. The substrates may also get coated by several types of proteins, which have negligible effects on the detection efficacy of the chip.
Figure 17B:
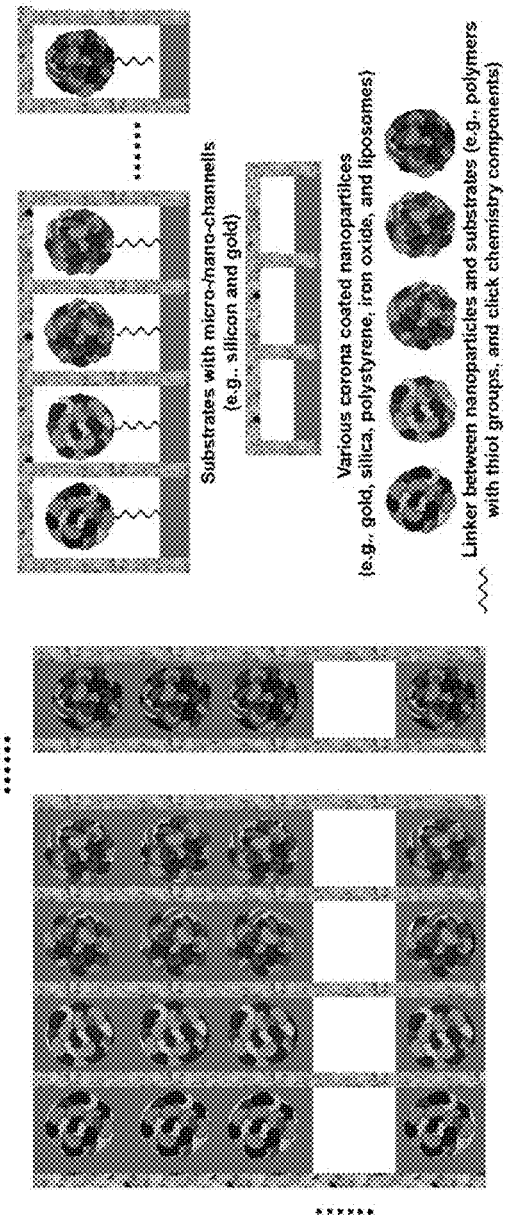
FIG. 17B. Examples of conjugation of nano-object materials to substrates to make a protein corona sensor array micro/nano fluidic chip after interactions with protein source (e.g., human plasma of various disease). The specific protein corona will form on the surface of nano-objects, with different physicochemical properties.
Figures 19A, 19B:
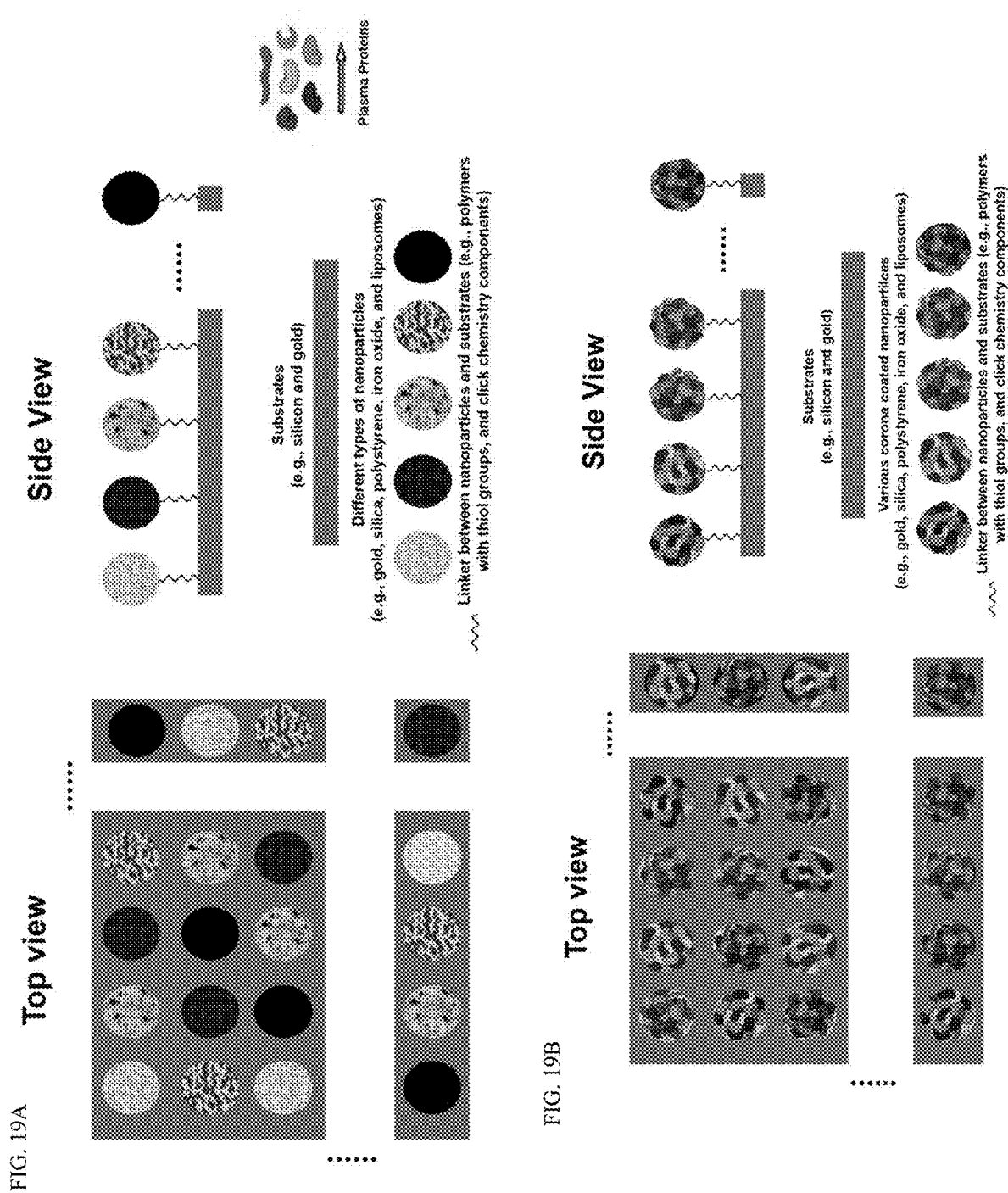
FIG. 19A. Examples of conjugation of random-ordered nano-object materials (with different physicochemical properties) to substrates (with different physicochemical properties) to make a protein corona sensor array chip before interactions with protein source (e.g., human plasma of various disease).
FIG. 19B. Examples of conjugation of random-ordered nano-object materials (with different physicochemical properties) to substrates (with different physicochemical properties) to make a protein corona sensor array chip after interactions with protein source (e.g., human plasma of various disease).
Figure 21A:
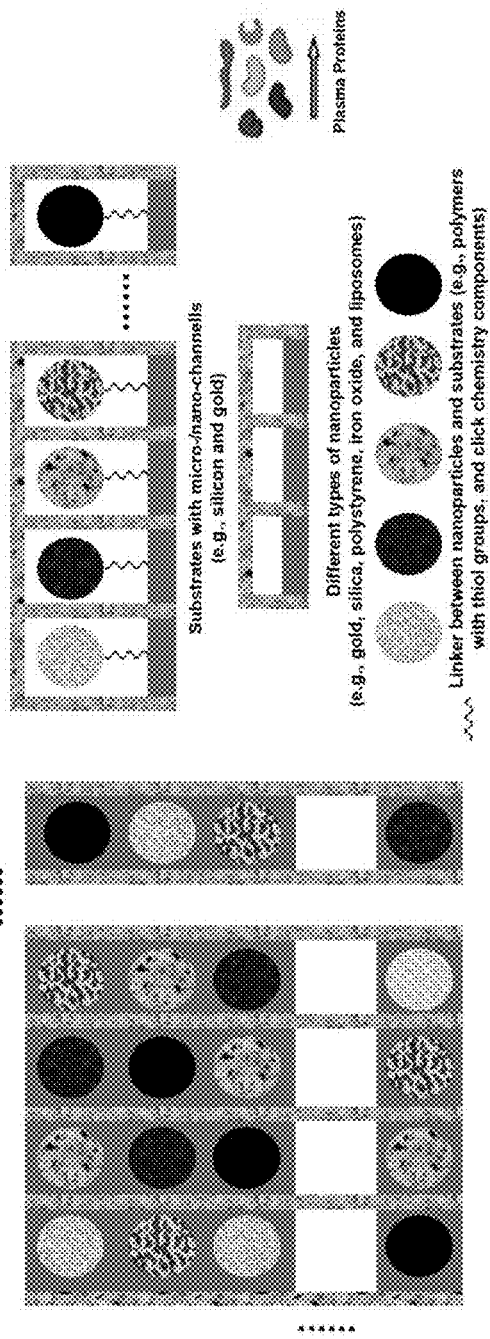
FIG. 21A. Examples of conjugation of random-ordered nano-object materials (with different physicochemical properties) to substrates (with different physicochemical properties) to make a protein corona sensor array micro/nano fluidic chip (A) before interactions with protein source (e.g., human plasma of various disease).
Figure 21B:
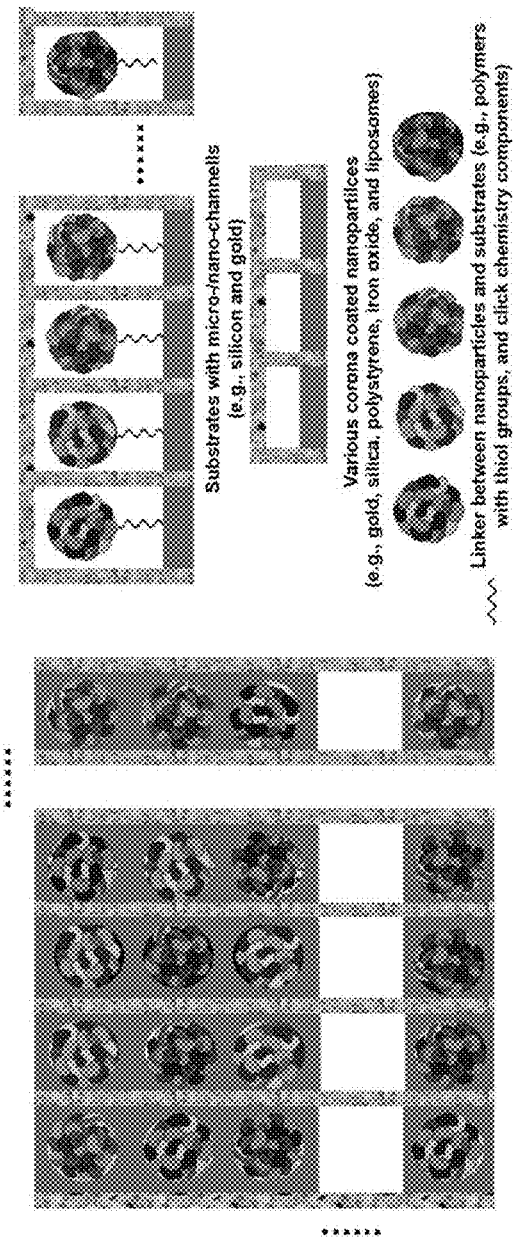
FIG. 21B. Examples of conjugation of random-ordered nano-object materials to substrates to make a protein corona sensor array micro/nano fluidic chip after interactions with protein source (e.g., human plasma of various disease).

The novelty of the sensor array is it not only can detect different proteins between the different sensor elements, but the ability to compare the levels of the same protein between the different sensor elements. For example, not to be bound by any theory but in order to illustrate the uniqueness of the present sensory array, a theoretical example is described. In some embodiments, the sample is contacted with a first sensor element A, a second sensor element B, and a third sensor element C, wherein each sensor element produces a distant protein corona signature (i.e., A', B' and C'). The compositions of each protein corona signature A', B' and C' can be different from one another. In some embodiments, A' B' and C' can comprise the same protein but in a different amount, which can provide additional proteomic information not obtainable by characterizing the sample with previously known approaches. In other words, each unique corona protein information from each nanoparticle serves as unique variables, and therefore provides more data proteomics data. For example, albumin may be found in the protein corona signature of only one sensor element A, in the signature of two sensors, e.g. A and B, B and C or A and C, or in all three sensor biomolecule signatures (A, B, C). Further, the sensor array does not just determine the presence or absence of the protein, e.g., albumin, but it also can determine the comparison of the amount of the protein from one sensor to the other. For example, albumin may be found at concentration X in the signature of A, the concentration of ⅓× in sensor B and at a concentration of 2× in sensor C for a specific biomolecule fingerprint. In another biomolecule fingerprint, the same protein, albumin, could be found in 3 different concentrations, for example, ⅛× in sensor D, 3× in sensor E and ¼× in sensor F. Thus, a plurality of sensors gives not only a data point for the concentration of a protein, but there can be a comparison of the concentration of the protein between two or more sensors. Further, the concentration or rare or low-abundant proteins can be compared to the concentration of a known protein providing further data regarding the protein coronas. For example, for illustrative purposes, the concentration of an unknown protein, e.g. protein Z, may be compared to the amount of a known protein, e.g. albumin in the different biomolecule coronas. For example, Z may be found at a ratio to albumin of 1:8 on sensor A, 1:50 on sensor B, and not present on sensor C. FIG. 12 provides an analysis of the comparison of rare proteins to albumin concentration within protein coronas analyzed. Thus, statistical analysis can take both the presence of a protein, the relative concentration between each sensor element, and the concentration of a rare or low-abundant protein as compared to a known protein of a particular concentration when analyzing the data.

In some embodiments, a channel is formed by lithography, etching, embossing, or molding of a polymeric surface. In general, the fabrication process may involve one or more of any of these processes, and different parts of the array may be fabricated using different methods and assembled or bonded together.

Lithography involves use of light or other form of energy such as electron beam to change a material. Typically, a polymeric material or precursor (e.g. photoresist, a light-resistant material) is coated on a substrate and is selectively exposed to light or other form of energy. Depending on the photoresist, exposed regions of the photoresist either remain or are dissolved in subsequent processing steps known generally as "developing." This process results in a pattern of the photoresist on the substrate. In some embodiments, the photoresist is used as a master in a molding process. In some embodiments, a polymeric precursor is poured on the substrate with photoresist, polymerized (i.e. cured) and peeled off.

In some embodiments, the photoresist is used as a mask for an etching process. For example, after patterning photoresist on a silicon substrate, channels can be etched into the substrate using a deep reactive ion etch (DRIE) process or other chemical etching process known in the art (e.g. plasma etch, KOH etch, HF etch, etc.). The photoresist is removed, and the substrate is bonded to another substrate using one of any bonding procedures known in the art (e.g. anodic bonding, adhesive bonding, direct bonding, eutectic bonding, etc.). Multiple lithographic and etching steps and machining steps such as drilling may be included as required.

In some embodiments, a polymeric substrate may be heated and pressed against a master mold for an embossing process. The master mold may be formed by a variety of processes, including lithography and machining. The polymeric substrate is then bonded with another substrate to form channels and/or a mixing apparatus. Machining processes may be included if necessary.

In some embodiments, a molten polymer or metal or alloy is injected into a suitable mold and allowed to cool and solidify for an injection molding process. The mold typically consists of two parts that allow the molded component to be removed. Parts thus manufactured may be bonded to result in the substrate.

In some embodiments, sacrificial etch may be used to form channels. Lithographic techniques may be used to pattern a material on a substrate. This material is covered by another material of different chemical nature. This material may undergo lithography and etch processes, or other machining process. The substrate is then exposed to a chemical agent that selectively removes the first material. Channels are formed in the second material, leaving voids where the first material was present before the etch process.

In some embodiments, microchannels are directly machined into a substrate by laser machining or CNC machining. Several layers thus machined may be bonded together to obtain the final substrate.

In some embodiments, the width or height of each channel ranges from approximately 1 µm to approximately 1000 µm. In some embodiments, the width or height of each channel ranges from approximately 5 µm to approximately 500 µm. In some embodiments, the width or height of each channel ranges from approximately 10 µm to approximately 100 µm. In some embodiments, the width or height of each channel a ranges from approximately 25 µm to approximately 100 µm. In some embodiments, the width or height of each channel ranges from approximately 50 µm to approximately 100 µm. In some embodiments, the width or height of each channel ranges from approximately 75 µm to approximately 100 µm. In some embodiments, the width or height of each channel ranges from approximately 10 µm to approximately 75 µm. In some embodiments, the width or height of each channel ranges from approximately 10 µm to approximately 50 µm. In some embodiments, the width or height of each channel ranges from approximately 10 µm to approximately 25 µm.

In some embodiments, the maximum width or height of a channel is approximately 1 µm, approximately 5 µm, approximately 10 µm, approximately 20 µm, approximately 30 µm, approximately 40 µm, approximately 50 µm, approximately 60 nm, approximately 70 µm, approximately 80 µm, approximately 90 µm, approximately 100 µm, approximately 250 µm, approximately 500 µm, or approximately 1000 µm.

In some embodiments, the width of each channel ranges from approximately 5 µm to approximately 100 µm. In some embodiments, the width of a channel is approximately 5 µm, approximately 10 µm, approximately 15 µm, approximately 20 µm, approximately 25 µm, approximately 30 µm, approximately 35 µm, approximately 40 nm, approximately 45 µm, approximately 50 µm, approximately 60 µm, approximately 70 µm, approximately 80 µm, approximately 90 µm, or approximately 100 µm.

In some embodiments, the height of each channel ranges from approximately 10 µm to approximately 1000 µm. In some embodiments, the height of a channel is approximately 10 µm, approximately 100 µm, approximately 250 µm, approximately 400 µm, approximately 500 µm, approximately 600 µm, approximately 750 µm, or approximately 1000 µm. In specific embodiments, the height of the channel(s) through which the sample flows is approximately 500 µm. In specific embodiments, the height of the channel(s) through which the sample flows is approximately 500 µm.

In some embodiments, the length of each channel ranges from approximately 100 µm to approximately 10 cm. In some embodiments, the length of a channel is approximately 100 µm, approximately 1.0 mm, approximately 10 mm, approximately 100 mm, approximately 500 mm, approximately 600 mm, approximately 700 mm, approximately 800 mm, approximately 900 mm, approximately 1.0 cm, approximately 1.1 cm, approximately 1.2 cm, approximately 1.3 cm, approximately 1.4 cm, approximately 1.5 cm, approximately 5 cm, or approximately 10 cm. In specific embodiments, the length of the channel(s) through which the sample flows is approximately 1.0 cm. In specific embodiments, the length of the channel(s) through which the sample flows is approximately 1.0 cm.

Biomolecule Corona Nanosystem

Provided herein is biomolecule corona nanosystem or sensor arrays comprising, consisting essentially of or consists of a plurality of sensor elements wherein the plurality of sensor elements differ from each other in at least one physiocochemical property. In some embodiments, a plurality of sensor elements are a plurality of nanoparticles. In some embodiments, a plurality of nanoparticles are a plurality of liposomes. In some embodiments, each sensor element is able to bind a plurality of biomolecules in a complex biological sample to produce a biomolecule corona signature. In some embodiments, each sensor elements has a distinct biomolecule corona signature.

The biomolecule corona signature refers to the composition, signature or pattern of different biomolecules that are bound to each separate sensor element or each nanoparticle. In some cases, the biomolecule corona signature is a protein corona signature. In another case, the biomolecule corona signature is a polysaccharide corona signature. In yet another case, the biomolecule corona signature is a metabolite corona signature. In some cases, the biomolecule corona signature is a lipidomic corona signature. The signature not only refers to the different biomolecules but also the differences in the amount, level or quantity of the biomolecule bound to the sensor element or the nanoparticle, or differences in the conformational state of the biomolecule that is bound to the sensor element or the nanoparticle. It is contemplated that the biomolecule corona signatures of each sensor elements may contain some of the same biomolecules, may contain distinct biomolecules with regard to the other sensor elements or nanoparticles, and/or may differ in level or quantity, type or confirmation of the biomolecule. The biomolecule corona signature may depend on not only the physiocochemical properties of the sensor element or the nanoparticle, but also the nature of the sample and the duration of exposure. In some embodiments, the biomolecule corona signature comprises the biomolecules found in a soft corona and a hard corona.

In some embodiments, the sensor array comprises, consists essentially of or consists of a first sensor element that produces a first biomolecule corona signature and at least one second sensor element or at least one nanoparticle that produces at least one second biomolecule corona signature when the sensor array is contacted with a complex biological sample. A biomolecule fingerprint is the combination of the first biomolecule signature and the at least one second biomolecule signature. It is contemplated that the biomolecule signature can be made from at least two biomolecule corona signatures to as many different biomolecule signatures are assayed, e.g. at least 1000 different biomolecule corona signatures. The biomolecule corona can be assayed separately for each sensor element to determine the biomolecule corona signature for each element each nanoparticle, or each liposome and combined to determine the biomolecule fingerprint or the two or more biomolecule corona can be assayed at the same time to develop the biomolecule fingerprint at once.

The biomolecule fingerprint can distinguish between different possible biological states (e.g., disease states) of a subject. In some embodiments, the biomolecule fingerprint is associated with the development of a disease or disorder and/or is able associated with a disease state of the subject.

In some embodiments, the biomolecule fingerprint is able to determine a disease state for a subject. The term "disease state" for a subject as used herein refers to the ability of sensor array of the present technology to be able to differentiate between the different states of a disease within a subject. This term encompasses a pre-disease state or precursor state of a disease or disorder (a state in which the subject may not have any outward signs or symptoms of the disease or disorder but will develop the disease or disorder in the future) and a disease state in which the subject has a stage of the disease or disorder (e.g., an early, intermediate or late stage of the disease or disorder). In other words, the disease state is a spectrum that encompasses a continuum regarding the health of a subject with respect to a disease or disorder. The array of the present invention is able to distinguish different diseases states for a subject by determining a biomolecule fingerprint which can be compared to differing biomolecule fingerprints that are associated with different disease states on the spectrum and to healthy subjects. In another example, the biomolecule fingerprint may be associated with a pre-disease state or precursor disease state, in which the subject appears healthy at the time with no outward signs or symptoms of a disease, but will develop the disease in the future. In another example, the biomolecule fingerprint may indicate that the subject has the disease, and is able to distinguish if the disease is in the early, intermediate or late stages by the unique biomolecule fingerprint associated with each stage.

As discussed above, the disease state also includes a precursor state of a disease or disorder. This precursor state is a state in which the subject does not have any outward signs or symptoms of the disease or disorder (although there may be submacro changes within the biomolecules of the subject found in their blood or other biological fluids) but will develop the disease or disorder in the future. This precursor state can also be described as a state in which the first pathological changes of a disease are seen, e.g. changes in the biomolecule fingerprint of a biological sample from the patient.

Another example of a biological state is a healthy, non-disease state. The array can also determine a specific biomolecule fingerprint associated with a healthy, non-disease state, where the subject will not develop the disease in the future. In this case, the subject has no evidence at the time of the test that they either have the disease or will develop the disease in the future.

Herein the term "biological state" encompasses any biological characteristic of a subject which can be manifested in a biological sample as defined herein. A biological state can be detected using the methods disclosed herein where two subjects who differ in the biological state manifest those differences in the composition of a sample. For example, a biological state includes a disease state of a subject. A disease state can be detected when the disease state gives rise to changes in the molecular composition (e.g., level of one or more proteins) of a sample of a subject expressing the disease state relative to a sample of a subject not having the disease state (i.e., where the biological state is a healthy state or non-disease state).

Another example of a biological state is a level of responsiveness of a subject to a particular therapeutic treatment (e.g. administration of one or a combination of drugs or pharmaceuticals). In some embodiments, a biological state is responsiveness (e.g., with respect to a particular threshold of analysis) of a subject to a particular drug. In another embodiment, a biological state is non-responsiveness (e.g., with respect to a particular threshold of analysis) of a subject to a particular drug. In some embodiments, the level of responsiveness of a subject to a drug (i.e., biological state of responsiveness to the drug or biological state of non-responsiveness to the drug) is associated with factors such as variability in metabolism or pharmacokinetics of the drug between subjects.

Another example of a biological state is the level of immune response exhibited by a subject. In some embodiments, the biological state can be increased immune response. In other embodiments, the biological state can be decreased immune response. Immune response can differ between subjects as a result of a number of variables. For example, immune response can differ between subjects as a result of differing exposure to an exogenously introduced antigen (e.g. associated with a virus or bacteria), as a result of differences in their susceptibility to an autoimmune disease or disorder, or secondarily as a result of a response to other biological states in a subject (e.g., disease states such as cancer).

Other examples of biological states that can be associated with a biomolecule fingerprint include susceptibility of a subject to adverse effects associated with administration of a drug, and identification of a subject's potential to exhibit an allergic reaction to administration of a particular composition or substance.

The innovation in this sensor arrays and associated methods differ from the current methods of detecting or measuring the presence or absence or levels of certain biomarkers to predict if a subject may have a pre-disposition or likelihood of developing a disease or disorder at a very early stages of the disease, before any signs or symptoms can be monitored can be assayed. Suitably, the array is able to differentiate the health of the subject from no disease or disorder, having a precursor of a disease or disorder, and having the disease or disorder. However, the invention is not limited to those embodiments and covers the spectrum of other disease states that may occur within the continuum of health and disease of a subject.

Further, the innovation of the present invention sensor arrays can be demonstrated by the following examples. The sensor array of the present invention is very sensitive and able to detect not only changes in small amounts of biomolecules within a sample, but rely on the interactions between the biomolecules. For example, not to be bound by any theory but in order to illustrate the uniqueness of the present sensory array, a theoretical example is described. If, for example, biological samples are collected from a subject over time (e.g., before any signs and symptoms of the disease, pre-disease state and during early and intermediate stages of a disease). In these samples, by just measuring a level of a biomolecule X in the sample (e.g. quantitation of amount) it may be found that the concentration does not alter over the different disease states. Thus, measuring biomolecule X would not be a useful marker for the disease However, using the present sensor array, although the level of biomarker X may be the same, the interaction of biomolecule X with other biomolecules, Y and Z, may change the composition of the protein corona signature associated with the sample over time and samples. For example, biomarker X may change its association from associating with biomolecule Y to biomolecule Z, or over time interaction of X with Y and Z leads to a conformational change in X. This type of changes, that does not change the overall concentration but will change the unique biomolecule fingerprint associated with the disease state (that includes biomolecule X) would allow for the distinction and association with other disease states. This would not be discovered if you use methods of the art of just measuring the quantitation of biomolecule X within the sample, as this level stayed the same throughout the entire disease. This is an unexpectedly highly specific and useful assay not seen before. With this assay, biomarkers of a disease that would not previously been characterized as biomarkers can be determined including, patterns of biomarkers, as these marker may not change in absolute amounts within the samples, but will have a consistent and measurable change with regard to the interaction with the sensor elements in the sensor array. The ability to distinguish patterns by analysis of the biomolecule corona allows for the ability to associate these patterns with different disease states.

As discussed above, the present sensor array has the ability to detect proteins over ten order of magnitude, which is a higher sensitivity than any previously described methods. The uniqueness of the present sensor array is found in the ability of the array to detect proteins regardless of the level of concentration within the sample. The assay relies on the ability of the biomolecule (e.g. protein), known or unknown, within the sample to interact with the sensor elements, and to interact differently and at different amounts with different sensor elements and also to interact with the other biomolecules associated with the sensor element. This in turn, allows for there to be the ability to detect low-abundance and rare proteins even in the presence of high abundant proteins (such as albumin) within the sample. As demonstrated in FIG. 12 of Example 1, the ability of the senor array to detect concentrations over 10 order of magnitude even in the presence of high abundant proteins has been shown. Further, the sensor array is also able to detect proteins with unknown/unreported plasma concentrations, which previously have not been found with current methods. One unique feature among others of the present sensor array is the ability of the present system to be able to detect low-abundant proteins and rare proteins. The present sensor array can be used to not only determine a disease state (no disease, pre-disease, or early and late stage disease) but in some cases to distinguish between subtypes of diseases (e.g. distinguish between different types of cancer, e.g. lung cancer, breast cancer, myeloma, etc).

Detection Methods

The present sensor array may be used in a variety of methods described herein. The ability to determine a unique biomolecule fingerprint for samples provides a novel and innovative means to measure a specific disease state in a subject. These biomolecule fingerprints can be used to determine the disease state of a subject, diagnosing or prognosing a disease in a subject or identifying unique patterns of biomarkers that are associated with a disease state or a disease or disorder. For example, the changes in the biomolecule fingerprint in a subject over time (days, months, years) allows for the ability to track a disease or disorder in a subject (e.g. disease state) which may be broadly applicable to determination of a biomolecule fingerprint that can be associated with the early stage of a disease or any other disease state. As discussed above, the ability to detect a disease early on, for example cancer, even before it fully develops or metastasizes allows for a significant increase in positive outcomes for those patients and the ability to increase life expectancy and lower mortality associated with that disease. Therefore, the sensor array of the present invention provides a unique opportunity to be able to develop biomolecule fingerprints associated with the pre-stages or precursor states of the disease.

It is understood that even before a disease has progressed into showing any measurable signs or symptoms, that at the macroscopic level, there are changes taking place within the body and biological systems of a subject. Being able to recognize these early pre-disease signs contemplated by use of the sensor array of the present invention. The inventors have found that by comparing the biomolecule fingerprint of a subject during different times of a disease state (e.g. before a disease has shown symptoms and developed, after early signs or symptoms of the disease, and/or at late stages of the disease) provides a unique biomolecule fingerprint linked to the different disease states linked to the disease progression. In other words, a biomolecule fingerprint can be determined that would allow one to be able to identify subjects that are going to develop a disease at a later time. This would allow for early monitoring and early treatment, greatly improving the outcome of the subject diagnosed with the disease.

In some embodiments, a method of detecting a disease or disorder in a subject are provided. The method comprises the steps of (a) obtaining a sample from the subject; (b) contacting the sample with a sensor array as described herein, and (c) determining a biomolecule fingerprint associated with the sample, wherein the biomolecule fingerprint differentiates the health of subject in a disease state, for example, from no disease or disorder, having a precursor of a disease or disorder, and having disease or disorder.

The step of determining a biomolecule fingerprint associated with the sample may comprise detecting the biomolecule corona signature for at least two sensor elements, wherein the combination of the at least two biomolecule corona signatures produces the biomolecule fingerprint. In some embodiments, the biomolecule corona signatures of the at least two sensor elements are assayed separately and the results combined to determine the biomolecule fingerprint. In some embodiments the biomolecule corona signatures of the at least two elements are assayed at the same time or in the same sample.

In some embodiments, the method of determining the biomolecule fingerprint comprises detecting and determining the biomolecular corona signatures of the at least two sensor elements. In some embodiments, this step can be done by separating the plurality of biomolecules attached to each sensor element (e.g. separating the biomolecule corona from the sensor element) and assaying the plurality of biomolecules to determine the composition of the plurality of biomolecule coronas to determine a biomolecule fingerprint. Depending on the design of the array, in some instances the composition of each biomolecule corona signature of each sensor element is assayed independently, and the results are combined to produce the biomolecule fingerprint (e.g. each sensor element is in a separate channel or compartment wherein the specific composition of the biomolecule corona for that specific sensor element can be separately analyzed (e.g. either by detaching the biomolecules and assaying by mass spectrometry and/or chromatography or by detecting the plurality of biomolecules still attached to the sensor element by fluorescence, luminescence or other means). In another embodiment, the at least two sensor elements are on the same array and the composition of the biomolecule corona for the at least two sensor elements is assayed at the same time by dissociating the biomolecule corona from both sensor elements into one solution and assaying that solution to determining a biomolecule signature. This later method would be the method of choice if using a chip array technology.

Methods of assaying the plurality of biomolecules that make up the biomolecule corona signature or the biomolecule fingerprint are known in the art and include, but are not limited to, for example, gel-electrophoresis, liquid chromatography, mass spectrometry, nuclear magnetic resonance spectroscopy (NMR), fourier transform infrared spectroscopy (FTIR), circular dichroism, Raman spectrometry, and a combination thereof. In a preferred embodiment, the assay is by liquid chromatography, mass spectrometry or a combination thereof.

In a preferred embodiment, the sensor assay is a non-label array.

In some embodiments, it is contemplated that labelled arrays may be used, wherein a corona signature is able to be determined as a change is signal (e.g. fluorescence, luminescence, charge, colormetric dyes). Suitable example is shown in FIGS. 42 and 43. For example, an array may include chemically responsive colorants in a printable formulation for detection and identification of biomolecules based on the equilibrium interactions with the biomolecules and responsive dyes.

In some embodiments, the sensor element comprises a complex with a first component and a polymer fluorophore or other quencher component chemically complementary to the first component where such a complex having an initial background or reference fluorescence. Once the first component comes into contact with the biomolecule corona, it will affect the quenching of the fluorophore and this change in fluorescence can be measured. After the sensor is irradiated and/or excited with a laser, the effect and/or change in fluorescence for each sensor element can be measured and compared to the background fluorescence to produce the biomolecule fingerprint.

The sensor arrays and methods described herein can be used to determine a disease state, and/or prognose or diagnose a disease or disorder. The diseases or disorders contemplated include, but are not limited to, for example, cancer, cardiovascular disease, endocrine disease, inflammatory disease, a neurological disease and the like.

In one embodiment, the disease or disorder is cancer. In suitable embodiments, the sensor array and methods described herein is not only able to diagnose cancer (e.g. determine if a subject (a) does not have cancer, (b) is in a pre-cancer development stage, (c) is in early stage of cancer, (d) is in a late stage of cancer) but in some embodiments is able to determine the type of cancer. As demonstrated in the examples below, a sensor array comprising six sensor elements was able to accurately determine the disease state of the presence or absence of cancer. Additionally, the Examples demonstrate that a sensor array comprising six sensor elements was able to distinguish between different cancer types (e.g. lung cancer, glioblastoma, meningioma, myeloma and pancreatic cancer).

The term "cancer" and "tumor" as used herein interchangeably and are meant to encompass any cancer, neoplastic and preneoplastic disease that is characterized by abnormal growth of cells. Cancer may, for example, be selected from the group consisting of lung cancer, pancreas cancer, myeloma, myeloid leukemia, meningioma, glioblastoma, breast cancer, esophageal squamous cell carcinoma, gastric adenocarcinoma, prostate cancer, bladder cancer, ovarian cancer, thyroid cancer, neuroendocrine cancer, colon carcinoma, ovarian cancer, head and neck cancer, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, fibrosarcoma, myxosarcoma, liposarcoma, chondrosarcoma, osteogenic sarcoma, chordoma, angiosarcoma, endotheliosarcoma, Ewing's sarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, endometrial cancer, lung carcinoma, small cell lung carcinoma, bladder carcinoma, epithelial carcinoma, glioblastomas, neuronomas, craniopharingiomas, schwannomas, glioma, astrocytoma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, childhood-null acute lymphoid leukemia (ALL), thymic ALL, B-cell ALL, acute megakaryocytic leukemia, Burkitt's lymphoma, and T cell leukemia, small and large non-small cell lung carcinoma, acute granulocytic leukemia, germ cell tumors, endometrial cancer, gastric cancer, hairy cell leukemia, thyroid cancer and other cancers known in the art. In a preferred embodiment, the cancer is selected from the group consisting of lung cancer, pancreas cancer, myeloma, myeloid leukemia, meningioma, glioblastoma, breast cancer, esophageal squamous cell carcinoma, gastric adenocarcinoma, prostate cancer, bladder cancer, ovarian cancer, thyroid cancer, and neuroendocrine cancer.

As used herein, the terms "cardiovascular disease" (CVD) or "cardiovascular disorder" are used to classify numerous conditions affecting the heart, heart valves, and vasculature (e.g., veins and arteries) of the body and encompasses diseases and conditions including, but not limited to atherosclerosis, myocardial infarction, acute coronary syndrome, angina, congestive heart failure, aortic aneurysm, aortic dissection, iliac or femoral aneurysm, pulmonary embolism, atrial fibrillation, stroke, transient ischemic attack, systolic dysfunction, diastolic dysfunction, myocarditis, atrial tachycardia, ventricular fibrillation, endocarditis, peripheral vascular disease, and coronary artery disease (CAD). Further, the term cardiovascular disease refers to subjects that ultimately have a cardiovascular event or cardiovascular complication, referring to the manifestation of an adverse condition in a subject brought on by cardiovascular disease, such as sudden cardiac death or acute coronary syndrome, including, but not limited to, myocardial infarction, unstable angina, aneurysm, stroke, heart failure, non-fatal myocardial infarction, stroke, angina pectoris, transient ischemic attacks, aortic aneurysm, aortic dissection, cardiomyopathy, abnormal cardiac catheterization, abnormal cardiac imaging, stent or graft revascularization, risk of experiencing an abnormal stress test, risk of experiencing abnormal myocardial perfusion, and death.

As used herein, the ability to detect, diagnose or prognose cardiovascular disease, for example, atherosclerosis, can include determining if the patient is in a pre-stage of cardiovascular disease, has developed early, moderate or severe forms of cardiovascular disease, or has suffered one or more cardiovascular event or complication associated with cardiovascular disease.

Atherosclerosis (also known as arteriosclerotic vascular disease or ASVD) is a cardiovascular disease in which an artery-wall thickens as a result of invasion and accumulation and deposition of arterial plaques containing white blood cells on the innermost layer of the walls of arteries resulting in the narrowing and hardening of the arteries. The arterial plaque is an accumulation of macrophage cells or debris, and contains lipids (cholesterol and fatty acids), calcium and a variable amount of fibrous connective tissue. Diseases associated with atherosclerosis include, but are not limited to, atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm or stroke.

For illustrative purposes, in one embodiment the sensor arrays may distinguish the different stages of atherosclerosis, including, but not limited to, the different degrees of stenosis in a subject.

Figure 53:
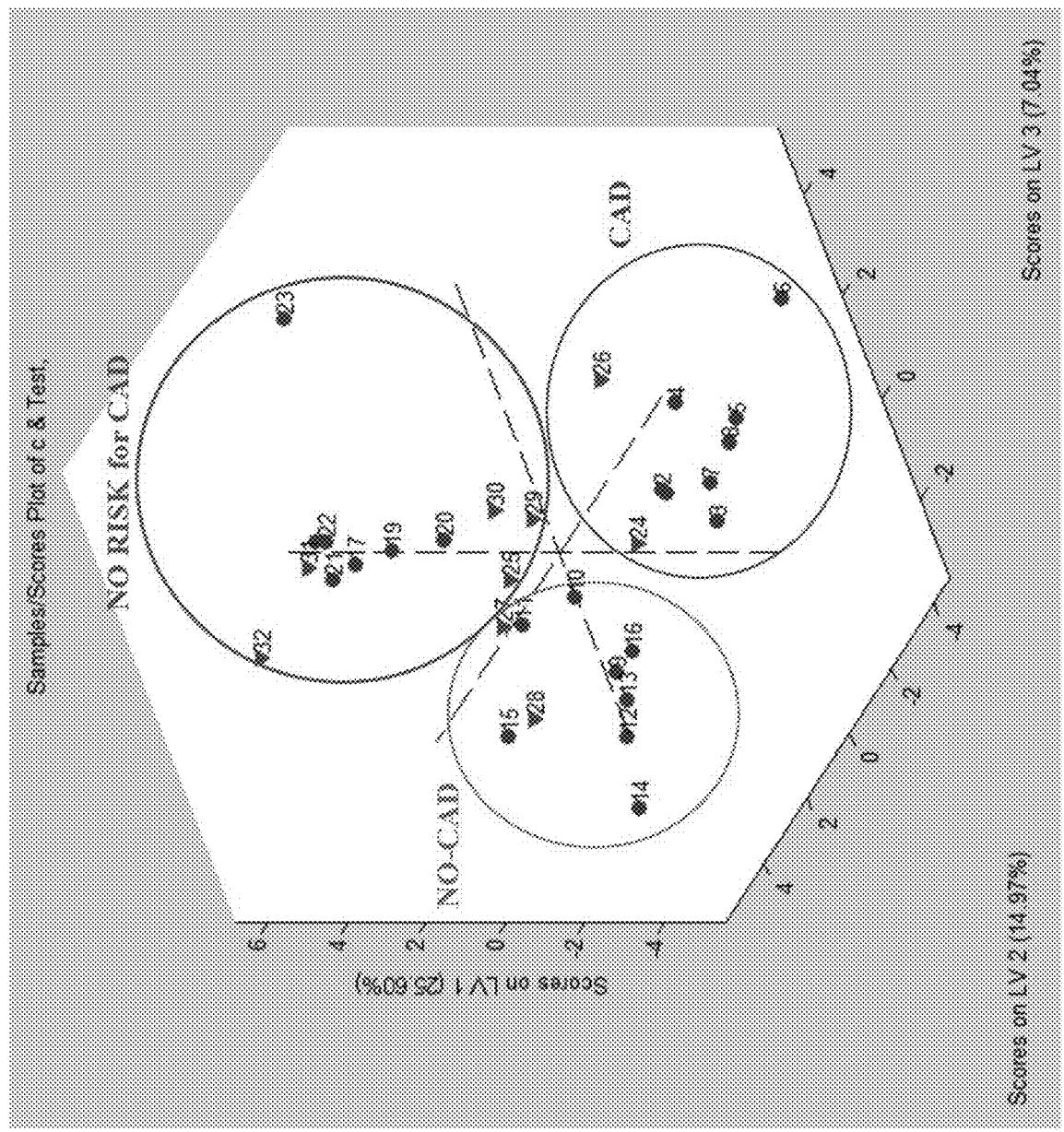
FIG. 53. Plot depicting the classification of the subject into CAD, NO CAD and CONTROL by analysis of the fingerprints produced by the protein-coated corona nanoparticles.

Further, for illustrative purposes only, the examples below demonstrate the use of a sensor array to detect the different state of coronary artery disease. A sensor array containing six sensor elements was able to distinguish subjects with CAD as diagnosed by coronary angiography, patients with symptoms that had healthy coronary vessels (NO CAD), patients with restenosis (reoccurrence of CAD after treatment) and healthy subjects with no risk factors (FIG. 53). The present sensor array was sensitive enough to detect the difference between people who ad symptoms of coronary artery disease but did not have stenosis of the arteries (e.g. NO CAD vs CAD groups). This provides a novel diagnostic CAD test that can be used as a non-invasive screening for at risk patients.

The term "endocrine disease" is used to refer to a disorder associated with dysregulation of endocrine system of a subject. Endocrine diseases may result from a gland producing too much or too little of an endocrine hormone causing a hormonal imbalance, or due to the development of lesions (such as nodules or tumors) in the endocrine system, which may or may not affect hormone levels. Suitable endocrine diseases able to be treated include, but are not limited to, e.g., Acromegaly, Addison's Disease, Adrenal Cancer, Adrenal Disorders, Anaplastic Thyroid Cancer, Cushing's Syndrome, De Quervain's Thyroiditis, Diabetes, Follicular Thyroid Cancer, Gestational Diabetes, Goiters, Graves' Disease, Growth Disorders, Growth Hormone Deficiency, Hashimoto's Thyroiditis, Hurthle Cell Thyroid Cancer, Hyperglycemia, Hyperparathyroidism, Hyperthyroidism, Hypoglycemia, Hypoparathyroidism, Hypothyroidism, Low Testosterone, Medullary Thyroid Cancer, MEN 1, MEN 2A, MEN 2B, Menopause, Metabolic Syndrome, Obesity, Osteoporosis, Papillary Thyroid Cancer, Parathyroid Diseases, Pheochromocytoma, Pituitary Disorders, Pituitary Tumors, Polycystic Ovary Syndrome, Prediabetes, Silent, Thyroiditis, Thyroid Cancer, Thyroid Diseases, Thyroid Nodules, Thyroiditis, Turner Syndrome, Type 1 Diabetes, Type 2 Diabetes, and the like.

As referred to herein, inflammatory disease refers to a disease caused by uncontrolled inflammation in the body of a subject. Inflammation is a biological response of the subject to a harmful stimulus which may be external or internal such as pathogens, necrosed cells and tissues, irritants etc. However, when the inflammatory response becomes abnormal, it results in self-tissue injury and may lead to various diseases and disorders. Inflammatory diseases can include, but are not limited to, asthma, glomerulonephritis, inflammatory bowel disease, rheumatoid arthritis, hypersensitivities, pelvic inflammatory disease, autoimmune diseases, arthritis; necrotizing enterocolitis (NEC), gastroenteritis, pelvic inflammatory disease (PID), emphysema, pleurisy, pyelitis, pharyngitis, angina, acne vulgaris, urinary tract infection, appendicitis, bursitis, colitis, cystitis, dermatitis, phlebitis, rhinitis, tendonitis, tonsillitis, vasculitis, autoimmune diseases; celiac disease; chronic prostatitis, hypersensitivities, reperfusion injury; sarcoidosis, transplant rejection, vasculitis, interstitial cystitis, hay fever, periodontitis, atherosclerosis, psoriasis, ankylosing spondylitis, juvenile idiopathic arthritis, Behcet's disease, spondyloarthritis, uveitis, systemic lupus erythematosus, and cancer. For example, the arthritis includes rheumatoid arthritis, psoriatic arthritis, osteoarthritis or juvenile idiopathic arthritis, and the like.

Neurological disorders or neurological diseases are used interchangeably and refer to diseases of the brain, spine and the nerves that connect them. Neurological diseases include, but are not limited to, brain tumors, epilepsy, Parkinson's disease, Alzheimer's disease, ALS, arteriovenous malformation, cerebrovascular disease, brain aneurysms, epilepsy, multiple sclerosis, Peripheral Neuropathy, Post-Herpetic Neuralgia, stroke, frontotemporal dementia, demyelinating disease (including but are not limited to, multiple sclerosis, Devic's disease (i.e. neuromyelitis optica), central pontine myelinolysis, progressive multifocal leukoencephalopathy, leukodystrophies, Guillain-Barre syndrome, progressing inflammatory neuropathy, Charcot-Marie-Tooth disease, chronic inflammatory demyelinating polyneuropathy, and anti-MAG peripheral neuropathy) and the like. Neurological disorders also include immune-mediated neurological disorders (IMNDs), which include diseases with at least one component of the immune system reacts against host proteins present in the central or peripheral nervous system and contributes to disease pathology. IMNDs may include, but are not limited to, demyelinating disease, paraneoplastic neurological syndromes, immune-mediated encephalomyelitis, immune-mediated autonomic neuropathy, myasthenia gravis, autoantibody-associated encephalopathy, and acute disseminated encephalomyelitis.

In a non-limiting example, the Examples below provide a method of diagnosing Alzheimer's in a patient using the sensor array and methods described herein. The sensor array was not only able to accurately distinguish between patients with or without Alzheimer's disease, but was also able to detect patients who were pre-symptomatic and developed Alzheimer's disease several years after the screening (as determined by cohort plasmas). This provides advantages of being able to treat a disease at a very early stage, even before development of the disease.

The sensor arrays and methods of the present invention in some embodiments are able to detect a pre-disease stage of a disease or disorder. A pre-disease stage is a stage at which the patient has not developed any signs or symptoms of the disease. A pre-cancerous stage would be a stage in which cancer or tumor or cancerous cells have not be identified within the subject. A pre-neurological disease stage would be a stage in which a person has not developed one or more symptom of the neurological disease. The ability to diagnose a disease before one or more sign or symptom of the disease is present allows for close monitoring of the subject and the ability to treat the disease at a very early stage, increasing the prospect of being able to halt progression or reduce the severity of the disease.

The sensor arrays and methods of the present invention in some embodiments are able to detect the early stages of a disease or disorder. Early stages of the disease refers to when the first signs or symptoms of a disease may manifest within a subject. Usually diseases able to be caught in either pre-disease development or in the early states are easier to treat and provide a more positive outcome for the patient. For example, for cancer, the early stages of a disease may include stage 0 and stage 1 cancer. Stage 0 cancer describes the cancer in situ, which means "in place" signifying that the cancer is still located in the place it started and have not spread to nearby tissues. This stage of cancer is often highly curable, usually by removing the entire tumor with surgery. Stage 1 cancer is usually a small cancer or tumor that has not grown deeply into nearby tissue and has not spread to lymph nodes or other parts of the body. Further, early stage of a disease may be a stage at which there are no outward signs or symptoms. For example, in Alzheimer's disease an early stage may be a pre-Alzheimer's stage in which no symptoms are detected yet the patient will develop Alzheimer's months or years later.

In some embodiments, the sensor arrays and methods are able to detect intermediate stages of the disease. Intermediate states of the disease describe stages of the disease that have passed the first signs and symptoms and the patient is experiencing one or more symptom of the disease. For example, for cancer, stage II or III cancers are considered intermediate stages, indicating larger cancers or tumors that have grown more deeply into nearby tissue. In some instances, stage II or III cancers may have also spread to lymph nodes but not to other parts of the body.

Further, the sensor arrays and methods are able to detect late or advanced stages of the disease. Late or advanced stages of the disease may also be called "severe" or "advanced" and usually indicates that the subject is suffering from multiple symptoms and effects of the disease. For example, severe stage cancer includes stage IV, where the cancer has spread to other organs or parts of the body and is sometimes referred to as advanced or metastatic cancer.

In some embodiments, the methods of the present technology include comparing the protein fingerprint of the sample to a panel of protein fingerprints associated with a plurality of diseases and/or a plurality of disease states to determine if the sample indicates a disease and/or disease state. For example, samples can be collected from a population of subjects over time. Once the subjects develop a disease or disorder, the present invention allows for the ability to characterize and detect the changes in biomolecule fingerprints over time in the subject by comparing the biomolecule fingerprint of the sample from the same subject before they have developed a disease to the biomolecule fingerprint of the subject after they have developed the disease. In some embodiments, samples can be taken from cohorts of patients who all develop the same disease, allowing for analysis and characterization of the biomolecule fingerprints that are associated with the different stages of the disease for these patients (e.g. from pre-disease to disease states).

For illustrative purposes only, the examples have shown that the methods and sensor arrays of the present invention are able to distinguish not only between different types of cancers, but also between the different stages of the cancer (e.g. early stages of cancer).

Methods of determining a biomolecule fingerprint associated with at least one disease or disorder and/or a disease state are contemplated. The methods comprise the steps of obtaining a sample from at least two subjects diagnosed with the at least one disease or disorder or having the same disease state; contacting each sample with a sensor array described herein to determining a biomolecule fingerprint for each sensor array, and analyzing the fingerprint of the at least two samples to determine a biomolecule fingerprint associated with the at least one disease or disorder and/or disease state.

Classification of Biomolecule Corona

The method of determining the biomolecule fingerprint associated with the disease or disorder and/or disease state include the analysis of the biomolecule fingerprints of the at least two samples. This determination, analysis or statistical classification is done by methods known in the art, including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive bayes, linear regression, polynomial regression, SVM for regression, K-means clustering, and hidden Markov models, among others. In other words, the biomolecule fingerprint of each sample are compared/analyzed with each other to determine with statistical significance what patterns are common between the individual fingerprints to determine a biomolecule fingerprint that is associated with the disease or disorder or disease state.

Generally, machine learning algorithms are used to construct models that accurately assign class labels to examples based on the input features that describe the example. In some case it may be advantageous to employ machine learning and/or deep learning approaches for the methods described herein. For example, machine learning can be used to associate the biomolecule fingerprint with various disease states (e.g. no disease, precursor to a disease, having early or late stage of the disease, etc.). For example, in some cases, one or more machine learning algorithms are employed in connection with a method of the invention to analyze data detected and obtained by the biomolecule corona and biomolecule fingerprints derived therefrom. For example, in one embodiment, machine learning can be coupled with the sensor array described herein to determine not only if a subject has a pre-stage of cancer, cancer or does not have or develop cancer, but also to distinguish the type of cancer.

The Examples below have shown the ability of the sensor array described herein to determine the disease state for a number of different diseases, including, cancer, cardiovascular disease and neurological disease (e.g. Alzheimer's disease) with statistical significance. This assay is not limited to these specific embodiments, as the sensor array can be applied to a variety of diseases and disease states as described herein.

In some embodiments, the method includes obtaining samples from control subjects which are contacted with the sensor array to produce a control biomolecule fingerprint. These control biomolecule fingerprints can then be used to compare to the biomolecule fingerprints of the subjects with a disease or disorder and/or specific disease state to determine a biomolecule fingerprint specific to that disease or disorder and/or specific disease state.

The method may include, for example, obtaining control sample from at least one control subject, contacting the control sample with the sensor array to produce a plurality of control biomolecule corona, and assaying the plurality of biomolecules of each control biomolecule corona. The method may further comprise comparing the plurality of biomolecules of the plurality of control biomolecule corona with the plurality of biomolecules of the plurality of biomolecule corona from the subject with the disease or disorder to determine a biomolecule fingerprint associated with the at least one disease or disorder.

Methods of diagnosing or prognosing a disease or disorder are also contemplated. The methods comprise obtaining a sample from a subject; contacting the sample with a sensor array to produce a biomolecule fingerprint, and comparing the biomolecule fingerprint to a panel of biomolecule fingerprints associated with a plurality of diseases or disorders; and diagnosing or prognosing the disease or disorder.

In some embodiments, methods of identifying patterns of biomarkers or specific biomarkers associated with a disease or disorder are contemplated. Suitable methods, include, for example, preforming the methods described above (e.g. obtaining a samples from at least two subjects diagnosed with the disease or disorder and at least two control subjects; contacting each sample with the sensor array to produce a biomolecule fingerprint, and comparing the biomolecule fingerprint of the subjects with the disease or disorder to the biomolecule fingerprint of the control subjects to determine at least one pattern and/or biomarker associated with the disease or disorder. Suitable, the method may comprise at least 2 disease subjects and at least two control subjects, alternatively at least 5 disease subjects and at least 5 control subjects, alternatively at least 10 disease subjects and at least 10 control subjects, alternatively at least 15 disease subjects and at least 15 control subjects, alternatively at least 20 disease subjects and at least 20 control subjects, and includes any variations in between (e.g. disease subjects from at least 2-100, and control subjects from at least 2-100).

In some embodiments, the arrays and methods allow for the determination of a pattern of biomarkers associated with the disease state or disease or disorder or, in some embodiments, specific biomarkers that are associated with the disease or disorder. Not only will biomarkers that may be associated with a disease state be able to be identified, for example, biomarkers listed herein, but new biomarkers or patterns of biomarkers that may be associated with a disease state or a disease or disorder may be determined. As discussed above, some biomarkers or patterns of biomarkers for a specific disease or disorder may be a change in a biomolecule associated with the sensor array of the present invention and differ from what is usually referred to as biomarkers in the art, e.g., and increase expression of a specific biomolecule associated with a disease. As discussed above, it may be the interaction of a biomolecule, e.g. biomolecule X, with other biomolecules, e.g. biomolecule Y and Z, that results in the ability to associate with a specific disease state and may not correlate with any change in the absolute concentration of biomarker X in the sample over time or disease state. Thus, a molecule that would not in the conventional sense be considered a biomarker since it does not change in absolute concentration in a sample from the pre-disease to disease state, may in view of the present disclosure be considered a biomolecule as its relative changes that are measured by the array of the present invention are associated with a disease state. In other words, it may be an increase or decrease in the interaction of biomolecule X (due to the interactions of X with the sensor elements and other biomolecules in the sample) with the array that provides a signal that a biomarker is associated with a disease state.

Suitable cancer biomarkers include, but are not limited to, for example, AHSG ($\alpha$2-HS-Glycoprotein), AKR7A2 (Aflatoxin B1 aldehyde reductase), AKT3 (PKB $\gamma$), ASGR1 (ASGPR1), BDNF, BMP1 (BMP-1), BMPER, C9, CA6 (Carbonic anhydrase VI), CAPG (CapG), CDH1 (Cadherin-1), CHRDL1 (Chordin-Like 1), CKB-CKM-(CK-MB), CLIC1 (chloride intracellular channel 1), CMA1 (Chymase), CNTN1 (Contactin-1), COL18A1 (Endostatin), CRP, CTSL2 (Cathepsin V), DDC (dopa decarboxylase), EGFR (ERBB1), FGA-FGB-FGG (D-dimer), FN1 (Fibronectin FN1.4), GHR (Growth hormone receptor), GPI (glucose phosphate isomerase), HMGB1 (HMG-1), HNRNPAB (hnRNP A/B), HP (Haptoglobin, Mixed Type), HSP90AA1 (HSP 90$\alpha$), HSPA1A (HSP 70), IGFBP2 (IGFBP-2), IGFBP4 (IGFBP-4), IL12B-IL23A (IL-23), ITIH4 (Inter-$\alpha$-trypsin inhibitor heavy chain H4), KIT (SCF sR), KLK3-SERPINA3 (PSA-ACT), L1CAM (NCAM-L1), LRIG3, MMP12 (MMP-12), MMP7 (MMP-7), NME2 (NDP kinase B), PA2G4 (ErbB3 binding protein Ebp1), PLA2G7 (Lp-PLA2/PAFAH), PLAUR (suPAR), PRKACA (PRKA C-$\alpha$), PRKCB (PKC-$\beta$-II), PROK1 (EG-VEGF), PRSS2 (Trypsin-2), PTN (Pleiotrophin), SERPINA1 ($\alpha$1-Antitrypsin), STC1 (Stanniocalcin-1), STX1A (Syntaxin 1A), TACSTD2 (GA733-1 protein), TFF3 (Trefoil factor 3), TGFBI (13IGH3), TPI1 (Triosephosphate isomerase), TPT1 (Fortilin), YWHAG (14-3-3 protein $\gamma$), YWHAH (14-3-3 protein eta), prostate cancer biomarkers, for example, PSA, Pro-PSA, PHI, PCA3, TMPRSS3:ERG, PCMT, MTEN, breast cancer markers, for example, epidermal growth factor receptor 2 (HER2) oncogene, melanoma biomarker BRAF, lung cancer biomarker EML4-ALK, A2ML1, BAX, C10orf47, Clorfl62, CSDA, EIFC3, ETFB, GABARAPL2, GUK1, GZMH, HIST1H3B, HLA-A, HSP90AA1, NRGN, PRDXS, PTMA, RABAC1, RABAGAP1L, RPL22, SAP 18, SEPW1, SOX1, EGFR, EGFRvIII, apolipoprotein AI, apolipoprotein CIII, myoglobin, tenascin C, MSH6, claudin-3, claudin-4, caveolin-1, coagulation factor III, CD9, CD36, CD37, CD53, CD63, CD81, CD136, CD147, Hsp70, Hsp90, Rabl3, Desmocollin-1, EMP-2, CK7, CK20, GCDF15, CD82, Rab-5b, Annexin V, MFG-E8, HLA-DR, a miR200 microRNA, MDC, NME-2, KGF, PlGF, Flt-3L, HGF, MCP1, SAT-1, MIP-1-b, GCLM, OPG, TNF RII, VEGF-D, ITAC, MMP-10, GPI, PPP2R4, AKR1B1, AmylA, MIP-1b, P-Cadherin, EPO and the like. For example, biomarkers for breast cancer include, but are not limited to, ER/PR, HER-2/neu, and the like. Biomarkers for colorectal cancer include, but are not limited to, for example, EGFR, KRAS, UGT1A1, and the like. Biomarkers associated with leukemia/lymphoma include, but are not limited to, e.g., CD20 antigen, CD30, FIP1L1-PDGFRalpha, PDGFR, Philadelphia Chromosome (BCR/ABL), PML/RAR alpha, TPMT, UGT1A1, and the like. Biomarker associated with lung cancer include but are not limited to, e.g., ALK, EGFR, KRAS and the like. Biomarkers are known in the art, and can be found in, for example, Bigbee W, Herberman R B. Tumor markers and immunodiagnosis. In: Bast R C Jr., Kufe D W, Pollock R E, et al., editors. Cancer Medicine. 6th ed. Hamilton, Ontario, Canada: BC Decker Inc., 2003; Andriole G, Crawford E, Grubb R, et al. Mortality results from a randomized prostate-cancer screening trial. New England Journal of Medicine 2009; 360(13):1310-1319; Schroder F H, Hugosson J, Roobol M J, et al. Screening and prostate-cancer mortality in a randomized European study. New England Journal of Medicine 2009; 360(13):1320-1328; Buys S S, Partridge E, Black A, et al. Effect of screening on ovarian cancer mortality: the Prostate, Lung, Colorectal and Ovarian (PLCO) Cancer Screening Randomized Controlled Trial. JAMA 2011; 305(22):2295-2303; Cramer D W, Bast R C Jr, Berg C D, et al. Ovarian cancer biomarker performance in prostate, lung, colorectal, and ovarian cancer screening trial specimens. Cancer Prevention Research 2011; 4(3):365-374; Sparano J A, Gray R J, Makower D F, et al. Prospective validation of a 21-gene expression assay in breast cancer. New England Journal of Medicine 2015; First published online Sep. 28, 2015. doi: 10.1056/NEJMoa1510764, incorporated by reference in their entireties.

Suitable, these methods can be used to determine biomarkers associated with cancer. For example, in one embodiment the cancer is glioblastoma, and wherein the biomarker is selected from the group consisting of HABP1, VTNC, CO3, ITIH2, ITIH1, C07, FHRS, CBPN, ALBU, PLMN, CO4A, PRDX2, VWF, C4BPA, APOB, HBB, CNDP1, CRP, SAA4, APOE, CSCL7 and combinations thereof. In another embodiment, the cancer is meningioma, and wherein the biomarker is selected from the group consisting of FCN3, RET4, HABP2, CBPN and combinations thereof. In another embodiment, the cancer is pancreatic cancer and wherein the biomarker is selected from the group consisting of KNG1, IC1, CBPB2, TRFE, GELS, CXCL7, HPTR, PGK1, AACT, LUM, APOE, FIBB, APOA2, A1BG, A1AT, LBP, APOA1, H4, FIBG and combinations thereof. In another embodiment, the cancer is lung cancer and the biomarker is selected from the group consisting of COO, CRP, SAA4, APOA1, A1AT, GELS and combinations thereof. In another embodiment, the cancer is myeloma and the biomarker is ALBU.

Biomarkers may also be associated with the cardiovascular disease which are known in the art and include, but are not limited to, lipid profile, glucose, and hormone level and physiological biomarkers based on measurement of levels of important biomolecules such as serum ferritin, triglyceride to HDLp (high density lipoproteins) ratio, lipophorin-cholesterol ratio, lipid-lipophorin ratio, LDL cholesterol level, HDLp and apolipoprotein levels, lipophorins and LTPs ratio, sphingolipids, Omega-3 Index, and ST2 level, among others. Suitable biomarkers for cardiovascular disease can be found in the art, for example, but not limited to, in van Holten et al. "Ciculating Biomarkers for Predicting Cardiovascular Disease Risk; a Systemic Review and Comprehensive Overview of Meta-Analyses" PLoS One, 2013 8(4): e62080, incorporated by reference in its entirety.

Biomarkers may also be associated with a neurological disease. Suitable biomarkers are known in the art and include, but are not limited to, e.g., Aβ1-42, t-tau and p-tau 181, α-synuclein, among others. See, e.g., Chintamaneni and Bhaskar "Biomarkers in Alzheimer's Disease: A Review" ISRN Pharmacol. 2012. 2012: 984786. Published online 2012 Jun. 28, incorporated by reference in its entirety.

Biomarkers for inflammatory diseases are known in the art and include, but are not limited to, e.g., cytokines/chemokines, immune-related effectors, acute-phase proteins [C-reactive protein (CRP) and serum amyloid A (SAA)], reactive oxygen species (ROS) and reactive nitrogen species (RNS), prostaglandins and cyclooxygenase (COX)-related factors, and mediators such as transcription factors and growth factors, which can include, for example, C-reactive protein (CRP), 5100, LIF, CXCL1, CXCL2, CXCL4, CXCL5, CXCL8, CXCL9, CXCL10, CCL2, CCL23, IL-Iβ, IL-IRa, TNF, IL-6, IL-10, IL-17A, IL-17F, IL-21, IL-22, IFNγ, CXCR1, CXCR4, CXCR5, GM-CSF, GM-CSFR, G-CSF, G-CSFR, EGF, VEGFA, LEP, SAA1, VCAM1, CRP, MMP1, MMP3, TNFRSF1A, RETN, CHI3L1, anti-nuclear antibodies (ANA), rheumatoid factor (RF), antibodies against cyclic citrullinated peptide (anti-CCP)] and for chronic IBD (fecal calprotectin), among others. Suitable biomarkers for inflammatory bowel disease, for example, include CRP, ESR, pANCA, ASCA, and fecal calprotectin. See, e.g., Yi Fengming and Wu Jianbing, "Biomarkers of Inflammatory Bowel Disease," Disease Markers, vol. 2014, Article ID 710915, 11 pages, 2014. doi:10.1155/2014/710915, incorporated by reference in its entirety.

The terms "individual," "subject," and "patient" are used interchangeably herein irrespective of whether the subject has or is currently undergoing any form of treatment. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Preferably, the subject is a human.

The arrays and methods described herein can be used under a number of different conditions to provide the desired biomolecule fingerprint. For example, the size of the sensor elements, the rate of flow of the sample through the sensor, the time of incubating the sensor array with the sample and the temperature at which the sensor array is incubated can all be changed to provide a reproducible biomolecule fingerprint. Suitable sizes of the sensor element include nanoscale sensor elements that have less than one micron in at least one direction.

Suitable time for incubating the array or plurality of sensor elements include, at least a few seconds, e.g. at least 10 seconds to about 24 hours, for example at least about 10 seconds, at least about 15 seconds, at least about 20 seconds, at least about 25 seconds, at least about 30 seconds, at least about 40 seconds, at least about 50 seconds, at least about 60 seconds, at least about 90 seconds, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, at least about 15 minutes, at least about 20 minutes, at least about 25 minutes, at least about 30 minutes, at least about 45 minutes, at least about 50 minutes, at least about 60 minutes, at least about 90 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 14 hours, at least about 15 hours, at least about 16 hours, at least about 17 hours, at least about 18 hours, at least about 19 hours, at least about 20 hours, and include any time and increment in between (e.g. 10 seconds, 11, 12, 13, 14, 15, 15, 17, 18, 19, 20, 21, 22, 23, 24, 25, 26, 27, 28, 29, 30, 31, 32 33, 34, 35, 36, 37, 38, 39, 40, 41, 42, 43, 44, 45, 46, 47, 48, 49, 50, 51, 52, 53, 54, 55, 56, 57, 58, 59, 60 seconds, etc.; 1 minute, 2, 3, 4, 5, 6, 7, 9, 10, 11, 12, 13, 14, 15, 15, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, etc.; 1 hour, 2 hours, 3, hours, 4, hours, 5 hours, 6 hours, 7 hours, 8 hours etc.)

Further, the temperature at which the assay is performed can be determined by one skilled in the art, and incudes temperatures between about 4° C. to about 40° C., alternatively from about 4° C. to about 20° C., alternatively from about 10° C. to about 15° C., alternatively from about 10° C. to about 40° C., for example, at about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 25° C., about 30° C., about 35° C., about 37° C., etc. Suitable, the assay may be performed at room temperature (e.g. around about 37° C., for example from about 35° C. to about 40° C.).

The methods of the present invention may comprise contacting the sample with the sensor array. The contacting of the sample with the sensor array may be using any suitable flow rate in which the sample can flow over the sensor array. In some aspects, the flow velocity of the streams, the Reynolds number, or the relative cross sectional areas of the flow streams can be altered to provide adequate contact between the sample and the sensor array.

For example, in embodiments using a nanochannel or microchannel the cross sectional area of the first stream can be more than 1% of the cross sectional area of the channel. In another example, the cross-sectional area of the first stream can be less than 90% of the cross sectional area of the channel. The cross sectional area ratio can be 10:1 to 1:10, 1:5 to 5:1, 1:3 to 3:1, 1:2 to 2:1 or 1:1.

In certain other circumstances, the flow of the sample over the array has a Reynolds number at the location of the introduction of the sample of between 300 and 1,000,000. In some instances, the location of the introduction of the sample is a nanochannel or microchannel.

Kits

Aspects of the present disclosure that are described with respect to methods can be utilized in the context of the sensor array or kits discussed in this disclosure. Similarly, aspects of the present disclosure that are described with respect to the sensor array and methods can be utilized in the context of the kits, and aspects of the present disclosure that are described with respect to kits can be utilized in the context of the methods and sensor array.

This disclosure provides kits. The kits can be suitable for use in the methods described herein. Suitable kits include a kit for determining a biomolecule fingerprint for a sample comprising a sensor array as described herein. In one aspect, the kit provides a sensor array comprising at least two sensor elements which have differing physiocochemical properties from each other. In some aspects, the kits provides a comparative panel of biomolecule fingerprints in order to use the biomolecule fingerprint to determine a disease state for the subject. In some aspects, instructions on how to determine the biomolecule fingerprint are included. In some suitable embodiments, the sensor arrays are provided as chip arrays in the kit.

In other aspects, kits for determining a disease state of a subject or diagnosing or prognosing a disease in a subject are provided. Suitable kits include a sensor array comprising at least two sensor elements which have differing physicochemical properties from each other to determining a biomolecule fingerprint. Further, the kit may further include a comparative panel of biomolecule fingerprint of different disease states or different diseases or disorders. Instructions on determining the biomolecule fingerprint and analysis are provided.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLES

Example 1A. Label-Free Sensor Array for Early Detection of Cancer

The present Example provides a label-free sensor array for early detection of various cancers. The sensor array consists of three different cross-reactive liposomes with various surface charges (i.e., cationic (DOPG (1,2-dioleoyl-sn-glycero-3-phospho-(1'-rac-glycerol)), anionic (DOTAP (1,2-Dioleoyl-3-trimethylammonium-propane)-DOPE (dioleoylphosphatidylethanolamine)), and neutral (CHOL (DOPC-Cholesterol)), whose protein corona composition changes in response to their interactions with the plasma of patients who have different types of various cancers, i.e., lung, pancreas, myeloma, meningioma, and glioblastoma. Although no single protein corona composition is specific for any one cancer type, the changes in the corona composition pattern provide a unique "fingerprint" for each type of cancer.

Figure 2A:
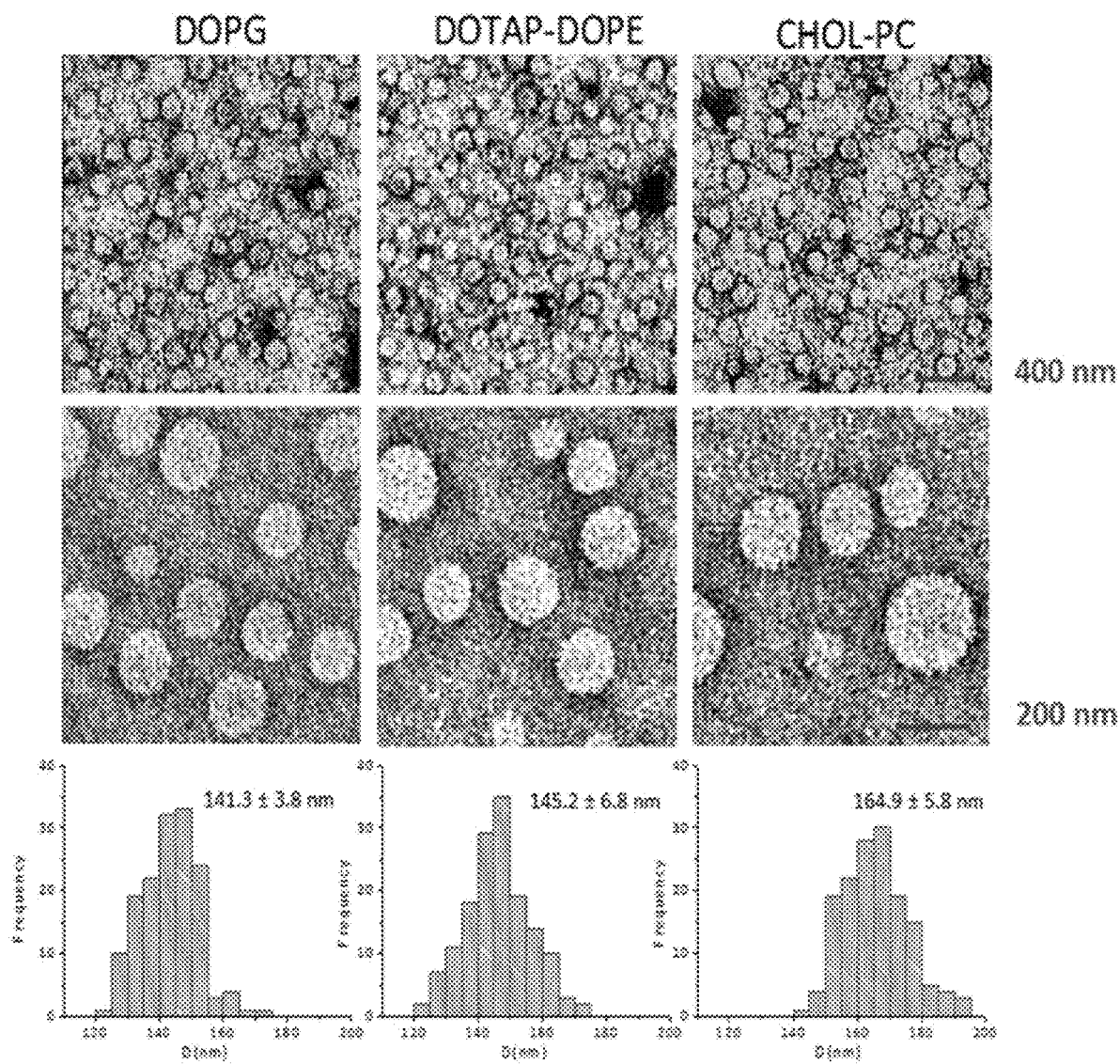
FIG. 2A. TEM images of liposomes with their size distribution profiles.

Hard corona profiles of the sensor array elements using plasma from patients with cancers at early, intermediate, and advanced stages. The composition of the protein corona that forms on the surface of sensor array elements (nanoparticles) is strongly dependent on the physicochemical properties of those nanoparticles and, at the same time, can be strongly affected by the type of disease present in the donor of the human plasma used for incubation. The size and charge of the corona-coated nanoparticles, after incubation with plasma from patients with five different types of cancers (i.e., glioblastoma multiforme, lung cancer, meningioma, multiple myeloma, and pancreatic cancer) and healthy individuals (see Table 1), were probed using dynamic light scattering (DLS/Nanosight) and transmission electron microscopy (TEM), and the results demonstrated that the physicochemical properties of the corona-coated nanoparticles depended substantially on the type of cancer (FIG. 2A,B).

TABLE 1

General information on patients (and their cancer types) whose plasma was used in this study.

| PATIENT LABEL | AGE | GENDER | CANCER STAGE | CANCER STAGE CATEGORY |
|---|---|---|---|---|
| HEALTHY 1 | 43 | F | — | — |
| HEALTHY 2 | 54 | M | — | — |
| HEALTHY 3 | 67 | F | — | — |
| HEALTHY 4 | 69 | M | — | — |
| HEALTHY 5 | 61 | F | — | — |
| PANCREAS 1 | 81 | M | TNM: cT4 N + M+ | Advanced |
| PANCREAS 2 | 76 | M | TNM: cT2 N+ | Moderate |
| PANCREAS 3 | 60 | F | TNM: cT4 N+ | Advanced |
| PANCREAS 4 | 75 | M | TNM: cT3 N + M+ | Advanced |
| PANCREAS 5 | 61 | F | TNM: cT3 N + M+ | Advanced |
| PANCREAS 6 | 71 | F | TNM: cT3 N+ | Advanced |
| PANCREAS 7 | 61 | M | TNM: cT3 N+ | Advanced |
| PANCREAS 8 | 67 | M | TNM: cT3 N+ | Advanced |
| LUNG 1 | 45 | F | TNM: TIA N0 M0 | Early |
| LUNG 2 | 24 | M | TNM: TIA N0 M0 | Early |
| LUNG 3 | 44 | F | TNM: TIA N0 M0 | Early |
| LUNG 4 | 48 | F | TNM: TIA N0 M0 | Early |
| LUNG 5 | 40 | M | TNM: TIA N0 M0 | Early |
| LUNG 6 | 47 | F | TNM: TIA N0 M0 | Early |
| LUNG 7 | 51 | M | TNM: TIA N0 M0 | Early |
| LUNG 8 | 52 | F | TNM: TIA N0 M0 | Early |
| MYELOMA 1 | 41 | F | Onset II (52% Plasma cells in Bone Marrow; Monoclonal IgG-k) | Moderate |
| MYELOMA 2 | 60 | F | Onset I (28% Plasma cells in Bone Marrow; Monoclonal IgG-k) | Early |
| MYELOMA 3 | 57 | F | Onset I (8% Plasma cells in Bone Marrow; Monoclonal IgG-k) | Early |
| MYELOMA 4 | 63 | M | Onset I (9% Plasma cells in Bone Marrow; Monoclonal IgG-k) | Early |
| MYELOMA 5 | 75 | M | Onset II (42% Plasma cells in Bone Marrow; Monoclonal IgG-k) | Moderate |
| MYELOMA 6 | 46 | F | Onset I (15% Plasma cells in Bone Marrow; Monoclonal IgG-L) | Early |
| MYELOMA 7 | 56 | F | Onset I (44% Plasma cells in Bone Marrow; Monoclonal IgG-L) | Early |
| MYELOMA 8 | 70 | F | Onset I (27% Plasma cells in Bone Marrow; Monoclonal IgG-L) | Early |
| GLIOBLASTOMA 1 | 58 | M | WHO 4 | Advanced |
| GLIOBLASTOMA 2 | 75 | M | WHO 4 | Advanced |
| GLIOBLASTOMA 3 | 76 | M | WHO 4 | Advanced |
| GLIOBLASTOMA 4 | 73 | M | WHO 4 | Advanced |
| GLIOBLASTOMA 5 | 76 | F | WHO 4 | Advanced |
| GLIOBLASTOMA 6 | 62 | M | WHO 4 | Advanced |
| GLIOBLASTOMA 7 | 48 | M | WHO 4 | Advanced |
| GLIOBLASTOMA 8 | 56 | M | WHO 4 | Advanced |
| MENINGIOMA 1 | 82 | F | WHO 2 | Moderate |
| MENINGIOMA 2 | 50 | F | WHO 2 | Moderate |
| MENINGIOMA 3 | 80 | M | WHO 2 | Moderate |
| MENINGIOMA 4 | 67 | M | WHO 2 | Moderate |
| MENINGIOMA 5 | 64 | M | WHO 2 | Moderate |
| MENINGIOMA 6 | 84 | M | WHO 2 | Early |
| MENINGIOMA 7 | 58 | F | WHO 2 | Early |
| MENINGIOMA 8 | 70 | M | WHO 2 | Early |

Quantitative evaluation of the total protein adsorbed onto the nanoparticles was performed via the BCA or NanoOrange assay, and the results showed significant differences in the amounts of adsorbed proteins after incubation in plasma from patients with various types of cancers (FIG. 2B). The quantitative evaluation of the total protein adsorbed on the surface of liposomes showed strong dependency of protein amount on cancer type (FIG. 2B). The protein corona composition at the surface of three liposomes was evaluated by liquid chromatography-mass spectrometry (LC-MS/MS) in which the abundance of 1,800 known proteins was defined. The contribution of individual proteins and their categories (i.e., complement, coagulation, tissue leakage, lipoproteins, acute phase, immunoglobulins, and other plasma proteins) to the corona composition were defined (FIG. 2C; FIG. 3A-F). These results demonstrated significant associations between the protein composition and not only the cancer type but also the type of sensor element (i.e., type of nanoparticle).

According to an extensive body of literature, there are considerable relationships between cancer development and variations in complement, coagulation, tissue leakage, lipoproteins, acute phase, and immunoglobulins. Therefore, the cross-reactive interactions of these protein categories with nanoparticles may provide unique "fingerprints" for each type of cancer, which may facilitate cancer identification and discrimination. Consequently, one would expect the protein corona sensor array to cross-reactively adsorb a wide range of proteins involved in cancer induction and development that could be used for cancer identification and discrimination.

Figure 4B:
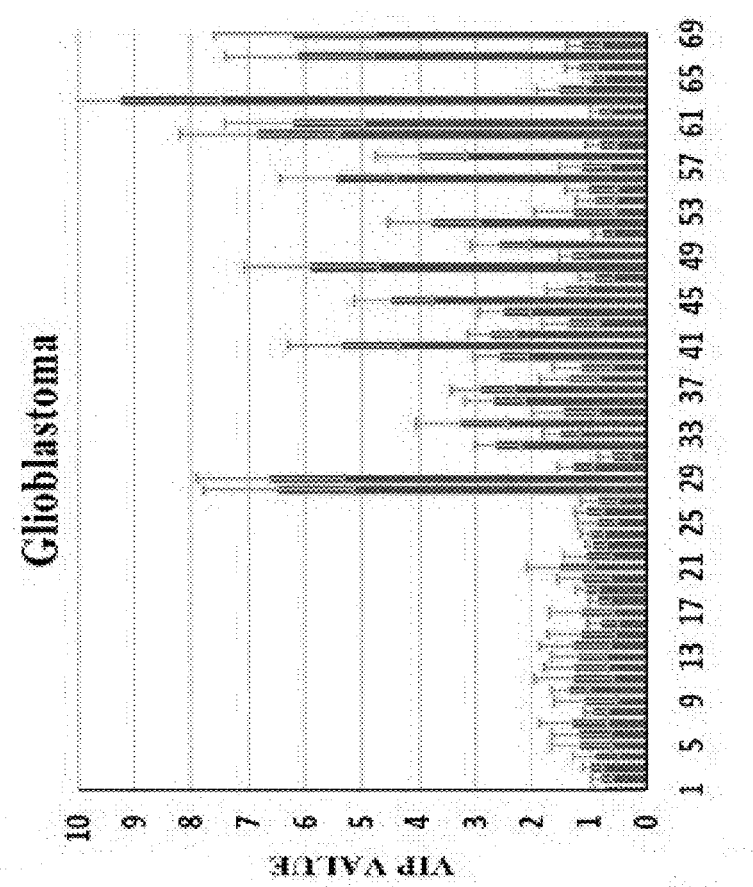
FIG. 4B depicts the results for the 69 variables for glioblastoma.
Figure 4A:
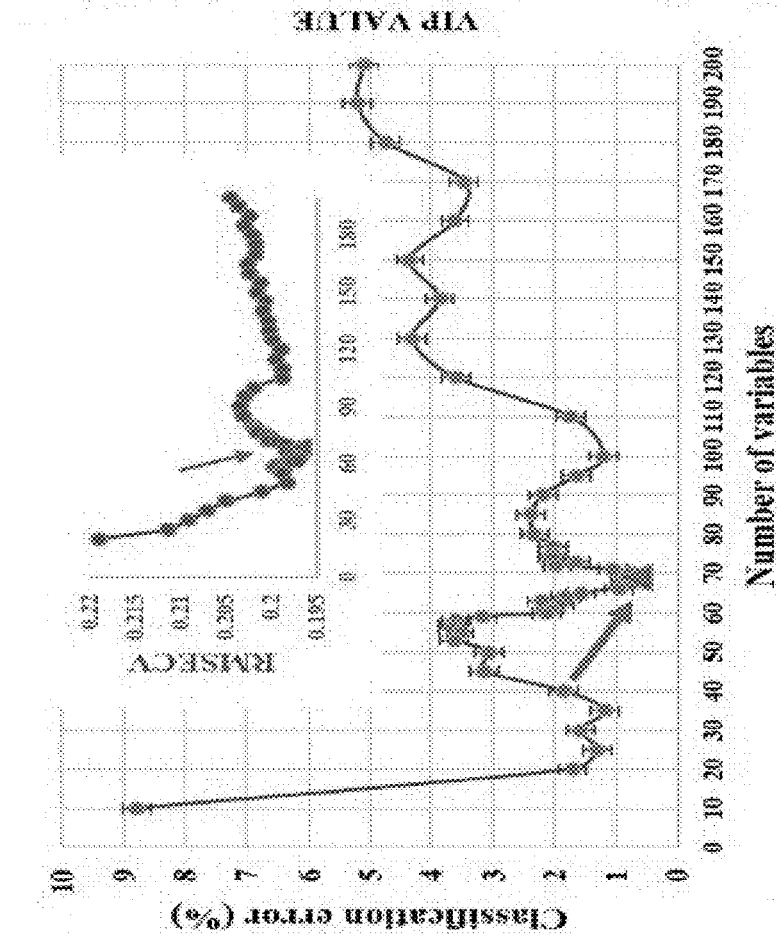
FIG. 4A. Predictor discovery and contribution from each individual predictor to separation of each class by PLS discrimination analysis. Predictor exploration by weighted VIP was performed by adding the ranked variables to the PLS-DA model one by one and calculating the classification error for internal cross-validation (10-fold). Decreasing the classification error led to the discovery of a minimal set of 69 predictors with the highest possible importance for separating each class from the others. The contribution of each individual marker to separation of each class based on the PLS discrimination analysis. VIP plot ranking markers of 69 selected variables for their contribution to separation of each class from PLS discrimination analysis. VIP score >1 indicates important protein leading to good prediction of class membership, whereas variables with VIP scores <1 indicate unimportant proteins for each class.
Figure 4C:
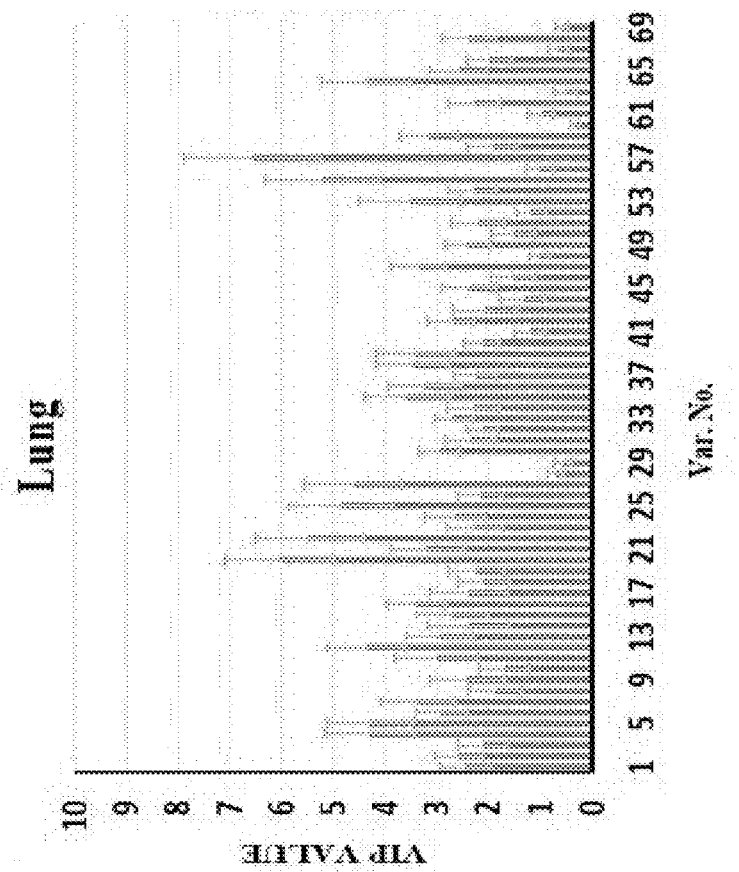
FIG. 4C. Depicts the VIP values for the 69 variables for meningioma.
Figure 4D:
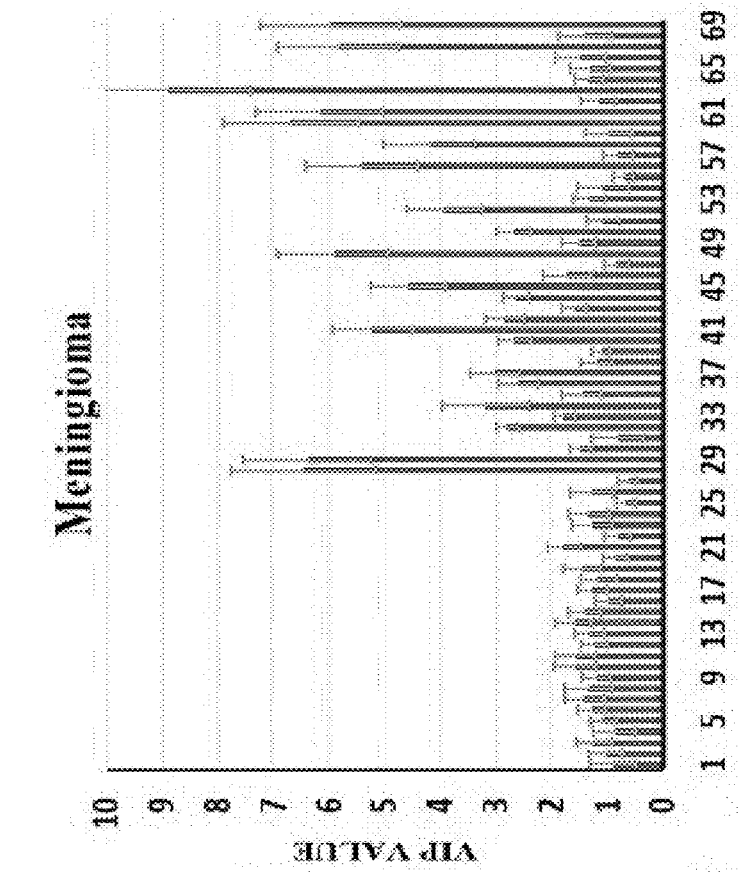
FIG. 4D. Depicts the VIP values for the 69 variables for lung cancer.
Figures 4E, 4F:
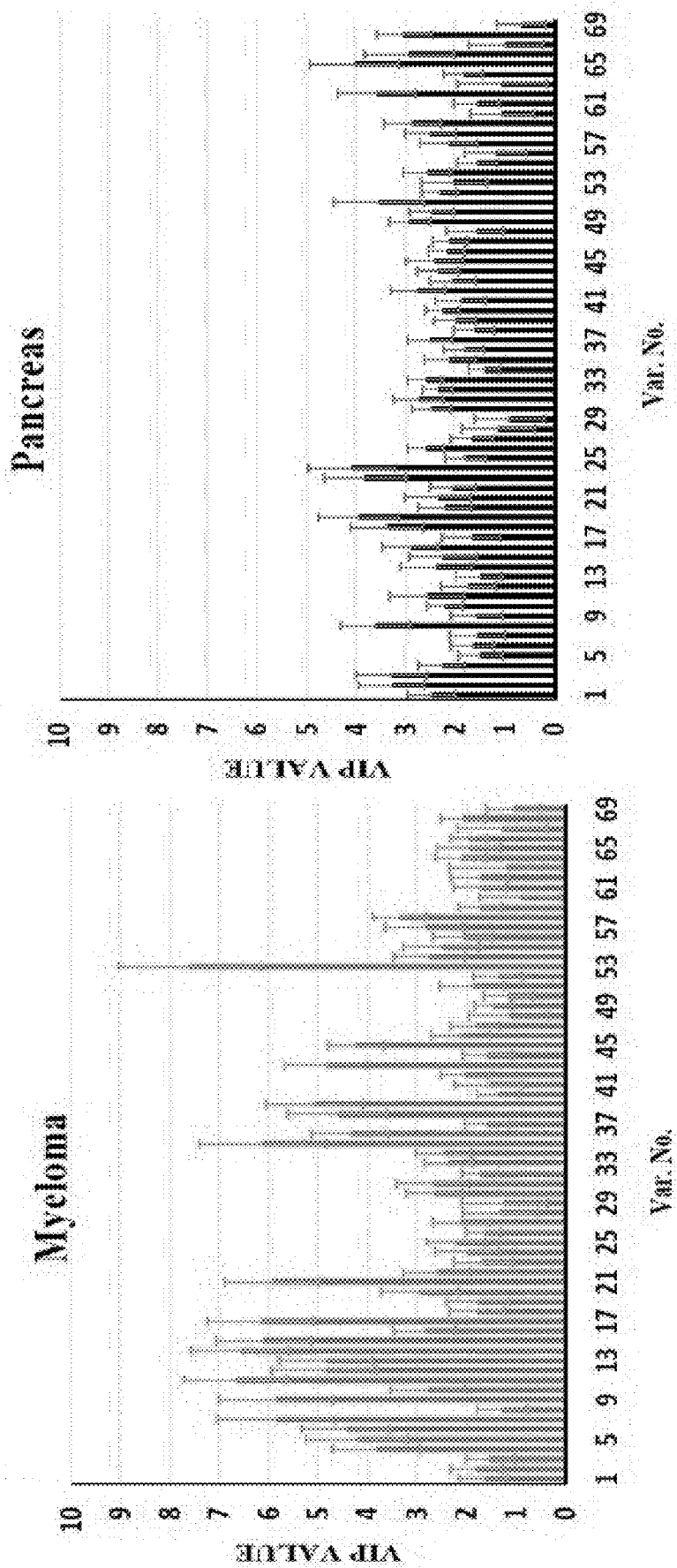
FIG. 4E. Depicts the VIP values for the 69 variables for myeloma.
FIG. 4F. Depicts the VIP Values for the 69 variables for pancreatic cancer.

Develop supervised classification analysis to identify and discriminate among cancers using the protein corona sensor array outcomes. In order to investigate whether protein corona fingerprints (PCFs) of various sensor elements could be utilized as a biosensors and form unique patterns for different diseases, we have applied focused classification approaches to proteomic data on three liposomes' protein corona composition (cationic, anionic, and neutral). Details of the methods are described in the Methods section. A weighted-variable importance in the projection (VIP) score is introduced and applied for ranking of variables based on partial least squares discriminant analysis (PLS-DA) as a linear projection method. Selection of the most relevant variables (proteins) in building the classification model can be guided by a set of obtained ranked variables. In this regard, top ranked variables were added to the model one by one, and the classification error of the PLS-DA model was monitored. We observed that the classification model has the minimum error by using only the top 69 features (FIG. 4A). The new 69-dimensional feature space was successfully used to discriminate 30 samples belonging to six classes by PLS-DA with a high classification accuracy (0.97) using leave-one-out and 10-fold cross-validation (FIG. 4A,B). The classification parameters are given in Table 2. The contribution of each single selected protein to the separation of each cancer group (VIP) is plotted on the y- and x-axis, respectively, to provide a visual representation of the relative specificity of the findings (FIG. 4B-F). The proteins with higher VIP scores could be considered the best informative or diagnostic set to discriminate each disease from controls and from among all cancer categories.

TABLE 2

Classification results obtained from two developed and non-linear models for six groups of samples.

| Models/ classification parameters | | PLS-DA, 10 fold CV, LV = 5 20 iteration | CPANN (8*8) 10 fold CV |
|---|---|---|---|
| Specificity (CV) | 1 | 1.00 | 1.00 |
| | 2 | 0.96 | 0.96 |
| | 3 | 1.00 | 1.00 |
| | 4 | 1.00 | 1.00 |
| | 5 | 1.00 | 1.00 |
| | 6 | 1.00 | 1.00 |
| Sensitivity (CV) | 1 | 1.00 | 1.00 |
| | 2 | 1.00 | 1.00 |
| | 3 | 1.00 | 0.80 |
| | 4 | 1.00 | 1.00 |
| | 5 | 1.00 | 1.00 |
| | 6 | 1.00 | 1.00 |
| Class error (CV) | 1 | 0.00 | 0.00 |
| | 2 | 0.03 | 0.02 |
| | 3 | 0.00 | 0.00 |
| | 4 | 0.00 | 0.00 |
| | 5 | 0.00 | 0.00 |
| | 6 | 0.00 | 0.00 |

1) Control
2) Glioblastoma
3) Meningioma
4) Myeloma
5) Pancreas
6) Lung cancers

PLS-DA and counter propagation artificial neural network (CPANN) were then applied to the selected variables, and whole samples as supervised classification, linear, and non-linear approaches, respectively. It should be noted that the primary data set with all variables before variable selection, has poor discrimination and could not be separated into six groups.

Figure 5A:
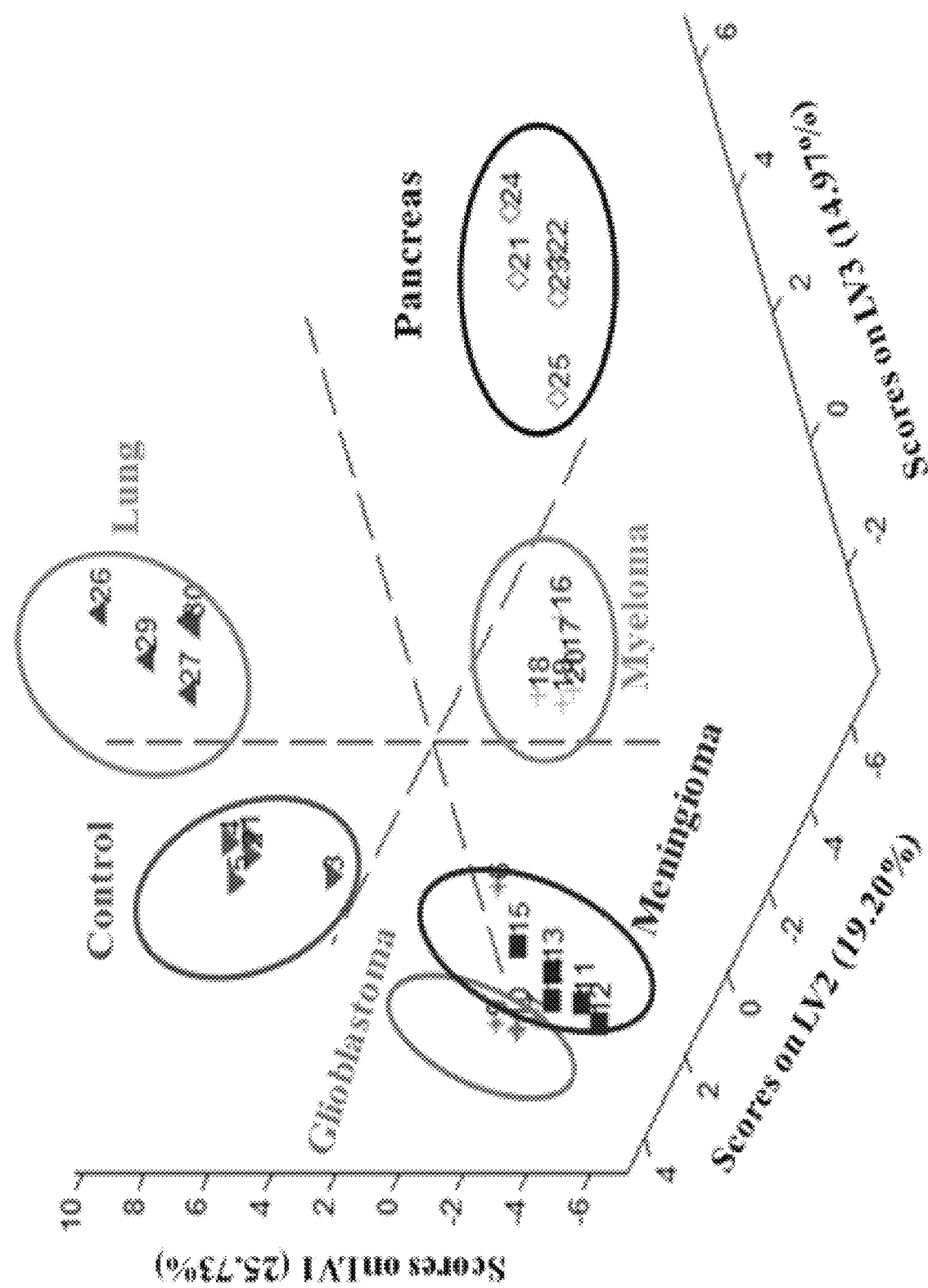
FIG. 5A. PLS-DA plot showing the separation of different cancerous samples from each other and from controls. PLS score-plot obtained using PLS-toolbox, projecting the objects into the subspace created by the 1st, 2nd, and 3rd latent variables of the model.
Figure 5B:
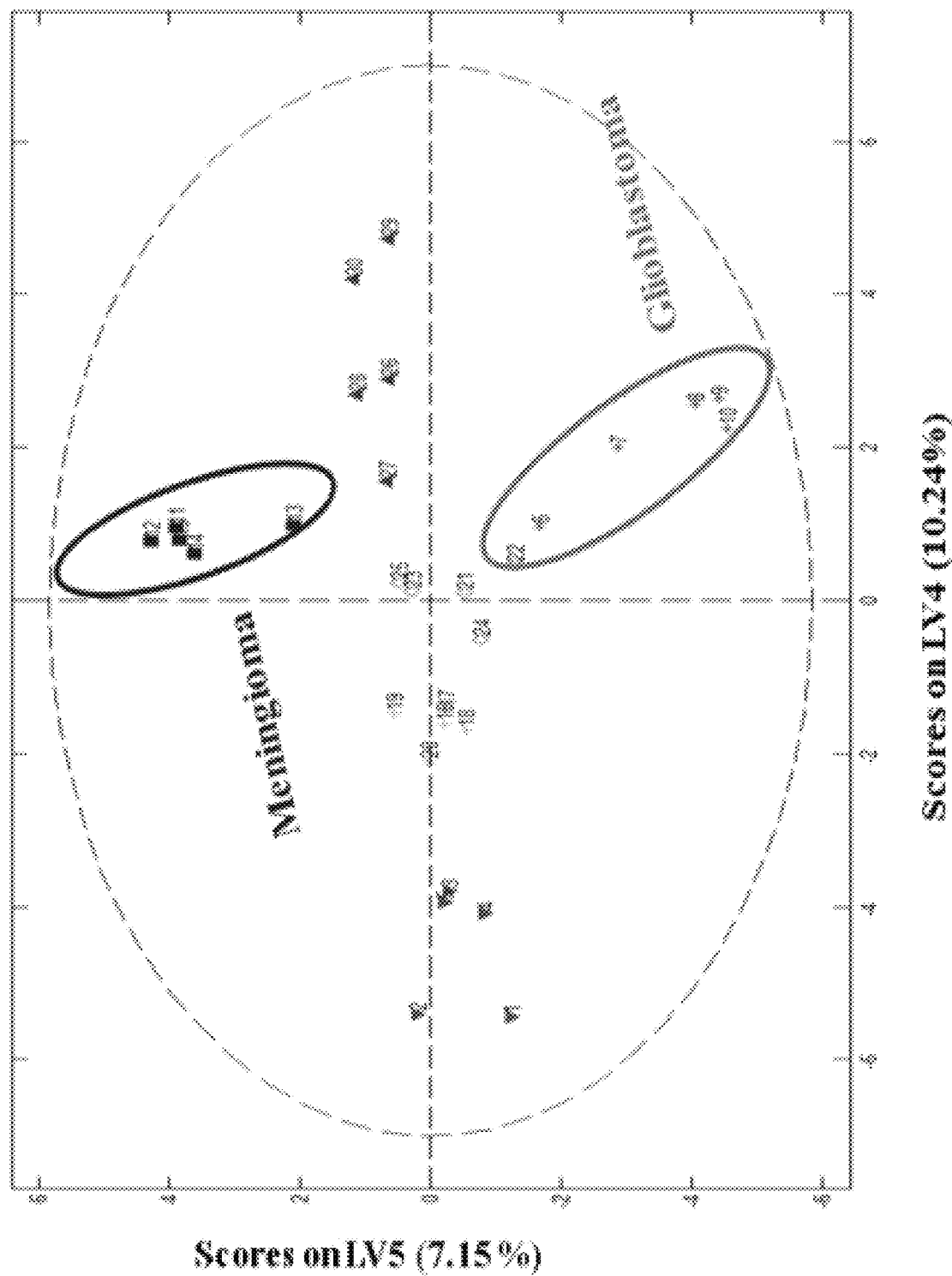
FIG. 5B. PLS-DA plot showing the separation of different cancerous samples from each other and from controls. Objects displayed where the 4th and 5th latent variables of the model are shown. As can be seen, meningioma and glioblastoma cases were not separated in three dimensions appropriately, but they can be separated in the fourth and fifth dimensions of the PLS model.
Figures 5C, 5D:
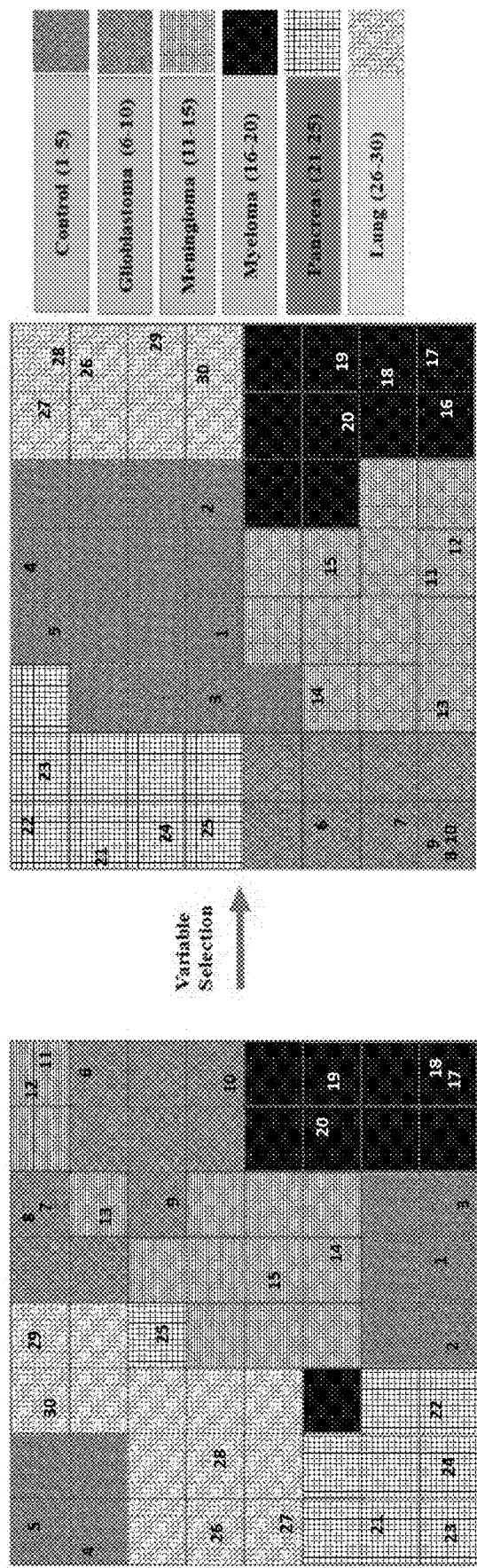
FIG. 5C. Assignation map obtained by CPANN with all variables and selected variables. The assignation map obtained by training of a CPANN network (8×8 neurons) using whole data set (1823 variables). The mapping quality is not good and there are conflicts of different types of cancer in term of mapping.
FIG. 5D. Assignation map attained by training of a CPANN network (8×8 neurons) using 69 variables. High dimensional input vectors (samples) are mapped on a two-dimensional network of neurons, preserving similarity and topology. Colors indicate the similarity of a neuron to a specific type of input vector (class type). This map also demonstrates the importance of the predictor selection step and the effect of deletion of non-informative and irrelevant predictors on the model quality.
Figure 9A:
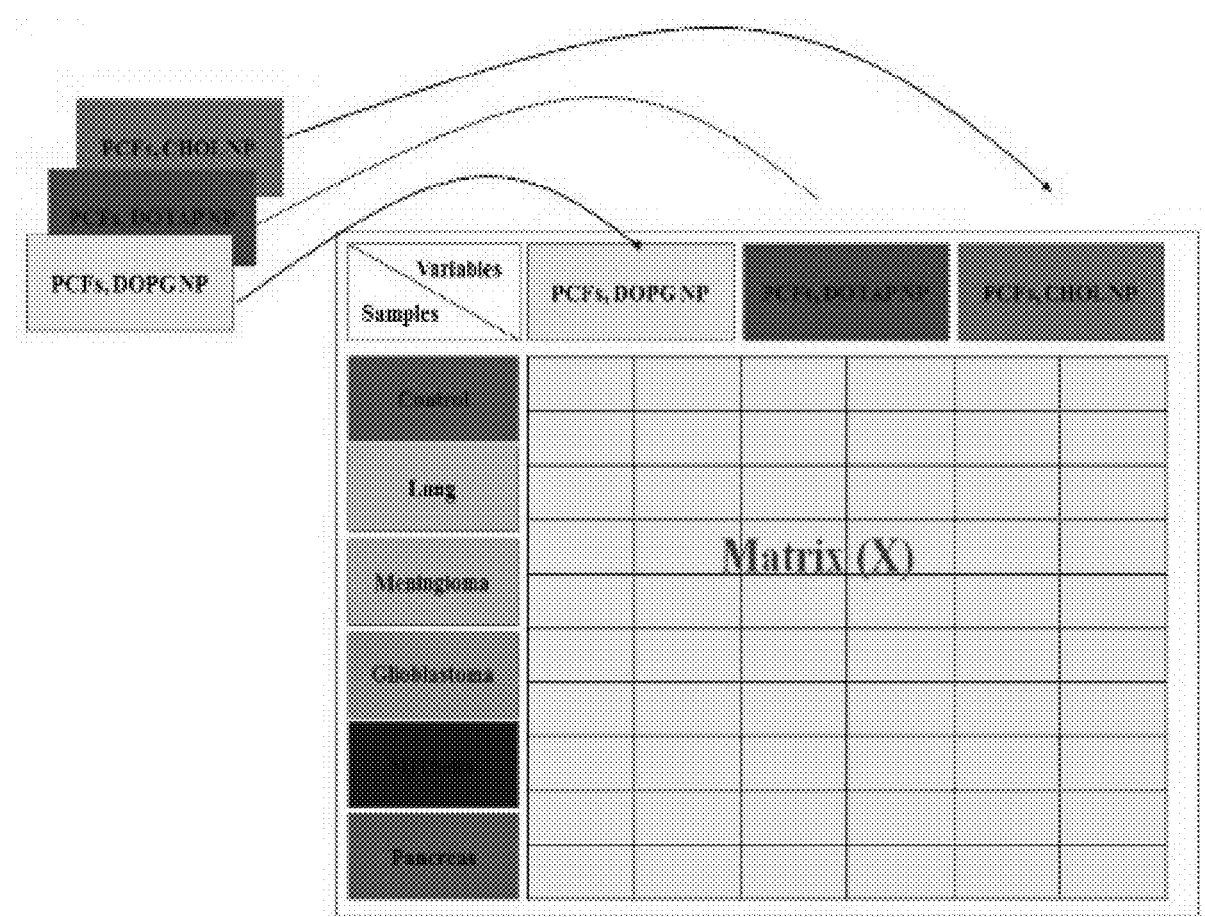
FIG. 9A. Schematic representation of unfolding a three-way data matrix into a two-way matrix.
Figure 9B:
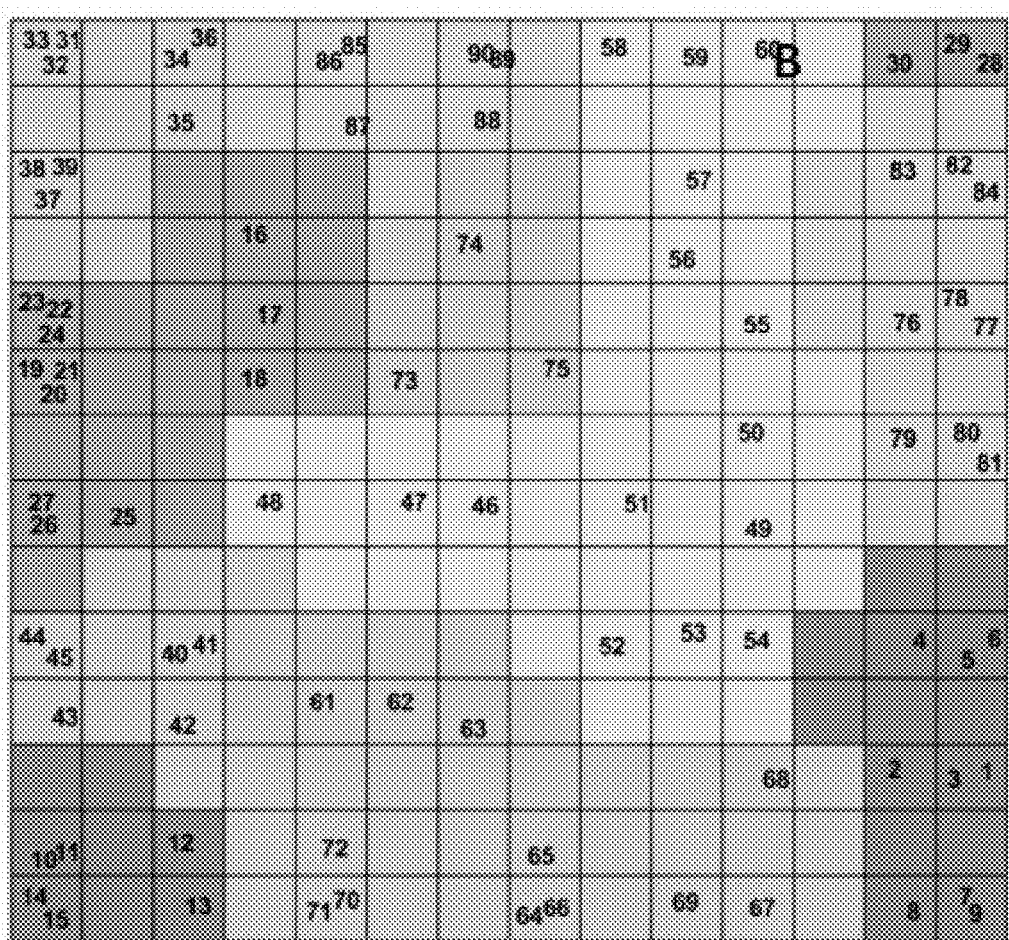
FIG. 9B. Assignation map obtained by CPANN (14×14) trained using 90 samples (replicates) with all 1823 variables. Sample numbers are indicated on each neuron. The neuron color (assigned label) is decided based on the similarity between the class label (a 6×1 binary vector) and the weight vector in the output layer of the corresponding neuron. Despite using all biomarkers, there are some distinct similarities between samples of the same cancer class. Replicated samples are also mapped on adjacent or the same neurons FIG. 9C. Classification error of CPANN map was calculated at different map size using 10-fold cross validation.
Figure 9C:
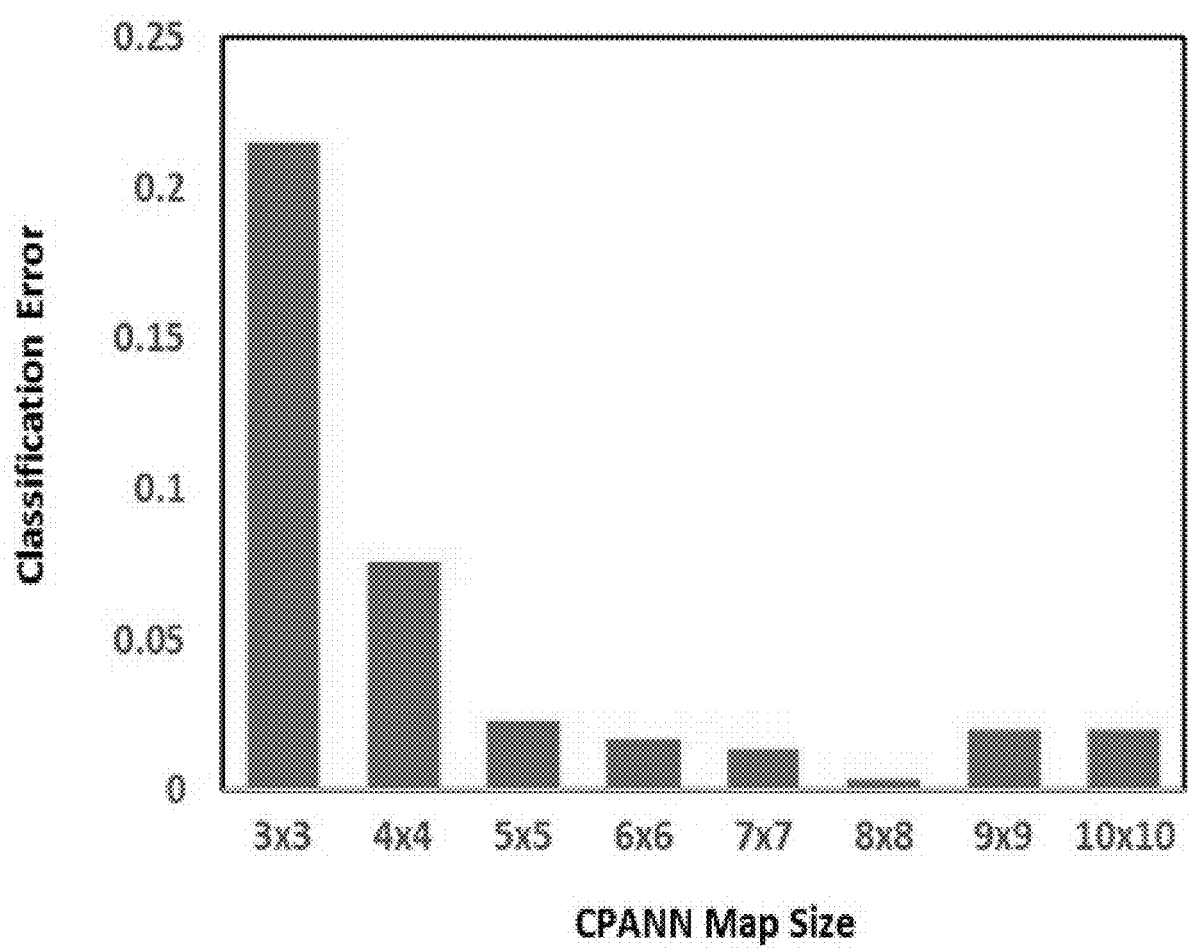
FIG. 9D. The CPANN network has 69 weight layers, which is equal to the number of variables used to train the model. The $i^{th}$ weight layer reflects the effect of the $i^{th}$ variable (biomarker) on the pattern of the assignation map.
FIG. 9E The correlation of the assignation map and 69 weight layers (weight maps) can be calculated and could help identify the biomarkers related to each cancer class. It can also be visually decided; similarity can be monitored by absolute value of Correlation Coefficient of two maps.
FIG. 9F. The correlation of the assignation map and 69 weight layers (weight maps) can be calculated and could help identify the biomarkers related to each cancer class. It can also be visually decided; similarity can be monitored by absolute value of Correlation Coefficient of two maps.
Figure 9D:
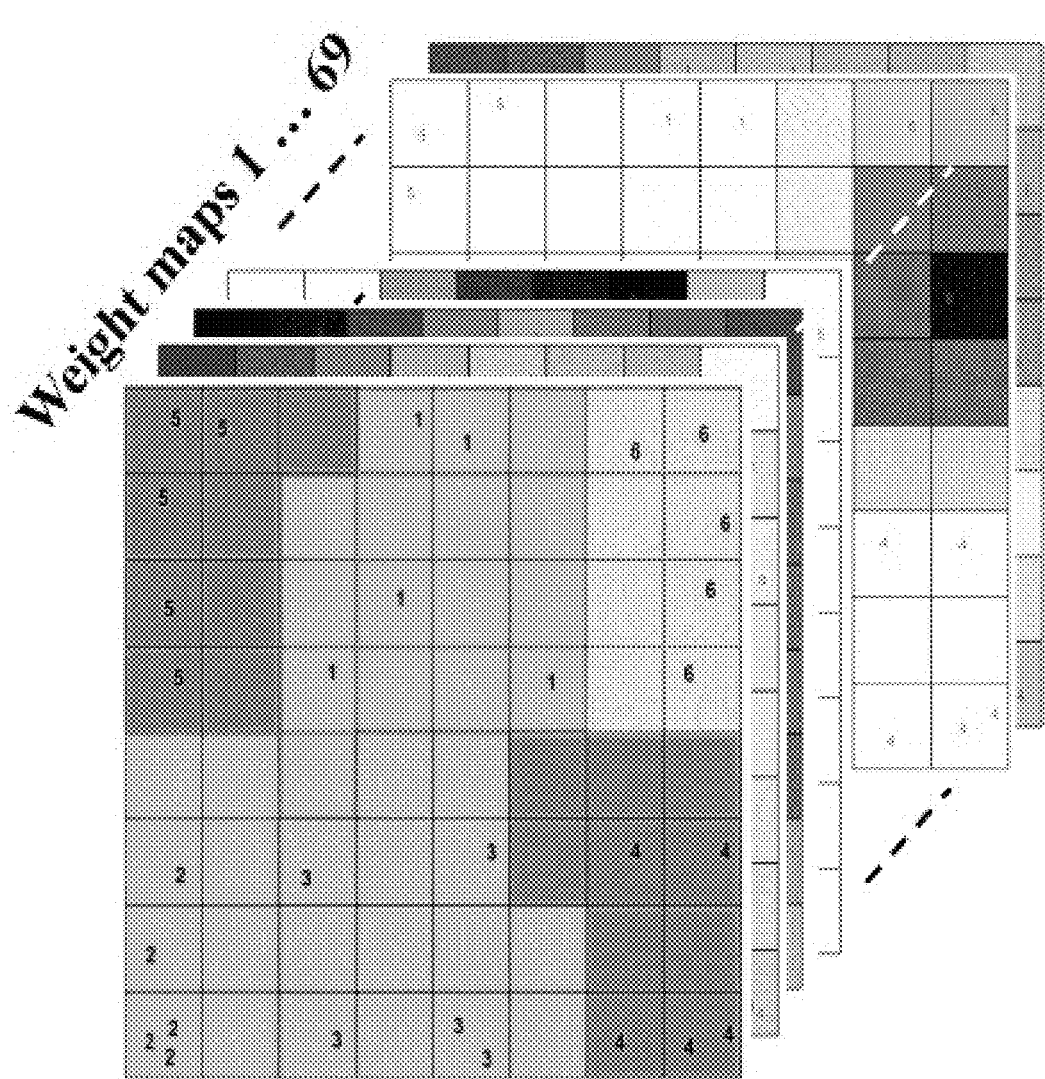
Figure 9F:
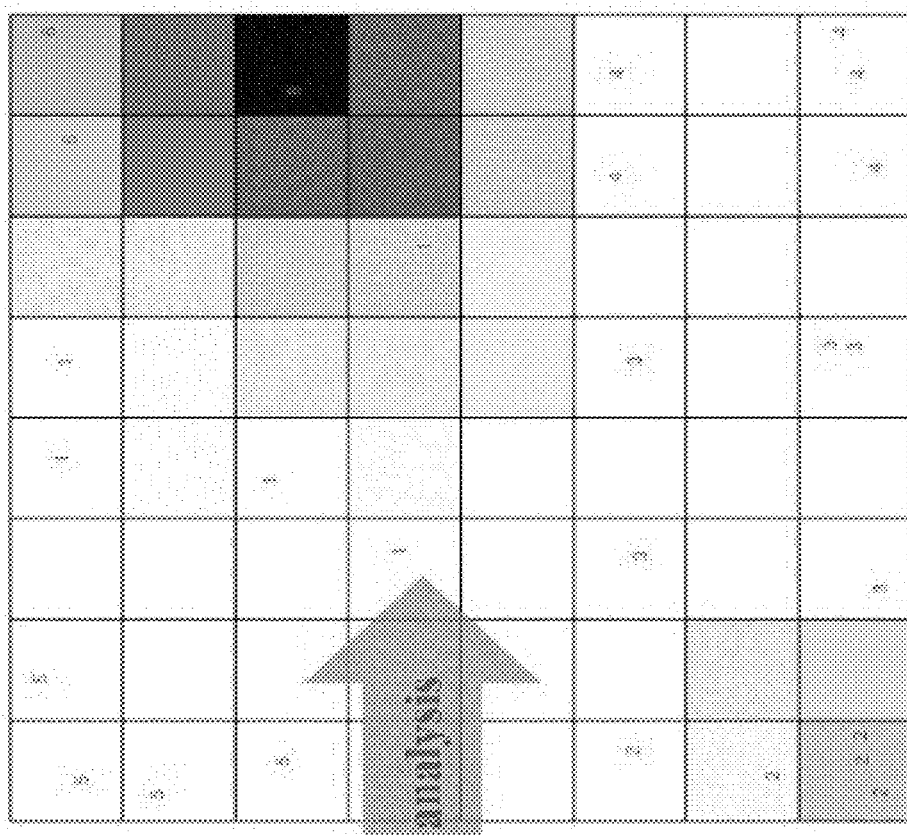
Figure 9E:
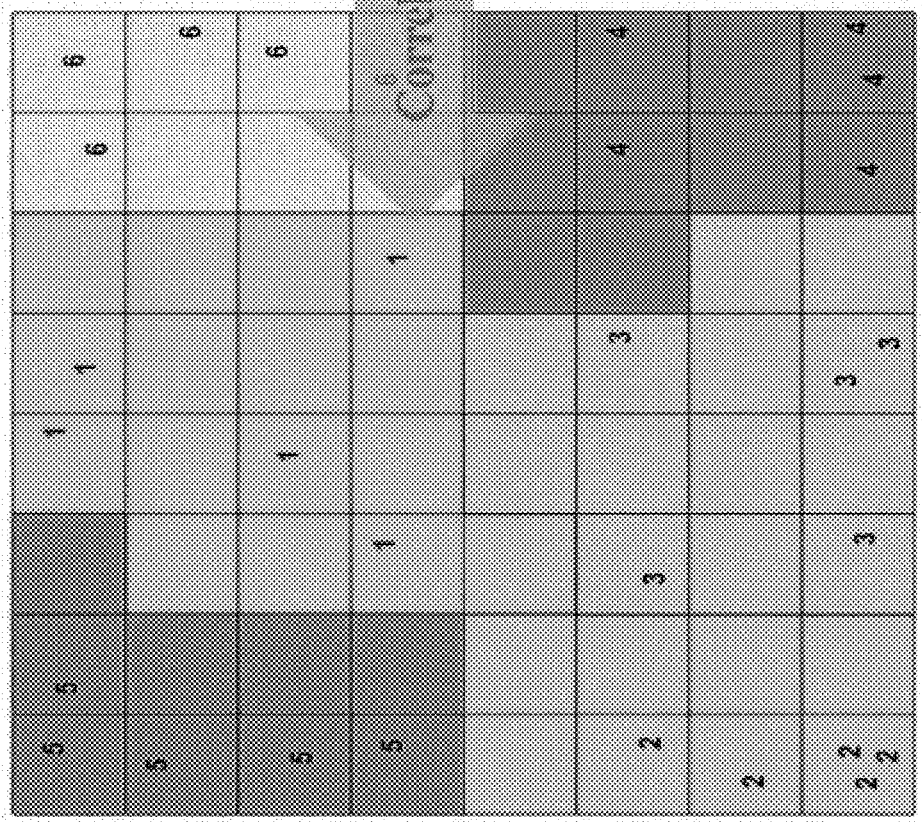

Next, to further verify and analyze the data, we decided to take advantage of a non-linear classification method. Visualizing the feature space can help us understand the hidden structures and topological relationships among the patterns. To reduce the dimensionality of the feature space while preserving the topological relation in the data structure, the CPANN (a supervised variant of self-organizing maps/ SOM) was used to learn and predict the class membership of the patterns, simultaneously producing a two-dimensional map of neurons and provide valuable information (from a non-linear approach) about the data structure. Details of the CPANN are provided in the Methods section. Different sizes for the CPANN map were checked using 10-fold cross-validation; a map including 64 (8×8) neurons was chosen due to the minimum classification error (FIG. 9C). Moreover, the topological structure of data in the high-dimensional space is reflected in the assignation map produced by CPANN (FIG. 5C,D). Considering the similarity of the neurons to the input vectors, the map can be partitioned into six distinct zones related to different type of cancers and control samples. Samples with the same class label are mapped onto nearby or the same neurons, which means that the selected variables provide information valuable in discriminating the samples in the feature space. The relative position and orientation of six zones on the map can contribute qualitative information on the similarities between types of cancers. To represent the effect of variable selection on the quality of mapping, another CPANN was trained with all 1823 variables, and the resulting map shows that the selected biomarkers (variables) play an important role in discriminating among cancer types and classifying them properly (FIG. 5C,D).

Figure 5E:
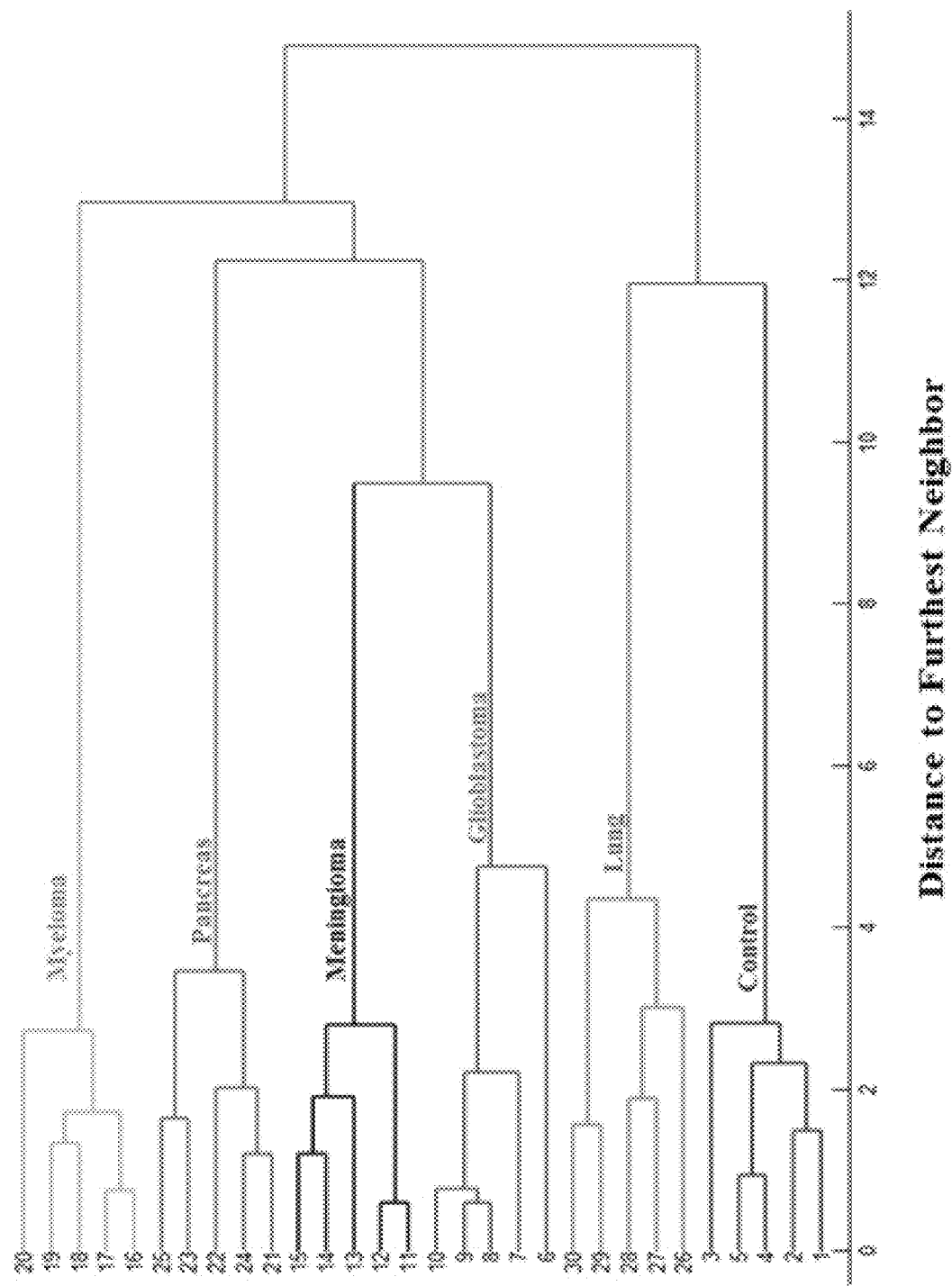
FIG. 5E. Dendrogram depicting the 51 proteins identified as capable of distinguishing among the six groups of cancer.
Figure 5F:
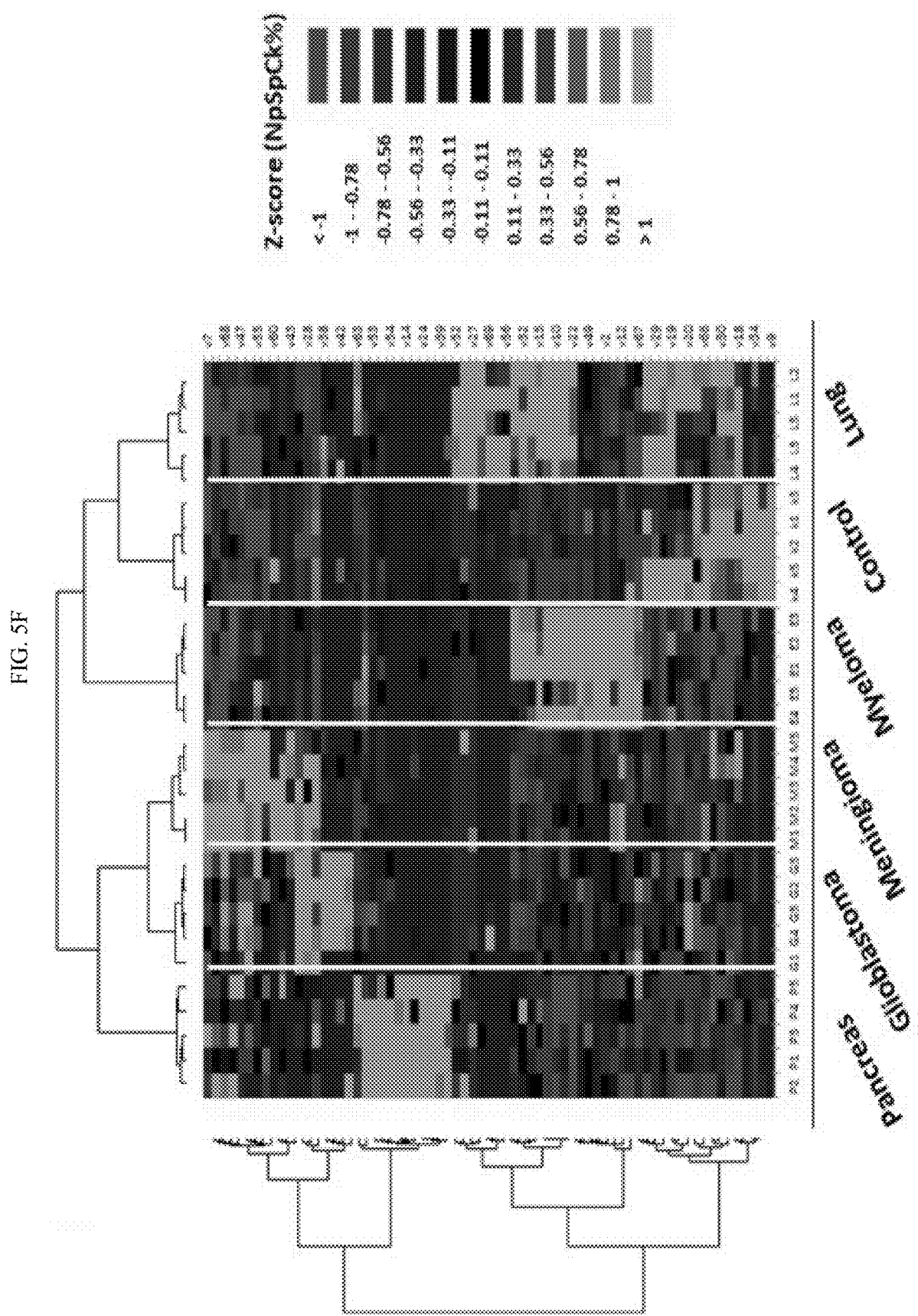
FIG. 5F. The 51 proteins identified as capable of distinguishing among the six groups are presented in a 'Heat Map' generated with an unsupervised cluster algorithm (Agglomerative HCA with furthest neighbor linkage). Visual inspection of both the dendrogram (FIG. 5E) and heat map (FIG. 5F) demonstrates cancer-specific protein corona signature and clear clustering of six groups of samples (five groups of cancerous samples plus normal samples) and also expected similarities among five patients from each group. The heat map also indicates substantial differences in the patterns of variables (markers) of different cancers (each column represents a patient, and each row represents a protein). Higher and lower protein levels are indicated in red and green, respectively.

On the basis of the obtained results, both linear and non-linear models showed high accuracy, deduced from their acceptable specificity, sensitivity, and class error values. Consistent with these findings, unsupervised clustering (HCA) based on 69 markers was able to strongly separate, various type of cancerous and control samples (FIG. 5E-F). As can be seen in FIG. 5, there is close similarity between the glioblastoma and meningioma groups of samples, implying difficulty in discrimination, most probably related to similar plasma proteomics patterns in these two brain cancers. These results reflect the fact that the plasma concentrations of many proteins in the corona differ considerably, not only among subjects with different types of cancers, but among healthy individuals as well.

To illustrate the biosensors' capability for pattern recognition, a set of analyses was performed on the data obtained from individual nanoparticles. As expected, the pattern of cancer-specific fingerprints could not be extracted solely from each nanoparticle's PCF. We found that pattern-recognition techniques applied to protein abundance in the protein corona formed on three different liposomes (cationic, anionic, and neutral) correctly distinguished not only cancerous from control samples, but also each type of cancer under consideration from the others.

Identification of proteins with crucial roles in cancer detection and discrimination as promising biomarkers for specific types of cancers. The use of biomarkers both before cancer diagnosis (in risk assessment and screening/early detection) and after diagnosis (in monitoring therapy, selecting additional therapy, and detecting recurrence) would yield substantial therapeutic and health-economic benefits. To understand the potential biological relevance of the 69 selected proteins that discriminate cancerous samples, we manually searched through previously published reports in PubMed on protein biomarkers of specific types of cancers that are upregulated or downregulated according to different disease stages. The resulting data were compared with the selected proteins in the model to identify matched markers and determine the biological relevance of the proposed model. Interestingly, we noted significant numbers of biomarkers specific to five investigated groups of cancers among the selected predictors that had been reported as specific cancer biomarkers (FIG. 7B).

The high specificity of the selected markers for discriminating among the five groups of cancers, which derives from the introduced protein corona sensor array approach, demonstrates a significant correlation with the work now under way in the complex cancer proteomics space; therefore this strategy not only provides a basis for cancer prediction but also translates that promise into reality. It is noteworthy that the discrimination between different groups occurs as a result of several predictors (and not individual biomarkers) that change simultaneously in a systematic manner, forming patterns unique to each specific type of cancer. On the basis of this evidence, the most informative predictors selected by the proposed model that have not already been reported as cancer-specific biomarkers may have great potential as new diagnosis biomarker candidates. To define their role in cancer development, the variation and functionality of these promising candidates in cancer patients should be carefully monitored. By focusing on the unique patterns derived from huge numbers of subjects via a set of informative predictors, researchers should be able to predict cancers at different stages more accurately than is possible using current methods.

Cohort data analysis. To probe the capacity of this innovative sensor array for very early detection of cancers, we used cohort plasma from healthy people who were diagnosed with one of the five types of cancers several years after plasma collection. Using the cohort samples, we evaluated whether our proposed models, both linear and non-linear, with 69 selected predictors could be utilized for cancer prediction.

Figure 6A:
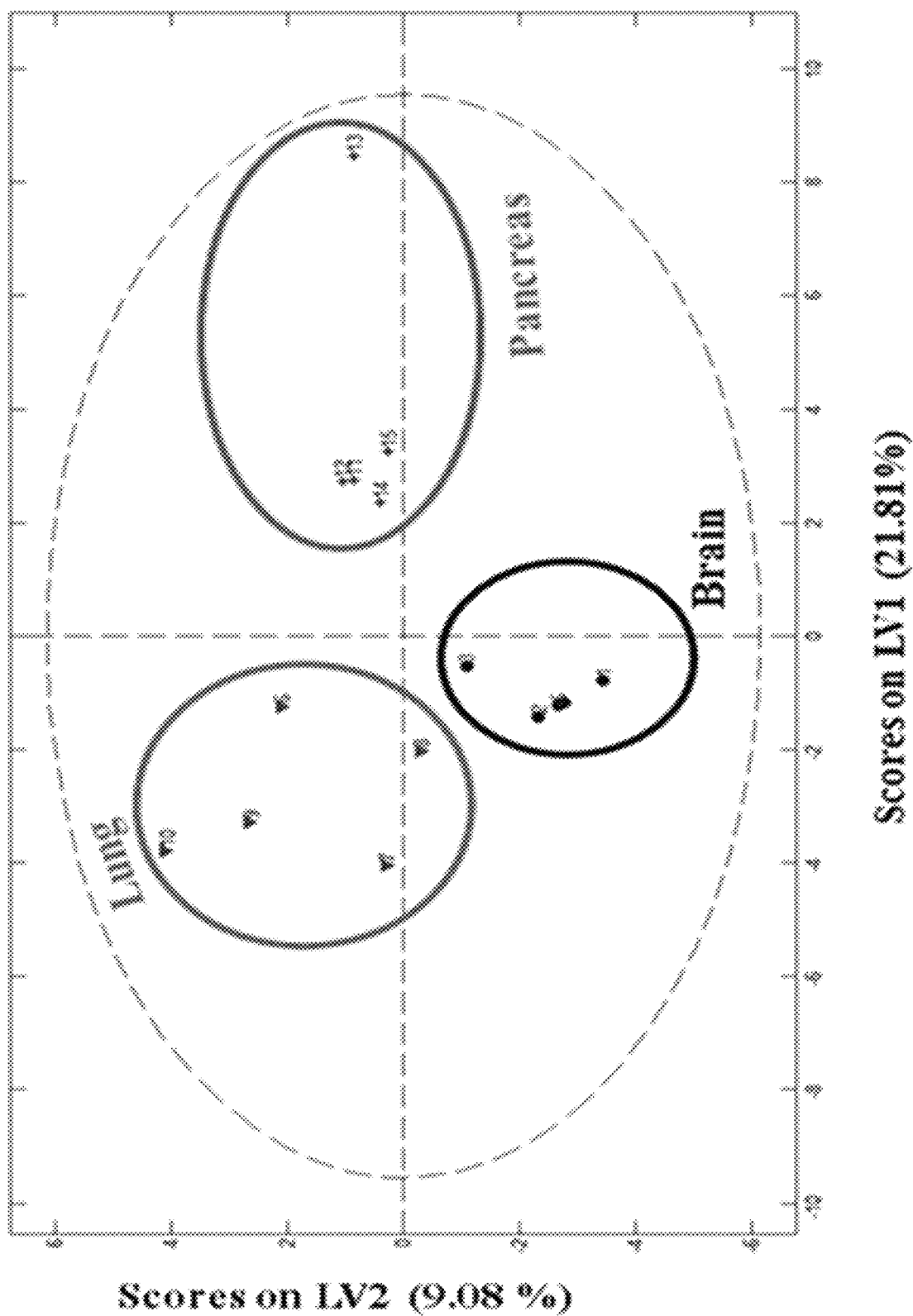
FIG. 6A. PLS score-plot obtained by considering 69 important markers, projecting the cohort objects into the subspace created by the 1st and 2nd latent variables of the model.
Figure 6B:
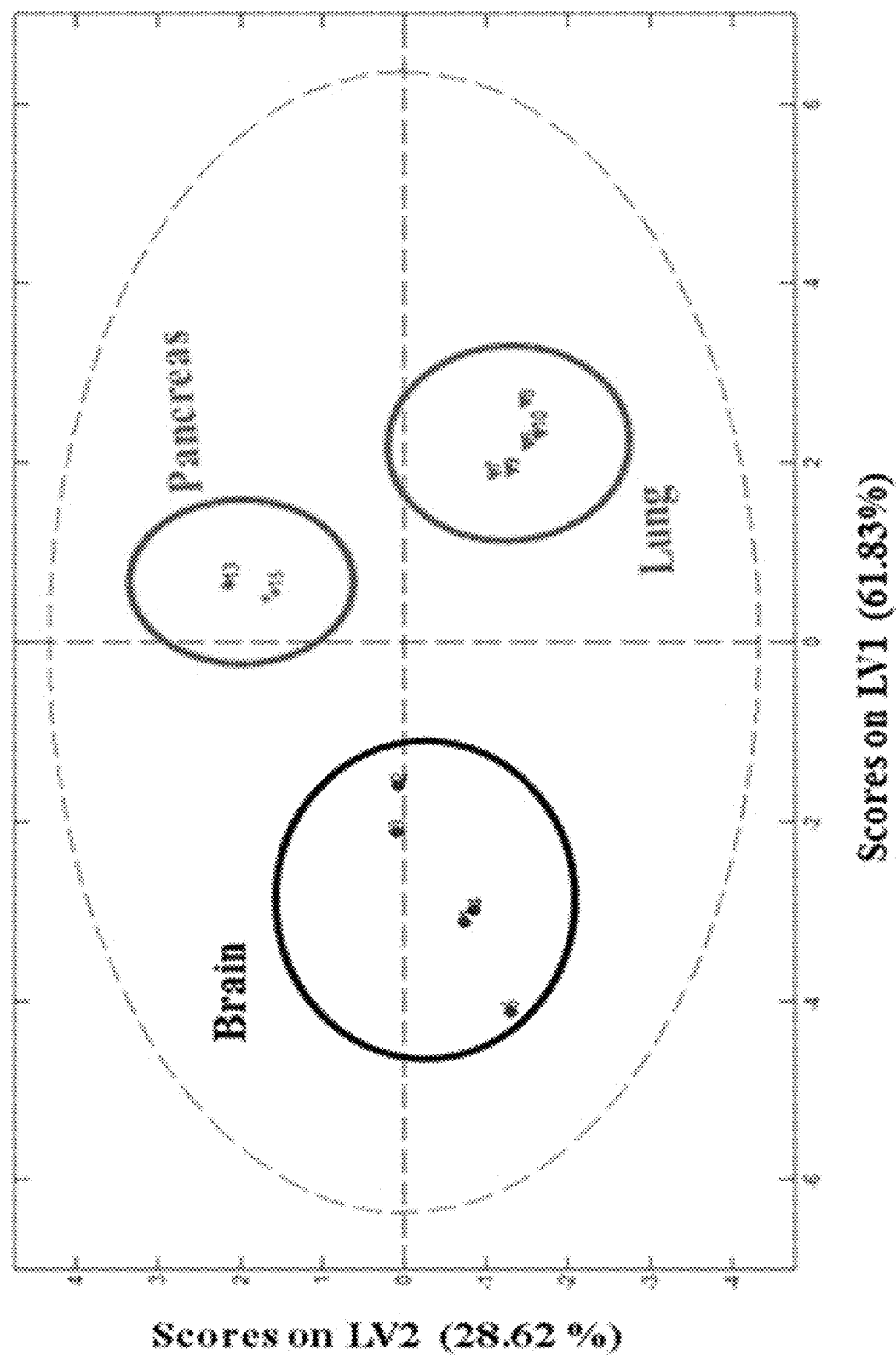
FIG. 6B. PLS-DA Model is generated using 8 variables projecting the cohort objects into the subspace created by the 1st and 2nd latent variables of the model, with excellent statistics.
Figure 6D:
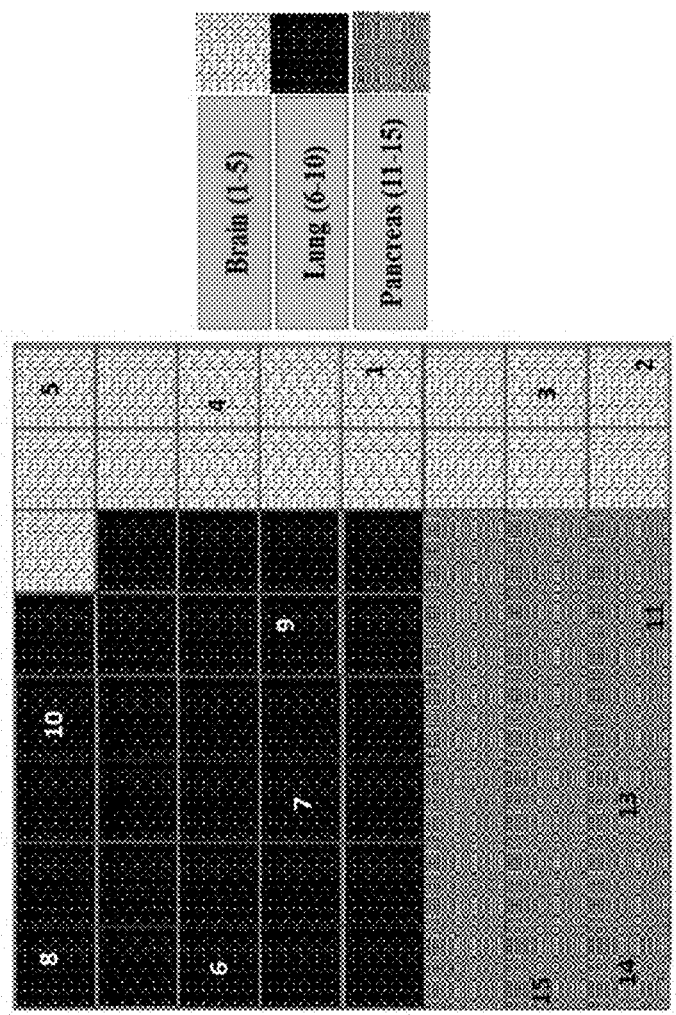
FIG. 6D. The assignation map obtained by training of a CPANN network (8×8 neurons) using only 8 markers without any misclassifications. Sample numbers are indicated on each neuron.
Figure 6C:
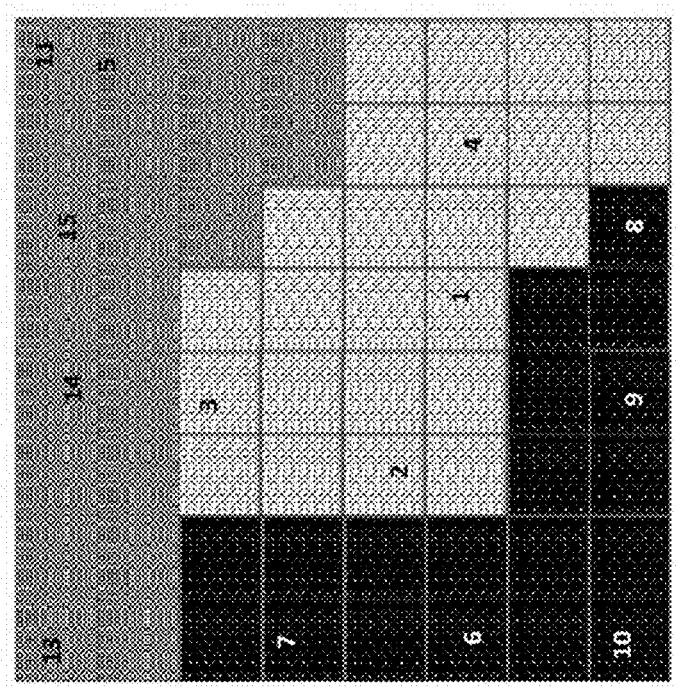
FIG. 6C. The assignation map obtained by training of a CPANN network (8×8 neurons) using 69 important markers.
Figure 8A:
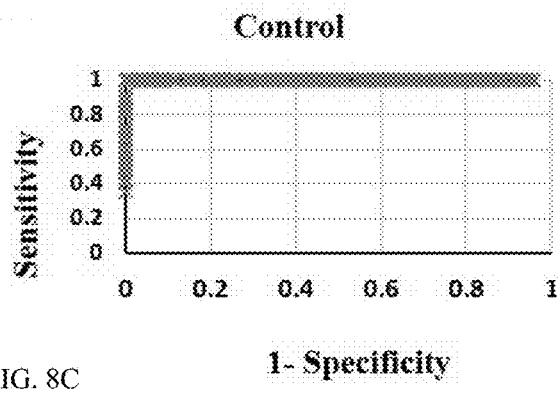
FIG. 8A. Receiver operating characteristic (ROC) plot derived from PLS-DA based on the top 69 ranked variables for control. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).
Figure 8B:
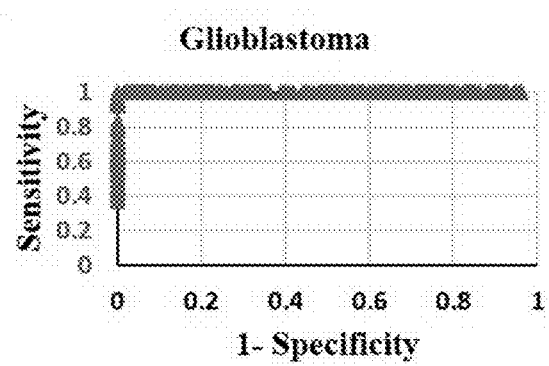
FIG. 8B. Receiver operating characteristic (ROC) plot derived from PLS-DA based on the top 69 ranked variables for glioblastoma. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).
Figure 8C:
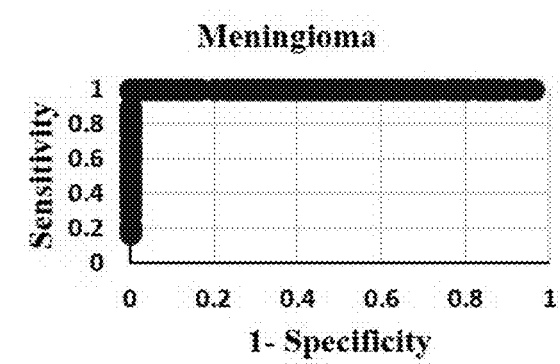
FIG. 8C. Receiver operating characteristic (ROC) plot derived from PLS-DA based on the top 69 ranked variables for meningioma. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).
Figure 8D:
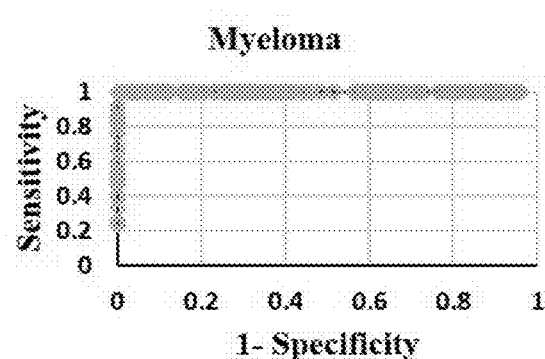
FIG. 8D. Receiver operating characteristic (ROC) plot derived from PLS-DA based on the top 69 ranked variables for myeloma. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).
Figure 8E:
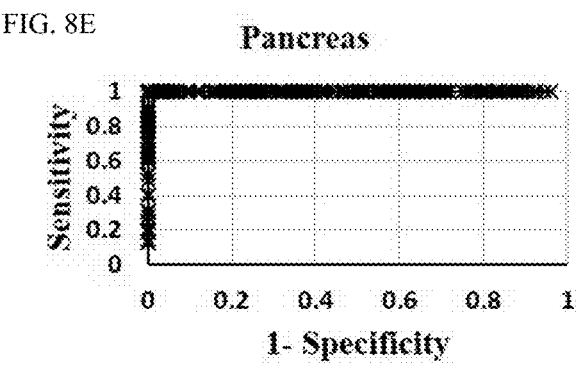
FIG. 8E. Receiver operating characteristic (ROC) plot derived from PLS-DA based on the top 69 ranked variables for pancreas. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).
Figure 8F:
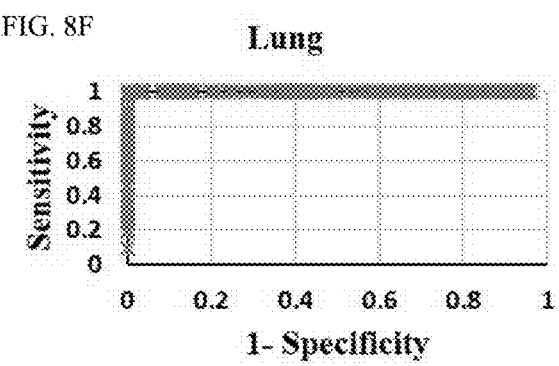
FIG. 8F. Receiver operating characteristic (ROC) plot derived from PLS-DA based on the top 69 ranked variables for lung. ROC plot of sensitivity (True Positive Rate, Y-axis) versus 1—specificity (False Positive Rate, X-axis) based on a PLS-DA built upon the 69 markers with the highest contribution for six classes (control, glioblastoma, meningioma, myeloma, pancreas, lung).

To this end, the values related to 69 variables were put into the model, and the class membership of each cohort object was predicted given the fixed optimum parameters values. It is noteworthy that 19 variables (proteins), out of the 69 variables, were absence in the proteomics profile of protein corona sensor array of cohort samples; therefore their amount in the validation data matrix was zero. Interestingly, both linear and non-linear models provided good predictions for all five samples. The observed distance between training and cohort samples (FIG. 6A,B), most probably influenced by zero values that were added to data matrix for those 19 absent variables. As shown in FIG. 6C, D, the cohort samples were placed in the correct neuron related to Glioblastoma in the CPANN map. METHODS Liposomes. Cholesterol (Chol) was purchased from Sigma Aldrich (St. Louis, Mo., USA). DOPC (dioleoylphosphatidylcholine), DOPE (dioleoylphosphatidylethanolamine), DOPG (1,2-dioleoyl-sn-glycero-3-phospho-(1'-rac-glycerol)), and DOTAP (1,2-Dioleoyl-3-trimethylammonium-propane) were purchased from Avanti Polar Lipids (Alabaster, Ala., USA). DOPG, DOTAP-DOPE (1:1 molar ratio) and DOPC-Chol (1:1 molar ratio) liposomes were prepared by dissolving appropriate amounts of lipids 9:1 (v/v) in chloroform:methanol. The chloroform:methanol mixture was evaporated by rotary-evaporation. Lipid films were kept under vacuum overnight and hydrated with phosphate saline buffer (PBS) 10 mmol/l (pH 7.4) to a final lipid concentration of 1 mg/ml. The liposome suspensions obtained were sized by extrusion through a 50-nm polycarbonate carbonate filter by the Avanti Mini-Extruder (Avanti Polar Lipids, Alabaster, Ala.).

Human plasma collection, preparation, and storage. Human plasma (HP) was collected from healthy and cancer patients diagnosed with glioblastoma multiforme, lung cancer, meningioma, multiple myeloma, or pancreatic cancer. The present study was approved by the Ethical Committees of the Sapienza University of Rome (glioblastoma multiforme, meningioma, multiple myeloma), the University of Napoli Federico II (lung cancer), and the University Campus Bio-Medico di Roma (pancreatic cancer). In brief, blood was collected by venipuncture of healthy subjects and cancer patients by means of a BD P100 Blood Collection System (Franklin Lakes, N.J., USA) with push-button technology that reduces blood waste while minimizing the risk of contamination. After clot formation, samples were centrifuged at 1000×g for 5 min to pellet the blood cells, and the supernatant was removed. After confirming the absence of hemolysis, plasma collected from each donor (1 ml) was split into 200-microliter aliquots and stored at −80° C. in labeled Protein LoBind tubes until use. For analysis, the aliquots were thawed at 4° C. and then allowed to warm at room temperature (RT).

Cohort plasma samples. We used human plasma from healthy people diagnosed with brain, lung, and pancreatic cancers within eight years after plasma collection. The plasma samples were collected through the NIH-funded Golestan Cohort Study, performed by the National Cancer Institute (NCI) in the USA, the International Agency for Research on Cancer (IARC) in France, and the Tehran University of Medical Sciences (TUMS) in Iran. This study involved the collection and storage of plasma from 50,000 healthy subjects, over 1,000 of whom went on to develop various types of cancers in subsequent years. Samples from five individuals per cancer were used in this study. These important plasma samples provide us the unique opportunity to probe the capacity of our innovative protein corona sensor array for early detection of cancers.

Size and zeta-potential. Bare liposomes were incubated with HP (1:1 v/v) for 1 hour at 37° C. Subsequently samples were centrifuged at 14000 rpm for 15 minutes at 4° C. to pellet liposome-HP complexes. The resulting pellet was washed three times with phosphate-buffered saline (PBS) and resuspended in ultrapure water. For size and zeta-potential measurements, 10 µL of each sample were diluted with 990 µL of distillated water. All size and zeta-potential measurements were performed at RT using a Zetasizer Nano ZS90 (Malvern, U.K.) equipped with a 5-mW HeNe laser (wavelength $\lambda$=632.8 µm) and a digital logarithmic correlator. The normalized intensity autocorrelation functions were analyzed by the CONTIN method to obtain the distribution of the diffusion coefficient D of the particles. D is converted into an effective hydro-dynamic radius $R_H$ by the Stokes-Einstein equation ($R_H$=$K_B$T/6$\pi\eta$1D), where $K_B$T is the thermal energy and $\eta$ is the solvent viscosity. Electrophoretic mobility of samples, u, was measured by laser Doppler electrophoresis. Zeta-potential was calculated by the Smoluchowski relation (zeta potential=u$\eta$/$\varepsilon$) where $\eta$ and $\varepsilon$ are the viscosity and the permittivity of the solvent phase, respectively). Size and zeta-potential of liposome-HP complexes are given as mean±standard deviation (S.D.) of five independent measurements.

Protein assay. Liposome formulations were incubated with HP (1:1 v/v) for 1 hour at 37° C. Afterwards, liposome-HP complexes were pelleted at 15000×g for 15 minutes at 4° C. and washed three times with PBS. Washed pellet was resuspended in urea 8 mol/l, $NH_4CO_3$ 50 mmol/l. 10 microliters of each sample were added to five wells of a 96-well plate. Protein quantification was made adding 150 microliters/well of Protein Assay reagent (Pierce, Thermo Scientific, Waltham, Mass., USA). The multiwell was shaken and incubated at room temperature for 5 minutes. Absorbance was measured with GloMax Discover System (Promega, Madison, Wis., USA) at 660 µm. Background effects were properly corrected and the protein concentration was calculated using the standard curve. Results are given as mean±S.D. of five independent replicates.

Protein identification and quantification. The incubation procedure was performed as described elsewhere (Label-free quantitative analysis for studying the interactions between nanoparticles and plasma proteins. Analytical and Bioanalytical Chemistry, 2013, 405, 2-3, 635-645, incorporated by reference in its entirety). Liposome formulations were incubated with HP (1:1 v/v) for 1 hour at 37° C. Samples were centrifuged at 15000×g for 15 min to pellet liposome-HP complexes. The pellet was washed three times with 10 mmol/l Tris HCl (pH 7.4), 150 mmol/l NaCl and 1 mmol/l EDTA. After washing, the pellet was air dried and resuspended in the digestion buffer. The digestion and peptide desalting were carried out as previously described (Shotgun proteomic analytical approach for studying proteins adsorbed onto liposome surface. Analytical and Bioanalytical Chemistry, 2013, 401, 4, 1195-1202, incorporated by reference in its entirety). In brief, pellet was resuspended in 40 microliters of urea 8 mol/l, $NH_4CO_3$ 50 mmol/l and digested by adding 2 micrograms of trypsin. The digested peptides were desalted using SPE C18 column, reconstituted with a suitable volume of a 0.1% formic acid solution, and stored at −80° C. until analysis. Digested peptides were analyzed by nano-high-performance liquid chromatography (HPLC) coupled to tandem mass spectrometry (MS/MS). NanoHPLC MS/MS analysis was carried out using a Dionex Ultimate 3000 (Dionex Corporation Sunnyvale, Calif., U.S.A.) directly connected to a hybrid linear ion trap-Orbitrap mass spectrometer (Orbitrap LTQ-XL, Thermo Scientific, Bremen, Germany) by a nanoelectrospray ion source. Peptide mixtures were enriched on a 300 μm ID×5 mm Acclaim PepMap 100 C18 precolumn (Dionex Corporation Sunnyvale, Calif., U.S.A.), employing a premixed mobile phase made up of ddH2O/ACN, 98/2 (v/v) containing 0.1% (v/v) HCOOH, at a flow-rate of 10 microliters/min. Peptide mixtures were then separated by reversed-phase (RP) chromatography. The largest set of peptides was detected using a 3-hour optimized LC gradient composed of a mobile phase A of ddH2O/HCOOH (99.9/0.1, v/v) and a mobile phase B of ACN/HCOOH (99.9/:0.1, v/v). MS spectra of eluting peptides were collected over an m/z range of 350-1700 using a resolution setting of 60,000 (full width at half-maximum at m/z 400), operating in the data-dependent mode. MS/MS spectra were collected for the five most abundant ions in each MS scan. Further details can be found elsewhere (Shotgun proteomic analytical approach for studying proteins adsorbed onto liposome surface. Analytical and Bioanalytical Chemistry, 2013, 401, 4, 1195-1202). For each experimental condition three independent samples (biological replicates) were prepared, each of which was measured in triplicate (technical replicates), yielding nine measurements for each experimental condition. RAW data files were submitted to Mascot (v2.3, Matrix Science, London, UK) using Thermo-Finnigan LCQ/DECA RAW file data import filter to perform database searches against the non-redundant Swiss-Prot database (09-2014, 546000 sequences, *Homo Sapiens* taxonomy restriction). For the database search, trypsin was specified as the proteolytic enzyme with a maximum of two missed cleavages. Carbamidomethylation was set as fixed modification of cysteine, whereas oxidation of methionine was chosen as variable modification. The monoisotopic mass tolerance for precursor ions and fragmentation ions were set to 10 ppm and 0.8 Da, respectively. Charge state of +2 or +3 were selected as precursor ions. Proteome output files were submitted to the commercial software Scaffold (v3.6, Proteome Software, Portland, Oreg., USA). Peptide identifications were validated if they surpassed a 95% probability threshold set by the PeptideproPhet algorithm. Protein identifications were accepted if they could be established at greater than 99.0% probability and contained at least two unique peptides. Proteins that contained shared peptides and could not be differentiated on the basis of MS/MS analysis alone were grouped to satisfy the principles of parsimony. Unweighted spectrum counts (USC) were used to assess the consistency of biological replicates in quantitative analysis, and normalized spectrum counts (NC S) was used to retrieve protein abundance.

Statistical Analysis. All statistical analyses were performed using PLS, Kohonen, and CPANN toolboxes, and graphs were created using Microsoft Excel, XLSTAT, and MATLAB.

Data matrix. Each raw of the predictor matrix (X) relating to each individual is derived from all proteins' abundance obtained from the three-protein corona sensor array (FIG. 4A). In the preprocessing step, the normalized data in matrix X, relative protein abundance (RPA), were auto-scaled.

Classification and Clustering.

Partial least squares discriminant analysis (PLS-DA). Partial least squares discriminant analysis is a well-known multivariate approach regarded as a linear classification and dimension reduction method consisting of two main parts a structural part, which searches for latent variables as linear combinations of original independent variables (i.e., data matrix X), which have the maximum covariation with the corresponding dependent-variables (i.e., class membership, Y). The measured components include the latent variables as scores and loadings, which show how the latent variables and their original ones are related. Based on the ability of PLSDA to reduce the dimensionality of the data, it allows a linear mapping and graphical visualization of the different data patterns. PLS-DA is particularly well suited to deal with highly collinear and noisy patterns. The main problems associated with the large dataset in proteomics are the large number of monitored variables (i.e., proteins) and relatively small number of samples. Hence, there may be a high redundancy among variables, which render many of them uninformative and irrelevant to the classification. In this way, eliminating uninformative variables or finding new uncorrelated ones may improve the predictive performance of classification. Since in biomedical applications such as the present work, we must not only make decisions about whether a sample belongs to one of a number of known groups, but also determine which variables are most relevant for the best discrimination between classes, a method like PLS-DA is a good candidate approach for finding uncorrelated new latent variables while preserving the variation of the data The impotence power of the original variables to produce latent projections can also be calculated by the variable importance in the projection (VIP) analysis and can play a significant role in to decide about variables.

Identifying the most relevant variables based on weighted VIP. The partial least squares discriminant analysis (PLS-DA) was used to explore the VIP values associated with variables. VIP is a combined measure of how much a variable contributes to a description of the two sets of data: the dependent (Y) and the independent variables (X). The weights in a PLS model reflect the covariance between the independent and dependent variables, and the inclusion of the weights allows VIP to reflect not only how well the dependent variable is described but also how important that information is for the model of the independent variables.

An approach based on VIP score was developed to identify the best subset of variables. VIP scores can be calculated by performing PLS-DA on the dataset. In that approach, VIP scores of variables are calculated 50 times, each time using a random permutation of training and validation sets (random training sets were selected iteratively by considering 80-percent coverage of each class of objects). Considering the most important variables, the large VIP-score values (>2), the top 200 variables can be selected at each repetition and added to the top-variables pool. Afterward, a frequency of occurrence ($Freq_i$) and an average VIP-score ($\overline{VIP}_i$) for each variable can be obtained according to the top-variables pool. Thus, the selection of variable i (which has a high $\overline{VIP}_i$ value and low $\overline{VIP}_i$ value) is less recommended because of dependency on the training and validation sets. Therefore, the VIP value of each variable can be weighted by $Freq_i$, and ranking of the most relevant variables can be done using the weighted $\overline{VIP}_i$. Fig_appr is a schematic diagram of the proposed approach. Selection of the most relevant variables to build the classification model can be guided by the obtained ranking as follows: The highly ranked variables were added one by one to the dataset, and the classification error of PLS-DA was calculated to find the minimum number of relevant predictors (FIG. 4A).

Counter-Propagation Artificial Neural Network (CPANN). The counter-propagation artificial neural network (CPANN) is a supervised variant of self-organizing map that consists of two layers of neurons arranged on a predefined N×N grid. CPANN can be used to map data from a high-dimensional feature space to a low-dimensional (typically 2) discrete space of neurons as well as to predict the class membership of the unknown samples. The input vectors (sample feature vector) and corresponding class membership vectors (a binary vector) are presented to the input and output layer of CPANN, respectively. The weight correction of the neurons in both layers performs based on competitive learning and cooperation of the neurons (See FIG. 67, Table 3). Hence, similar input vectors can be mapped on the same or adjacent neurons and vice versa. The final assignment map properly reveals the structure of the data in feature space and preserves the distance of patterns in the low-dimensional grid of neurons. FIG. 9C shows a high-quality assignment map of CPANN using top-ranked biomarkers. According to the distinct regions for each class, the risk of classification error is minimized. The proper size of the map can be decided by performing 10-fold cross-validation at different map sizes. The trained CPANN can be used to assign a class membership to an unlabeled sample. Presence of redundant and uninformative variables in training data will affect the quality of the map and increase the risk of an error of classification (FIG. 5C). The process is a nonlinear mapping, which helps visualize a high-dimensional input object on a two-dimensional neuron grid. It is a self-organized procedure and solves the issue of classification in a transparent way. More details about the CPANN method can be found in the following references.

Hierarchical clustering analysis (HCA). Hierarchical clustering analysis is an unsupervised method widely used to explore and visualize whole heterogeneous large data sets like those often used in proteomics into distinct and homogeneous clusters. Strategies for hierarchical clustering can be divided into two categories: agglomerative and divisive methods. The agglomerative procedure first separates each object into its own individual cluster and then combines the clusters sequentially; similar objects or clusters are merged until every object belongs to only one cluster. The divisive procedure, in contrast, starts with all of the objects in one large cluster and gradually partitions them into smaller clusters until each object is in an individual cluster. Finally, objects are organized into a dendrogram whose branches are the defined clusters. In cluster analysis, to identify homogeneous sub-groups, the two important concepts, similarity (determining a numerical value for the similarity between objects and constructing a similarity matrix) and linkage (connection of an object to a group or not) should be defined. Herein, we applied agglomerative hierarchical clustering with furthest-neighbor linkage algorithm for unsupervised analysis based on the selected variables.

Cohort sample prediction. The predictive ability of both linear and non-linear variables, with 69 selected predictors, were assessed by cohort samples analysis. To this end, the values related to 69 variables were put into the model, and the class membership of each cohort object was predicted at the fixed optimum parameters values. The 19 variables (proteins) in the proteomics profile of our protein corona sensor array of cohort samples were not detected, and zero were considered for these variables in validation data matrix. Interestingly, both linear and non-linear models provide good predictions for all five samples. The distance between training and cohort samples shown in FIG. 6A is most probably related to zero values that were added to the data matrix for those 19 absent variables. We examined the effect of replaced zero values for absent variables by deleting these 19 proteins from both data matrices of the training and prediction sets; then the PLS-DA model was built and cohort samples were predicted. As expected, no large distance between cohort and training samples was observed.

Table 3. See FIG. 67 Correlation coefficient of CPANN weight map for each variable in the six classes.

For each variable, the correlation coefficient of corresponding weight map with the assignation map pattern can be calculated.

CC=0: indicates no correlation between biomarker and the related class; 1>CC(i)>0: accordance between the biomarker intensity and cancer related class. 0<CC<−1: an inverse correlation between biomarker value and cancer-related class. The CC values >0.5 or <−0.5 are colored. For example, the weight map of biomarker 1282 is highly correlated with the cancer class 4 pattern on the assignation map, and it may be an important biomarker for the samples from patients with myeloma.

Example 1B. In Depth Analysis of Human Proteome Using Multi-Nanoparticle Protein Corona Characterization and Machine Learning Enable Accurate Identification and Discrimination of Cancers at Early Stages In a second embodiment, the collective protein corona data for a given plasma sample, derived from individual nanoparticles' protein corona profiles, is able to identify and discriminate different types of cancers using machine learning (e.g., random forest approach) to analyze the data. The sensor array as described in Example 1A was used and the data collected was further analyzed by machine learning in further detail. This sensor array (i.e. protein corona nanosystem) unambiguously and robustly identified cancer and allows for the discrimination among different types of cancers. This system can be used to predict cancer types using blind plasma samples. The capacity for very early detection by using the plasma of healthy people in existing cohorts who were diagnosed with cancers several years after plasma collection to determine a pre-cancer biomolecule fingerprint.

Figure 1:
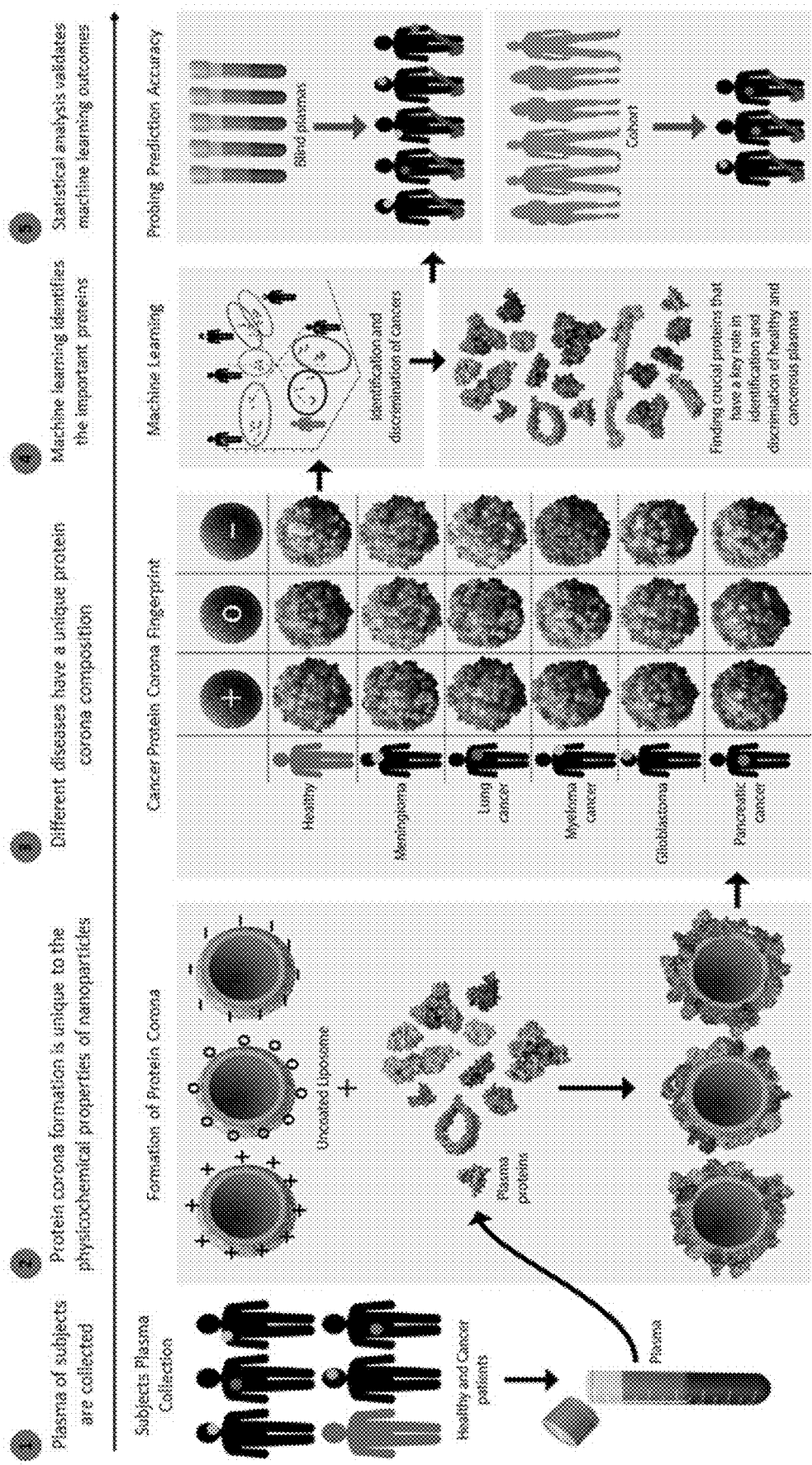
FIG. 1. Scheme of one embodiment showing an example of study design of the protein corona pattern approach for cancer detection. Three types of liposomes are incubated with plasma of healthy people and cancer patients, and the protein corona pattern forming on each liposome in each subject's plasma (healthy and different cancers) is characterized by liquid chromatography-tandem mass spectrometry (LC-MS/MS). The formation of protein coronas on the three liposomes results in the enrichment of an overlapping but distinct pool of selected plasma proteins, and the enriched proteins are the bases for subsequent multivariate analysis. Via classification approaches, the important proteins in the corona patterns were identified and used to predict cancers using both blind plasmas and cohort samples to test the accuracy of the multi-nanoparticle protein corona nanosystem. 29 human subjects (25 cancerous patients, i.e., 5 patients per 5 cancer types; and 4 healthy subjects) representing 261 distinct runs of LC-MS/MS (3 liposomes, 29 subjects, 3 replicates) were used to train a classification model. 16 human subjects (3 patients per 5 cancer types; and 1 healthy subject) of blind plasma and 144 distinct runs of LC-MS/MS (3 liposomes, 16 subjects, 3 replicates) were used for cancer prediction, i.e., to test the classification model. 15 human subjects (5 patients per 3 cancer types) of cohort plasma representing 135 distinct runs of LC-MS/MS (3 liposomes, 15 subjects, 3 replicates) were used for very early cancer prediction as well.

FIG. 1 presents a schematic overview of the use of the sensor array (nanoparticle system) to use multi-protein-corona proteomics for cancer detection in known cancer patients and for cancer prediction using both blind plasma and cohort samples.

Results

Protein Corona Profiles of the Nanosystem Using Plasma from Patients with Cancers at Early, Intermediate, and Advanced Stages Our protein corona nanosystem consists of three different cross-reactive liposomes with various surface charges [anionic (DOPG (1,2-dioleoyl-sn-glycero-3-phospho-(1'-rac-glycerol))), cationic (DOTAP (1,2-Dioleoyl-3-trimethylammonium-propane)-DOPE (dioleoylphosphatidylethanolamine)), and neutral (CHOL (DOPC-Cholesterol))], whose protein corona profiles were measured after exposure to the plasma of healthy subjects or patients with one of five cancers: lung, pancreas, myeloma, meningioma, or glioblastoma.

We performed proteomic analysis on each patient (5 patients/group) in triplicate for each of the three liposomes (see FIG. 2A,B for details on the size and charge of the liposomes) in our protein corona nanosystem (i.e., total trials: 3*(29)*3=261). Although no single protein corona composition is specific for any one cancer type as also described in Example 1A, the collective protein corona composition for a given plasma sample derived from different liposomes provided a unique "fingerprint" for each type of cancer.

Though the composition of the protein corona that forms on the surface of liposomes is strongly dependent on their physicochemical properties, it can also be strongly affected by the unique type, concentration, and conformation of proteins and other biomolecules present in a given patient's plasma. The size and charge of corona-coated liposomes were probed using dynamic light scattering (DLS/Nanosight), after incubation with plasma from patients with five different types of cancers (see Table 1) and healthy individuals. The results confirmed that the physicochemical properties of the corona-coated nanoparticles varied across different types of cancer (FIG. 2A,B).

Quantitative evaluation of the total protein adsorbed onto the liposomes was performed via the BCA (bicinchoninic acid) or NanoOrange assays, and the results confirmed significant differences in the amounts of adsorbed proteins after incubation in plasma from patients with various types of cancers (FIG. 3A-F). Quantitative evaluation of the total protein adsorbed onto the surface of liposomes showed the dependency of protein amount on cancer type (FIG. 3A-F). The protein corona composition at the surface of three liposomes was evaluated by liquid chromatography-tandem mass spectrometry (LC-MS/MS) in which 876 known proteins were defined. The contributions of individual proteins and their categories (i.e., complement, coagulation, tissue leakage, lipoproteins, acute phase, immunoglobulins, and other plasma proteins) to the corona composition were defined (FIG. 3A-F). The results demonstrated associations between the protein composition and not only the cancer type but also the type of liposomes. The mechanism behind this variation is that the high surface-to-volume ratio of the nanoparticles provides a unique opportunity for a wide range of human plasma proteins (highly abundant proteins, less-abundant plasma proteins, and very rare proteins) to participate in the corona composition, without need for depletion of highly abundant proteins, and without a direct correlation to plasma protein concentrations. Furthermore, in our system, conformational changes in plasma proteins can also change the protein corona composition, via significantly altering the interaction site of proteins with nanoparticles. These characteristics make the protein corona profile unique among other approaches developed for the analysis of proteins in human plasma.

The protein corona compositions at the surface of liposomes contained a wide range of human plasma proteins including highly abundant proteins (e.g., albumin, transferrin, complement proteins, apolipoproteins, and alpha-2-macroglobulin) and very rare proteins (defined as <100 ng/ml) such as transforming growth factor beta-1-induced transcript 1 protein (~10 ng/ml), fructose-bisphosphate aldolase A (~20 ng/ml), thioredoxin (~18 ng/ml), and L-selectin C92 ng/ml). We also identified 388 proteins without a known previous plasma concentrations (see website at plasmaproteomedatabase.org). The obtained protein information was then analyzed by a machine learning approach to probe the capacity of our protein corona nanosystem for robust and accurate cancer detection.

Development of Classifier to Detect and Discriminate Among Cancers Using Protein Corona Nanosystem Outcomes.

To evaluate the ability of the protein corona nanosystem to detect various cancers, we used proteomic data collected from the 3 distinct liposomes on 29 plasma samples (5 patients each from 5 cancer types; and 4 healthy samples) to train a classifier, specifically an algorithm that receives array measurements from a patient and outputs one of six labels (either one of the five cancer types, or healthy). Before training the classifier, raw data from the 3 nanoparticles were first 'de-noised' via a low-rank tensor factorization discussed in depth in a later section. This de-noising implicitly mitigates the significant variability observed in individual corona elements. We then trained a random forest classifier, a popular non-linear classification algorithm, on the resulting de-noised data.

We tested the accuracy of this classifier on 16 blind samples (3 patients each from 5 cancer types; and 1 healthy sample). We measured overall classification accuracy for the task of correctly assigning these blind samples to one of the six labels, along with sensitivity and specificity for each of the five cancer types separately (Table 4). Due to the relatively small number of plasma samples (45 in total), and to ensure the robustness of our results, we performed this procedure (training a random forest classifier on 29 samples and measuring accuracy, sensitivities and specificities on the remaining 16 samples) a total of 1000 times. The training and tests sets in each of the 1000 replications of the experiment were chosen randomly from amongst all class-stratified partitions of the data. This approach allows us to calculate unbiased estimates of the p-value for the classification accuracies we report (see Table 4). Specifically, the last row of Table 4 shows that the average overall accuracy across the 1000 replications was 96.2%, or equivalently an overall error of 3.8%. We also observe a p-value of 0.04 for the null hypothesis that the overall classification error is lower than 87.5%, and therefore we can reject this null hypothesis with 95% confidence. Sensitivities for the five individual cancer types range from 87.4% to 100.0%, and individual specificities range from 97.0% to 100.0%.

TABLE 4

Overall classification accuracy, sensitivity, and specificity. Overall classification accuracy for protein corona nanosystem with one, two, and three liposomes (Column 2). Both classification accuracy and the associated p-values improve with additional liposomes. Individual sensitivity and specificity for glioblastoma, lung, meningioma, myeloma, and pancreatic cancers (Columns 3-12) also show that sensitivity and specificity improve with additional liposomes. Experimental results are averaged over 1000 independent draws of a training set comprising 29 plasmas, with evaluation on the remaining 16 plasmas. p-values are for the null hypothesis of a classification error lower than 87.5%.

|  |  | Glioblastoma | | Lung | | Meningioma | | Myeloma | | Pancreatic | |
| --- | --- | --- | --- | --- | --- | --- | --- | --- | --- | --- | --- |
| Array Size | Accuracy | Sens. | Spec. | Sens. | Spec. | Sens. | Spec. | Sens. | Spec. | Sens. | Spec. |
| One | 86.0 (0.43) | 80.1 | 96.5 | 85.9 | 98.4 | 83.9 | 96.3 | 88.1 | 97.1 | 89.6 | 97.7 |
| Two | 92.4 (0.18) | 89.6 | 97.5 | 94.0 | 99.5 | 91.6 | 96.2 | 99.9 | 99.6 | 85.8 | 99.9 |
| Three | 96.2 (0.04) | 100.0 | 98.9 | 94.0 | 100.0 | 98.5 | 97.0 | 100.0 | 100.0 | 87.4 | 99.5 |

The Value of Multi-Liposomes in the Protein Corona Nanosystem

To assess the importance of including multi-liposomes in the protein corona nanosystem, we repeated the entire classification procedure using 1000 different splits of the data into training and testing samples, but this time using data measured from only a single liposome. This was done for each of the three liposomes, and the results are reported in the first row of Table 4. Relative to the entire array including all three liposomes, the single-liposome arrays showed significantly lower accuracy, sensitivity, and specificity. We also re-performed the procedure for sets of two liposomes (there are three such unique sets); these results are found in the second row of Table 4. The two-liposome systems are more accurate than a one-liposome system, but still weaker than the entire array of three liposomes. Overall, this indicates the value of changes in the corona composition pattern between different liposomes and the necessity of including such multiple observations.

Variable and Protein Importance and Stability

The random forest model also yields an importance score for each variable (i.e. each liposome-protein pair). This score essentially measures how important that variable was in discriminating patients of different cancer types. On an individual 'tree' of the random forest, the importance score of any variable used in constructing the tree is defined as the proportion of the training set that lies in the 'leaves' of nodes utilizing that variable (variables not used in constructing the tree are assigned a score of zero); then the overall importance score for a variable is the average of its importance scores on each tree.

Figure 2C:
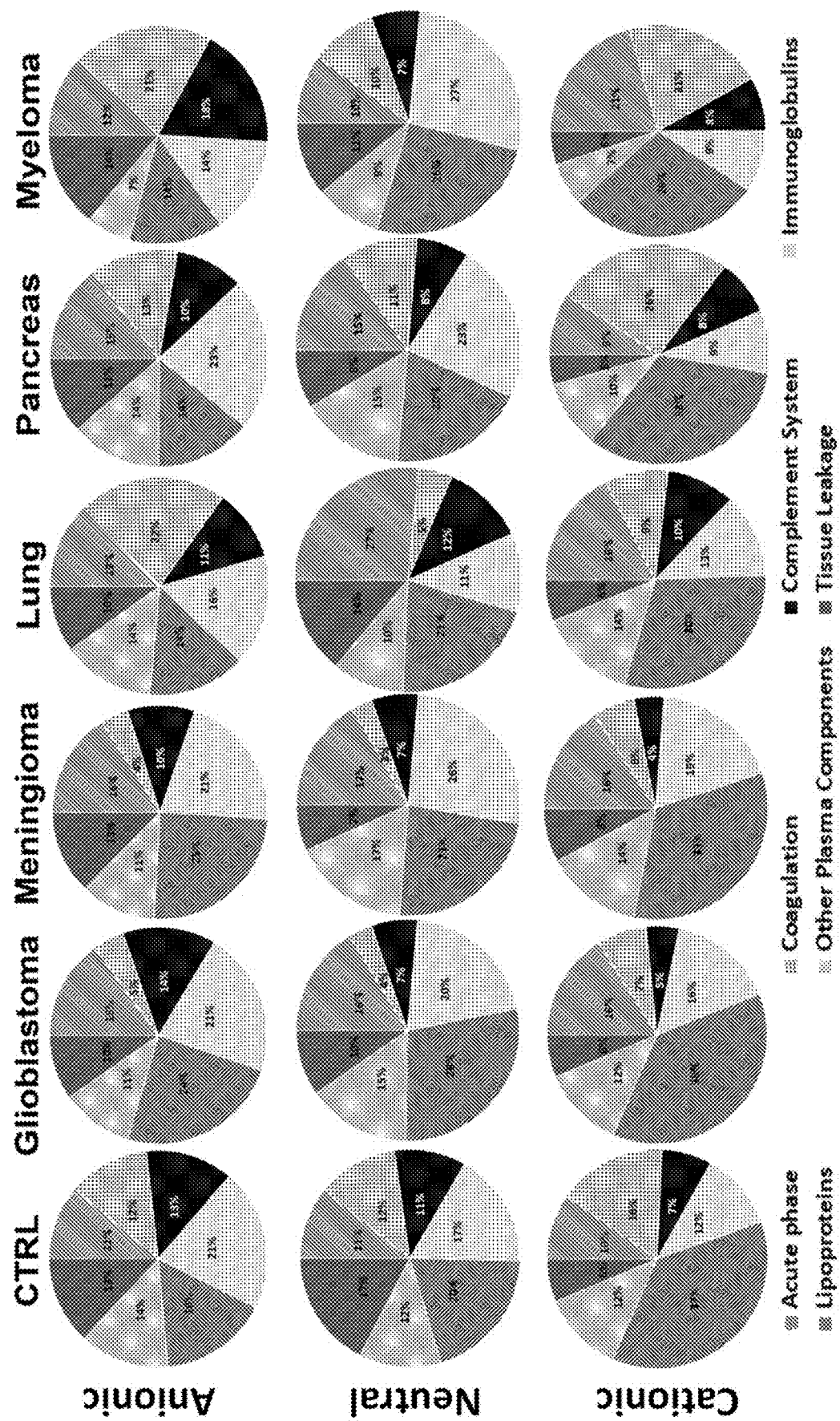
FIG. 2C. Classification of the identified corona proteins from liposomes according to their physiological functions in human plasma of healthy individuals and of patients having different types of cancers (the data presented reflect a calculation from five biological plasmas per group and three technical replicates per plasma)
Figure 3A:
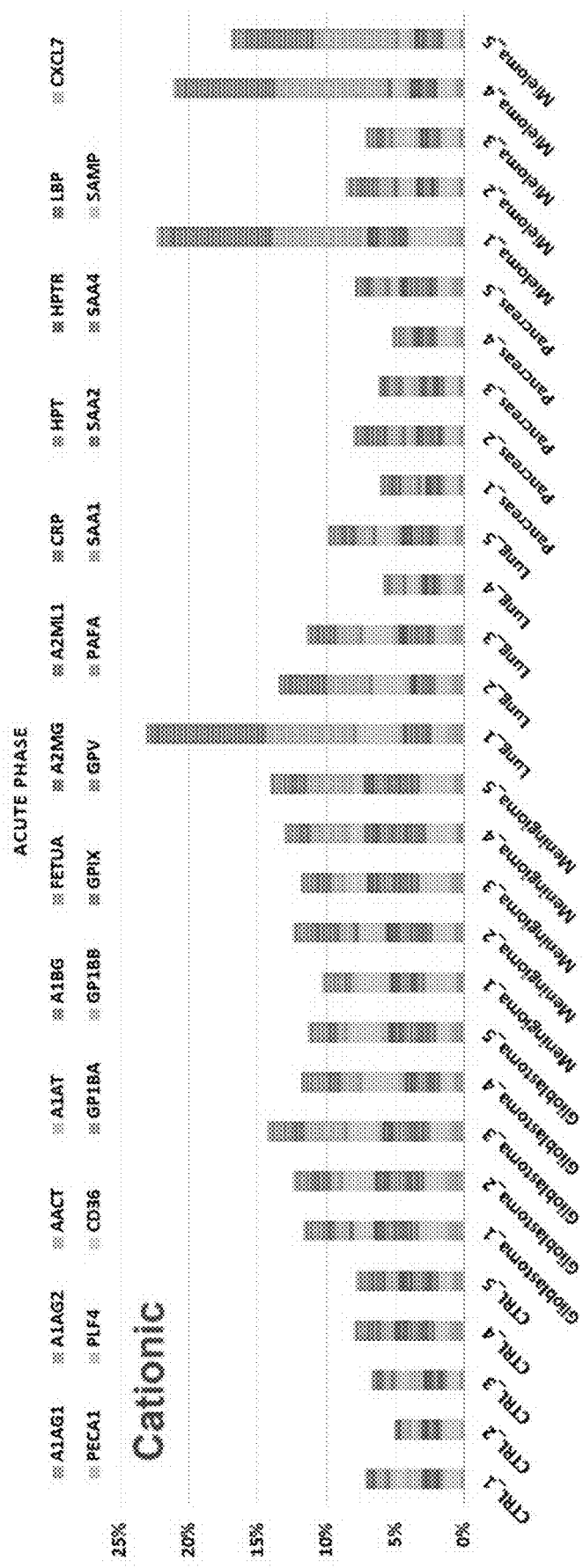
FIG. 3A. Classification of identified coronas by sensor array elements according to their physiological functions including acute phase, in human plasma of healthy subjects and patients having different types of cancers.
Figure 3A:
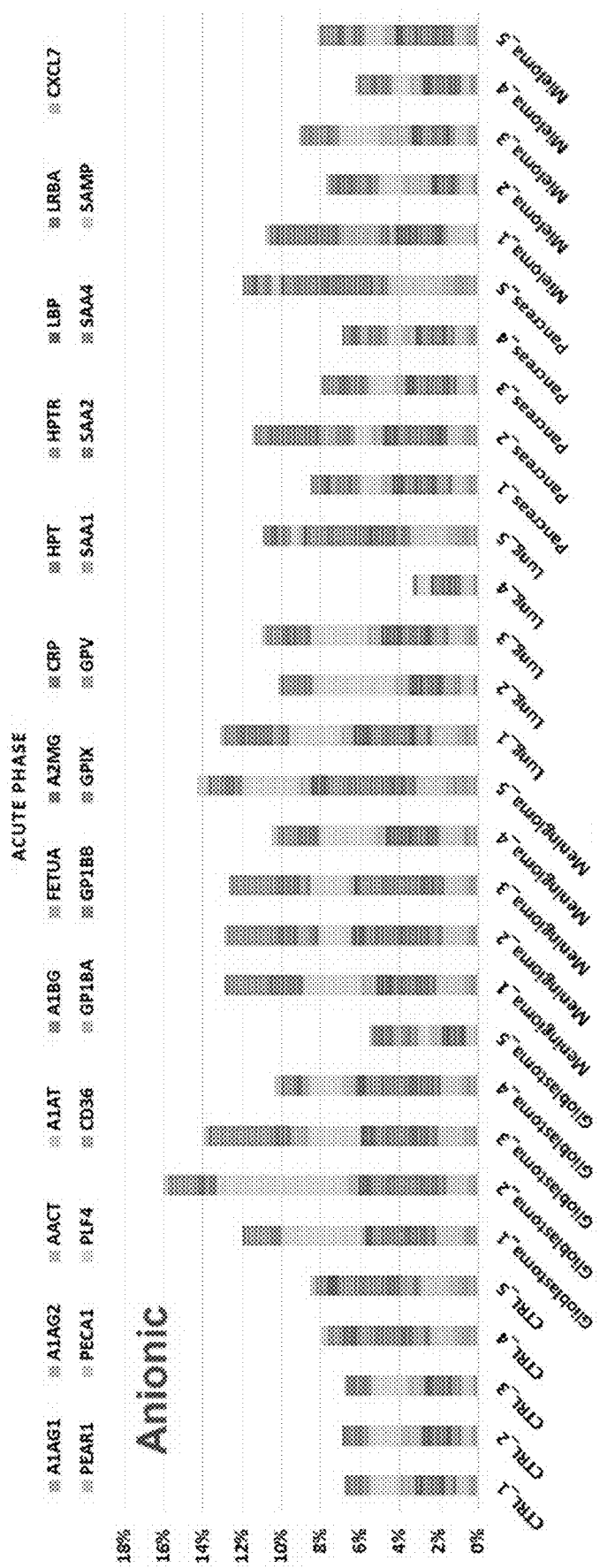
Figure 3A:
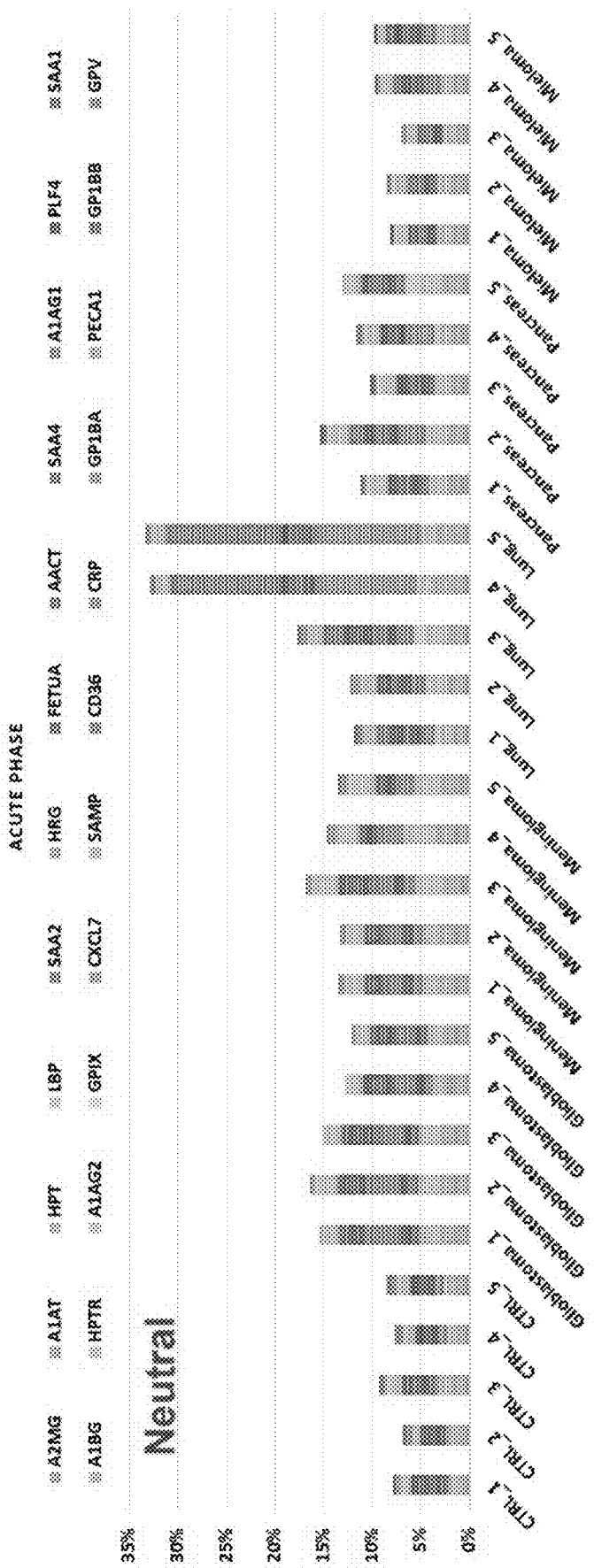
Figure 3B:
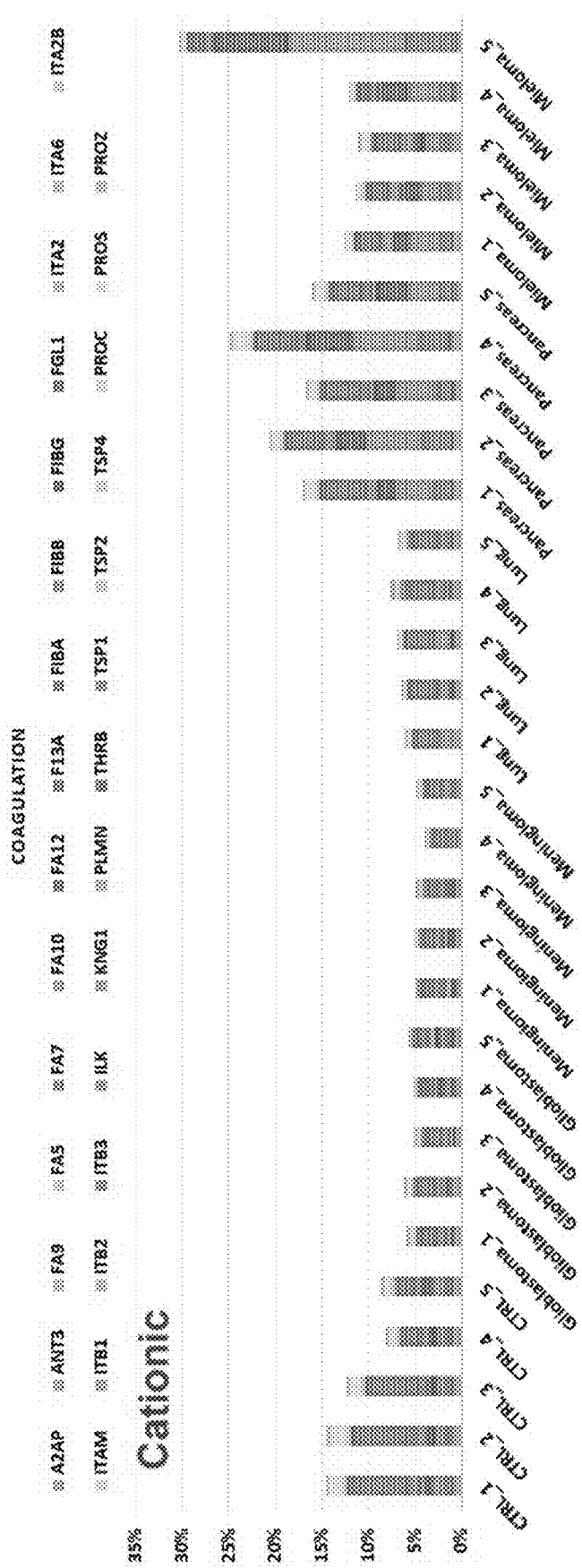
FIG. 3B. Classification of identified coronas by sensor array elements according to their physiological functions, including coagulation in human plasma of healthy subjects and patients having different types of cancers.
Figure 3B:
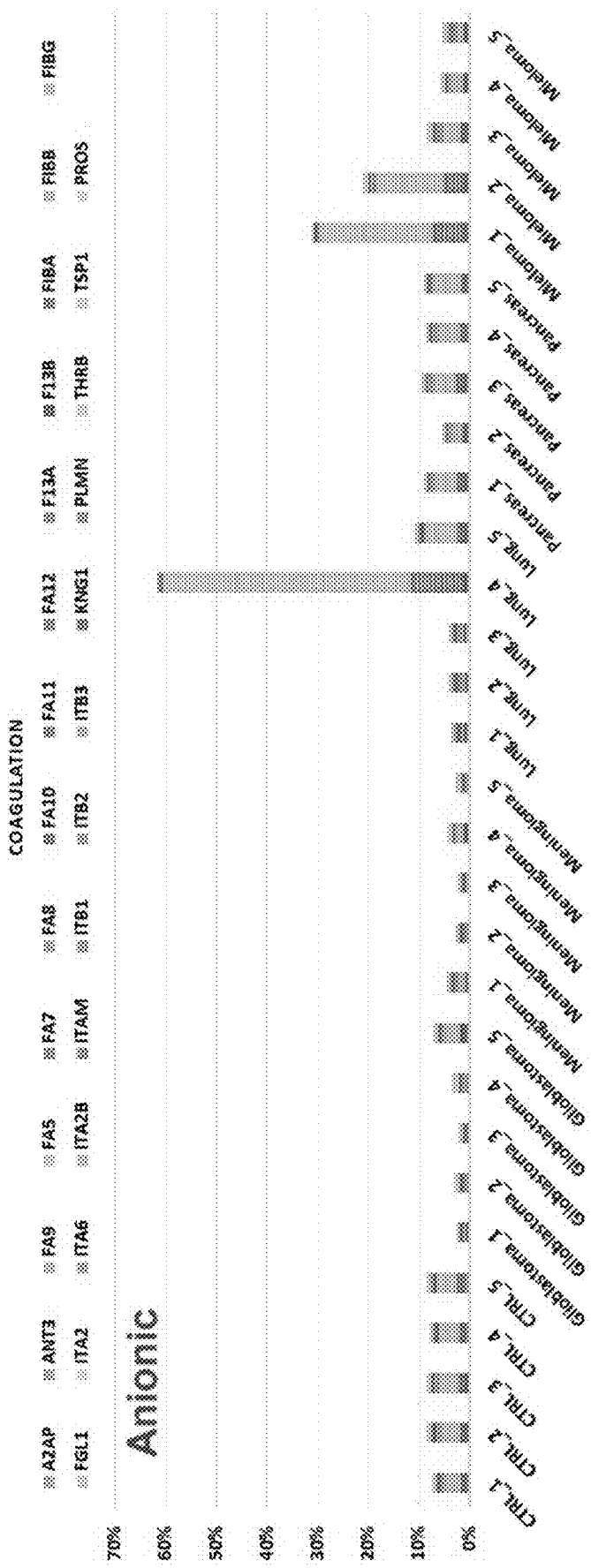
Figure 3B:
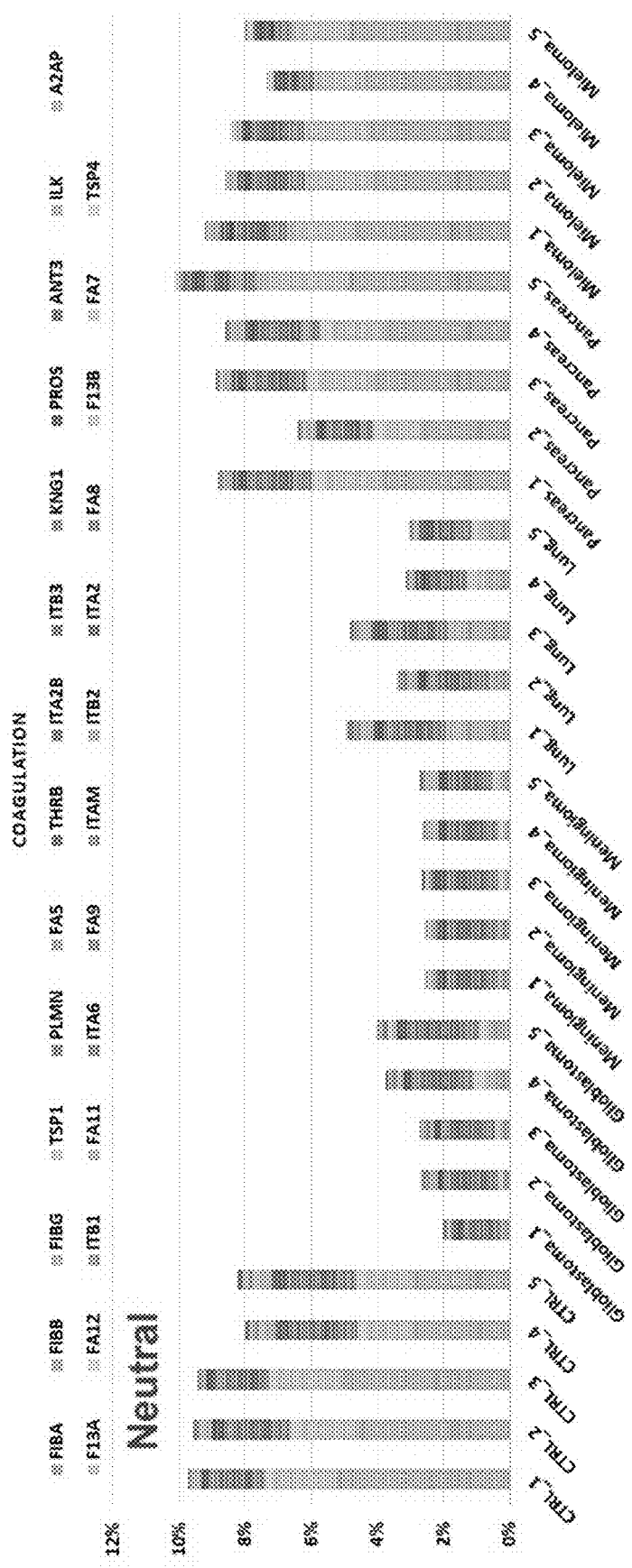
Figure 3C:
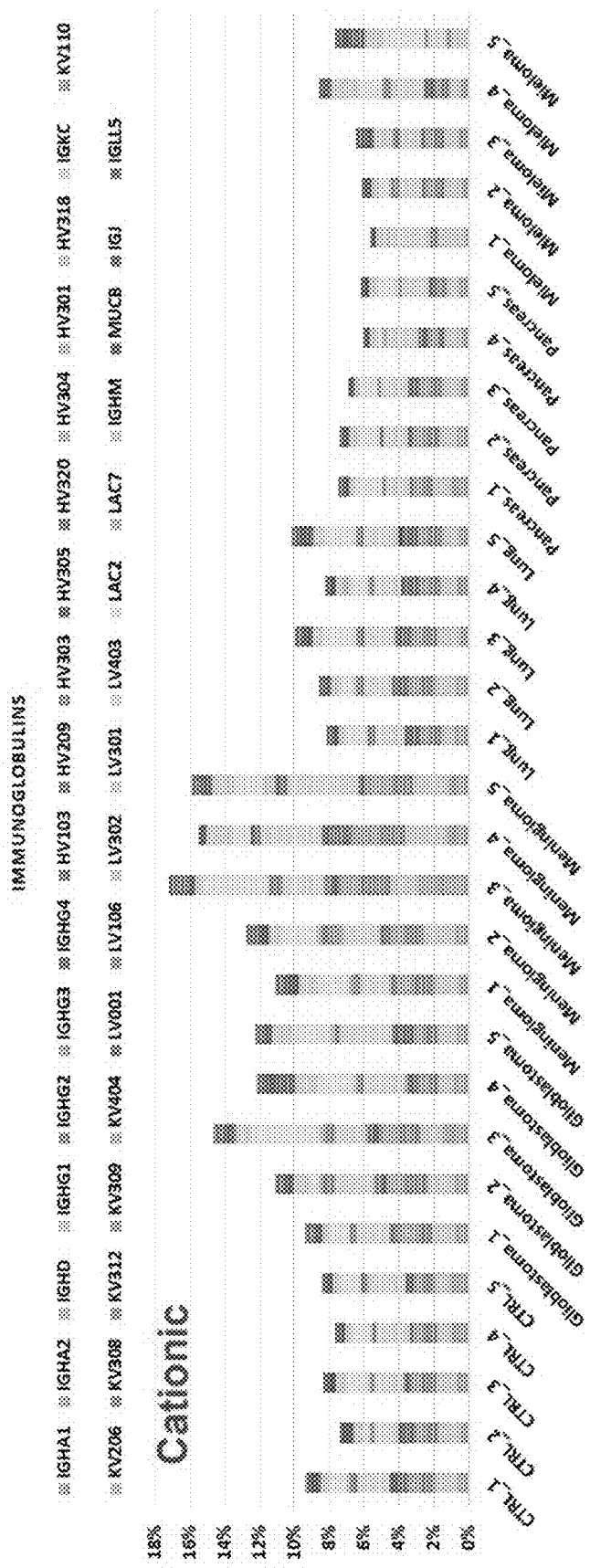
FIG. 3C. Classification of identified coronas by sensor array elements according to their physiological functions, including immunoglobulins in human plasma of healthy subjects and patients having different types of cancers.
Figure 3C:
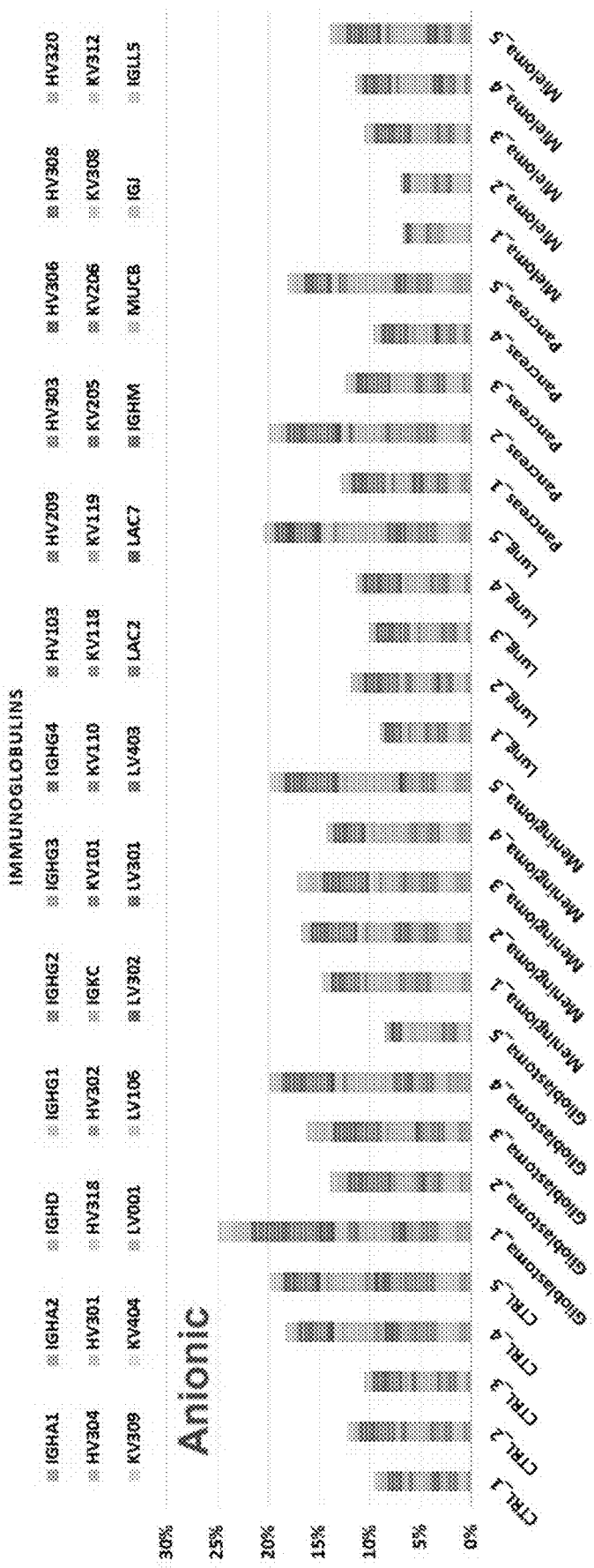
Figure 3C:
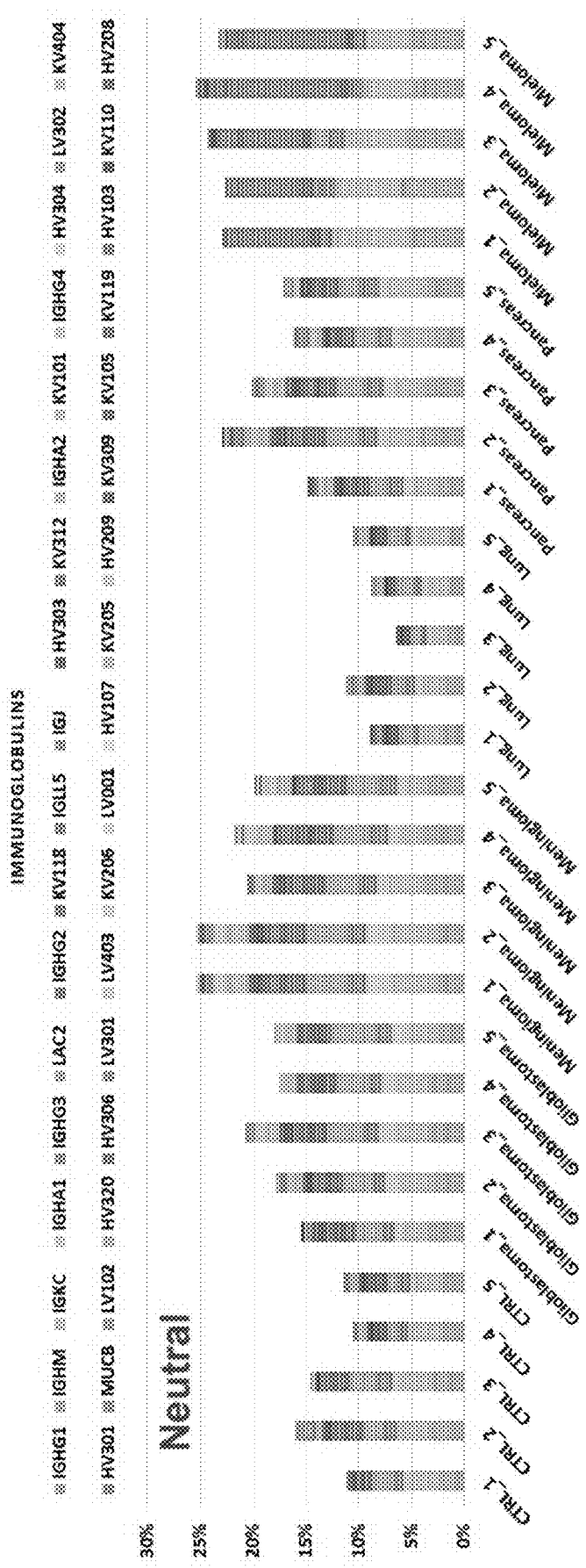
Figure 3D:
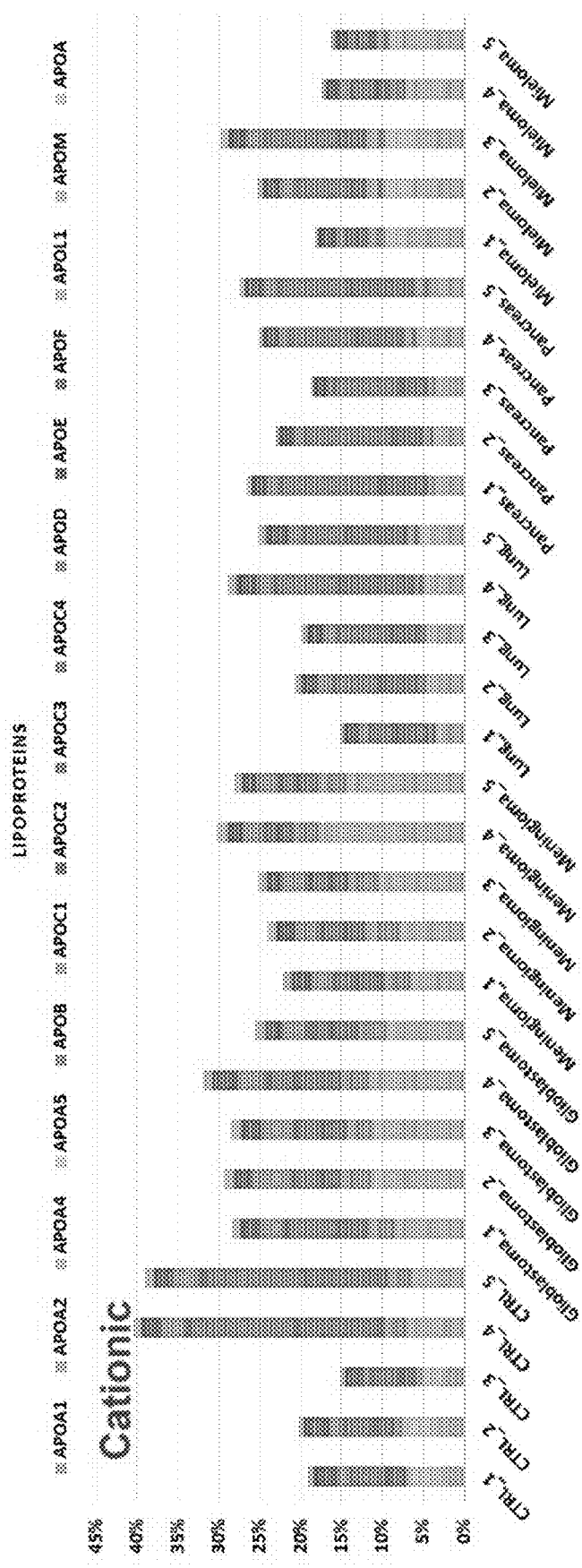
FIG. 3D. Classification of identified coronas by sensor array elements according to their physiological functions, including lipoproteins in human plasma of healthy subjects and patients having different types of cancers.
Figure 3D:
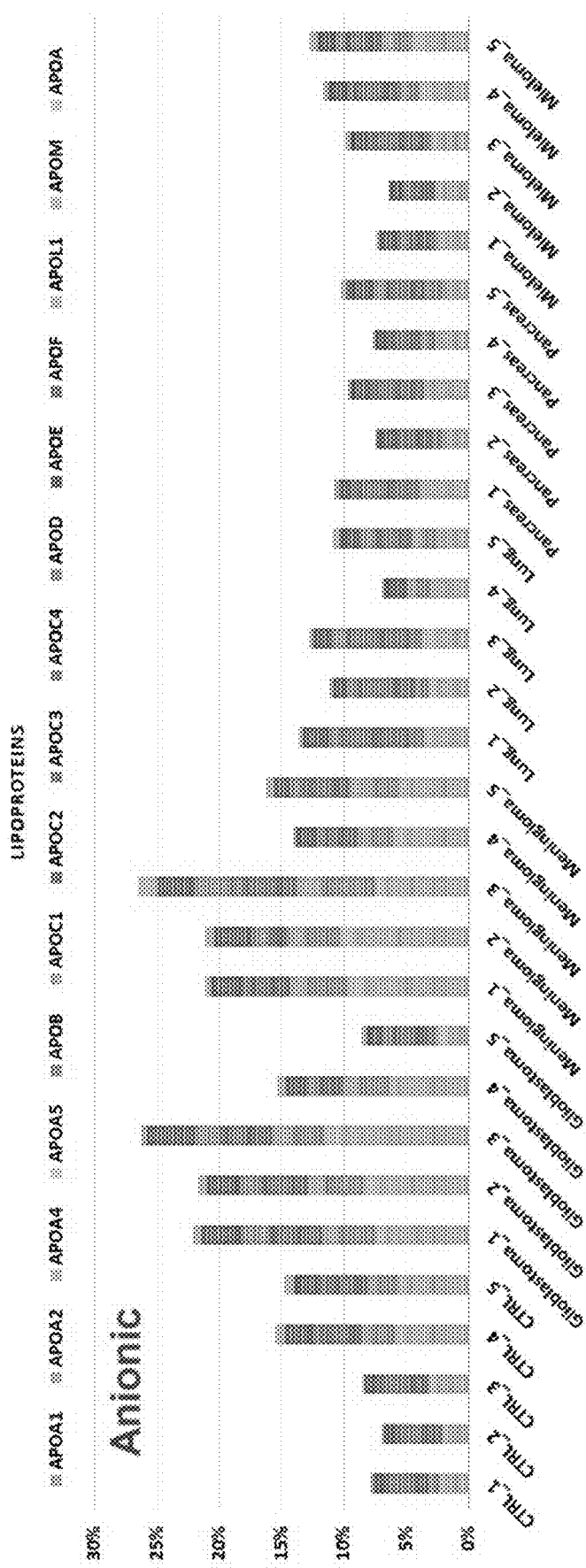
Figure 3D:
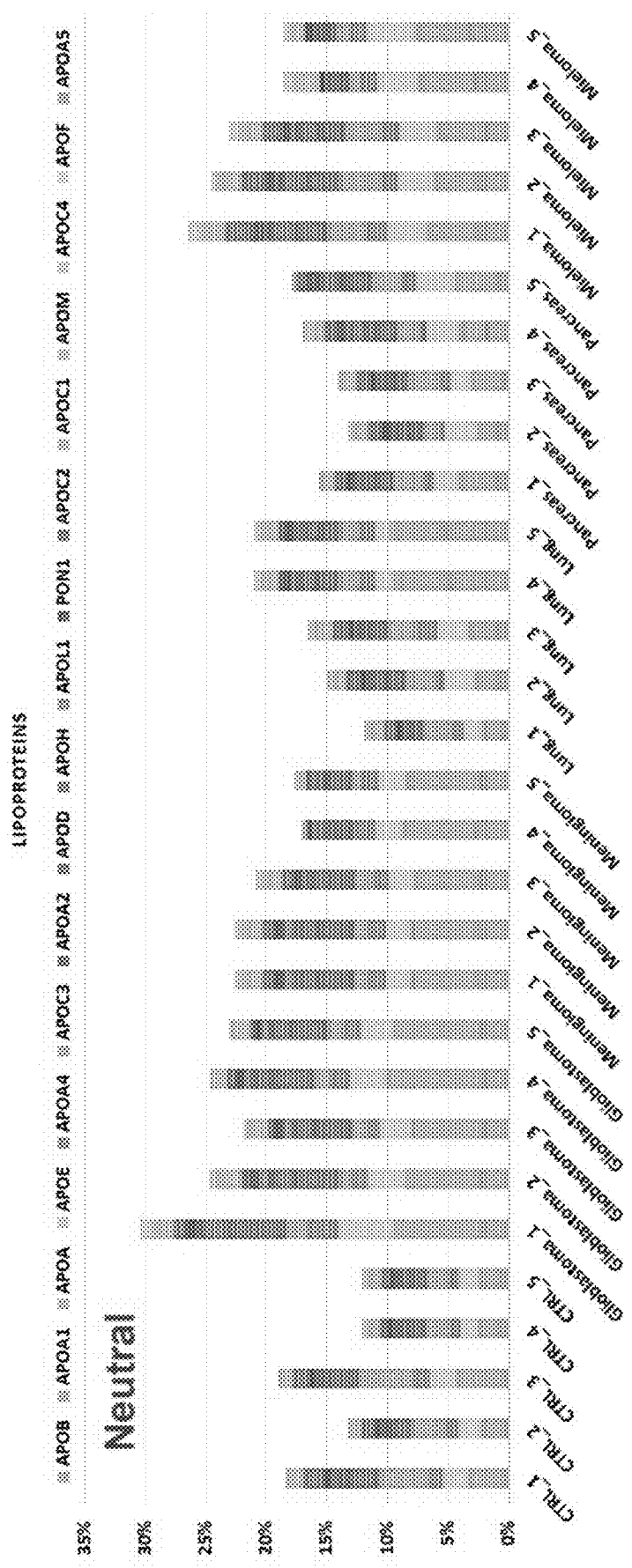
Figure 3E:
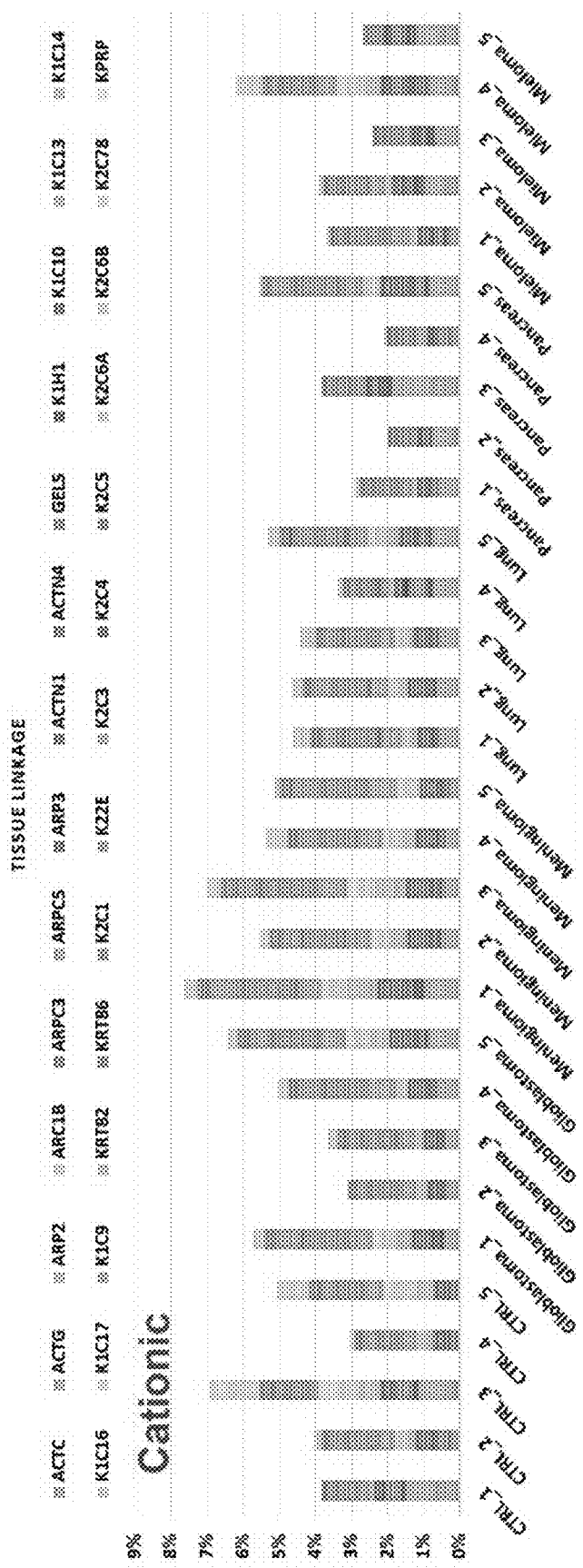
FIG. 3E. Classification of identified coronas by sensor array elements according to their physiological functions, including tissue leakage in human plasma of healthy subjects and patients having different types of cancers.
Figure 3E:
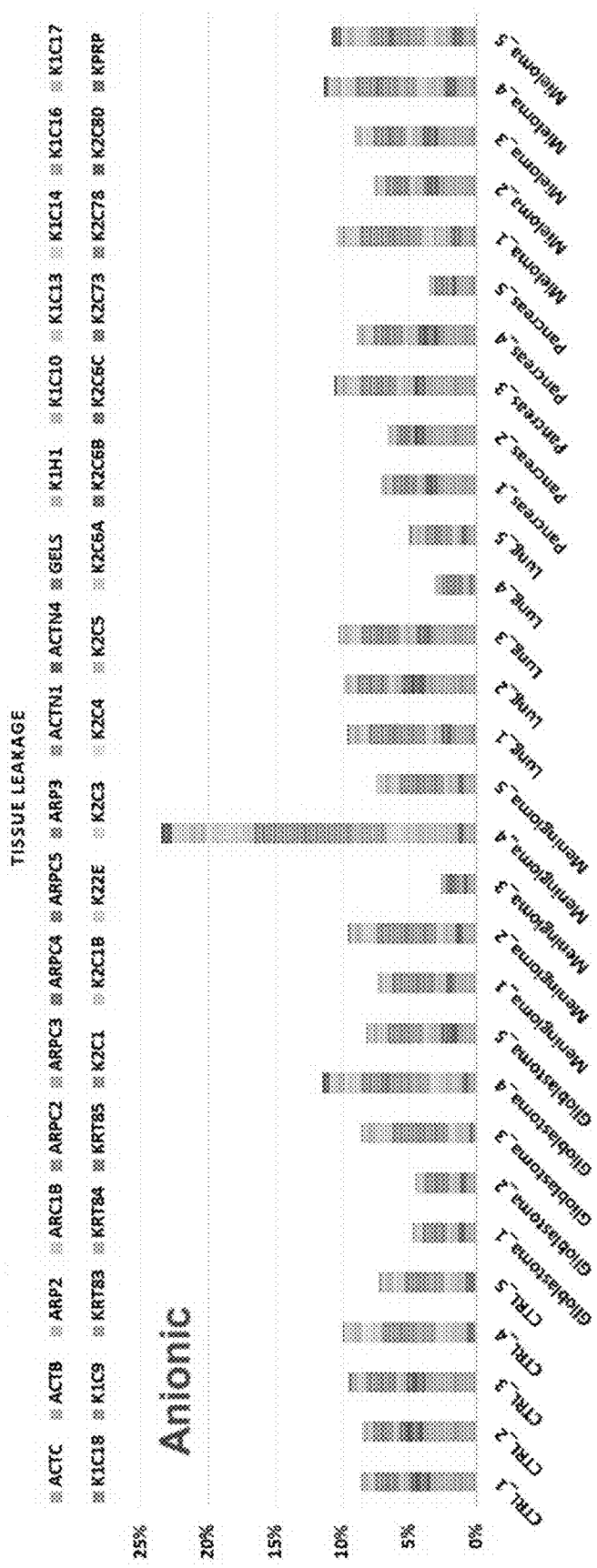
Figure 3E:
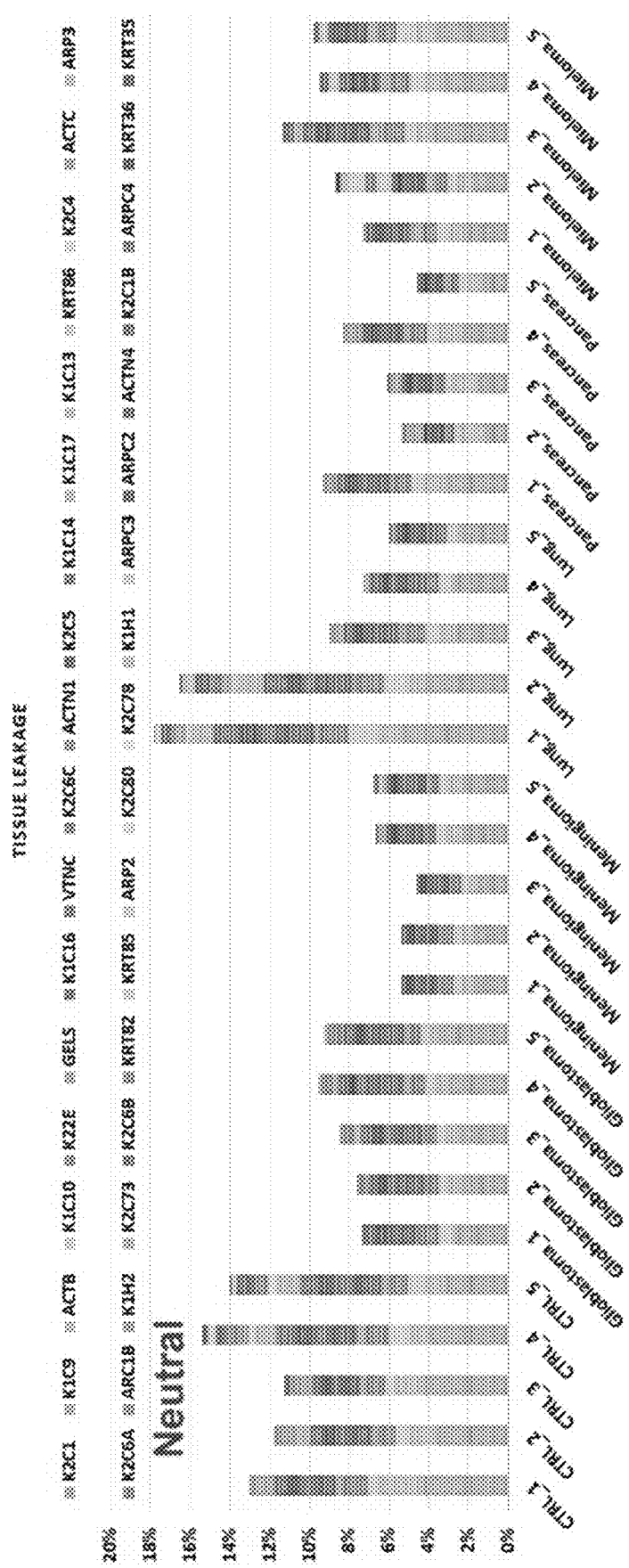
Figure 3F:
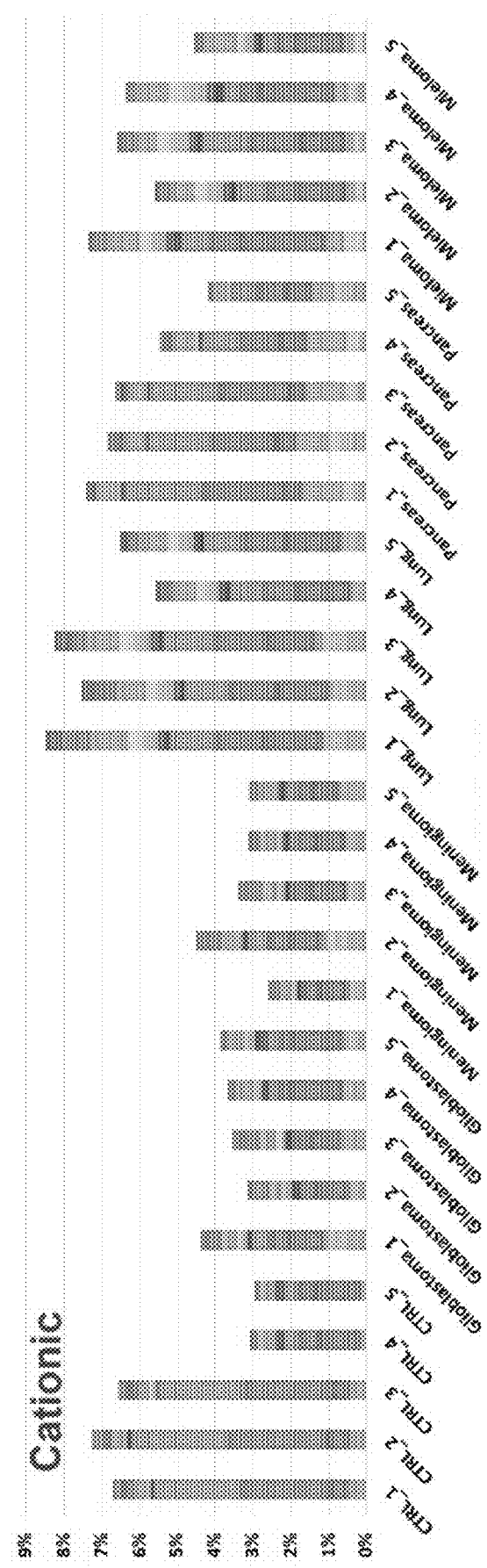
FIG. 3F. Classification of identified coronas by sensor array elements according to their physiological functions, including complement proteins in human plasma of healthy subjects and patients having different types of cancers.
Figure 3F:
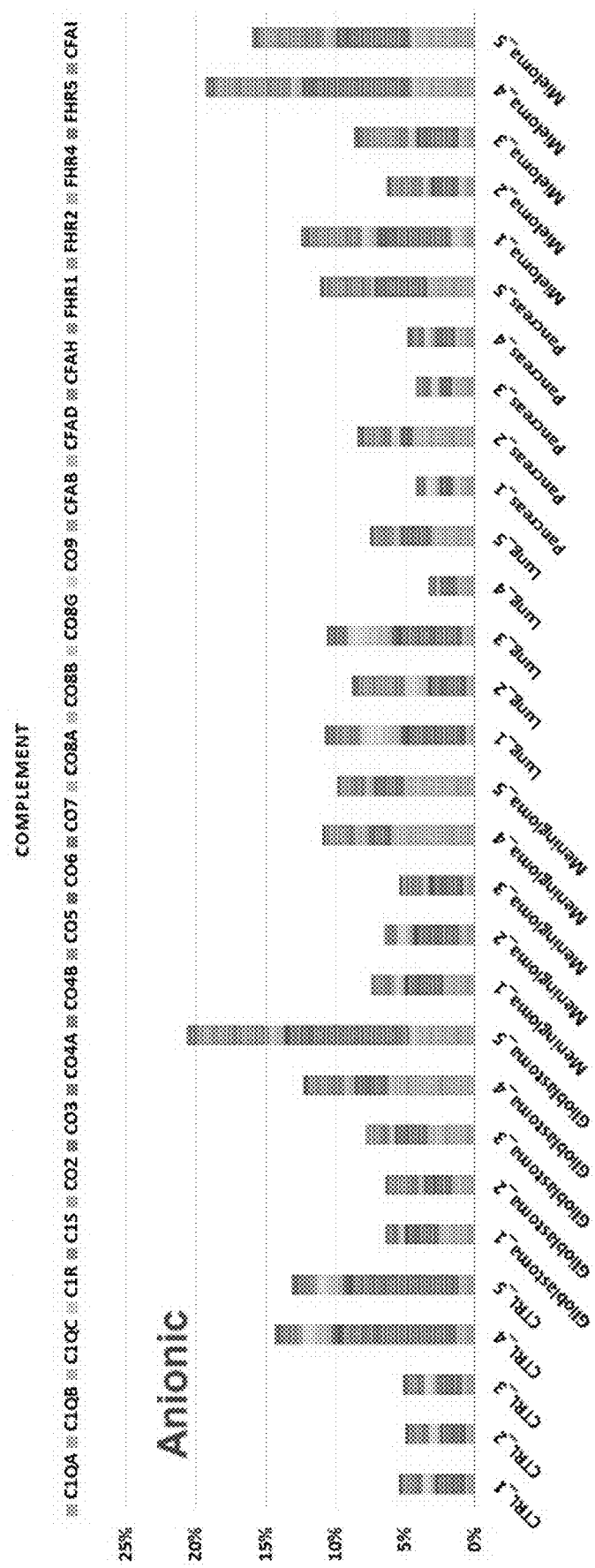
Figure 3F:
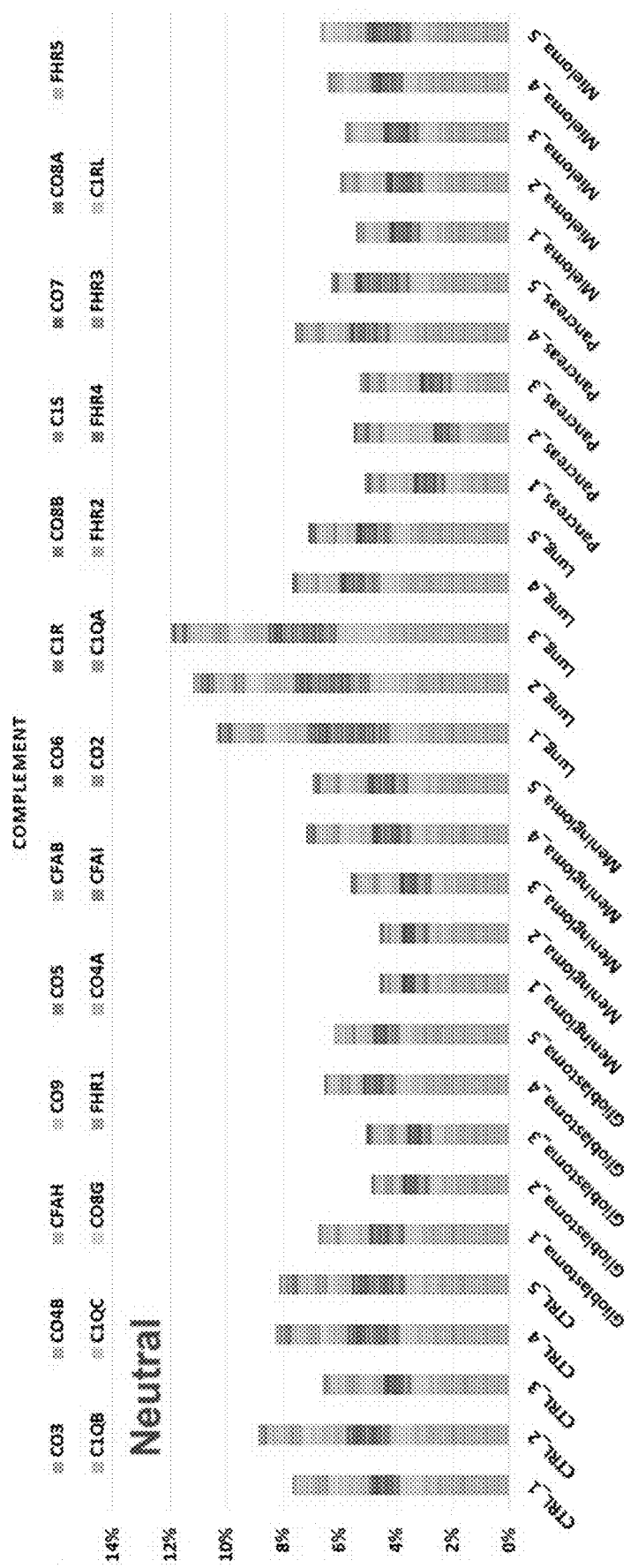
Figure 3G:
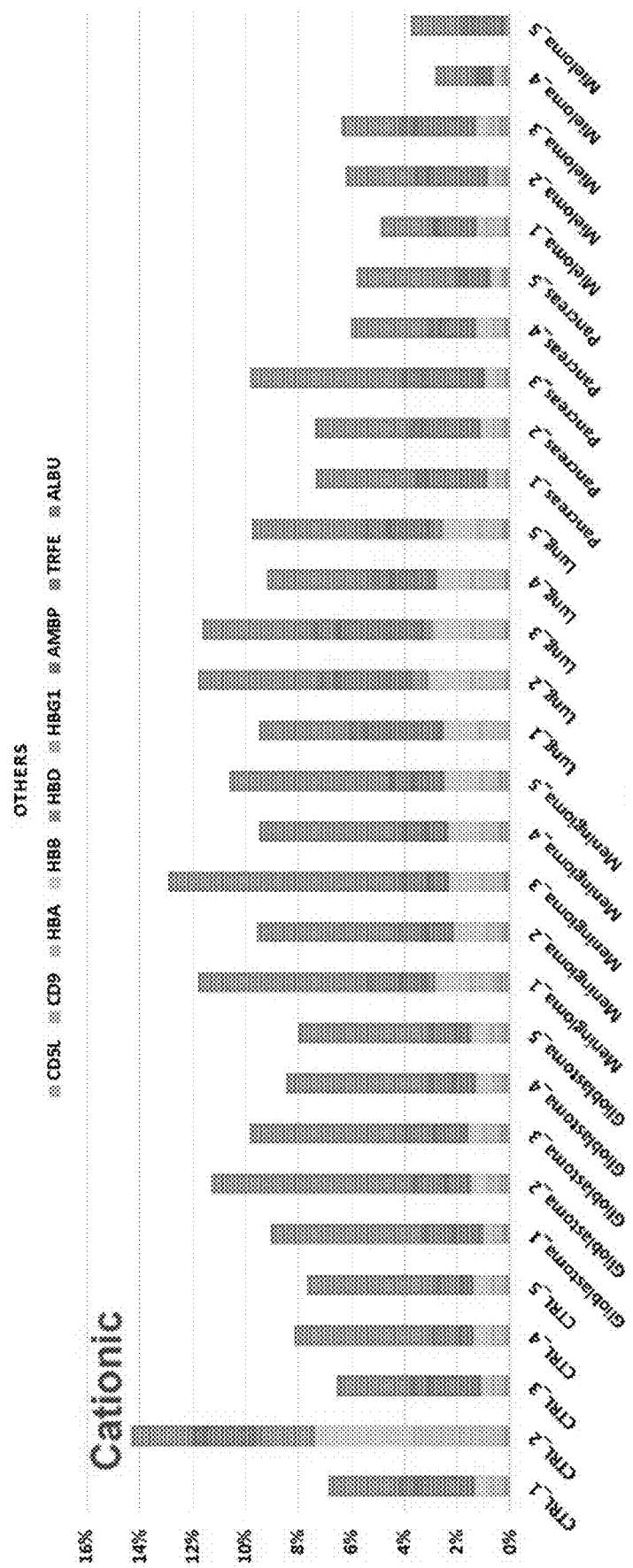
FIG. 3G. Classification of identified coronas by sensor array elements according to their physiological functions, including other plasma proteins in human plasma of healthy subjects and patients having different types of cancers.
Figure 3G:
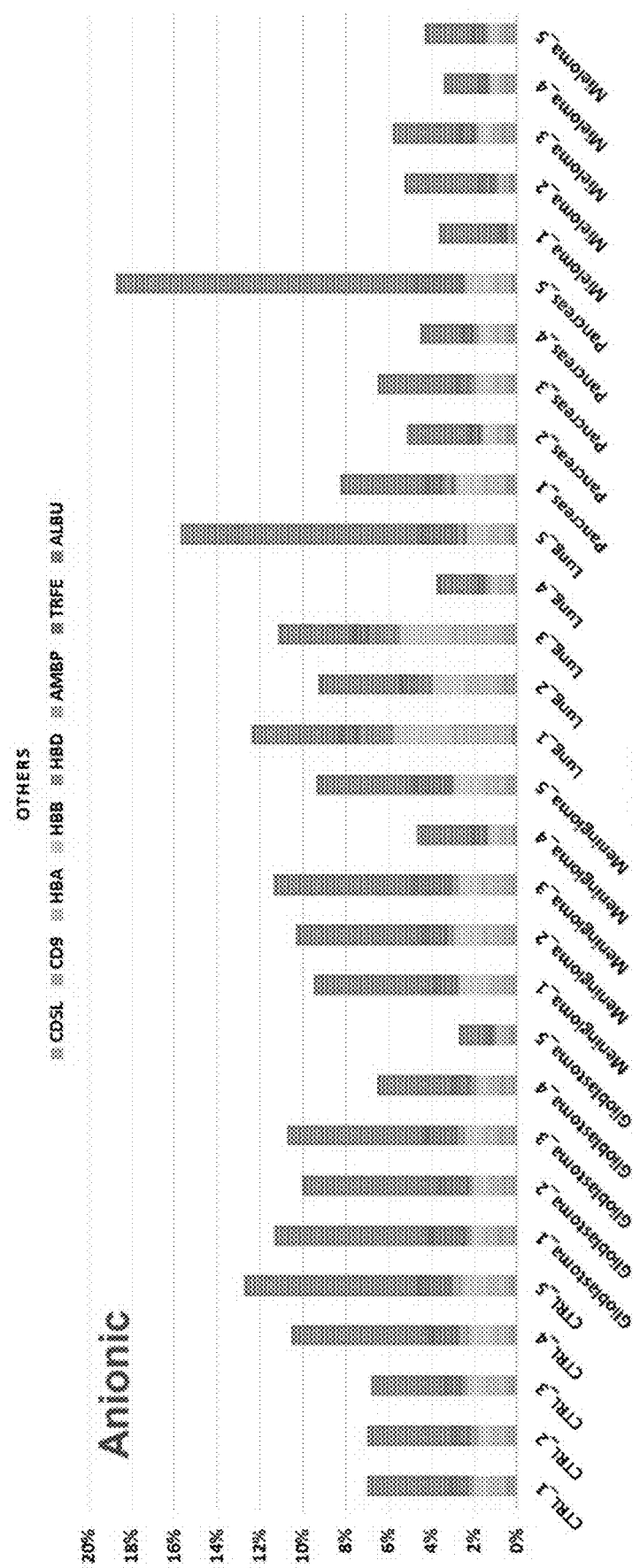
Figure 3G:
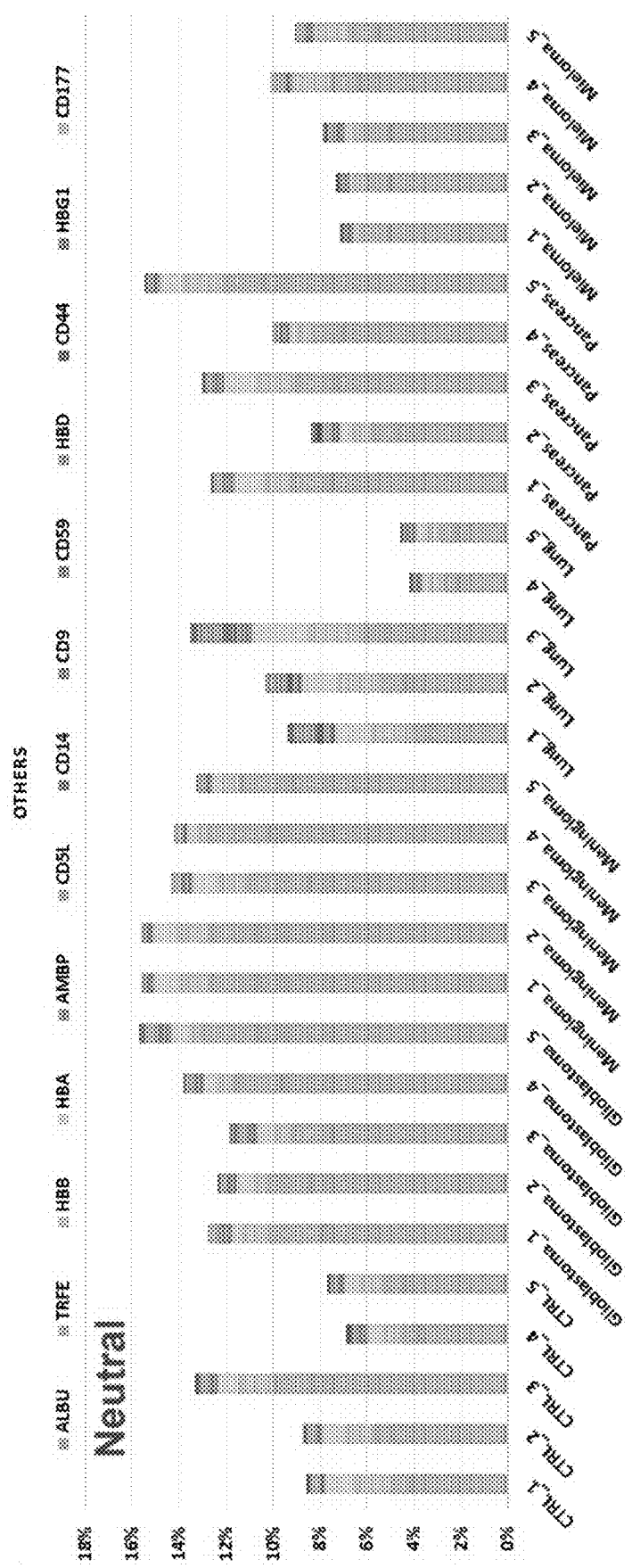
Figure 10A:
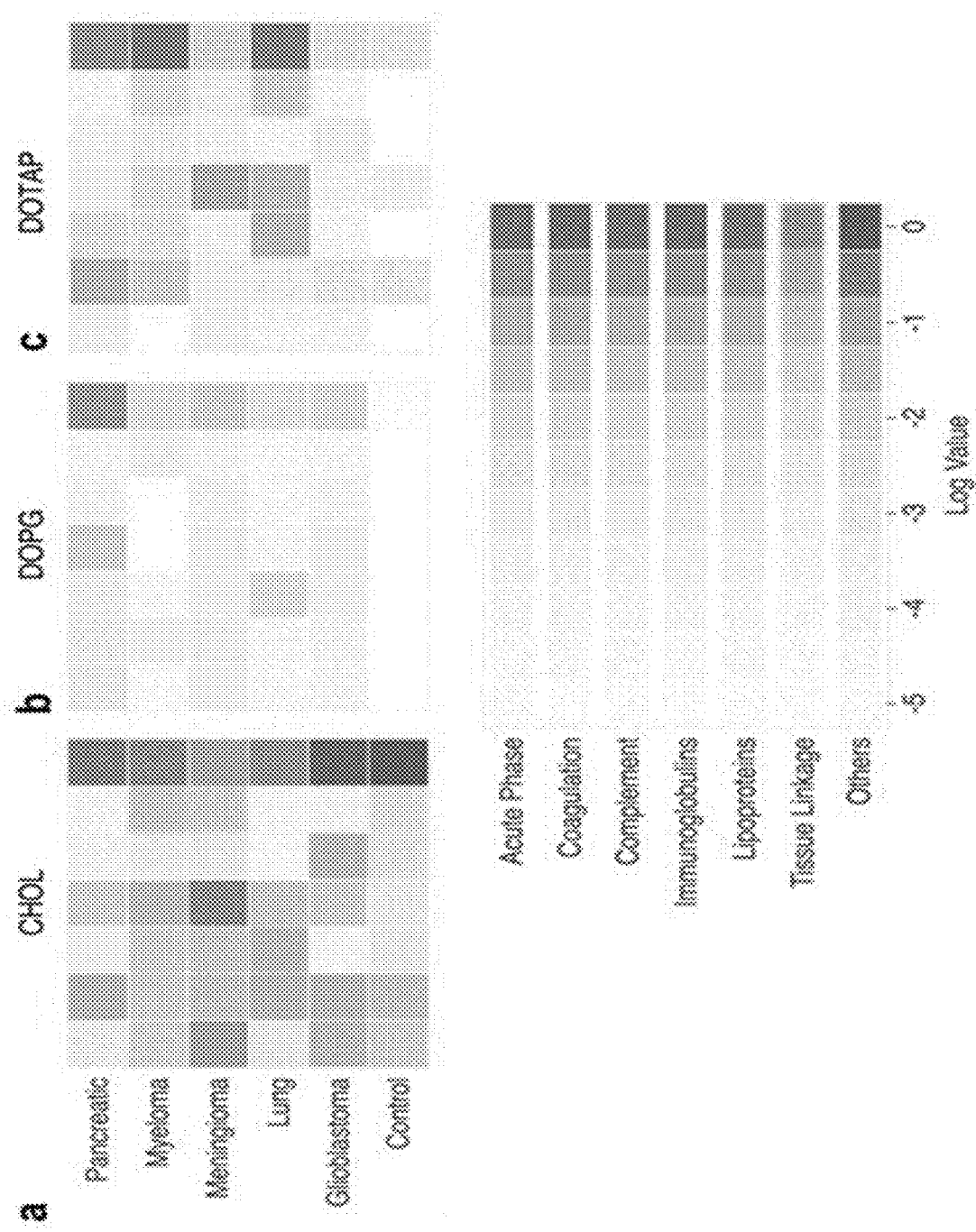
FIG. 10A. Protein importance for classification vs. percentage of proteins adsorbed on protein corona nanosystem. Panels (a)-(c) illustrate the importance of the observed protein-liposome interactions ('variables') in predicting specific cancers. Proteins are grouped by their physiological functions. Panels (d)-(f) illustrate the percentage of proteins adsorbed on each liposome. The protein-liposome groups that emerge as relevant to the prediction of a cancer are highly distinct across cancers (panels (a)-(c)). Moreover, this distinction is substantially more pronounced than the variance in the percentage of proteins adsorbed on the liposomes across those cancers (panels (d)-(f)).

For different biological families of proteins (the same as those used in FIG. 3A-F), we calculated the overall importance in discriminating different cancer types (FIG. 10A, (a)-(c)). The results suggest that different families of proteins are important in detecting different cancers. For example, acute phase proteins were relatively important in detecting meningioma, and lipoproteins were relatively important in detecting glioblastoma. Notably, these variations were distinct from the variations in the percentage of each category adsorbed onto the liposomes (FIG. 10A, (d)-(f)). Interestingly, these results are in good agreement with the biological function of these protein categories. For example, it is well-accepted that lipid metabolisms are substantially altered in glioblastoma compared to the healthy tissue, which may be the main reason for the observed substantial changes in the interaction of lipoproteins with liposomes (FIGS. 2C and 10A). Details on the numbers of identified proteins and unique proteins in the corona composition of different liposomes and their combinations are provided FIG. 10B.

Figure 10B:
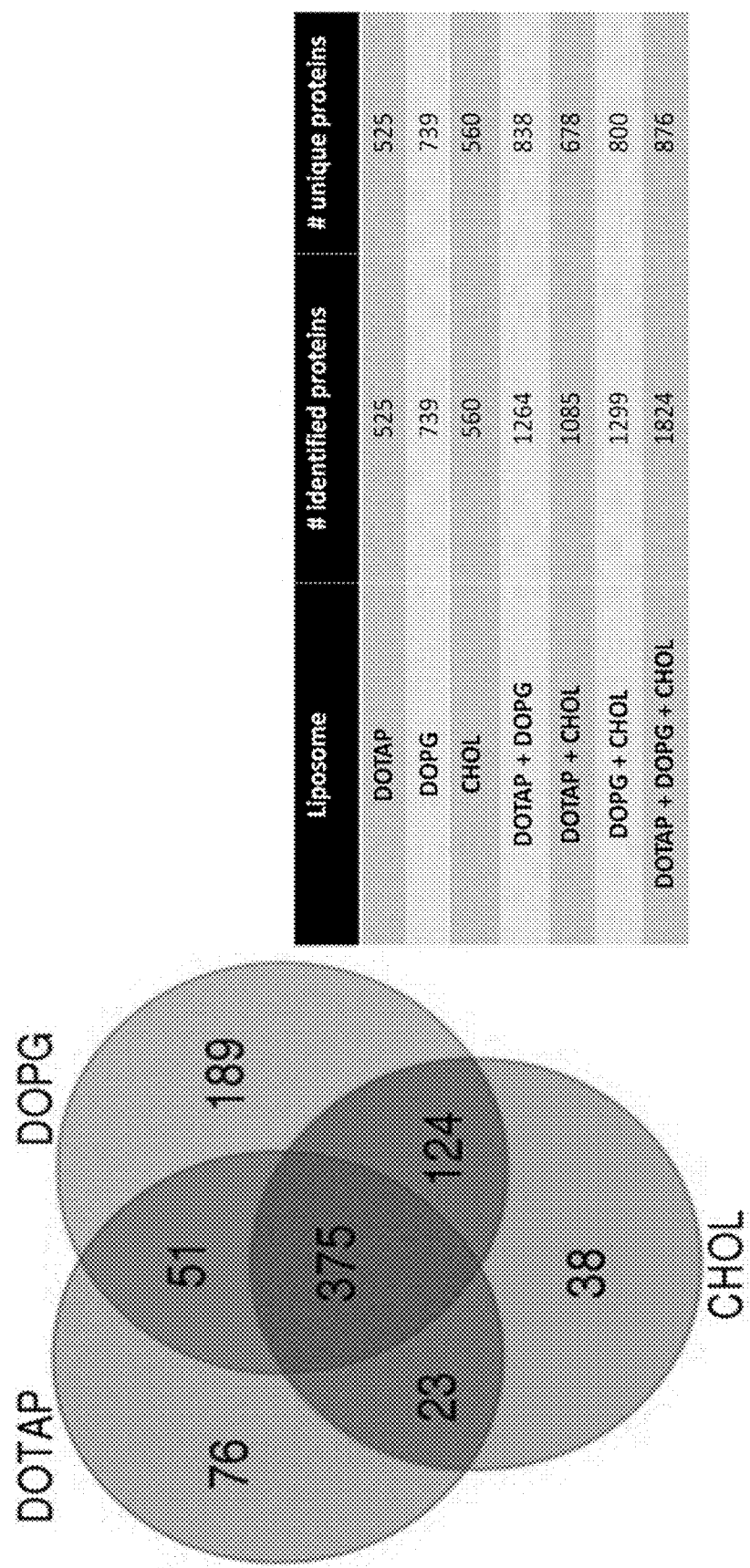
FIG. 10B. Venn diagram showing the number of unique proteins identified in the corona composition of each liposome and their combinations (the table at right presents the same data numerically).
Figure 10C:
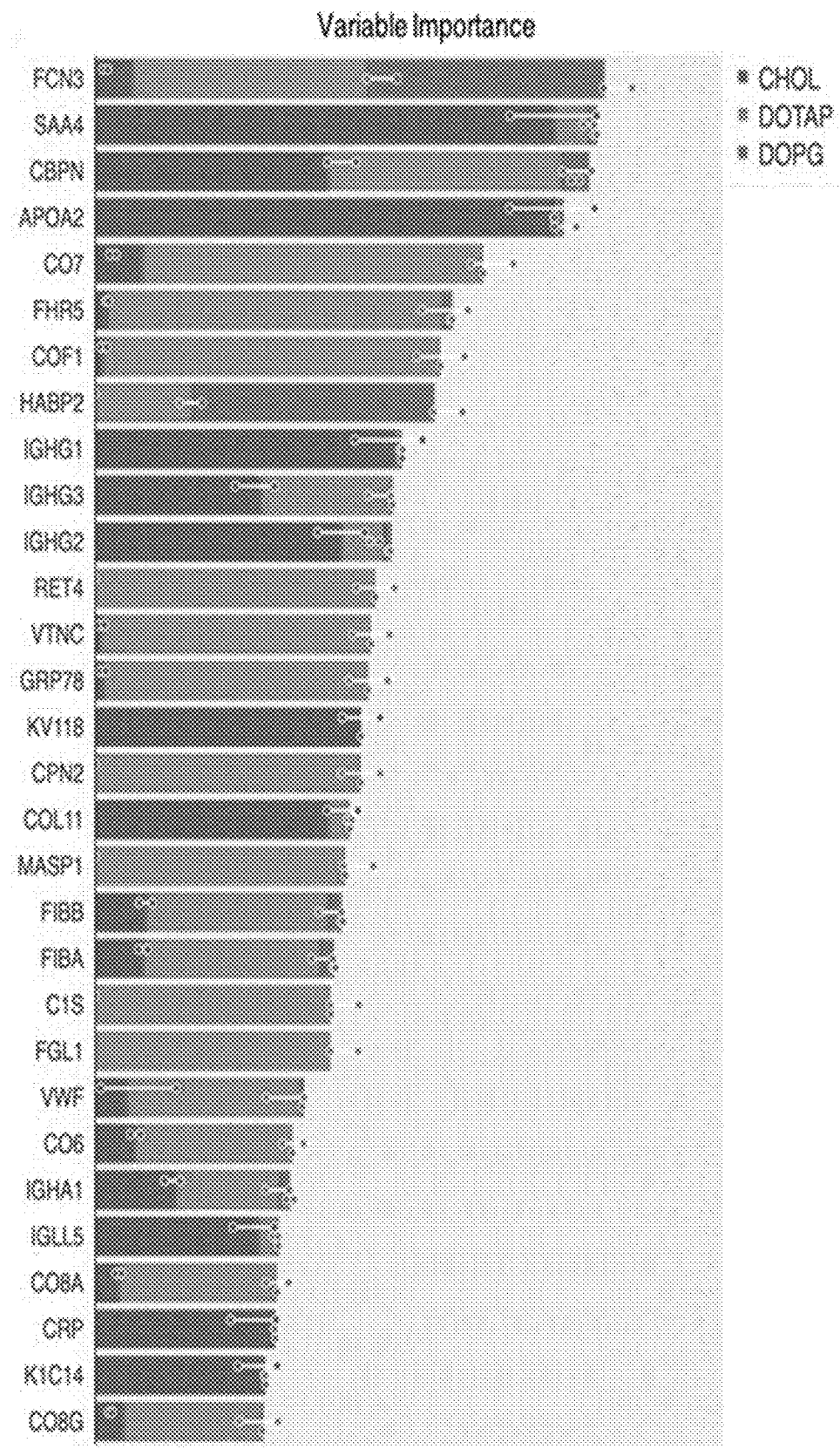
FIG. 10C. Variable importance for classification. Each row indicates the importance of a specific protein. The three dots on each row correspond to the importance of the observed interaction with each of the three liposomes. Horizontal lines straddling the dots indicate the 25th and 75th percentiles of the importance across classifiers trained on 1000 random draws of the training set from the data. These confidence intervals indicate the 'stability' of the trained model in terms of the protein-liposome interactions upon which it crucially relies, with respect to random draws of data.

We also calculated the most important overall proteins (FIG. 10C and Table 5). These proteins were detected in combinations of all three liposomes, again showing the critical role of multi-liposomes in the nanosystem. We also evaluate the robustness of this set of 'important' proteins across the classifiers estimated on the 1000 splits of training data discussed earlier. Specifically, FIG. 10B shows the 25th to 75th percentiles of the importance scores for the 30 most important proteins on average. These show that the set of important proteins is robust to the split of data used for model training. Among these most important proteins (see Table 5), some have been recognized as playing critical roles in cancer development. For example, Ficolins (both Ficolin 2 and Ficolin 3) are serum pattern recognition molecules with opsonic properties with a substantial capacity to regulate complement activation. The serum concentrations of Ficolin 3 have been demonstrated to be higher in patients with ovarian cancer than in healthy subjects. Moreover, Ficolin 3 was identified in a differential proteomic analysis of prostate cancer serum, suggesting a role for this protein in prostate cancer as well. On the other hand, it is well established that Apolipoprotein A2 and its isoforms are overexpressed in prostate cancer serum and that the concentration of acute-phase proteins (e.g., complement proteins) can change by ≥25% in the presence of inflammatory disorders such as cancer. A clear association between cancer and the hemostatic system has long been documented. Hemostasis modulates blood flow by regulating the adhesion of platelets and deposition of fibrin. Several proteins involved in hemostasis have been connected to the regulation of angiogenesis. Among these, fibrinogen is the main protein in the hemostasis process and has been found in many tumors; it modulates angiogenesis and tumor growth and has been implicated in metastasis formation. Indeed, plasma levels of fibrinogen have been used to forecast clinical outcomes in patients with non-metastatic renal cell carcinoma, and to predict distant metastasis in pancreatic cancer.

Table 5. Information about the most important overall proteins, found to be detected on combinations of all three liposomes. * The concentrations are values obtained using spectral counting from the plasma proteome database (see website at plasmaproteomedatabase.org).

TABLE 5

Information about the most important overall proteins, found to be detected on combinations of all three liposomes.

| Uniprot entry name | Protein description | Function | Amount in plasma* |
|---|---|---|---|
| FCN3 | Ficolin-3 | complement activation, lectin pathway | 1 µg/ml |
| SAA4 | Serum amyloid A-4 protein | chemoattractant activity | 30 µg/ml |
| CBPN | Carboxypeptidase N catalytic chain | protects the body from vasoactive and inflammatory peptides containing C-terminal Arg or Ly | 720 ng/ml |
| APOA2 | Apolipoprotein A2 | acute inflammatory response, lipid transport | 750 µg/ml |
| CO7 | Complement component C7 | regulator of innate and adaptive immune response | 2.6 µg/ml |
| FHR5 | Complement factor H-related protein 5 | complement activation, alternative pathway | 11 ng/ml |
| COF1 | Cofilin-1 | actin cytoskeleton organization | 140 ng/ml |
| HABP2 | Hyaluronan-binding protein 2 | serine-type endopeptidase activity | 1.1 µg/ml |
| IGHG1 | Immunoglobulin heavy constant gamma 1 | antigen binding | N.A. |
| IGHG3 | Immunoglobulin heavy constant gamma 3 | antigen binding | N.A. |
| IGHG2 | Immunoglobulin heavy constant gamma 2 | antigen binding | N.A. |
| RET4 | Retinol-binding protein 4 | retinol transporter | 580 µg/ml |
| VTNC | Vitronectin | cell adhesion | 35 µg/ml |
| GRP78 | 78 kDa glucose-regulated protein | ATPase activity | 100 ng/ml |
| KV118 | Ig kappa chain V-I region WEA | Antigen binding | N.A. |
| CPN2 | Carboxypeptidase N subunit 2 | regulation of complement activation | 2 µg/ml |
| COL11 | Collectin-11 | mannose binding, complement activation | N.A. |
| MASP1 | Mannan-binding lectin serine protease 1 | complement activation, lectin pathway | 240 ng/ml |
| FIBB | Fibrinogen beta chain | hemostasis | 706 µg/ml |
| FIBA | Fibrinogen alpha chain | hemostasis | 2.5 mg/ml |
| C1S | Complement C1s subcomponent | regulation of complement activation | 50 µg/ml |
| FGL1 | Fibrinogen-like protein 1 | hemostasis | 2.3 ng/ml |
| VWF | von Willebrand factor | hemostasis | 110 µg/ml |
| CO6 | Complement component C6 | regulation of complement activation | 40 µg/ml |
| IGHA1 | Immunoglobulin heavy constant alpha 1 | antigen binding | N.A. |
| IGLL5 | Immunoglobulin lambda-like polypeptide 5 | antigen binding | N.A. |
| CO8A | Complement component C8 alpha chain | regulation of complement activation | 70-90 µg/ml |
| K1C14 | Keratin, type I cytoskeletal 14 | structural constituent of cytoskeleton | 210 ng/ml |
| CRP | C-reactive protein | complement activation, classical pathway | 2 µg/ml |
| CO8G | Complement component C8 gamma chain | regulation of complement activation | 1.1 µg/ml |

*The concentrations are values obtained using spectral counting from the plasma proteome database (www.plasmaproteomedatabase.org).

To further probe the role of the important proteins identified by our machine learning approach, we searched for them in the Open Targets database, a platform for therapeutic target identification and validation. That database calculates a disease-association score for each protein based on evidence from various other databases (including GWAS Catalog, UniProt, Gene2Phenotype, Cancer Gene Census, IntOGen, Europe PMC, and Reactome) to derive a score on a scale of 0 (lowest) to 1.0 (highest) of disease association. Of the proteins listed, three have strong associations with cancers. Hyaluronan Binding Protein has a very strong general association (1.0) with cancers; Fibrinogen Beta Chain has a moderately strong association (0.4) with lung cancer; while Keratin, Type 1 cytoskeletal 14 is strongly associated (0.72) with prostate cancer. Almost all the other proteins in Table 5 have some degree of weak association (0.05-0.4) with various types of cancers. Hence, overall, the proteins have a linkage with known cancer associations.

Overcoming Variability in Single Measurements with Tensor Factorization

Figure 11:
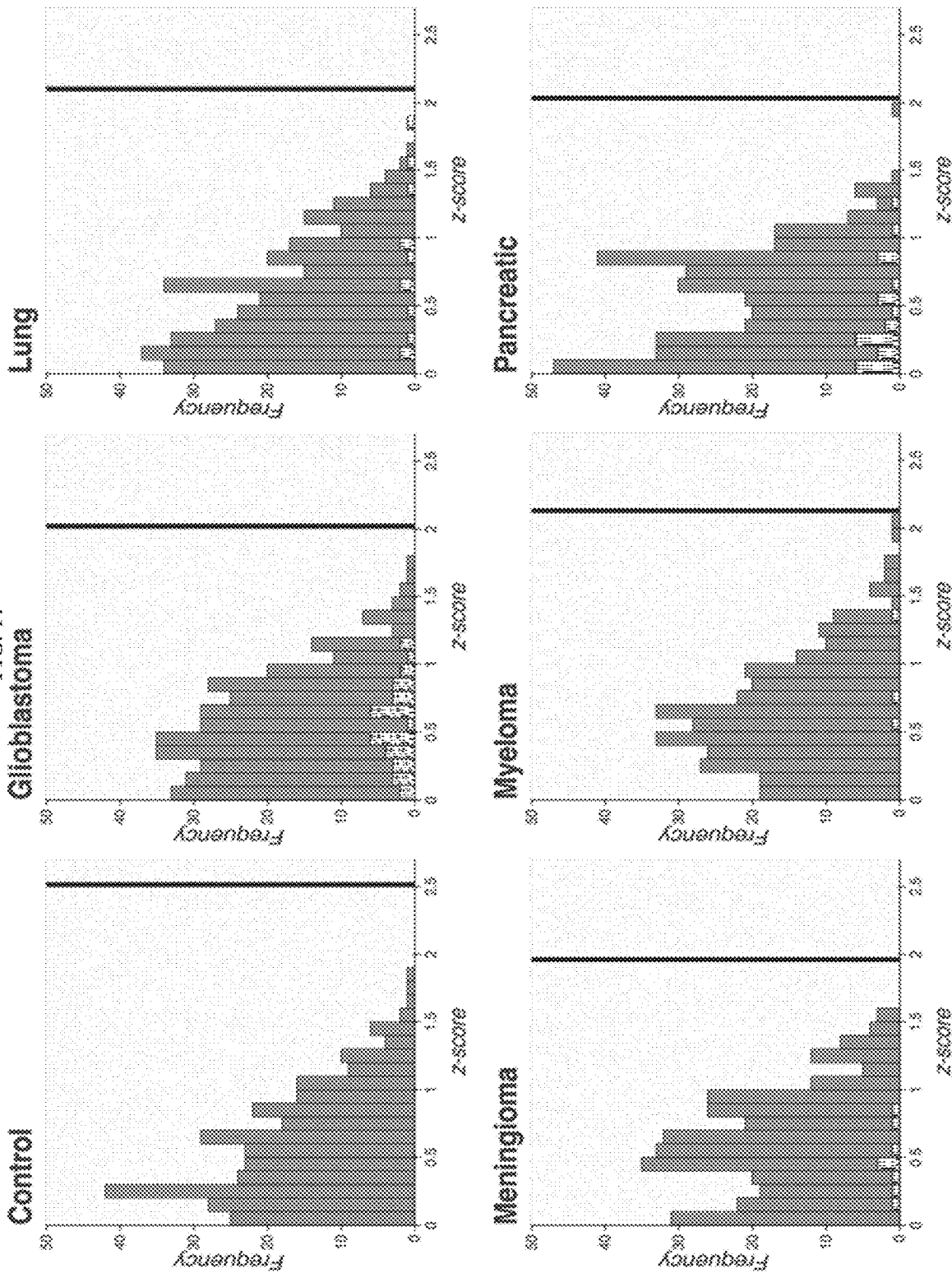
FIG. 11. Weighted averages of protein-liposome interactions classify cancers. Distribution of the absolute z-scores for each patient group, histogrammed across the 100 most abundant proteins (gray) and previously identified biomarkers (white with black dots). The long black bar corresponds to the z-score for a linear combination of the protein-liposome interactions. A large z-score for a specific protein-liposome interaction indicates that the group 'separates' from the rest of the patients in that particular interaction. The figure consequently indicates that whereas no individual protein-liposome interaction suffices to classify any of the cancers, their weighted combinations induce a separation of between 2 and 2.5 standard deviations.

Due to significant variability in patient populations, along with noise introduced through measurement error, we found that any single protein was insufficient for classification. For each of the 100 most-abundant proteins (yielding 3*100=300 variables), we calculated the average absolute z-score of that proteins concentration in the observed corona across patients of each cancer type. A higher z-score for a cancer type on a given protein indicates that this protein may be useful in detecting this cancer type. FIG. 11 (blue bars) shows a histogram of these average absolute z-scores for each cancer type and the healthy group. We also measured average absolute z-scores for proteins previously linked to these specific cancer types, which are displayed in the same histogram in FIG. 10 (light grey bars). Across all of these hundreds of variables, only a single protein has an absolute z-score above 2.0, and on only a single cancer type (Myeloma), suggesting that no single protein suffices for accurate classification.

The tensor decomposition that precedes our construction of a random forest effectively serves the role of computing a small number of weighted averages of protein composition in the observed corona on a given sample. This average is across all proteins and nanoparticles in a given plasma sample, and serves the role of mitigating the variability in the observed concentration of any given protein. For example, in FIG. 11 (long, black bars), the average absolute z-score for one of these weighted averages is plotted for each cancer type. The absolute z-scores of these weighted averages are significantly higher than those of any single variable. In addition to the intuition this provides for how our approach overcomes variations in a single protein across samples with the same indication, this de-noising also materially impacts our ability to classify. Absent de-noising, simply training a random forest classifier on the raw corona data would yield a classification accuracy of 94% (at a p-value of 0.07) as opposed to 96.2% (at a p-value of 0.04) reported in Table 4. For the cohort data reported in Table 7 de-noising enabled us to increase classification accuracy from 92% (at a p-value of 0.04) to 94.1% (at a p-value of 0.01).

Dependence of Classification Accuracy on Data

Our final evaluation on the 45 non-cohort patients was of the value of data. Our original classifier was trained on 5 samples per cancer type. To measure the value of including more or less training data, we repeated the classification procedure (splitting the data into training and testing samples, training a classifier on the training samples, and measuring performance on the testing samples, all done 1000 times) for a varying number of training samples per class, ranging from four to six (Table 6. Classification accuracy, sensitivity, and specificity all increased with increasing numbers of training samples. With six training samples per class, overall accuracy reaches 96.8% (i.e. an overall error rate of 3.2%). This strongly suggests that accuracy, sensitivity, and specificity will continue to increase as more data are included in training the classifier.

Detection of low-abundance proteins in human plasma requires depletions of highly abundant proteins and post-depletion plasma-fractionation strategies; however, even using these depletion strategies, plasma proteomics has not been robustly successful in early detection of cancers. The results obtained with our system indicate that, in contrast to human plasma proteins, the protein corona composition contains a wide range of less-abundant and very rare plasma proteins, without need for depletion (which may cause

TABLE 6

Classification accuracy improves with more data. (Column 2) Overall classification error when the training set consists of four, five, and six samples from each cancer, and associated p-values. Both classification error and the associated p-values improve with additional samples from each cancer. (Columns 3-12) Sensitivity and specificity for glioblastoma, lung, meningioma, myeloma, and pancreatic cancers when the training set consists of four to six samples. Experimental results are averaged over 1000 independent draws of a training set with four healthy patients, and four to six patients with each cancer type. p-values are for the null hypothesis of at least two classification errors.

| | | Glioblastoma | | Lung | | Meningioma | | Myeloma | | Pancreatic | |
|---|---|---|---|---|---|---|---|---|---|---|---|
| # Samples | Accuracy | Sens. | Spec. | Sens. | Spec. | Sens. | Spec. | Sens. | Spec. | Sens. | Spec. |
| Four | 94.4 (0.14) | 98.8 | 98.1 | 91.2 | 100.0 | 93.0 | 96.7 | 100.0 | 99.9 | 88.0 | 98.4 |
| Five | 96.2 (0.04) | 100.0 | 98.9 | 94.0 | 100.0 | 98.5 | 97.0 | 100.0 | 100.0 | 87.4 | 99.5 |
| Six | 96.8 (0.01) | 100.0 | 99.4 | 96.6 | 100.0 | 98.9 | 97.0 | 100.0 | 100.0 | 87.8 | 99.6 |

Sampling of Low- and High-Abundance Plasma Proteins with Liposomes without the Requirement of Protein Depletion The multi-liposome protein corona nanosystem, using machine-learning techniques, produces a unique "fingerprint" protein pattern for each type of cancer and for healthy individuals. In pursuit of the mechanism underlying the unique capacity of the protein corona in cancer identification and discrimination, we have thoroughly analyzed the corona composition for the contribution of both high- and low-abundance proteins, and compared those outcomes with the concentration of corona proteins in human plasma. In this regard, the contribution of each protein (e.g., protein X) to the corona composition and plasma was normalized with respect to albumin using (total peptides of albumin in protein corona)/(total peptides of protein X in protein corona) and (concentration of albumin in plasma)/(concentration of protein X in plasma), respectively. It is noteworthy that we manually searched the concentrations of identified corona proteins in plasma using an online proteome database (see website at plasmaproteomedatabase.org). As the total peptides of the albumin in the protein corona are proportional to albumin's total weight in the protein corona, dividing these peptides to the peptides of protein X is comparable with the ratio of albumin concentration to concentration of protein X in plasma. As shown in FIG. 12, we found that the plasma concentrations vary over 10 orders of magnitude (in log-log scale), while the liposomes detect these same proteins over 4-5 orders of magnitude. In other words, we revealed that the protein corona composition has a great capacity to concentrate a wide range of low-abundance proteins (≤100 ng/mg) and very rare proteins (≤10 ng/mg). This means that obtaining data on highly abundant proteins in the protein corona does not interfere with detection of peptides derived from less-abundant and rare proteins. It is worth noting that most of the detected proteins are low-abundance, rare, or unknown/unreported proteins. Participation of the low-abundance proteins in the corona composition is mainly due to the exchange of corona proteins with low affinity for proteins with higher affinity and slower adsorption kinetics.

unintended removal of low-abundance proteins/biomarkers). In addition, we found several proteins in the protein corona whose concentrations in human plasma are unknown/unreported, possible due to their very low concentration in human plasma. More specifically, anionic, neutral, and cationic liposomes account for 323, 189, and 155 of proteins with unknown/unreported plasma concentration, respectively). The contribution of these proteins to the protein corona is indicated by the rectangular box on the right in FIG. 12.

The use of multi-liposomes (with distinct surface properties) provides a unique opportunity to increase the detection depth of the low-abundant proteins and very rare proteins (see FIG. 12), which substantially enhanced the sensitivity, specificity, and predictive accuracy of the protein corona nanosystem. Each liposome provided different patterns of contributed proteins with a strong dependency on cancer type.

Cancer Detection and Discrimination Among Cohort Samples

Finally, to investigate the ability of the protein corona nanosystem to detect cancers at very early stages, we used cohort plasma (obtained from the NIH-funded Golestan Cohort Study; details are provided in the Methods section) from healthy people who were diagnosed several years after plasma collection with pancreatic, lung, and brain cancers. We followed the same procedure, performing 1000 experiments. In each experiment, we partitioned the data into 12 (4 each from 3 cancer types) training samples and 3 testing samples (one each from 3 cancer types). Observations were denoised via the previously described procedure, and then a random forest classifier was trained on the training samples. Finally, overall accuracy, sensitivity, and specificity were measured on the test samples (Table 7). Overall accuracy was 94.1% (an error rate of 5.9%), with a p-value of 0.01 for the null hypothesis of an overall accuracy <66.7% (thus rejected with 95% confidence). Sensitivities across the three cancer types ranged from 83.2% to 100.0%, and specificities ranged from 91.6% to 100.0%. These relatively high values suggest that the protein corona array can successfully detect cancers at their earliest stages.

TABLE 7

Overall Classification Accuracy, Sensitivity, and Specificity for Cohort Samples. (Column 2) Overall classification accuracy for one, two, and three liposomes. Both classification error and the associated p-values improve with the addition of liposomes to the nanosystem. (Columns 3-8) Sensitivity and Specificity for Brain, Lung, and Pancreatic cancers, respectively. Again, sensitivity and specificity improve with the addition of liposomes. Experimental results are averaged over 1000 independent draws of a training set comprising 12 patients, with evaluation of the remaining 3 patients. p-values are for the null hypothesis of a classification accuracy <66.7%.

| Array Size | Accuracy | Brain | | Lung | | Pancreatic | |
| --- | --- | --- | --- | --- | --- | --- | --- |
| | | Sens. | Spec. | Sens. | Spec. | Sens. | Spec. |
| One | 75.4 (0.23) | 74.7 | 86.1 | 90.7 | 90.9 | 60.8 | 86.9 |
| Two | 80.5 (0.11) | 92.3 | 89.7 | 76.3 | 92.1 | 73.1 | 88.9 |
| Three | 94.1 (0.01) | 100.0 | 100.0 | 83.2 | 99.6 | 99.2 | 91.6 |

We also performed the same experiments with smaller subsets of liposomes, including each liposome individually, and all three unique sets of two liposomes. Again, overall accuracy, sensitivities and specificities were shown to increase dramatically as the number of liposomes increased, again indicating the value of the array system.

Discussion

No prior study using protein corona or any other approach for fractionation of the plasma proteome has enabled concurrent multi-cancer screening with acceptable specificity, sensitivity, and predictive accuracy. This is the first time a sensor array has been developed with the specificity, sensitivity and predictive accuracy for not only cancer, but specific cancer subtypes.

The fractionation of the plasma proteome by the protein corona has been demonstrated to be unrelated to the abundance of specific plasma proteins and occurs instead via many factors including protein affinity for the nanoparticle surface through a wide range of forces including Coulomb forces, London dispersion, hydrogen-bond acidity and basicity, polarizability, lone-pair electrons, and protein-protein interactions between participating proteins in the corona structure. Protein corona composition has been shown to be dynamic and initially dominated by abundant proteins including albumin, immunoglobulin, and fibrinogen, which together with 19 other proteins comprise over 99% of the protein mass in the plasma proteome. The remaining 1% of the plasma proteome is comprised of over 10,000 proteins; a subset of these proteins with higher affinities and/or lower absorption kinetics for the nanoparticle surface compete with the high-abundance proteins for inclusion in the corona composition. In addition to the exchange of the proteins with higher binding affinity for those with lower binding affinity at the surface of nanoparticles, there is a chance for a contribution by other low-affinity proteins in the outer protein corona layer due to their favorable protein-protein interactions with the already-formed protein corona layer. This means that the exchanged low-abundant proteins may be able to direct the formation of the protein corona toward adsorption of more low-abundance proteins.

Herein we analyze for the first time the relative concentration capacity of the protein corona in enriching low-abundance proteins (defined as <100 ng/ml), demonstrating that many of these proteins are at concentrations <10 ng/ml and approaching 1 pg/ml. More importantly, we show that many of these proteins play a crucial role in cancer identification and discrimination via machine-learning approaches. The role of the protein corona in concentrating a wide range of low-abundance and very rare proteins may go a long way towards overcoming the main reasons behind the limited success of current mass spectrometry techniques (including LC-MS/MS) in early detection of cancers, as these techniques can detect proteins at a dynamic range of 4-6 orders of magnitude. In other words, the protein corona composition enables sampling across a vast dynamic range of the plasma proteome, which can substantially enhance the depth of protein coverage without protein depletion. Since the protein corona obtained from a single nanoparticle constitutes at most several hundred distinct proteins (a small subset of the total proteome), we postulated that using multi-nanoparticles with distinct physiochemical properties might create additional dimensions of proteomic information: 1) each additional nanoparticle with distinct physicochemical properties potentially enables the recruitment of additional unique low-abundance proteins (FIG. 12); 2) corona proteins that overlap more than one nanoparticle surface participate at different corona contribution percentages, and thus alter the concentration and identity of other participating corona proteins; and $3^{rd}$) both unique and overlapping corona protein information from each nanoparticle serve as unique variables, and therefore provide more data to our machine learning approach. Combining more nanoparticles for plasma fractionating and proteomic analysis provides significantly more information for cancer detection and discrimination with superior sensitivity, specificity, and prediction accuracy compared to fewer nanoparticles (Table 4). Conceptually, our multi-nanoparticle approach is similar to the olfactory system, in which the specificity of odorant recognition originates from the pattern of responses from several hundred highly cross-reactive olfactory receptors, where any one receptor provides incomplete information but the combination is highly specific in identifying a given odorant (i.e., in humans ~400 active receptors can detect and differentiate ~10,000 odorants, and in dogs ~1200 active receptors can detect ~1,000,000 odorants). Similar approaches have also been used by other investigators to detect and differentiate among diverse families of analytes, various foods and beverages, pathogenic bacteria and fungi, biomolecules, and even nanoparticles themselves.

Three different cross-reactive liposomes (with negative, neutral, and positive surface charges) were used whose protein corona profiles were measured after exposure to the plasma of individual patients who had one of five cancers: lung, pancreas, myeloma, meningioma, or glioblastoma. To identify and discriminate among cancers using the protein corona nanosystem outcomes, we used a well-defined random forest machine learning approach. We have designated 1000 different sets of samples as training (i.e., plasmas with known cancers and healthy conditions) or testing (i.e., blind plasmas) samples to ensure that our protein corona nanosystem is robust and accurate for cancer detection with excellent predictive accuracy. Although no one protein corona composition from a single nanoparticle was specific for any particular cancer type with acceptable predictive accuracy (i.e., 86.0% with p-value of 0.43 for the classification error lower than 87.5%), we found that the pattern of corona composition derived from the multi-liposomes provides a unique "fingerprint" for each type of cancer with excellent predictive accuracy (i.e., 96.2% with p-value of 0.04 for the classification error lower than 87.5%). These results, based on the deep analysis of the human proteome using multi-liposome protein corona characterization and machine learning, confirmed the promise of this system for unambiguous identification and discrimination of cancers and error-free discrimination against healthy subjects with excellent specificity (from 97.0% to 100.0%).

To probe the capacity of the protein corona nanosystem for very early detection of cancers, cohort plasma samples were used. These samples were collected from healthy people who were diagnosed with lung, pancreas, or brain cancer eight years after plasma collection. The outcomes of the protein corona nanosystem, using plasma from 15 patients in the cohort study, revealed that our approach accurately identified and discriminated cancers even in these pre-diagnosis cohort samples, for which cancer detection was not possible with current alternatives. In agreement with our findings on the fresh plasma samples, multi-liposome plasma sampling provided superior classification accuracy (94.1% vs. 75.4%) and specificity [i.e., brain (100.0% vs. 86.1%) lung (96.6% vs. 90.9%), and pancreatic (91.6% vs. 86.9%)] compared to single-liposome sampling. It is noteworthy that the protein corona profiles of the cohort samples were different compared to the previous fresh cancer samples. This is mainly because of the long-frozen storage (around 10 years) of the cohort samples, as the samples were collected at the time of screening of healthy individuals. It is increasingly accepted that long-term storage of plasma samples can strongly affect the concentration and integrity of a subset of proteins, in turn altering the protein corona composition and decreasing the sensitivity of our protein corona nanosystem. Therefore, the maximal sensitivity of the nanosystem may be realized when using fresh plasma, either as part of a cancer screening or cancer work-up after diagnosis. The value in the latter setting may be that changes in the protein corona pattern over time may provide valuable information relevant to early tumor recurrence or the presence of residual disease after tumor resection.

In summary, we present proof-of-concept that the multi-nanoparticle protein corona nanosystem has considerable potential for increasing the depth of protein detection and thus a unique capacity to accurately detect and discriminate cancers even at their earliest stages, when existing technologies fail to detect disease. The multi-nanoparticle protein corona pattern derived from our protein corona nanosystem provides a unique multivariate "fingerprint" for cancer detection, which is not possible when the protein corona of only a single nanoparticle is analyzed. Furthermore, the protein corona pattern represents the collective enrichment of a wide range of plasma proteins (including both abundant and rare proteins) using distinct nanoparticles, clearly distinguishing it from other multivariate whole-plasma proteomic approaches that have failed to produce suitable results for early cancer detection. The depth of protein detection (the main limitation of protein analysis in human plasma) and predictive accuracy of the nanosystem may be further enhanced by using additional nanoparticles with different physicochemical properties. The successful predictive outcome of our machine-learning and protein-corona characterization approach for both blind fresh plasmas and retrospective cohort plasmas provides a suitable foundation for subsequent prospective studies in cancer. Furthermore, the utility of the multi-nanoparticle protein corona nanosystem can be applied to other important human diseases for which early detection can significantly improve both longevity and quality of life.

Liposomes were prepared as described in Example 1A.

Human plasma collection, preparation, and storage was performed as described in Example 1A.

Cohort plasma samples were prepared as described in Example 1A.

Transmission electron microscopy (TEM). Liposome formulations have been characterized by TEM as reported previously. Briefly, 10 µl of each sample was deposited onto Formvar-coated grids, negatively stained using 1% uranyl acetate, washed with ultrapure water, and air-dried. Measurements were performed with a Zeiss Libra 120, and image analysis was performed with Image) software.

Size and zeta-potential was determined as detailed in Example 1A.

Protein assay was carried out as described in Example 1A.

Protein identification and quantification was performed as in Example 1A. Unweighted spectrum counts (USC) were used to assess the consistency of biological replicates in quantitative analysis, and normalized spectrum counts (NC S) were used to retrieve protein abundance.

Statistical Analysis. All statistical analyses in the main text were performed in Python using the scikit-learn, numpy, and scipy packages, and figures and graphs were created using the bokeh package in Python, along with Microsoft Excel, XLSTAT, and MATLAB.

Data matrices. For all 60 plasma samples (45 non-cohort and 15 cohort), labeled as i=1, . . . , 60, a data matrix $X_i$ (with 3 rows and ~900 columns) was generated such that each row of the matrix corresponds to the protein abundances of a single nanoparticle, as obtained from the protein corona nanosystem. As a preprocessing step, we converted the protein abundances to relative protein abundances (RPA) by normalizing the rows of all of the matrices.

Classification and Clustering

Tensor factorization. We treated the data as a three-mode tensor, the first two modes corresponding to nanoparticles and proteins, and the third mode corresponding to plasma samples; this is essentially equivalent to stacking the observation matrices corresponding to each sample, $X_i$, on top of each other. The data were de-noised via a low Tucker rank tensor factorization (135,136,137) using code implemented in Python for this project (available for academic use upon request). Each matrix $X_i$, is approximated by a tensor decomposition that takes the form $$X_i \sim US_iV^T,$$

where U is a matrix whose rows can be viewed as latent features corresponding to each of the nanoparticles, and similarly V is a matrix whose rows can be viewed as latent features corresponding to each of the proteins; these latent features are shared across all of the data matrices. Finally, each $S_i$ is a matrix encoding interactions between nanoparticle and protein features, and these are allowed to be unique between samples. We estimated this decomposition in two steps: we (a) estimated U and V via a truncated singular-value decomposition on the mode-1 and mode-2 unfoldings of the tensor, and then given these estimates, we (b) fit each $S_i$ matrix separately via a least-squares calculation.

Random forest classification. The random forest model is a well-known machine learning algorithm for classification. A random forest is made up of multiple decision trees that each make simple classification decisions based on relatively few variables. These trees are created (or "trained") with different, randomly drawn subsets of variables so that it is likely that no two trees are identical. Given a new sample, each tree is traversed top-down until a set of training samples is reached at the bottom. Using the forest as a whole for classification amounts to having the multiple decision trees "vote" on a label (in this case, one of five cancer types, or healthy), where each tree's vote is made from the labels of the bottom set of training samples. For our own algorithm, each random forest consisted of 1000 decision trees and was trained using the scikit-learn package. Importance scores were also calculated using the same package.

Example 2. Additional Sensor Array Construction for Detection of Diseases

A sensor array consisting of 12 different cross-reactive nanoparticles including three liposomes, three superparamagnetic iron oxide nanoparticles, and six gold nanoparticles are made. These types of liposomes (DOPG (1,2-dioleoyl-sn-glycero-3-phospho-(1'-rac-glycerol)), DOTAP (1,2-Dioleoyl-3-trimethylammonium-propane)-DOPE (dioleoylphosphatidylethanolamine), and CHOL (DOPC-Cholesterol)) with negative, neutral, and positive surface charges are synthesized according to our previous reports. Ultra-uniform PEG-coated superparamagnetic iron oxide nanoparticles 20 μm in size and of various PEG molecular weights (i.e., 300, 3000, and 6000) are obtained from Micromod®. Gold nanoparticles, with core size of ~2 nm, and different surface functionalities are synthesized.

All of the nanoparticles are the same size but have different surface properties, which are expected to form significantly different protein corona compositions in response to the plasma of patients developing various types of cancers. The sensor array probes the capability of the protein corona sensor array to identify and discriminate among cancer types via the patient's plasma proteins, as described in Example 1.

Samples from a wide range of cancers including lung, pancreas, myeloma, meningioma, glioblastoma, esophageal squamous cell carcinoma, and gastric adenocarcinoma are probed. Protein corona arrays based on different nanoparticles (liposomes, iron oxide, and gold) are designed to probe the variation in biomolecule fingerprint among various cancer types. The sensor assay will also allow for the identification of proteins that are markers for specific types of cancers, including new and unknown biomarkers for different cancer cell types. The pattern recognition that can be determined based on the different types of cancer or the stage of cancer.

A wide range of human plasmas from healthy people that were later diagnosed with various types of cancers several years after plasma collection will be analyzed. The plasma samples were collected through a NIH-funded cohort study, named the Golestan Cohort Study, performed by the National Cancer Institute (NCI) in the USA, the International Agency for Research on Cancer (IARC) in France, and the Tehran University of Medical Sciences (TUMS) in Iran. This study involved the collection and storage of plasma from 50,000 healthy subjects. Over 1,000 of these subjects went on to develop various types of cancers in subsequent years. The samples are stored at IARC and being used by our team for analysis. These important plasma samples provide us a unique opportunity to probe the capacity of our innovative protein corona sensor array for early detection of cancers. In addition, we will also assess and identify proteins useful for the identification and discrimination of these cancers.

We believe that the outcomes from applying this innovative sensor array to cohort plasma samples will not only be instrumental in the detection and screening of cancers at early stages but also help identify novel protein markers involved in cancer development. Our sensor array component choices have more specific capability compared to other developed methods to provide fingerprints for a wide variety of proteins in a non-specific, cross-reactive manner for identification and discrimination of cancers.

The Hard Corona Profiles of the Sensor Array Elements are Probed Using Plasma from Patients with Cancers at Intermediate and Advanced Stages:

The composition of the protein corona that forms on the surface of sensor array elements is strongly dependent on the physicochemical properties of those nanoparticles and, at the same time, can be strongly affected by the type of disease present in the donor of the human plasma used for incubation. To prepare the corona-coated nanoparticles, the 12 nanoparticles prepared are incubated with human plasma (separately) of nine types of cancers (lung, pancreas, myeloma, myeloid leukemia, meningioma, glioblastoma, breast, esophageal squamous cell carcinoma, and gastric adenocarcinoma) and isolated from free proteins via a well-defined centrifugation approach. Centrifugation is usually performed at 13000 g for 30 min at 15° C. The supernatant will be removed and the collected particles would be redispersed in 500 microlitter of PBS. The procedure will be repeated to get the loosely attached proteins removed. In order to remove the loosely attached proteins from the surface of nanoparticles, the collected nanoparticles will be redispersed in cold PBS (15° C.) and collected via centrifugation. The size and charge of the corona-coated nanoparticles will then be determined using DLS/Nanosight and compared to their initial values obtained in buffer. Quantitative evaluation of the total protein adsorbed onto the nanoparticles will be performed via the BCA or NanoOrange assay, while qualitative shotgun proteomics analysis identify the proteins adsorbed onto the surface of the 12 nanoparticles. Briefly, after separation of proteins from the surface of nanoparticles (according to the protocol (Saha, K.; Rahimi, M.; Yazdani, M.; Kim, S. T.; Moyano, D. F.; Hou, S.; Das, R.; Mout, R.; Rezaee, F.; Mahmoudi, M. ACS nano 2016, 10, (4), 4421-4430, incorporated by reference), proteins are injected into a liquid chromatography-mass spectrometry (LC-MS/MS) apparatus. The proteins are identified from the resulting data through screening of relevant databases. To obtain the total number of LC-MS/MS spectra for all peptides attributed to a matched protein, semi-"Polydispersity index from cumulant fitting quantitative assessment of the protein amount will be conducted through spectral counting (SpC). The normalized SpC (NpSpC) amounts of each protein identified in the LC-MS/MS spectra will be calculated using the following equation:

$$NpSpCk = \left( \frac{\frac{SpC}{(M_w)_k}}{\sum_{t=1}^{n} \left( \frac{Spc}{(M_w)_t} \right)} \right) \times 100$$

where NpSpCk is the normalized percentage of spectral count (i.e., raw counts of ions) for protein k, SpC is the spectral count, and Mw is the molecular weight (in kDa) of the protein k.

Develop Supervised and Unsupervised Clustering Analysis to Identify and Discriminate Among Cancers Using the Sensor Array Outcomes:

In order to investigate whether protein corona fingerprints (PCFs) of various sensor elements could be utilized as a biosensors and form unique patterns for different diseases (biomolecule corona signature), we have applied focused classification approaches to proteomic data from three liposomes' protein corona composition (cationic, anionic, and neutral) as described in Example 1.

Example 3. Conjugation of Nanoparticles to the Substrate to Make Sensor Arrays

Different types of particles may be used as nanoscale sensor elements in the practice of this invention. Further, different methods of conjugation of the nanoscale sensor elements to the substrate are provided. Additionally, the nanoscale sensor elements may be attached to substrate in different patterns.

Specific examples of different configurations of sensor elements on different substrates are exemplified in FIG. 15-43.

Example 4. Sensor Array Comprising Silica and Polystyrene Nanoparticles for Screening for Cancer This Example demonstrates that a sensor array of the present invention with different nanoparticles than those used in Example 1 is still able to detect cancer samples from healthy patient samples.

Utilizing the experimental protocol of Example 1, a sensor array was designed using functionalized silica and polystyrene particles. In this Example, a total of six nanoparticles: two nanoparticles types, i.e. polystyrene (P) and silica (S), with three different surface functionalization, i.e. none, amine modification and carboxyl modification (P—NH2, P—COOH, S—NH2 and S—COOH), were used.

Characterization of bare polystyrene and silica nanoparticles with different functionalization (none, amine modification (NK2) and carboxyl modification (COOH) is shown in FIGS. 44A-44D demonstrating their sizes, DLS and zeta potential of the bare particles and TEM images. The characterization of protein corona-coated polystyrene and silica nanoparticles with different functionalization is demonstrated in FIGS. 45A-45D with their sizes, DLS, zeta potential and TEMs of the protein-corona loaded polystyrene and silica nanoparticles.

Figure 46:
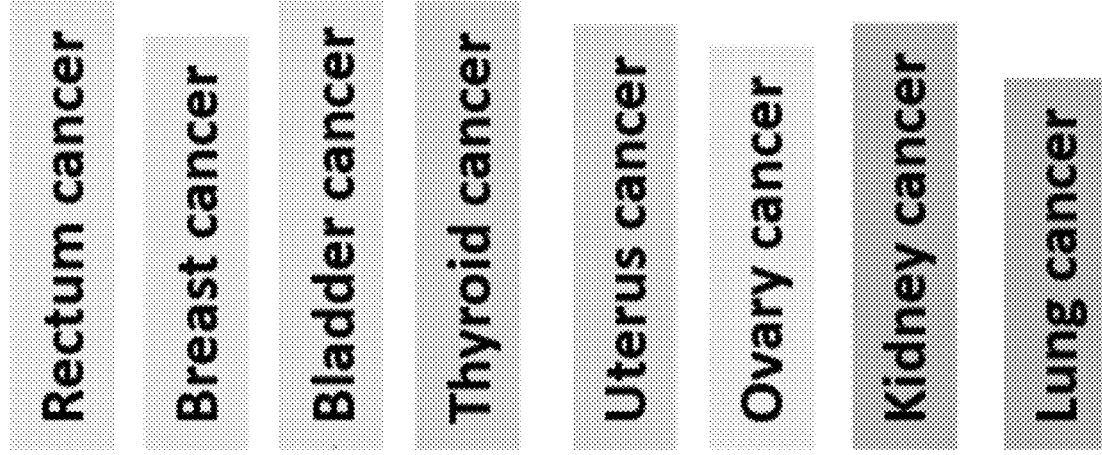
FIG. 46. A diagram of the type of cancer plasma samples screened with the polystyrene and silica nanoparticles.
Figure 47:
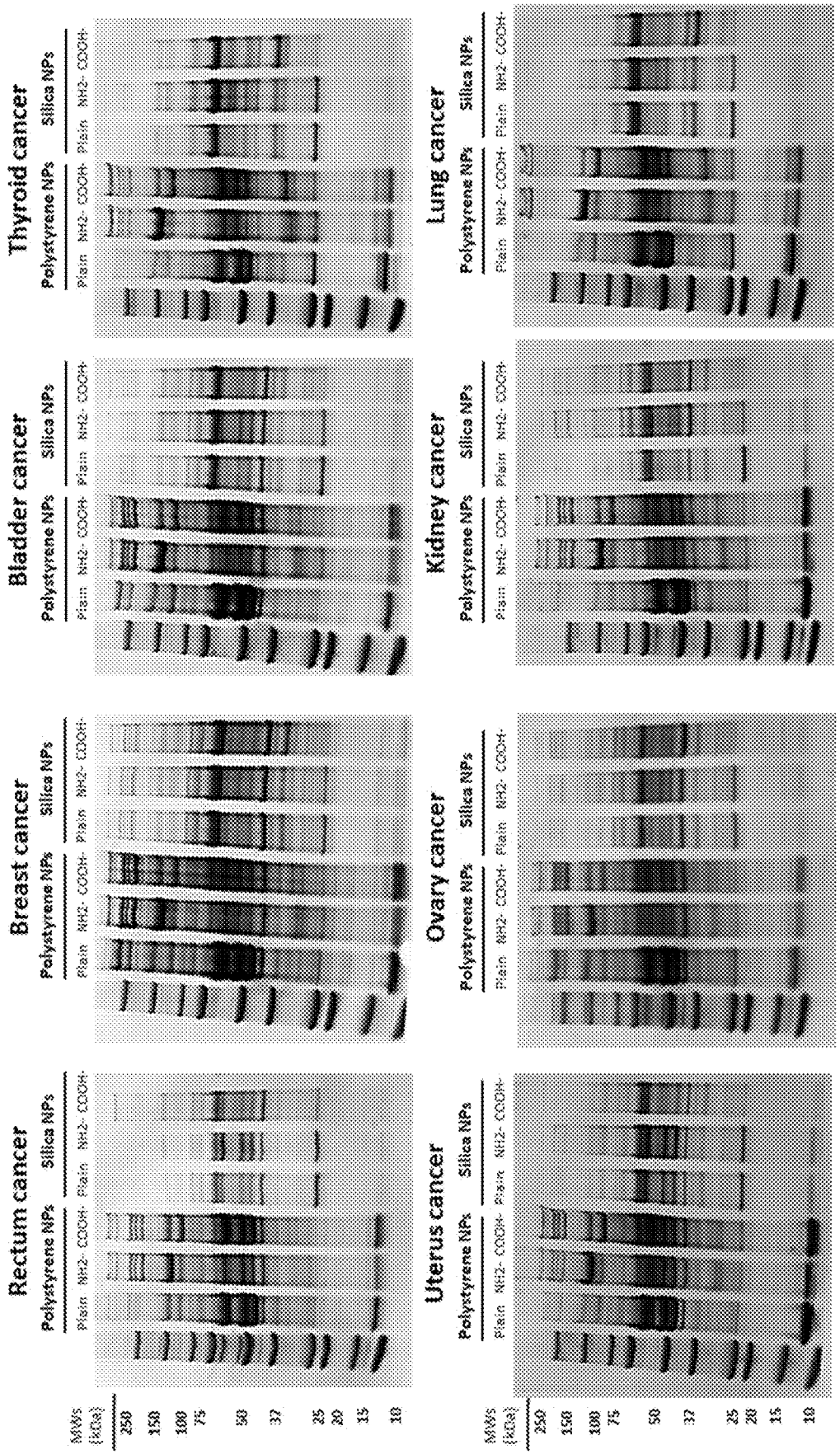
FIG. 47. Protein corona profiles of polystyrene and silica nanoparticles (100 nm) with plain, amine-modified and carboxyl-modified surfaces after incubation with plasma of patients having different cancers, analyzed by SDS PAGE.

The 6 nanoparticle sensor array was contacted with the plasma of healthy individuals or patients with rectum cancer, breast cancer, bladder cancer, thyroid cancer, uterus cancer, ovary cancer, kidney cancer (5 patients per cancer) as depicted in FIG. 46 by the method described in Example 1. The protein corona profiles of polystyrene and silica nanoparticles (100 μm) were analyzed by SDS PAGE. Comparison of the protein corona of plain, amine-modified and carboxyl-modified particles by SDS PAGE is shown in FIG. 47.

Figure 48:
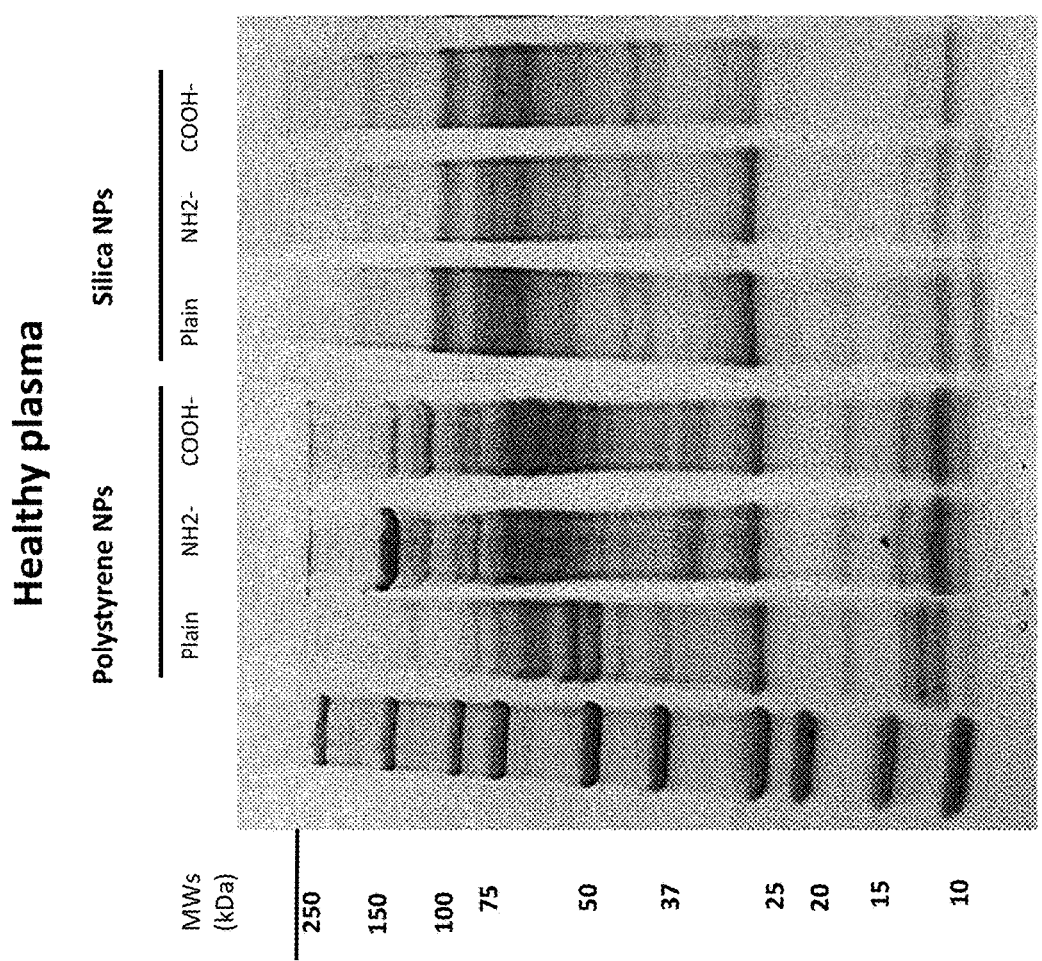
FIG. 48. Protein corona profiles of polystyrene and silica nanoparticles (100 nm) with plain, amine-modified and carboxyl-modified surfaces after incubation with plasma of healthy individuals as analyzed by SDS-Page FIG. 49. Plot depicting the separation of patients with cancer from the healthy individuals using a sensor array of the present invention.

The protein corona profiles for healthy plasma for polystyrene and silica nanoparticles (100 μm) analyzed by SDS-PAGE is shown in FIG. 48. Comparison of the protein corona of plain, amine-modified and carboxyl-modified particles.

Figure 49:
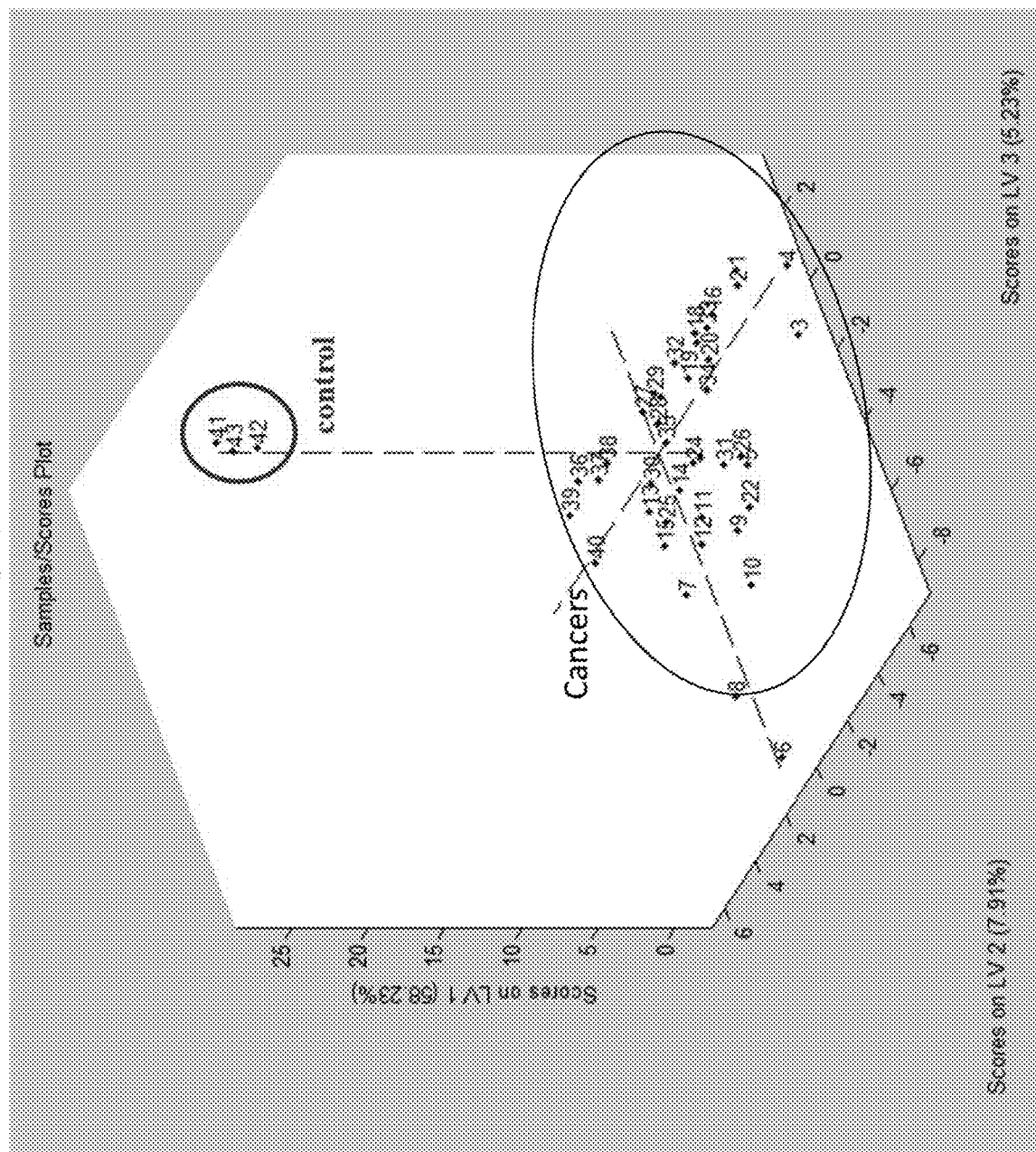

The data was analyzed as described in Example 1. The statistical analysis and clustering results are depicted in FIG. 49. As depicted, the healthy individuals are able to be identified and classified as compared to the cancer patients (healthy controls are in the orthogonal space vs the cancer patient samples as seen in FIG. 49).

This Example demonstrates that this sensor array using a six nanoparticle array can discriminate and detect a patient with cancer from a healthy individual.

Materials: Three differently functionalized silica particles were purchased by Kisker-Products (see website at kisker-biotech.com); three differently functionalized polystyrene particles were purchased by Polyscience, Inc. (see website at polysciences.com). All the particles had the same size (100 μm). Their morphology, average size, polydispersity index (PDI) and zeta potential were characterized by TEM, DLS and zeta potential measurements.

Experimental info: 1 h incubation in 50% human healthy plasma. SDS PAGE: 4-20% acrylamide 45 min 40 mA/gel. Staining: Colloidal Blue Comassie overnight. nanoparticles used: 0.5 mg).

Example 5. Protein Corona Sensor Array Nanosystem Identifies Coronary Artery Disease Coronary artery disease (CAD) is the most common type of heart disease and represents the leading cause of death in both men and women. Early detection of CAD is crucial in preventing death, prolong the survival and ameliorate quality of life of patients. This Example describes the non-invasive, sensor array nanosystem containing six nanoparticles for ultraprecise detection of CAD using specific PC pattern recognition. While the PC of a single nanoparticle do not provide the required specificity, the multivariate PCs across six distinct nanoparticles with different surface chemistries provides the desirable information to selectively discriminate each cardiovascular condition under investigation.

CAD is a chronic condition which starts during adolescence and progresses gradually throughout the affected person's entire life. It is characterized by the presence of atherosclerotic plaques in the coronary arteries. The genesis of atherosclerosis lies in the dysfunction of the endothelium: when subjected to stress stimuli and inflammatory factors (e.g. oxidative stress and hemodynamic forces), endothelial cells express surface adhesion molecules inducing the recruitment of circulating leukocytes and low density lipoproteins (LDL) containing cholesterol.[5] These events induce the formation of the atherosclerotic plaques, which narrows the coronary artery and thus impairs the blood flow. Depending on the velocity of the plaque's development and on the severity of the artery obstruction, the symptoms can culminate in myocardial infarction.[5]

An accurate and in-time diagnosis of CAD in at-risk subjects is very important to promptly start an ad hoc therapy and avoid further complications. Coronary angiography is to date the most accurate and trustable method for CAD diagnosis. However, inserting a catheter into an artery of the arm (or neck or upper tight) up to the heart is invasive, costly and causes many side effects, including infections, injury to the catheterized artery, allergy and excessive bleeding. Therefore, there is an urgent need to develop new tests for CAD detection. While several inflammatory biomarkers have been reported as useful for diagnosis, unfortunately, however, none of them are used in clinical practice, highlighting the still very prevalent need for new diagnostic tests. The inventors have developed a nano-based blood test as a new tool for diagnosis of CAD.

As demonstrated in the previous Examples for cancer, personalized PCs act as fingerprint of a given plasma condition. This Example uses the same approach to accurately define the formation of the atherosclerotic plaque, through its induced changes in plasma composition. Indeed, the plaque-associated cells (e.g. foam cells, macrophages, mast cells, monocytes, and T-cells) shed a wide range of biomolecules (e.g., cytokines, proteases, and vasoactive biomolecules) to the blood,[22] and thus may induce changes in the pattern of PC composition at the surface of various nanoparticles in respect to the PC of patients with no plaque formation.

This Example analyzed the PC formed around nanoparticles using plasma derived from i) patients who are diagnosed with CAD following coronary angiography (CAD), ii) patients with symptoms who had coronary angiography and their coronary vessels were found healthy (NO CAD), iii) restenosis (recurrence of CAD after treatment) and iv) healthy volunteers with no risk factors (e.g. family history, tobacco use, obesity, hypertension) for cardiovascular disease (CONTROL).

In order to have a wider spectrum of adsorbed proteins, the Example used six commercially available nanoparticles as the sensor array elements, with different composition and surface chemistry and/or functionalization, creating a 6 nanoparticles PC-based sensor array able to be used as an easy and non-invasive diagnostic test. This novel diagnostic CAD test to be used as pre-non-invasive screening for at-risk patients. Notably, these results demonstrated that PC patterns allowed the ultra-accurate discrimination between CAD, NO CAD, restenosis, and control patients, thus providing a novel, precise, non-invasive never developed before tool for blood-based diagnosis of CAD.

Results

Figures 50A, 50B:
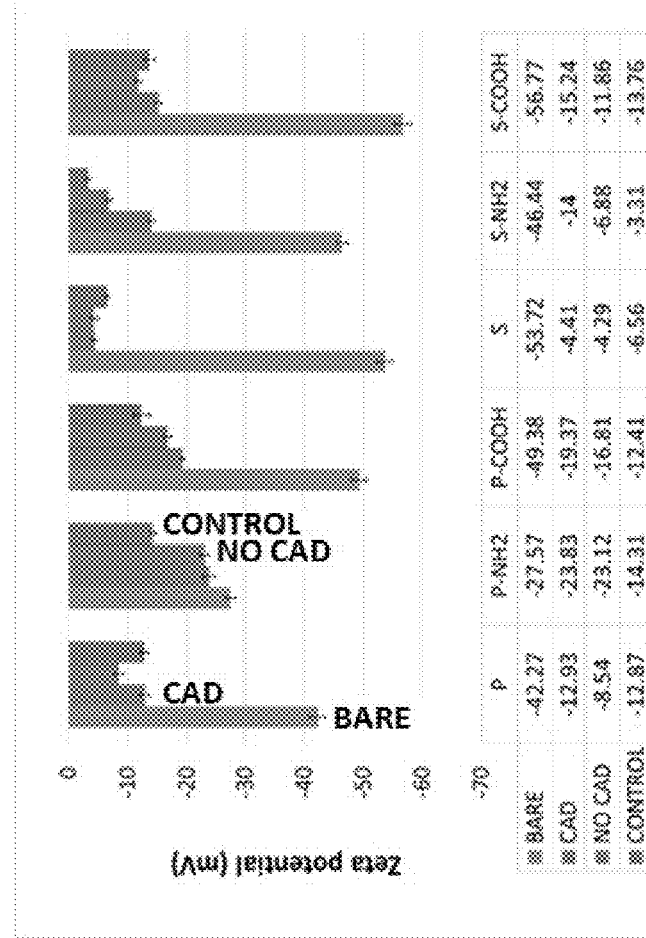
FIG. 50A. Characterization of polystyrene and silica nanoparticles used for CAD screening, showing profile of bare, CAD, NO CAD, and CONTROL treated nanoparticles.
FIG. 50B. Characterization of polystyrene and silica nanoparticles used for CAD screening, showing zeta potential for the different groups of nanoparticles.

In this Example, a total of six nanoparticles: two nanoparticles types, i.e. polystyrene (P) and silica (S), with three different surface functionalization, i.e. none, amine modification and carboxyl modification (P—NH2, P—COOH, S—NH2 and S—COOH), as described in FIG. 50 were used. The size, zeta potential and morphology of nanoparticles before and after incubation in plasma have been measured to compare differences in results between the synthetic identity of bare nanoparticles and their corresponding biological identity (PC-coated nanoparticles). Dynamic light scattering analysis showed that bare nanoparticles were all highly monodispersed, as demonstrated by polydispersity index 0.02, and homogeneous in size of about 100 nm, being in the range from 93 μm up to 120 μm (FIG. 50A). Following 1 h incubation with plasma of patients, sizes of all nanoparticles increased due to the presence of a layer of adsorbed proteins (PC), whose thickness and composition have been demonstrated to be dependent on protein concentration, surface properties and size of nanoparticles. All bare nanoparticles had negative surface charge (FIG. 50B), with those amine-functionalized slightly less negative than others due to the contribution of positive amine groups. These results were in line with specifications provided by the supplier and other studies. Modification with amine groups was not sufficient to switch the surface charge of silica and polystyrene nanoparticles characterized by all negatively charged residues on their surfaces at physiological pH.

Figure 50C:
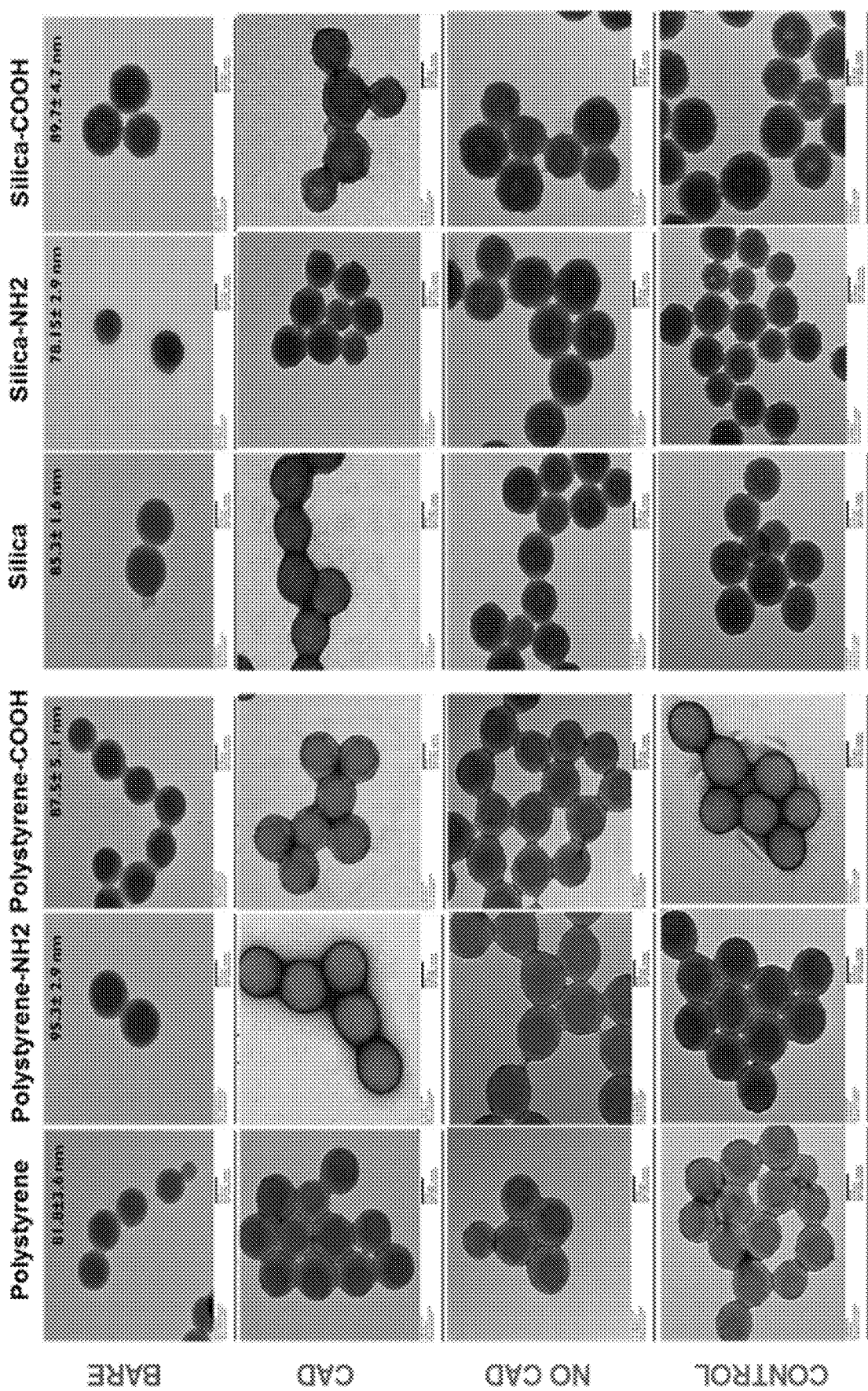
FIG. 50C. Characterization of polystyrene and silica nanoparticles used for CAD screening, showing TEM of the different nanoparticle in the CAD screen.
Figure 51A:
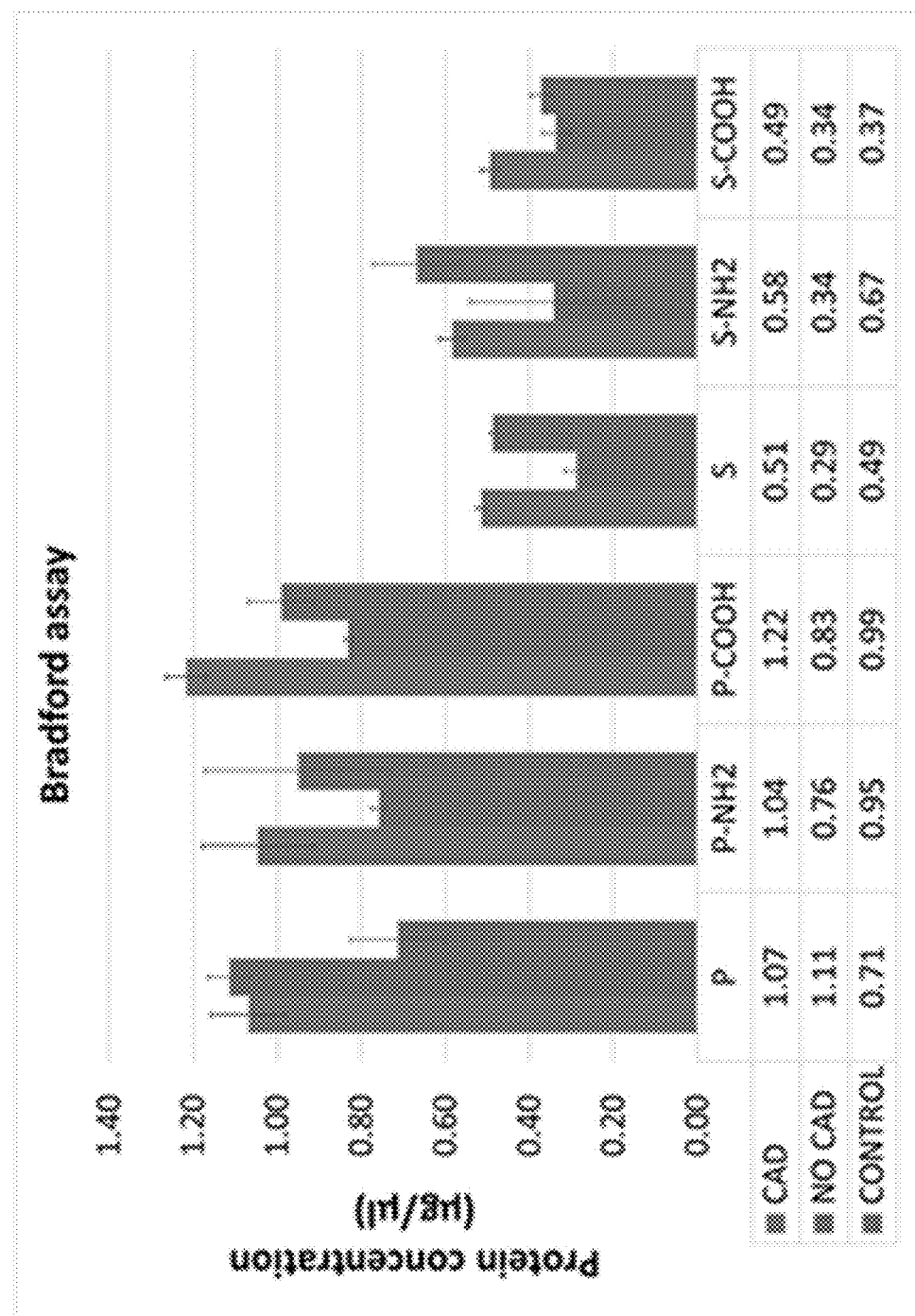
FIG. 51A. Protein concentrations of different protein corona from analysis of the CAD, NO CAD, and no risk for CAD (CONTROL) nanoparticles, showing Bradford assay of protein concentrations of the different protein coronas.
Figure 51B:
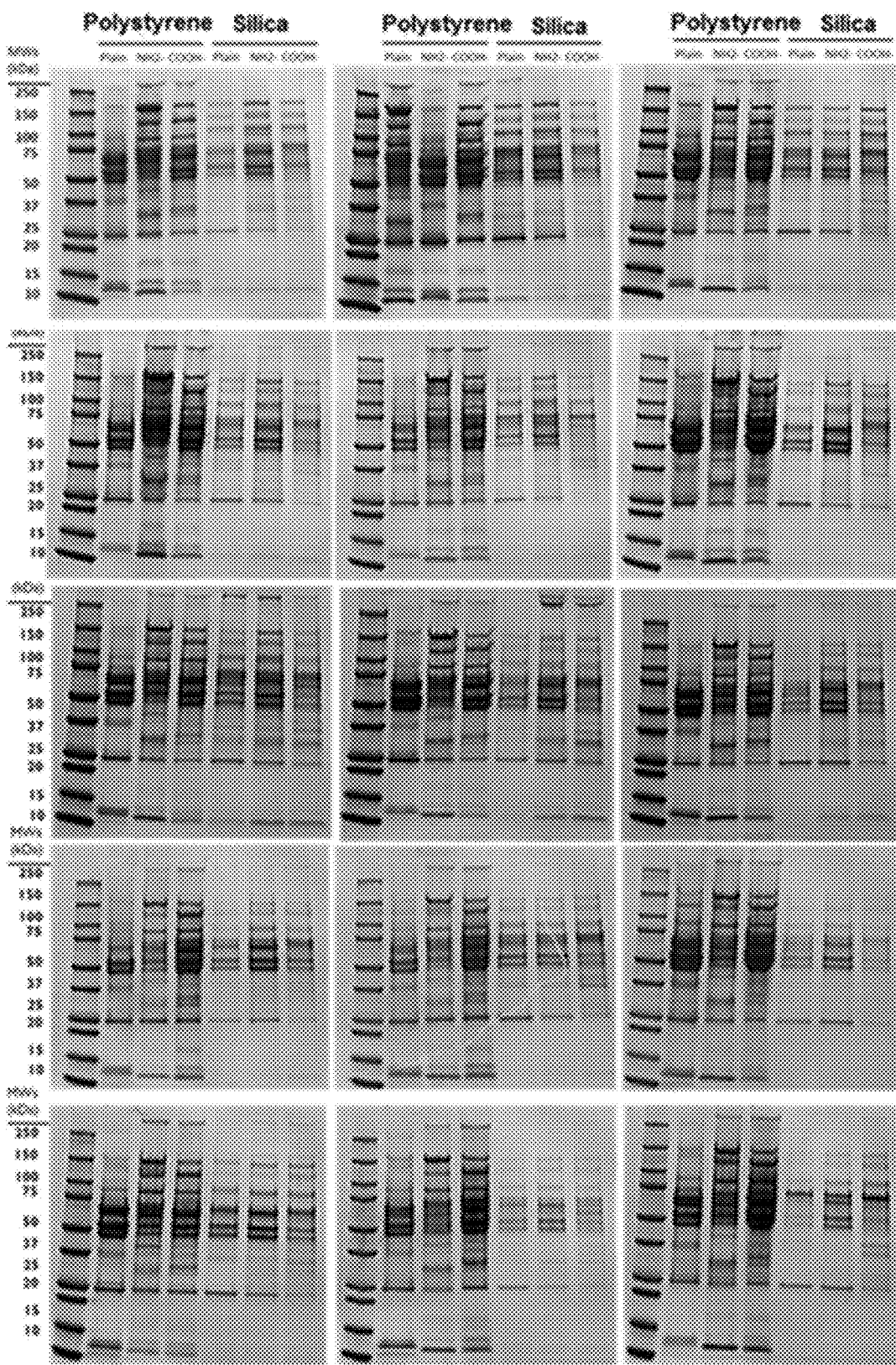
FIG. 51B. Protein concentrations of different protein corona from analysis of the CAD, NO CAD, and no risk for CAD (CONTROL) nanoparticles, showing personalized protein corona profiles have been analyzed and compared through 1D-SDS-PAGE.
Figure 51C:
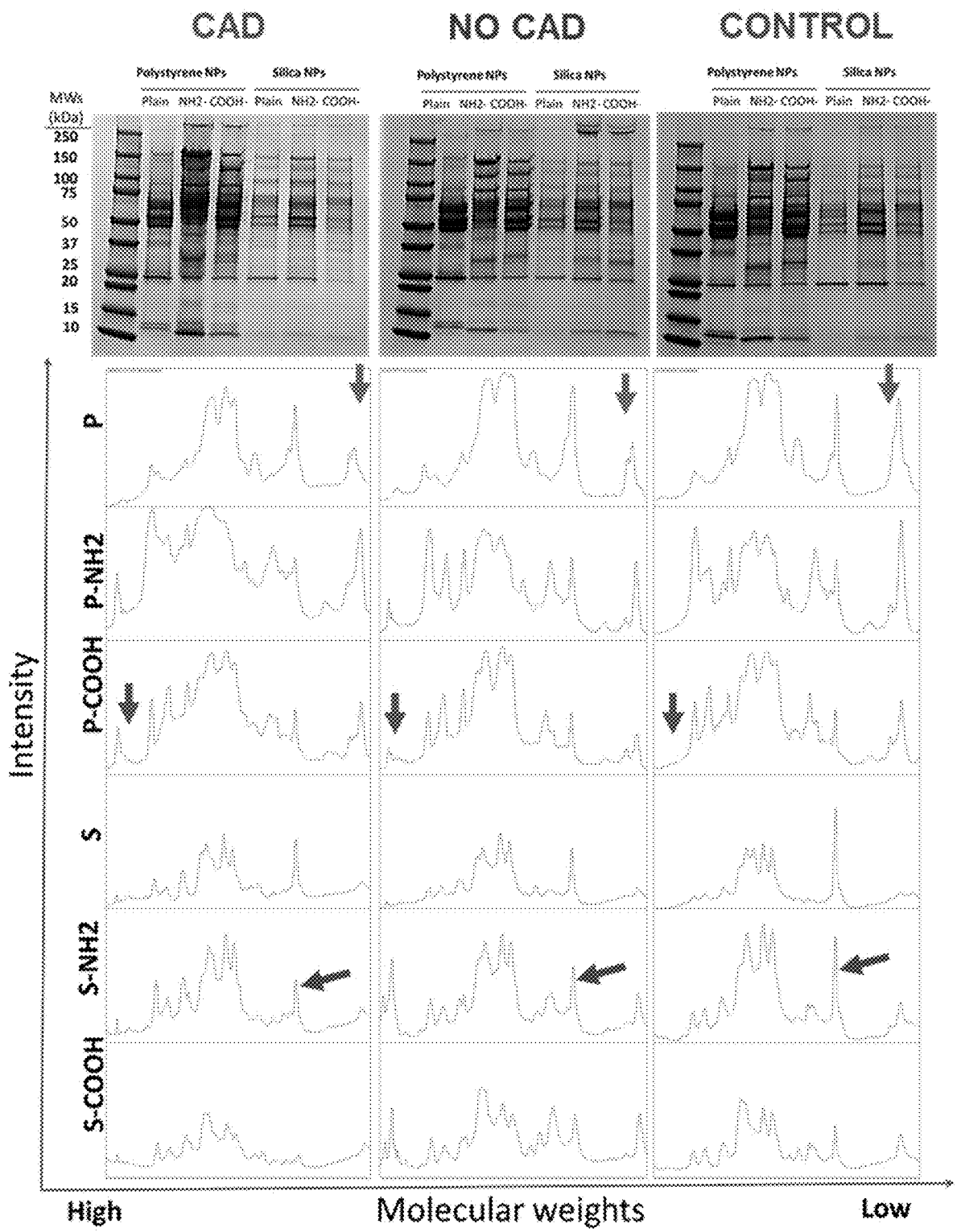
FIG. 51C. Protein concentrations of different protein corona from analysis of the CAD, NO CAD, and no risk for CAD (CONTROL) nanoparticles, showing gel analysis by densitometry determined differences in the amount of protein in the CAD, NO CAD and CONTROL PCs.
Figure 52:
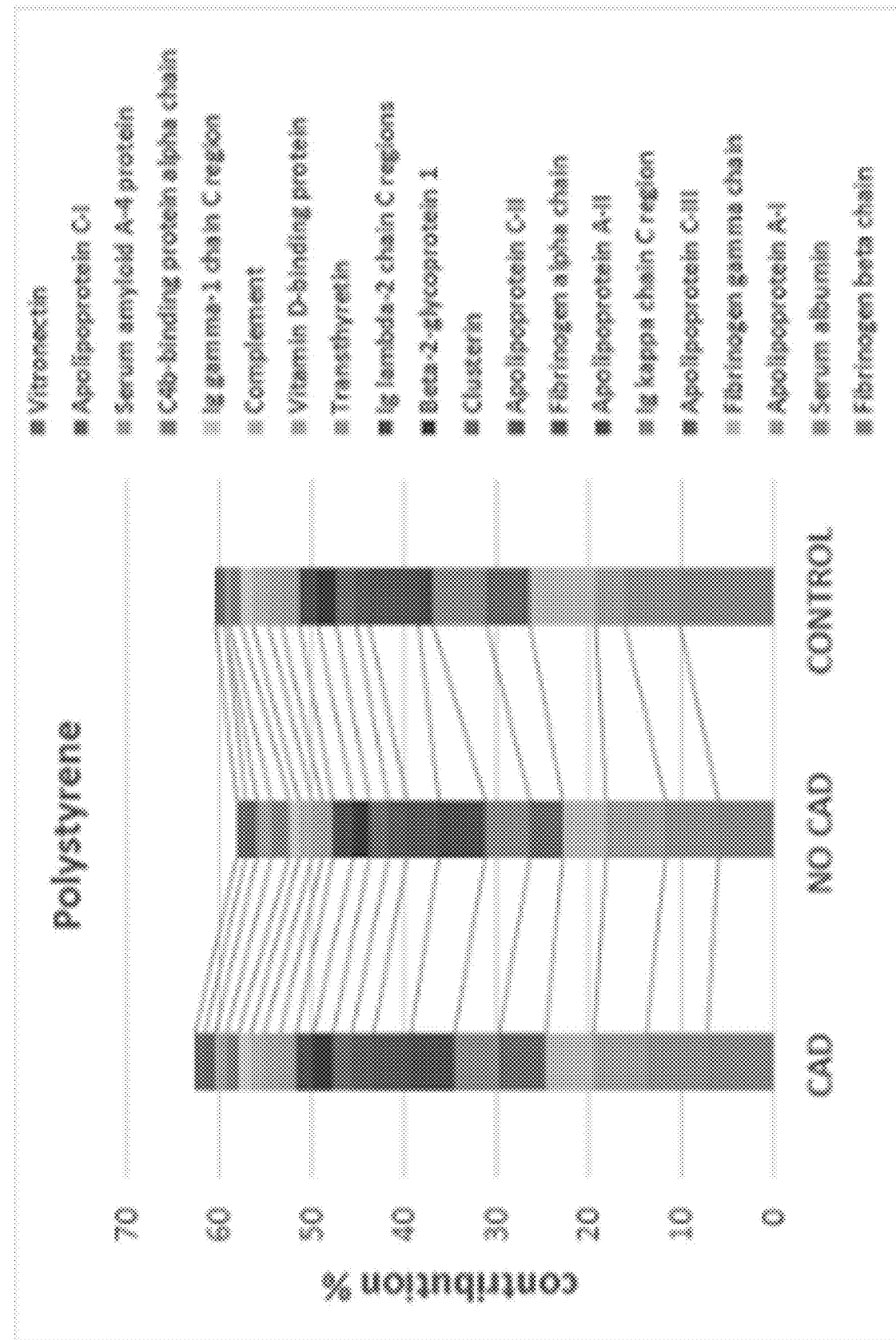
FIG. 52. Bars depicting the differences in the percentage contribution of the top 20 abundant proteins in the PCs.
Figure 52:
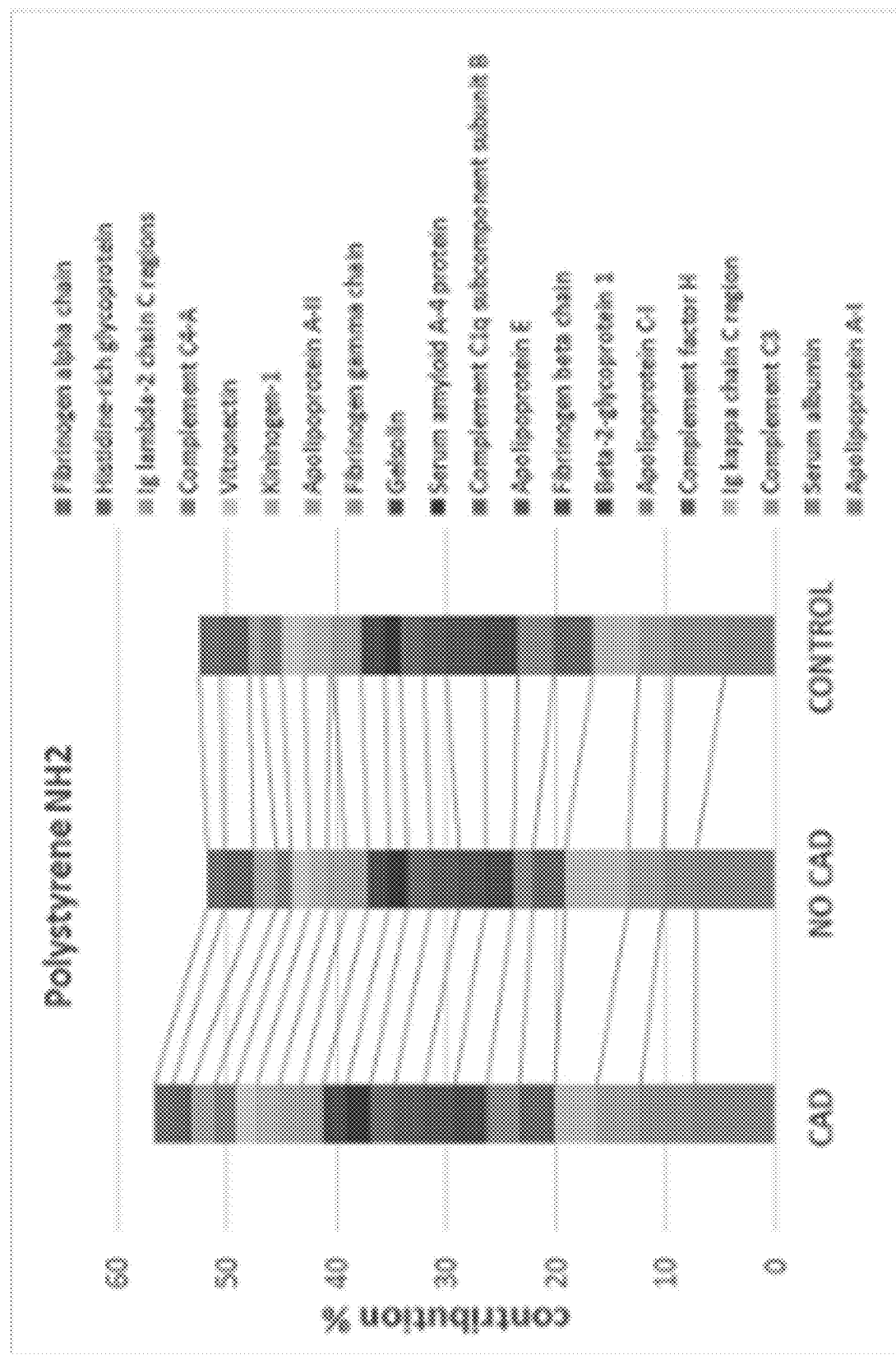
Figure 52:
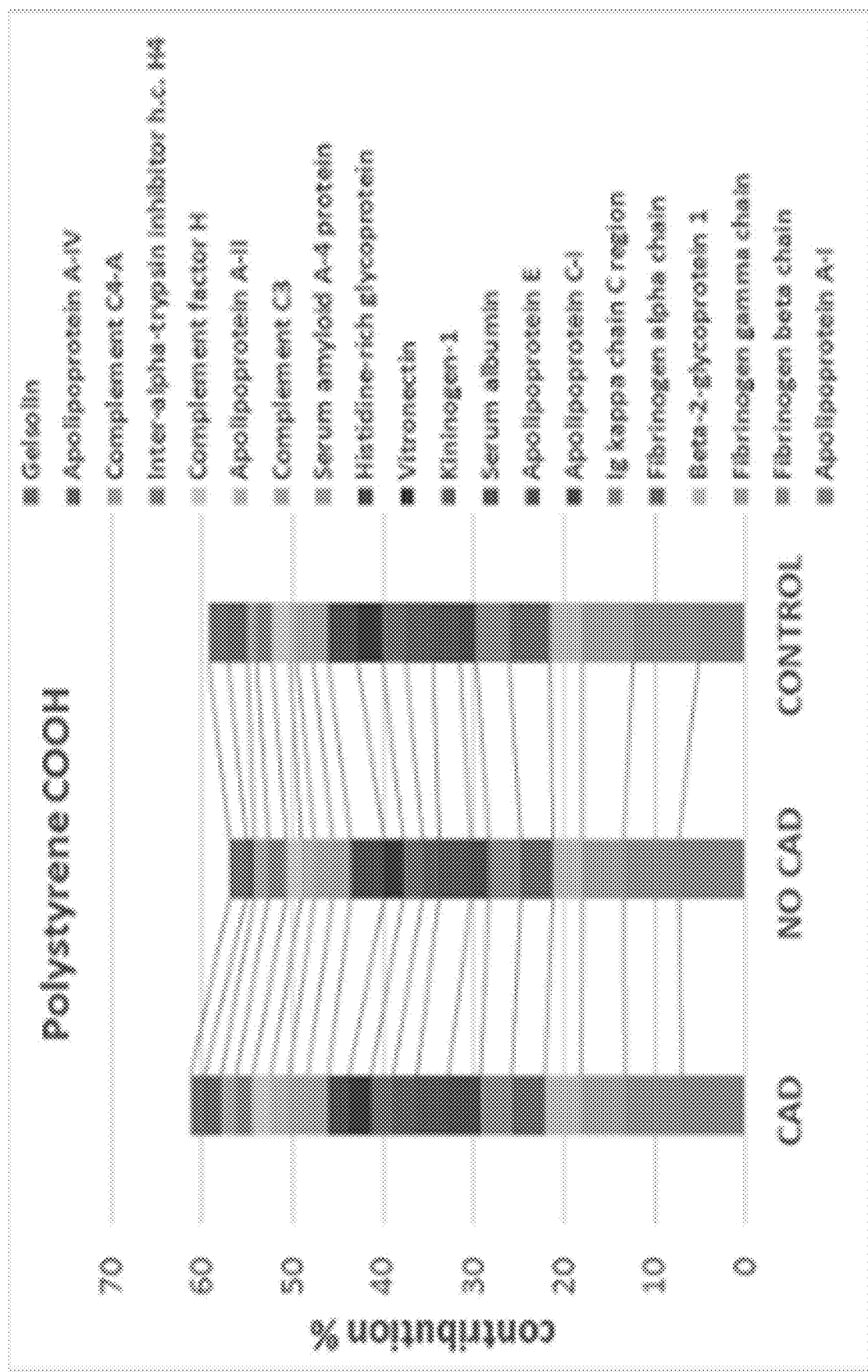
Figure 52:
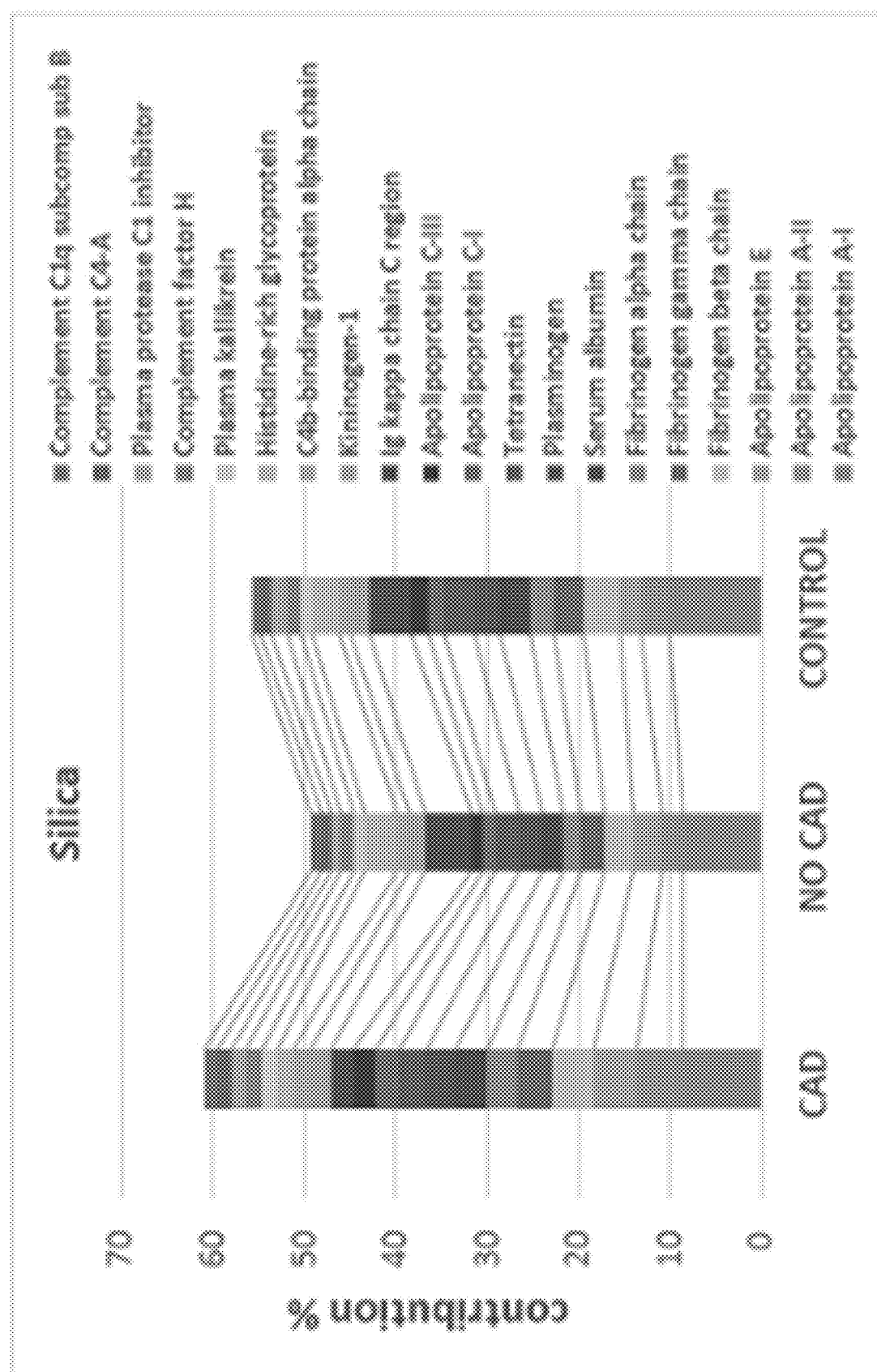
Figure 52:
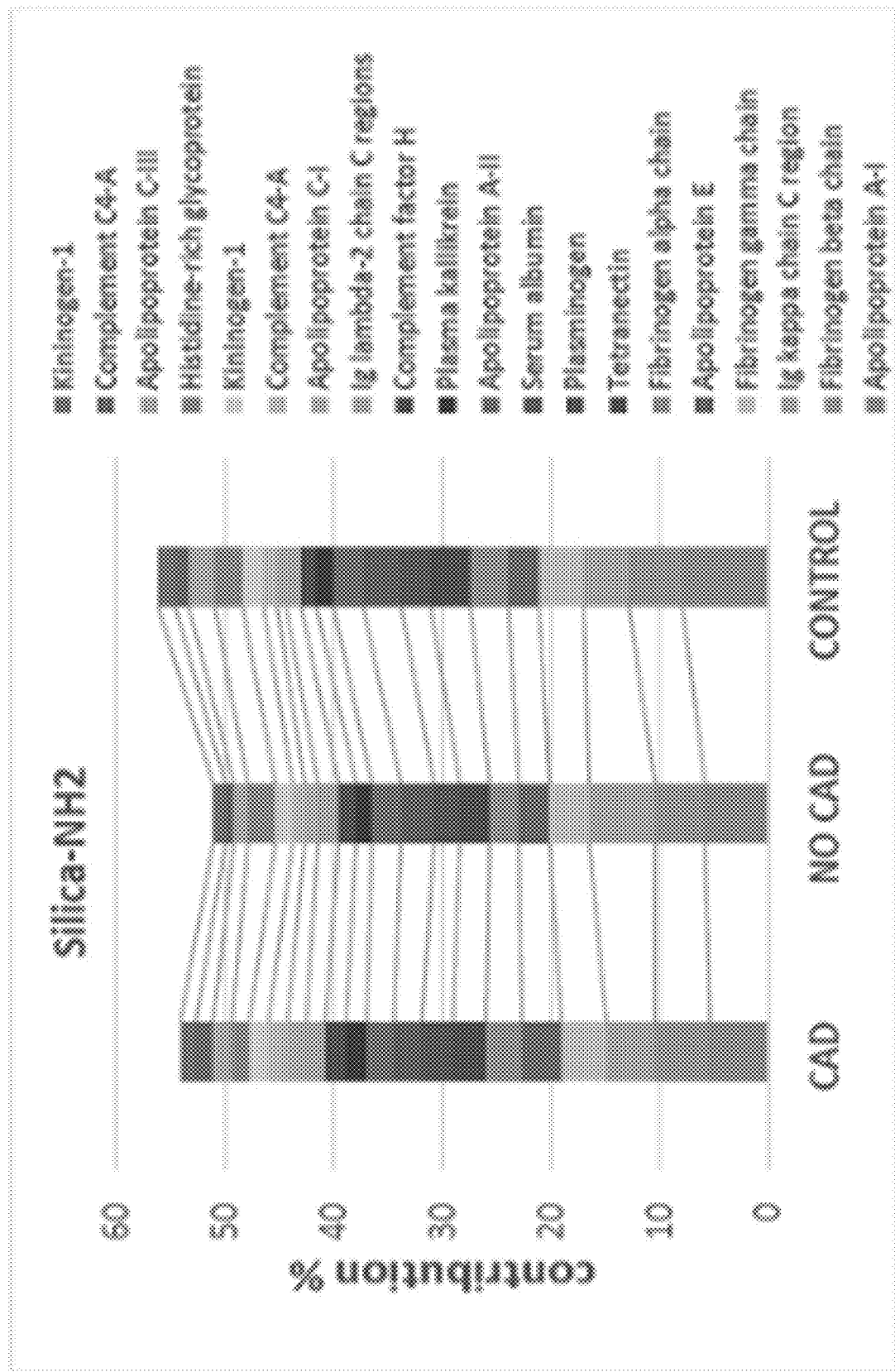
Figure 52:
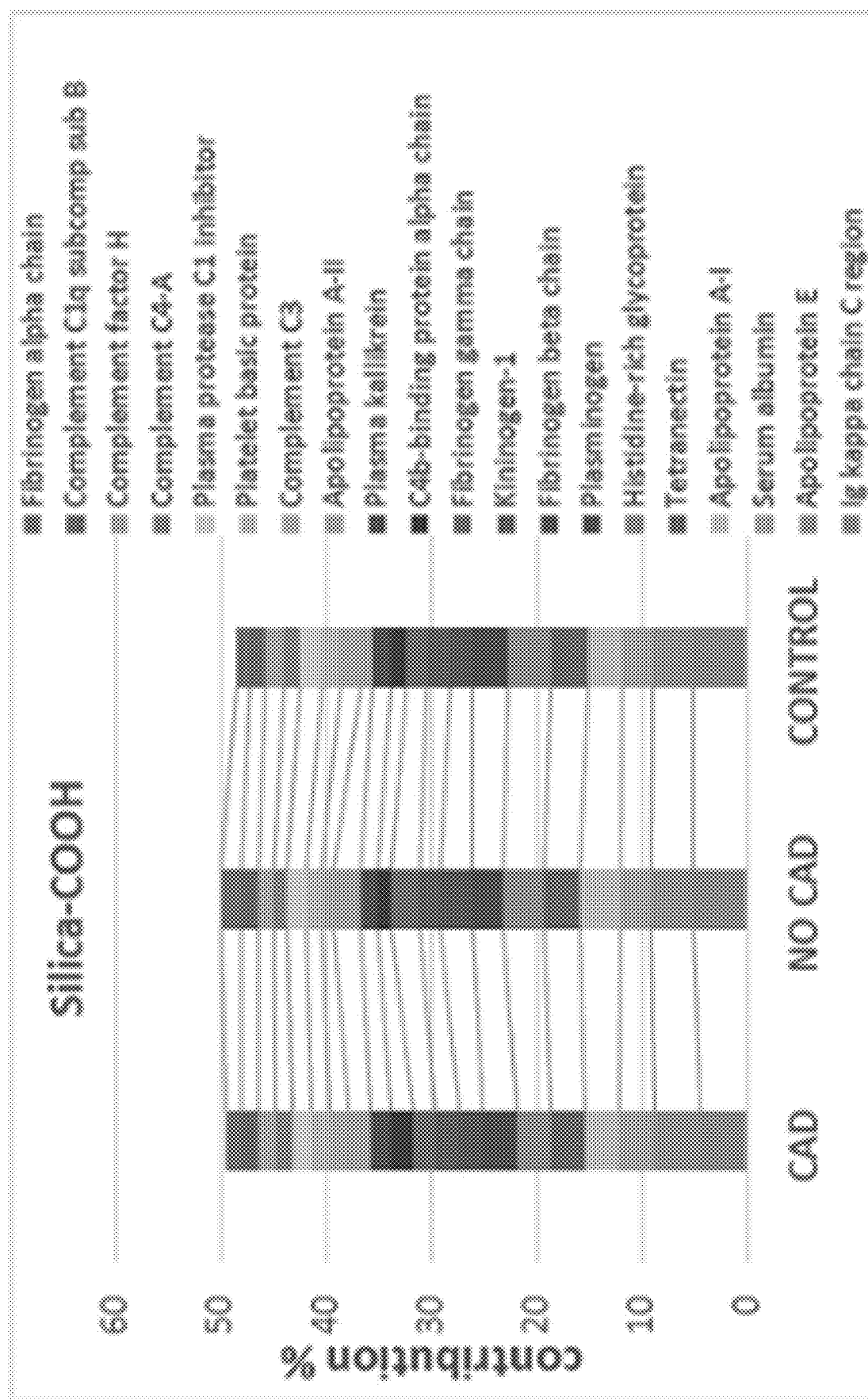

Once exposed to plasma, all the surface charges became less negative (from −5 mV to −25 mV) due to the charge of most plasma proteins at physiological pH. Overall, the physicochemical properties of the PC-coated nanoparticles showed similar trends, being always bigger and less negative than their bare counterparts, irrespective of the plasma used for the incubation. However, when incubated with NO CAD plasma, P and S nanoparticles exhibited an increase in size of ≈85 μm, bigger than that showed using plasma of other conditions (40-50 μm). On the other hand, PC thickness of S—NH2 nanoparticles incubated with CAD plasma was bigger (≈40 μm) than those derived from incubation of the same nanoparticles with other plasma types (≈30 μm). Transmission electron microscopy showed that nanoparticles did not change their morphology and structure after incubation in plasma (FIG. 50C). Furthermore, an increase in the size after coating was observed, thus confirming results obtained by dynamic light scattering. Protein concentrations of different PCs were evaluated by Bradford assay, showing that overall all silica nanoparticles adsorbed less proteins in the PC than polystyrene nanoparticles (FIG. 51A). This observation was confirmed through analysis of PCs by 1D-SDS PAGE. Five patients with CAD, NO CAD and no risk for CAD (CONTROL) have been used to collect plasma and the PCs obtained for all nanoparticles have been resolved onto Comassie stained SDS PAGE gels (FIG. 51B). Gels have been analyzed by densitometry and differences in the amount of proteins in the CAD, NO CAD and CONTROL PCs of the same nanoparticle have been detected (FIG. 51C, arrows). In some cases, we also noticed the presence and/or absence of some proteins in specific PCs (FIG. 51C, blue arrows). These results confirm that the formation of atherosclerosis plaque induces changes in plasma composition and, consequently, differences in PC. The protein corona were analyzed by LC-MS/MS analysis. More than 150 proteins have been identified in each PC-coated nanoparticle sample. In addition, spectral counting values, which represent the total number of fragmentation spectra for all peptides attributed to a specific protein, have been used to obtain information about the abundance of the proteins and, consequently, the percentage contribution of each identified proteins in the PCs. Differences in the percentage contribution of the top 20 abundant proteins in the PCs are reported in FIG. 52. The results demonstrated correlation between the PC composition, the plasma condition, the type of nanoparticle and the surface functionalization.

Data obtained from all samples have been collected, analyzed and classified: a key for each measurement was created by concatenating nanoparticle, surface modification, type of plasma and label. Proteins identified with less than 2 peptides were removed from consideration and TIBCO Spotfire Analyst 7.6.1 was used to pivot the data so that rows were identified by protein accession, columns by the key and values containing the percentage contribution.

Besides mathematical analysis, we analyzed the presence of exclusive proteins in the corona of a given condition. To do this, we created Venn Diagrams which facilitate the research of common and unique proteins in big data set of proteins or genes. The PCs of each nanoparticle have been analyzed separately, for a total of 6 classifications. We looked for exclusive proteins by comparing proteins common to all 5 patients-derived PCs for CAD, NO CAD and control. Our results show that for each nanoparticle used in this study, various specific proteins are exclusively identified in specific PC patterns. Among these, several proteins involved in the regulation of complement activation (complement factor H related protein 3, complement component C8 gamma) were exclusively identified in the PC pattern of CAD patients. This result is in line with the recently described role of complement activation in the pathogenesis of cardiovascular diseases (development of atherosclerosis, plaque rupture, and thrombosis). Another example is represented by apolipoprotein (a), considered an attractive biomarker candidate for use into clinical practice for CAD, which we have detected exclusively in the PC pattern of CAD patients. Apolipoprotein (a) is the main component of lipoprotein (a), is well known to be subjected to proteolytical cleavage and its fragments accumulate in atherosclerotic plaques.

We confirmed the accuracy of the approach in discrimination of patients with CAD and NO CAD by analyzing 9 blind plasma samples (3 per each condition and 3 control). The PC was formed around the 6 nanoparticles of our PC sensor array nanosystem. Then, proteins in the PCs have been identified by LC-MS/MS (Supporting Information) and the results have been analyzed using the same classification and clustering approaches.

Figure 54A:
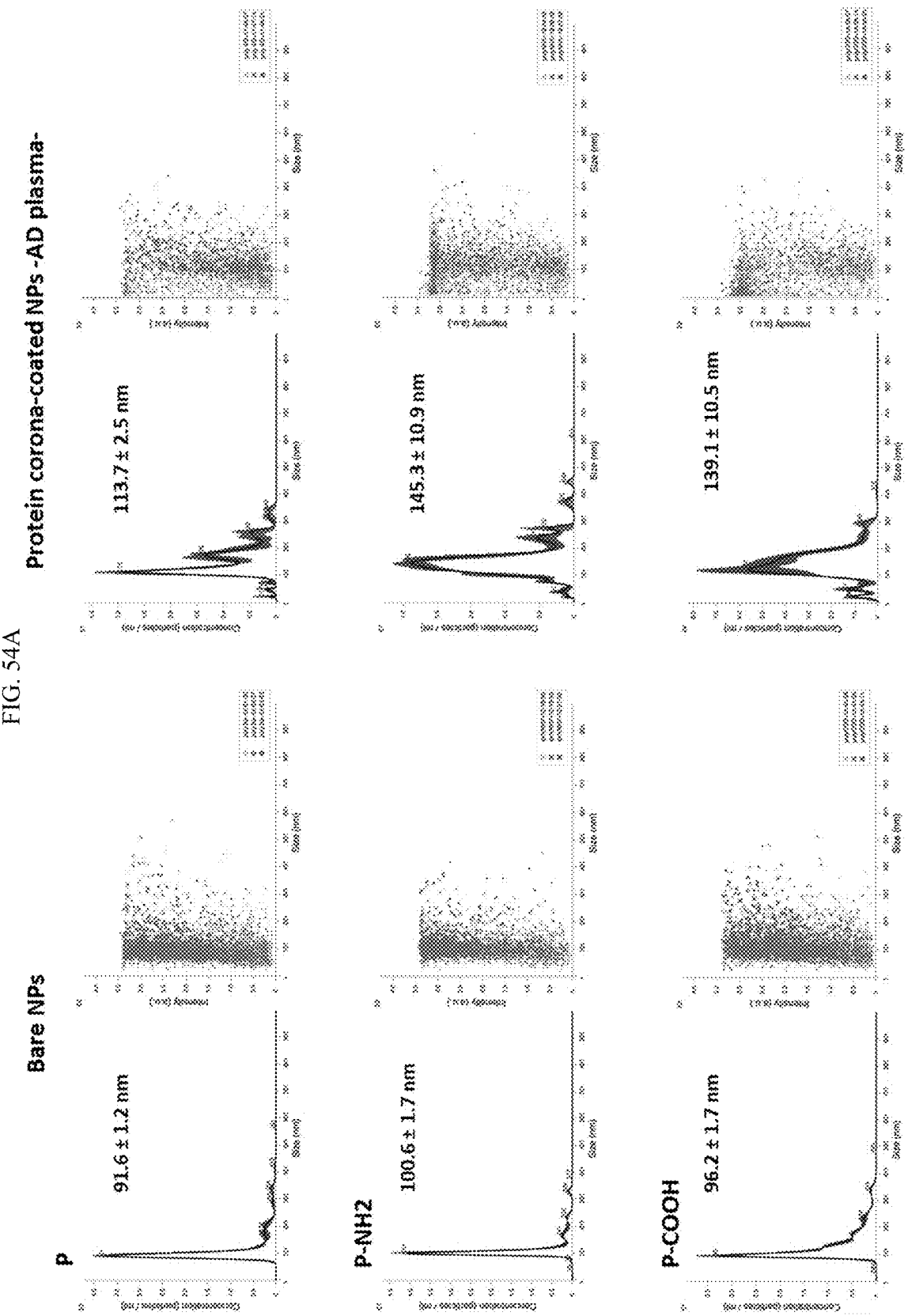
FIG. 54A. Synthetic and biological identity of nanoparticles after incubation in Alzheimer's disease plasma. Nanosight nanoparticles tracking analysis (size). Polystyrene nanoparticles before and after coating with AD protein coronas. Bare nanoparticles are 90-100 µm and homogenous in size. AD PC-coated nanoparticles are bigger and less homogenous in size. Intensity profiles and scatter plot of each measurements are reported. Values are average±SD (n=3).
Figure 54B:
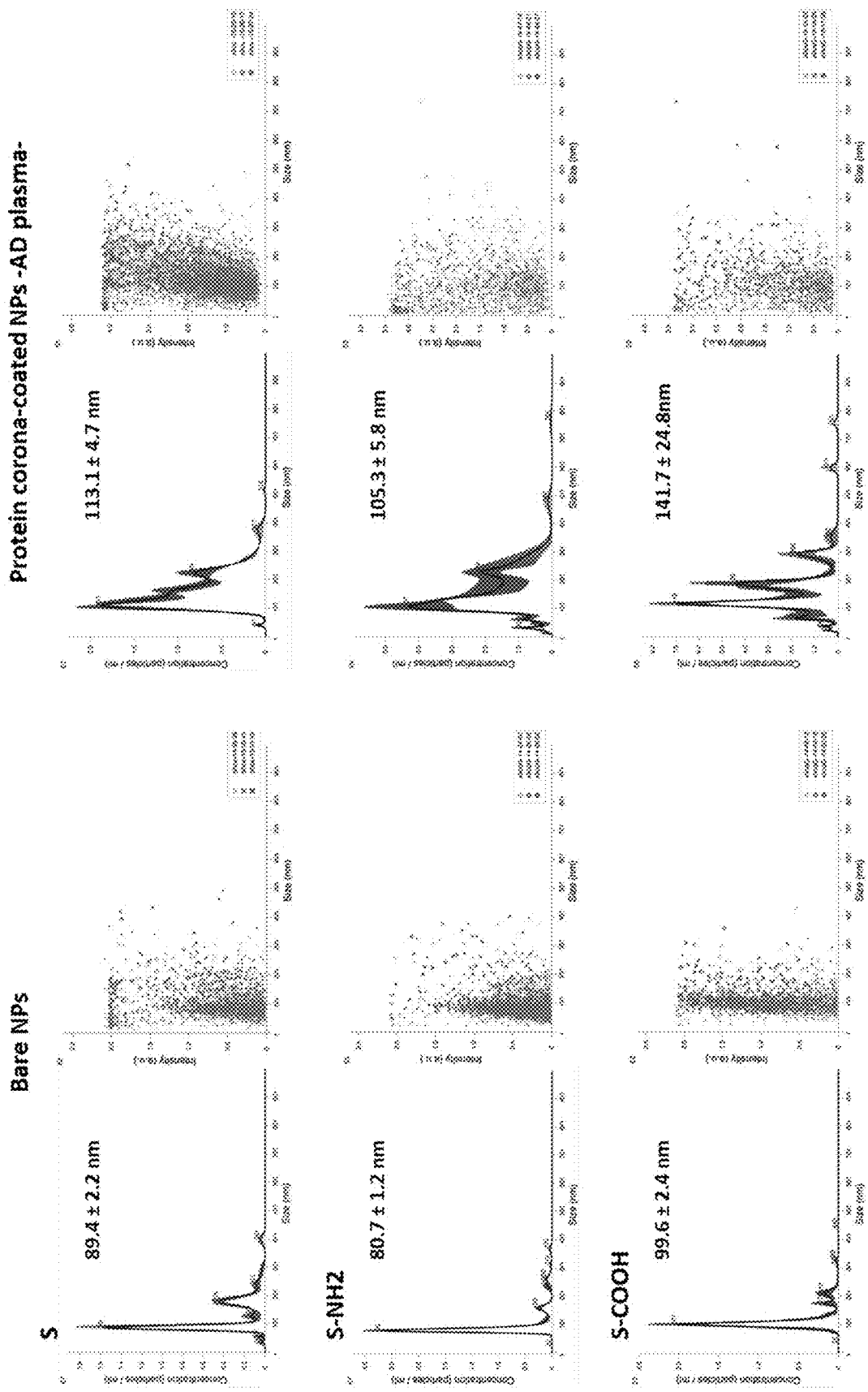
FIG. 54B. Synthetic and biological identity of nanoparticles after incubation in Alzheimer's disease plasma. Nanosight nanoparticles tracking analysis (size). Silica nanoparticles before and after coating with AD protein coronas. Bare nanoparticles are 90-100 µm and homogenous in size. AD PC-coated nanoparticles are bigger and less homogenous in size. Intensity profiles and scatter plot of each measurements are reported. Values are average±SD (n=3).

Statistical and data analysis is graphically represented in FIG. 54 showing the discrete isolation of the classification of the CAD, NO CAD and CONTROL (no risk of CAD).

In conclusion, we have demonstrated the accuracy of a 6 nanoparticles PC sensor array for the detection of CAD. The PC sensor array nanosystem developed in this work demonstrated to also be sensitive and accurate in the discrimination of CAD, restenosis, NO CAD, and healthy individual, which further showing its own great potential value as technology platform to be used in clinical setting. Indeed, despite the presence of many symptoms typically associated to atherosclerotic plaque, the NO CAD group of patients under investigation in this work did not have any obstruction in their arteries.

The PC patterns resulting from this platform represent a unique multivariate fingerprint, which is more accurate and broad-spectrum than those obtained using the PCs of a single nanoparticle. The approach presented here may be of great value for the detection of not only CAD, but also other various human diseases, improving many patients' quality of life. Especially due to the non-invasiveness of the test, we envision that such a test would be used more willingly and more frequently than angiography by patients. And unlike angiography, this test is easy to administer and has no side effects, allowing patients to check the status of arteries from the very first symptoms, and have significantly reduced CAD complications due to the early detection.

Methods

Nanoparticles. Three differently functionalized silica particles were purchased by Kisker-Products (see website at kisker-biotech.com); three differently functionalized polystyrene particles were purchased by Polyscience, Inc. (see website at polysciences.com). All the particles had the same size (100 μm). Their morphology, average size, polydispersity index (PDI) and zeta potential were characterized by TEM, DLS and zeta potential measurements.

Protein corona formation. The PCs were created by incubating 0.5 mg of nanoparticles in deionized $H_2O$ with the same volume of human plasma. Incubation was performed in 37° C. under agitation for 1 h. Immediately after incubation, centrifugation was executed at 14,000 rpm and 10° C. for 30 minutes to form a pellet. Next, the pellet was washed and suspended in 200 μl of phosphate-buffered saline (PBS) at 4° C. The centrifugation measures were repeated three times under the same previous conditions. The pellet of the PC-coated nanoparticles was resuspended in 8M Urea, 50 mM ammonium bicarbonate to later run SDS-PAGE gels and LC/MSMS analysis or in deionized $H_2O$ to later analyze the size and ζ-potential.

Nanoparticles characterization. Size and ζ-potential of bare and protein corona-coated nanoparticles have been characterized by diluting 10 μl of each sample in 1 ml total of distilled water. Measurements have been performed using a Zetasizer Nano ZS90 (Malvern, UK). Size and surface charge values are given as mean±S.D. of three independent measurements.

Protein concentration assay. The amount of proteins within the corona was determined by Bradford assay (Biorad) using bovine serum albumin at a known concentration as the standard to build a 5-point standard curve ($R^2$=0.99). Protein concentrations are recorded as an average of three experiments±S.D.

1D-SDS PAGE gels. Proteins in the corona were dissolved in in 8M Urea, 50 mM ammonium bicarbonate. An equal amount of Laemmli buffer 2× was added to the pellet and heated for 5 min at 90° C. before being loaded and resolved onto a 4-20% Mini-PROTEAN® TGX™ Precast Gels (Bio-Rad Laboratories, Hercules, Calif.) for 1 h at 120V. Proteins were stained with Coomassie Brilliant Blue (Fisher Scientific, Fair Lawn, N.J., USA) overnight followed by extensive washing in ultra-pure water.

Mass spectrometry/Statistics/PLS-DA. Mass spectrometry, statistical analysis and PLS-DA were performed as described in Example 1.

Example 6. A Multi-Nanoparticle Protein Corona Test for Detection of Alzheimer's Disease at Early Stage The pathology of Alzheimer's disease begins decades before the detection of clinical symptoms. The need for accurate and noninvasive early diagnosis for Alzheimer's disease is rapidly growing. To address the issue, a state-of-the-art sensor array nanosystem was developed, which successfully detects minuscule changes in plasma protein patterns and uses clustering techniques to determine the presence of Alzheimer's disease. The developed technology can also be applied in the future to diagnose other diseases since the sensor array creates unique fingerprints for each plasma proteome change due to diseases and is sensitive enough to capture such changes unlike current technologies.

As discussed in the previous Examples, PCs' composition changes based on the plasma proteome that can be altered as a consequence of disease, which results in "personalized protein coronas" (PPCs). The PPCs, however, cannot provide a robust and precise strategy for early detection of diseases mainly due to the huge overlapping of the similar proteins in the protein corona composition. In this study, using the PPCs formed around a multi-NP platform containing six nanoparticles, we provided a fingerprint-patterns for robust and precise detection of AD with unprecedented prediction accuracy and specificity. The developed sensor array test successfully distinguished between patients with and without AD, as well as patients who developed AD several years afterwards (using cohort plasmas). This Examples provides a feasible, noninvasive alternative to current AD detection, allowing the ability to provide unparalleled early detection and treatment.

Results and Discussion

The sensor array test consists of incubating plasma samples with 6 different nanoparticles. The latter are 100 µm polystyrene and silica nanoparticles, each with tunable surface chemistries (plain, -amino and -carboxyl conjugated here after referred to as P, P—NH2, P—COOH, S, S—NH2, S—COOH) and narrow size distribution as described in Example 5 for CAD analysis. As initial proof-of-concept, to search for differences between AD and control plasmas, the size, surface charge and morphology of the nanoparticles before and after PC formation have been analyzed. Nanoparticle tracking analysis (Nanosight) has been applied to characterize the size of nanoparticles. During such analysis, a laser beam illuminates the nanoparticles, from which the scattered light is visualized through an optical microscope. Meanwhile, a video is recorded by a camera aligned to the beam showing the movement of the nanoparticles (30-60 frame/sec). Before incubation in plasma, all nanoparticles were homogeneous in size (FIG. 58, polystyrene nanoparticles 90-100 µm; silica nanoparticles 80-100 µm) with a negative surface charge consistent with those provided by the manufacturer (Table 8). After 1 h incubation at 37° C. under agitation in plasma, PC-coated nanoparticles have been recovered by centrifugation followed by extensive washings to remove unbound and loosely attached proteins. In all cases, we revealed an increase in the size of PC-coated nanoparticles and a wider size distribution, which indicates a less homogeneous population (FIG. 54, scatter plot). The average increase in size was 30 µm, thus indicating a 15-nm thickness of the PC layer, which is consistent with data reported in literature[1] and with what was observed using plasma from healthy volunteers (data not shown). The presence of plasma proteins on the nanoparticles' surface induced a change in their charge, which became less negative reaching the values typical of the plasma proteins (−20 mV to −0 mV to Table 8).

TABLE 8 zeta potentials of nanoparticles bare or after contacted with plasma

| Zeta Potentials (mV) | Bare nanoparticles | Healthy plasma | AD plasma |
|---|---|---|---|
| P | −42.27 ± 0.54 | −20.36 ± 1.54 | −26.56 ± 2.14 |
| P—NH2 | −27.57 ± 1.63 | −29.81 ± 1.55 | −30.62 ± 0.74 |
| P—COOH | −49.38 ± 1.1 | −34.87 ± 0.78 | −27.02 ± 0.71 |
| S | −53.72 ± 1.05 | −23.22 ± 1.55 | −21.23 ± 0.54 |
| S—NH2 | −46.44 ± 0.86 | −24.26 ± 0.95 | −21.21 ± 0.38 |
| S—COOH | −56.77 ± 0.14 | −28.37 ± 0.87 | −25.69 ± 1.31 |

Figure 55:
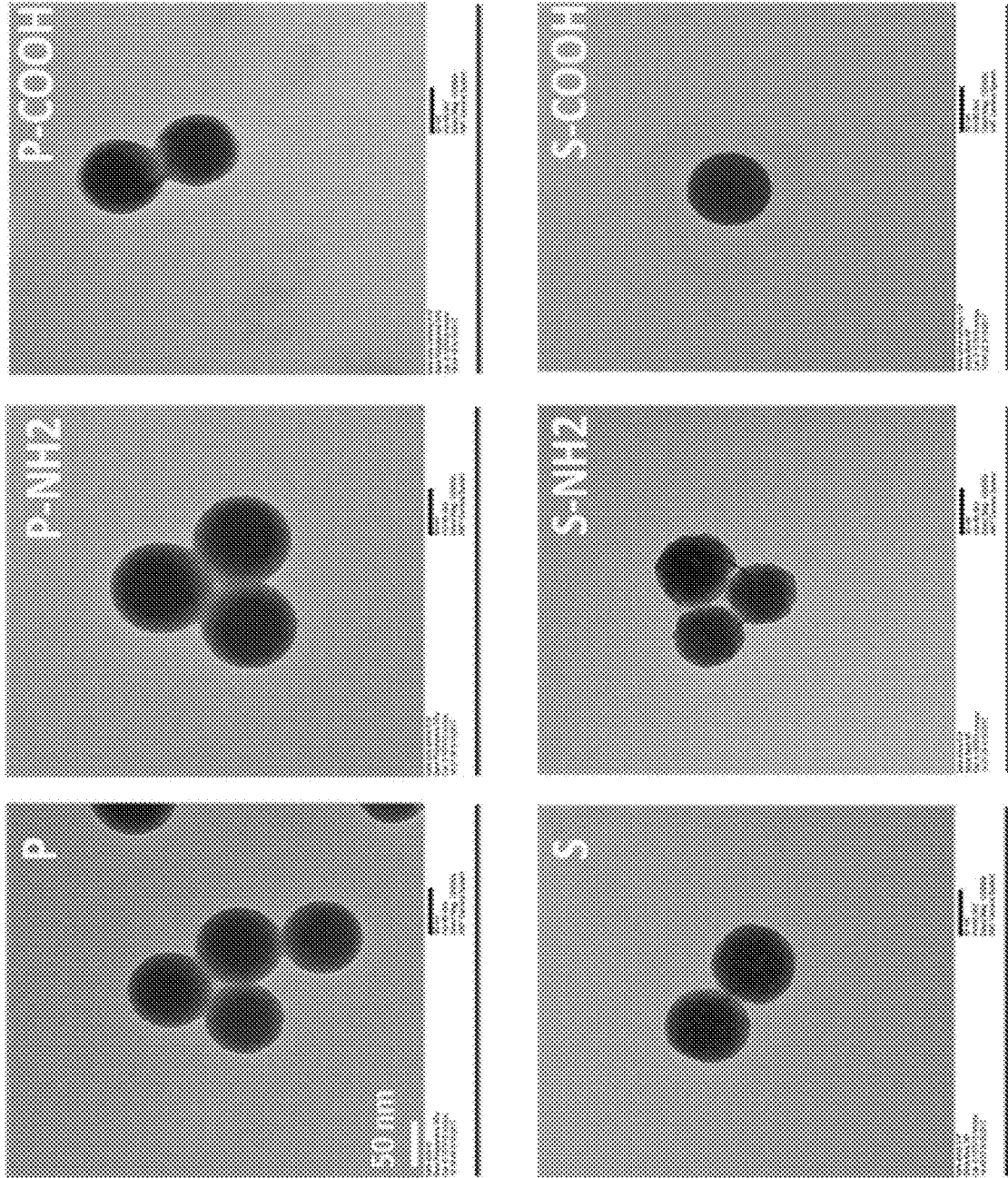
FIG. 55. TEM analysis. Nanoparticles before and after coating with AD protein coronas have been analyzed by transmission electron microscopy to evaluate potential changes in morphology and size. P: polystyrene; PN: polystyrene-$NH_2$, PC: polystyrene-COOH; S: silica; SN: silica-$NH_2$; SC: silica-COOH. All the nanoparticles show a size increase following incubation in plasma.
Figure 55:
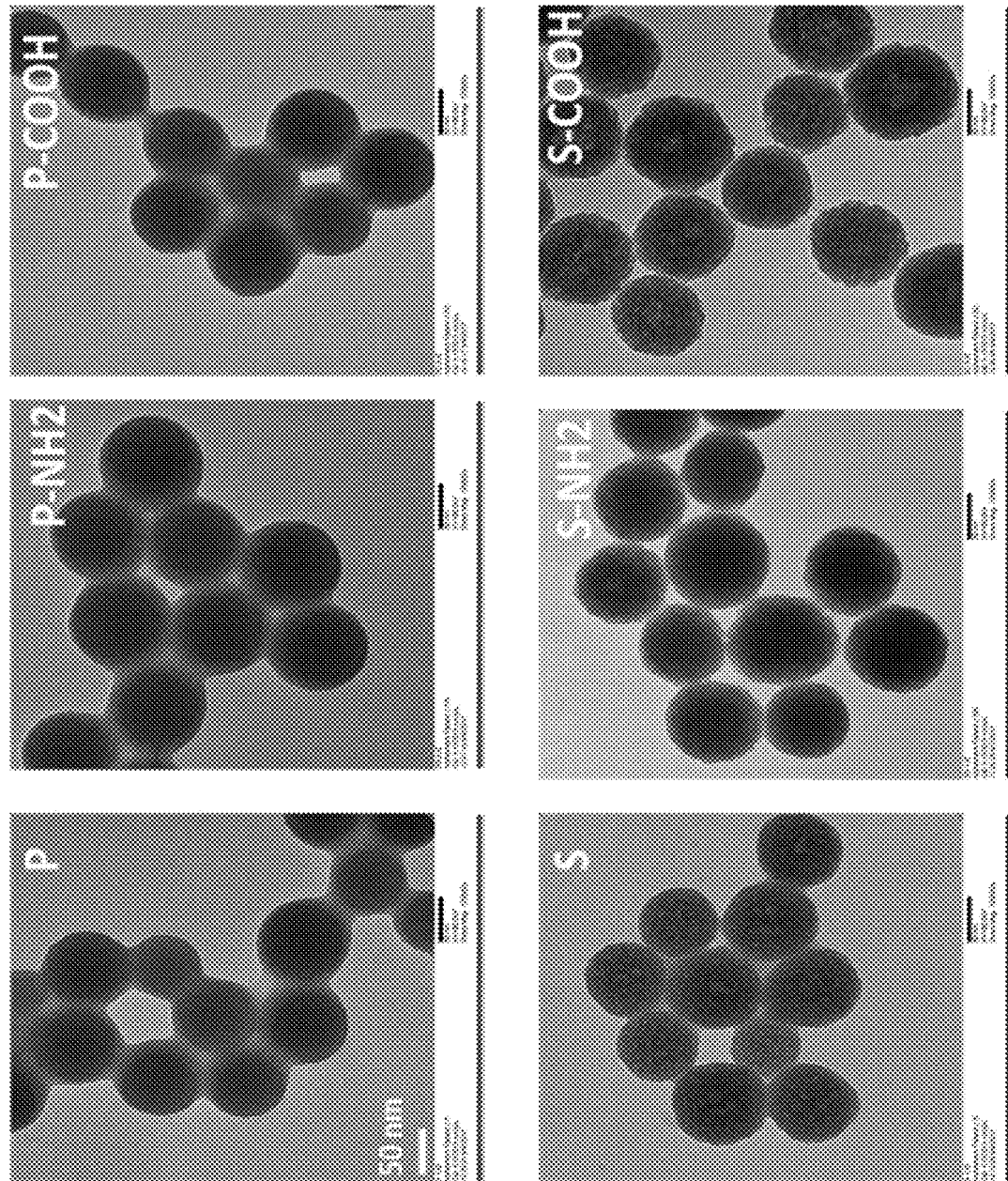

Slight differences in the surface charge of the same nanoparticle incubated with AD plasma and healthy plasma were observed (Table 8). However, those differences were not substantial and thus not useful in the discrimination between different plasma's conditions. Transmission electron microscopy (TEM) was also used to evaluate the morphology of nanoparticles, which remained unchanged after PC formation. Indeed, both before and after incubation with plasma, all nanoparticles had a round homogeneous shape (FIG. 55). The presence of a thin layer of proteins, associated to an increase in the size of PC-coated nanoparticles, confirming the results obtained by Nanosight, was observed (FIG. 55).

Figure 56:
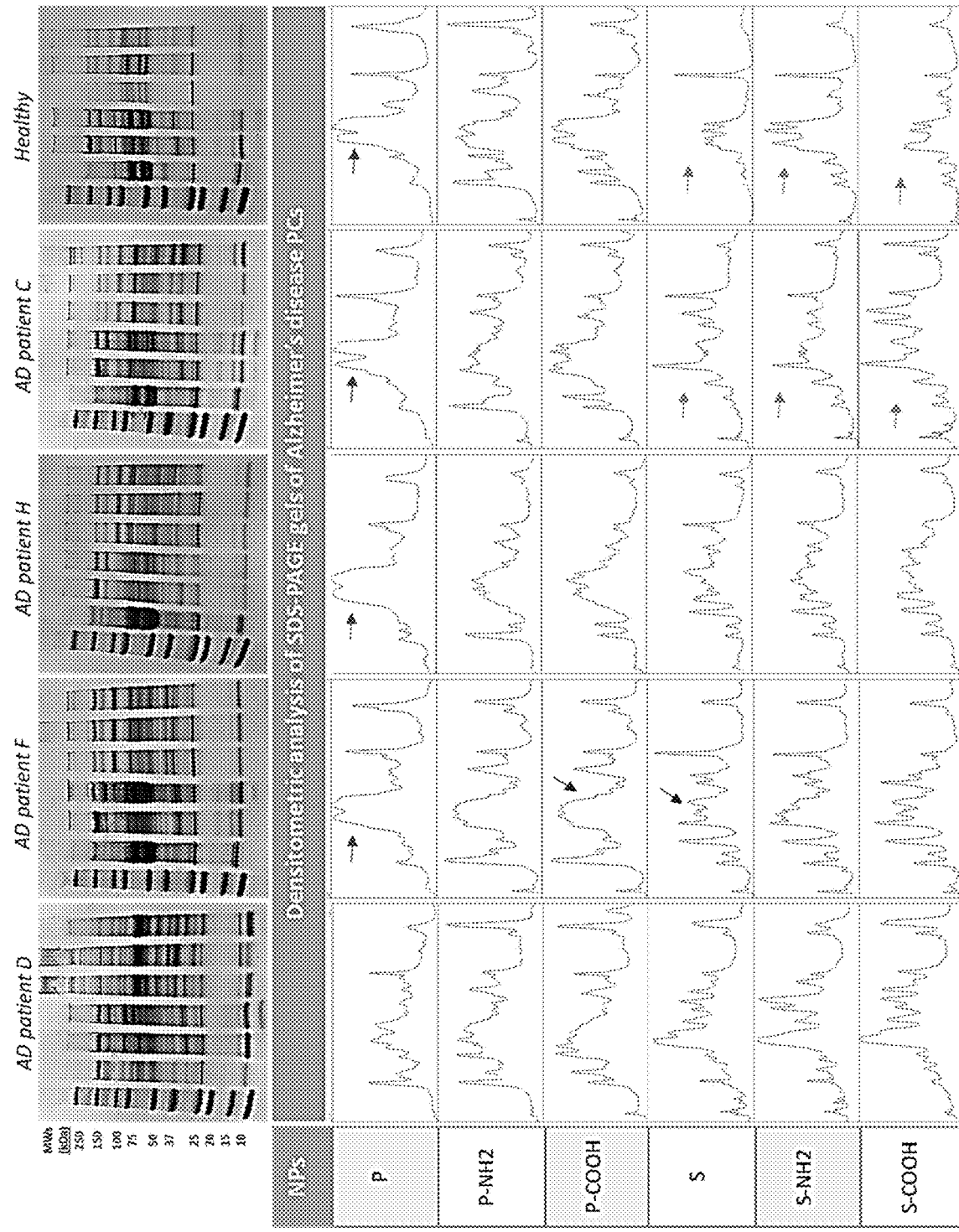
FIG. 56. SDS-PAGE gels and densitometric analysis of the bands. Loading order: P, P—$NH_2$, P—COOH, S, S—$NH_2$, S—COOH where P: polystyrene; PN: polystyrene-$NH_2$, PC: polystyrene-COOH; S: silica; SN: silica-$NH_2$; SC: silica-COOH. Personalized protein corona profiles have been analyzed and compared through SDS-PAGE. Four representative gels of Alzheimer's protein corona and one healthy protein corona are showed. Intensity of bands relative to plasma proteins adsorbed on nanoparticles was analyzed by Image) (y-axis: intensity, x-axis: molecular weight).
Figure 57:
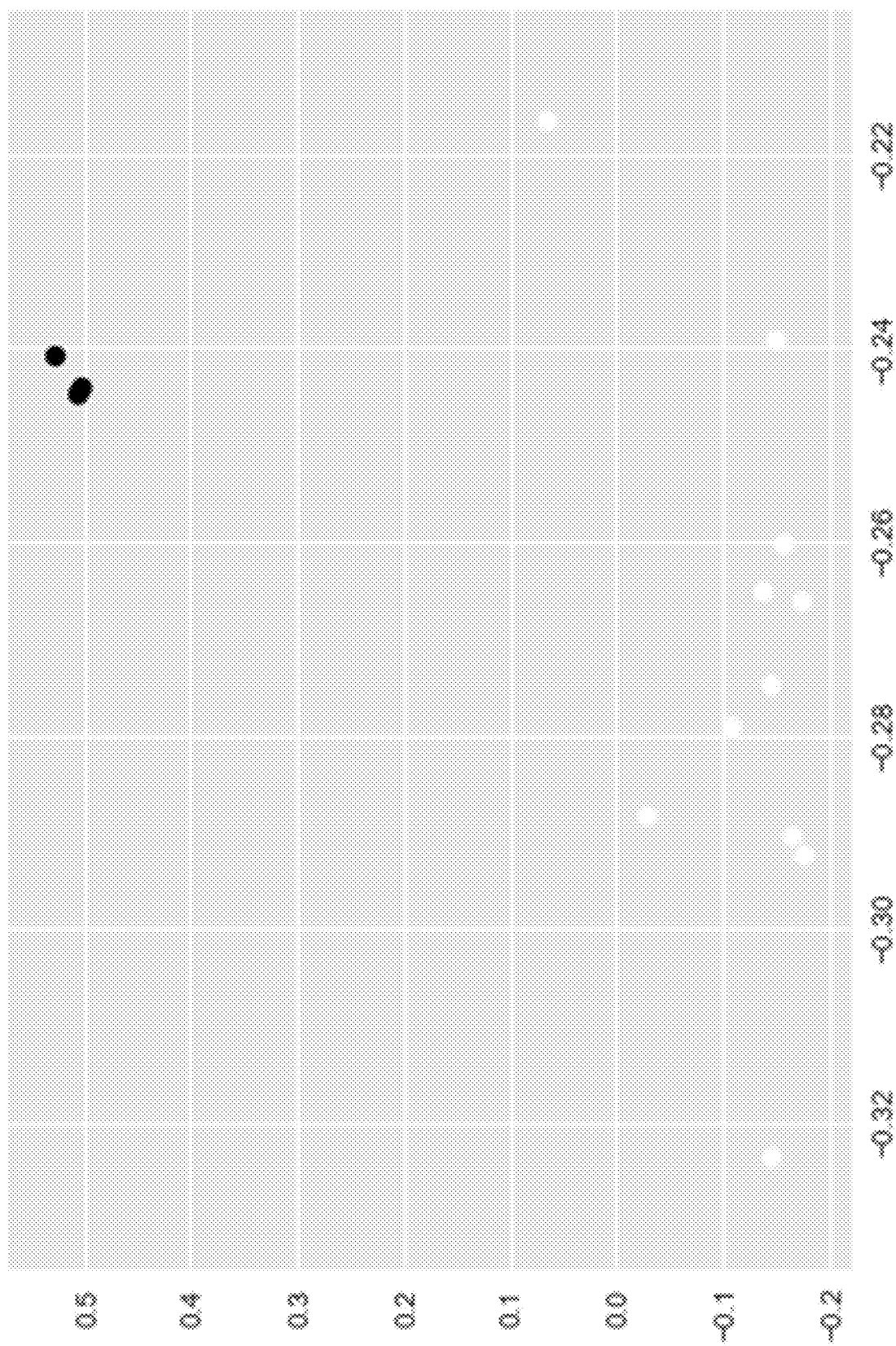
FIG. 57. Classification of healthy and AD disease. The white dots are AD and black dots are healthy samples.

PCs associated with the particles were resolved by gel electrophoresis (SDS-PAGE) and later visualized by staining with Coomassie Brilliant Blue (FIG. 56). In general, by visually evaluating the lanes, the 6 nanoparticles had different PCs patterns, which was what expected and desired for the best performances of our approach. Silica nanoparticles seemed to adsorb less proteins on their surface than polystyrene nanoparticles. In most samples, the PC of plain polystyrene was more enriched than others in proteins at molecular weight ≈60 kDa, which are most likely attributable to Albumin. This was true both for AD patients' plasma and for control plasma (FIG. 56, arrows). The densitometric analysis of bands associated to each PC confirmed that silica nanoparticles generally adsorbed lower amount of proteins, but revealed also that a higher number of proteins constitute their PCs: as for example, more than one band is present at level of Albumin for polystyrene nanoparticles' PC (FIG. 56, arrows). On the other hand, several differences were recorded in the PPCs profiles of AD patients and healthy individual, particularly in the case of silica nanoparticles (FIG. 56, arrows). However, those differences were not statistically significant and not sufficient to accurately discriminate between the two groups of patients under investigation. To deeper investigate the PCs and to know the exact identity and amount of proteins composing the different PCs, all the samples have been analyzed by mass spectrometry. Spectral-counting label free analysis, widely employed for quantitative profiling of the PCs around nanoparticles[2-4], was used to determine the percentage contribution of each protein in the PCs. This calculation was done six times for each plasma patient (incubated separately with each nanoparticle), thus allowing the formation of an AD-specific PC profile derived from the combination of the contribution of the PCs related to six nanoparticles. Table 9 (See FIG. 68) describes the patient population used.

CONCLUSION

This work represents a proof-of-concept study for the development of a MNPC blood test for the diagnosis of AD. The MNPC test showed unprecedented prediction accuracy and specificity. While individual biomarkers blood-based tests are often associated with false positive and thus require further analyses to confirm the diagnosis, our approach records the interactions of all the high-affinity proteins with the set of 6 nanoparticles, thus allowing the creation of a high-specificity PC fingerprint of a given disease. The nanoparticles act as nano-concentrator of plasma proteins on their surface (each nanoparticle concentrates the plasma proteins with higher affinity towards its surface): this helps in the revelation of proteins whose levels only change slightly in pathological conditions with respect to a healthy status. These little changes may belong both to high abundance and low abundance plasma proteins. In this study, we reported a relatively small number of patients because each patient's plasma was analyzed 6 times using different nanoparticles, and so the results obtained for each patient are 6 times more specific than those obtained when a single analysis is performed.

Materials and Methods

Nanoparticles. Silica particles (plain, amino and carboxyl-conjugated) were purchased by Kisker-Products (see website at kisker-biotech.com). Polystyrene particles (plain, amino and carboxyl-conjugated) were purchased by Polyscience, Inc. (see website at polysciences.com). According to manufacturer's all the particles had the same size (90-100 µm). Their morphology, average size and zeta potential were characterized as described later in this section.

Personalized Protein Corona Formation.

The PCs were created by incubating 0.5 mg of nanoparticles in deionized $H_2O$ with the same volume of human plasma. Incubation was performed in 37° C. under agitation for 1 h. Immediately after incubation, PC-coated nanoparticles have been recovered by centrifugation (14,000 rpm and 10° C. for 30 minutes) and extensive washing in cold phosphate-buffered saline (PBS) to remove unbound or weakly bound proteins. The pellet of PC-coated nanoparticles was resuspended in 8M Urea, 50 mM ammonium bicarbonate for SDS-PAGE gels and LC/MSMS analysis or in deionized H$_2$O for dynamic light scattering and ζ-potential analyses.

Physicochemical characterization of nanoparticles. Size was measured by Nanoparticle tracking analysis (Nanosight, Malvern, UK). The software calculates the size according to ζ-potential of bare and PC-coated nanoparticles has been determined using a Zetasizer Nano ZS90 (Malvern). nanoparticles were diluted in water before the analysis to a concentration of 50 ng/ml. Size and surface charge values are given as mean±S.D. of three independent measurements. For transmission electron microscopy (TEM) analysis, samples and grids have been labeled with 1% uranyl acetate. Tecnai G2 Spirit BioTWIN Transmission Electron Microscope equipped with an AMT 2k CCD camera was used.

One-dimensional gel electrophoresis. Personalized protein coronas were dissolved in 8M Urea, 50 mM ammonium bicarbonate. An equal amount of Laemmli buffer 2× was added to the pellet and heated for 5 min at 90° C. before being loaded and resolved onto a 4-20% Mini-PROTEAN® TGX™ Precast Gels (Bio-Rad Laboratories, Hercules, Calif.) for 1 h at 120V. Proteins were stained with Coomassie Brilliant Blue (Fisher Scientific, Fair Lawn, N.J., USA) overnight followed by extensive washing in ultra-pure water. Densitometric analysis of the band intensities have been performed by ImageJ (website: imagej.nih.gov/ij/).

Protein identification and quantification by mass spectrometry. Proteins were reduced with 10 mM dithiothreitol (Sigma) for 1 h at 56° C. and then alkylated with 55 mM iodoacetamide (Sigma-Aldrich, St Louis, Mo., USA) for 1 h at 25° C. in the dark. Proteins were then digested with modified trypsin (Promega, Madison, Wis., USA) at an enzyme/substrate ratio of 1:50 in 100 mM ammonium acetate, pH 8.9 at 25° C. overnight. Trypsin activity was halted by addition of acetic acid (99.9%, Sigma-Aldrich) to a final concentration of 5%. Peptides were desalted using C18 SpinTips (Protea, Morgantown, W. Va.) then vacuum centrifuged and stored at −80° C. until the day of the analysis. Peptides were separated by reverse phase HPLC (Thermo Fisher, Waltham, Mass. Easy nLC1000) using a precolumn (made in house, 6 cm of 10 μm C18) and a self-pack 5 μm tip analytical column (12 cm of 5 μm C18, New Objective) over a 140-minute gradient before nano-electrospray using a QExactive mass spectrometer (Thermo Fisher). Solvent A was 0.1% formic acid and solvent B was 80% MeCN/0.1% formic acid. The gradient conditions were 2-10% B (0-3 min), 10-30% B (3-107 min), 30-40% B (107-121 min), 40-60% B (121-126 min), 60-100% B (126-127 min), 100% B (127-137 min), 100-0% B (137-138 mM), 0% B (138-140 min), and the mass spectrometer was operated in a data-dependent mode. The parameters for the full scan MS were: resolution of 70,000 across 350-2000 m/z, AGC 3e6, and maximum IT 50 ms. The full MS scan was followed by MS/MS for the top 10 precursor ions in each cycle with a NCE of 28 and dynamic exclusion of 30 s. Raw mass spectral data files (.raw) were searched using Proteome Discoverer (Thermo Fisher) and Mascot version 2.4.1 (Matrix Science). Mascot search parameters were: 10 ppm mass tolerance for precursor ions; 15 millimass units (mmu) for fragment ion mass tolerance; 2 missed cleavages of trypsin; fixed modification was carbamidomethylation of cysteine; variable modifications were methionine oxidation. Only peptides with a Mascot score 25 were included in the data analysis. Spectral counting was performed by summing the total number of peptides selected for fragmentation each protein.

Example 7. Size of Particles Effects Amount of Protein Bound

This Example demonstrates that the use of different size nanoparticles made of the same material provide a different biomolecule fingerprint for each size. Silica nanoparticles of three different diameters (100 μm (0.1 μm), 3 μm and 4 μm) were incubated with the same plasma sample. The beads where analyzed by SDS-PAGE. As demonstrated in FIG. 58, the larger the beads, the more proteins are comprised within the biomolecule signature. Further, each bead size has a distinct biomolecule corona signature and thus the combination of different sizes of nanoparticle alone allow for the development of a distinct biomolecule fingerprint. As shown, there are distinct differences in the pattern or proteins between the three different sized beads.

A sensor array can be made using nanoparticles of different sizes which each will give a different biomolecule fingerprint.

Figure 59:
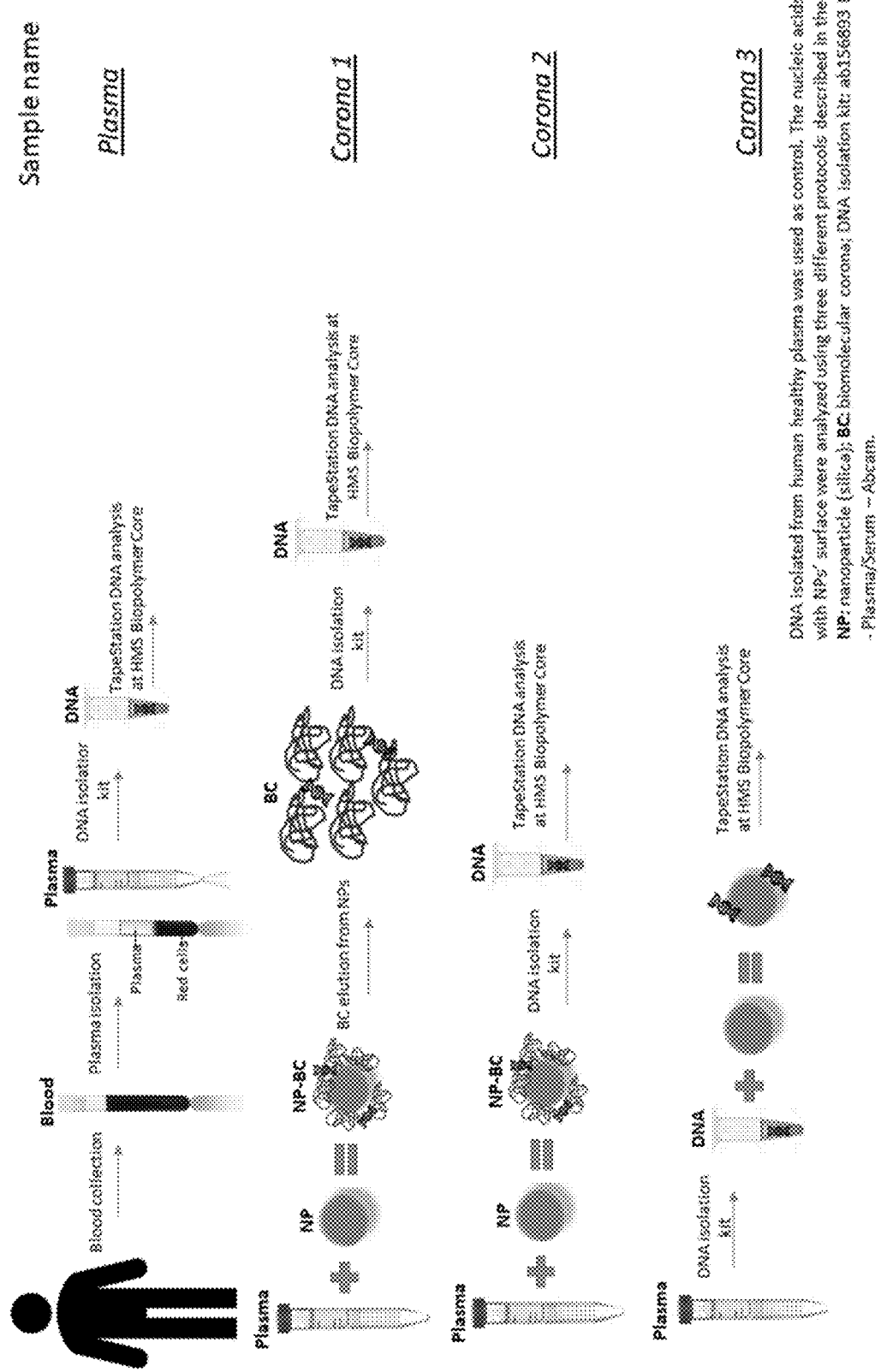
FIG. 59. Scheme showing the conducted experiments to probe the existence of nucleic acids in biomolecular corona.
Figure 60:
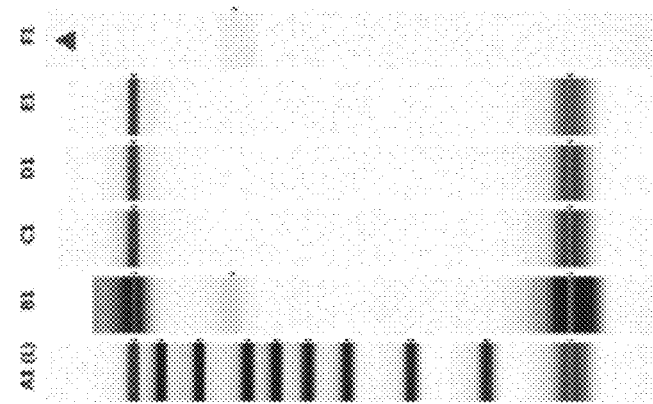
FIG. 60. Agarose gel analysis of nucleic acid binding to three different nanoparticles.
Figure 61:
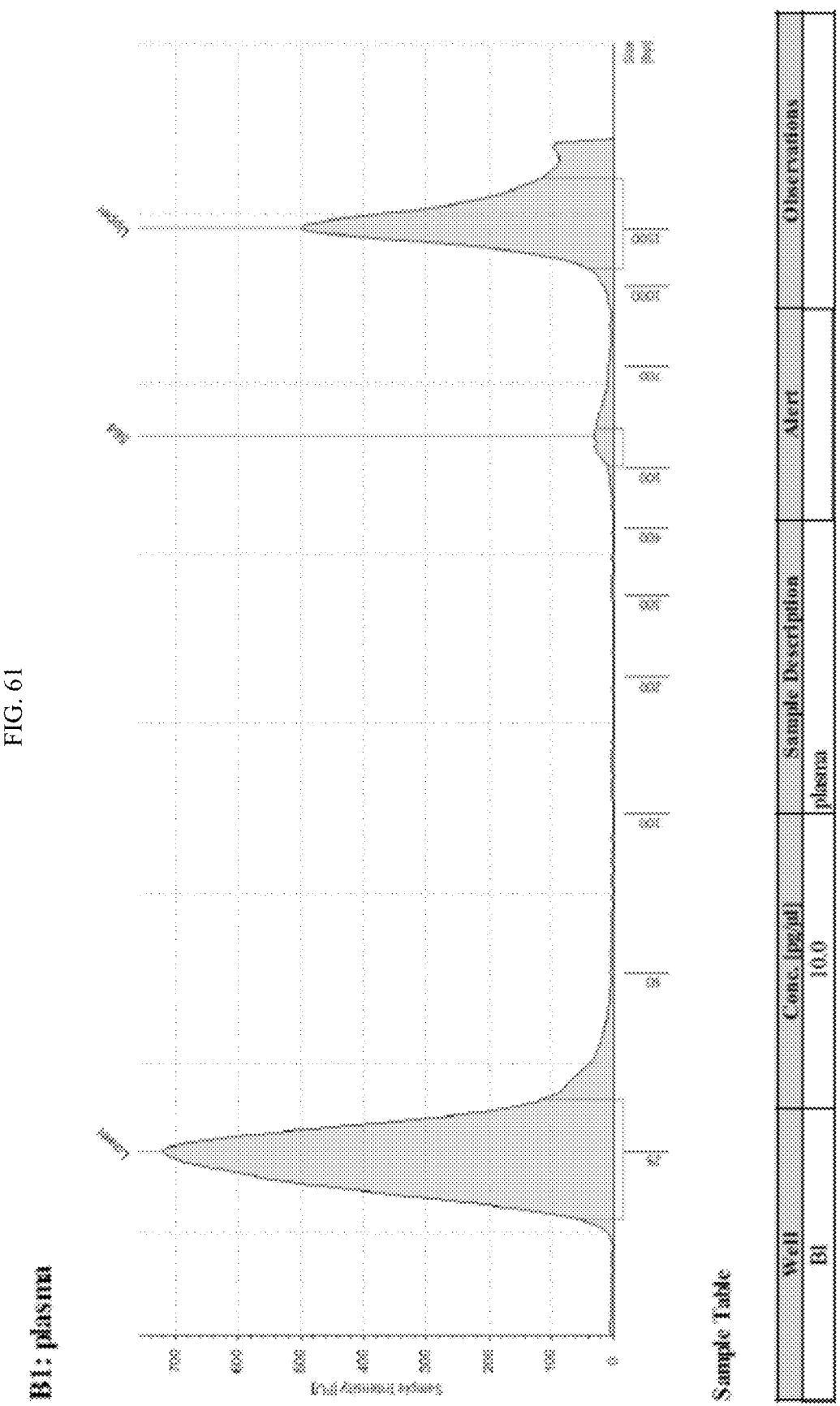
FIG. 61. Analysis of nucleic acid content in plasma.
Figure 61:
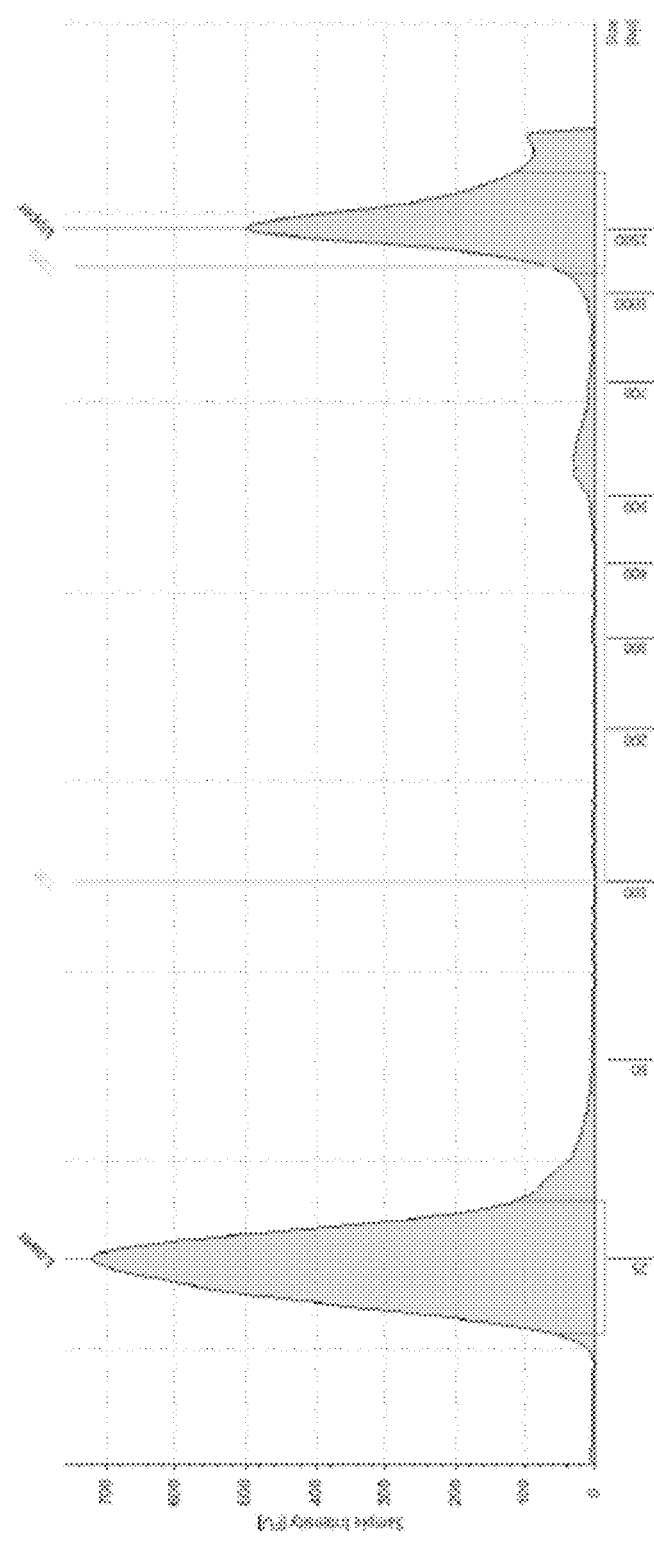

Example 8. Sensor Array can Provide a Biomolecule Fingerprint Comprising Nucleic Acids The sensor array and associated biomolecule corona signature along with proteins contains nucleic acids that make up the biomolecule corona. This Example demonstrates the composition of nucleic acids that bind to silica nanoparticles with neutral surface nanoparticles. Nanoparticles were incubated with plasma, and the associated nucleic acids were analyzed (FIG. 59). FIGS. 60 and 61 depict the analysis of nucleic acid in all samples and its content in plasma, (nucleic acid amount in plasma was 33.8 pg/μl). The nucleic acid content of the biomolecule coronas associated with the nanoparticle was analyzed. The proteins were either dissociated from nanoparticle using urea and the nucleic acids subsequently analyzed (FIG. 62, nucleic acid amount 14.0) or the proteins were not dissociated from the corona and the nucleic acids analyzed (FIG. 63, 14.4 pg/μl). Alternatively, the nanoparticles can be incubated with nucleic acids that have been purified from the plasma with a plasma kit and then incubated with the bare particles (FIG. 64, nucleic acid amount 13.2 pg/μl). The outcomes revealed the capacity of nanoparticles in adsorption of nucleic acid in the biomolecular corona composition.

The invention claimed is:
1. A method for assaying a biological sample, comprising:
(a) contacting the biological sample with a plurality of particles comprising different particle types to permit biomolecules of the biological sample to bind to the plurality of particles and form coronas around the plurality of particles, wherein the coronas corresponding to the different particle types (i) differ based on particle type, and (ii) comprise overlapping and distinct proteins;
(b) separating at least a subset of the plurality of particles comprising the coronas from the biological sample by removing the subset of the plurality of particles thereby producing a subset of proteins from the biological sample;
(c) assaying the subset of proteins of (b) with an instrument to detect, in the subset, proteins in the biological sample at concentrations across a dynamic range comprising at least 6 orders of magnitude, thereby assaying the biological sample.

2. The method of claim 1, wherein the detecting of proteins in the biological sample comprises detecting a protein present in the sample at a concentration greater than 1 mg/ml and a protein present in the sample at a concentration of less than 10 ng/ml.

3. The method of claim 1, wherein the plurality of particles comprise iron oxide.

4. The method of claim 1, wherein the assaying is performed using gel-electrophoresis, liquid chromatography, mass spectrometry, nuclear magnetic resonance spectroscopy, Fourier transform infrared spectroscopy, circular dichroism, Raman spectroscopy, or any combination thereof.

5. The method of claim 1, wherein the dynamic range of the proteins detected exceeds a detection limit of the assaying.

6. The method of claim 1, wherein the dynamic range of the proteins detected spans 6 or more orders of magnitude.

7. The method of claim 1, wherein the detected proteins comprise proteins present in concentrations of 100 ng/ml or less in the biological sample.

8. The method of claim 1, wherein the assaying comprises quantitative determination of the total protein adsorbed onto a particle from among the plurality of particles.

9. The method of claim 1, wherein the assaying comprises quantitative determination of the relative amounts of different types of proteins adsorbed onto a particle from among the plurality of particles.

10. The method of claim 1, wherein step (b) further comprises removing loosely attached proteins from the particles prior to (c).

11. The method of claim 1, wherein a particle from among the plurality of particles forms a corona that is at least 15 nm thick.

12. The method of claim 1, wherein the contacting in (a) is performed for at least 1 minute.

13. The method of claim 1, wherein the assaying comprises detecting a protein from the corona of a first particle from among the plurality of particles and a protein from the corona of a second particle from among the plurality of particles at the same time, wherein the first particle and the second particle are different particle types.

14. The method of claim 13, wherein the detecting is performed on an array.

15. The method of claim 1, wherein the assaying comprises determining the quantity of a protein in the corona of a particle from among the plurality of particles.

16. The method of claim 1, wherein the assaying comprises determining a ratio of two proteins in a corona of a particle from among the plurality of particles.

17. The method of claim 1, wherein the assaying further comprises digesting the proteins.

18. The method of claim 1, wherein the biological sample is divided into a plurality of sample volumes, wherein, in (a), contacting comprises separately incubating a particle of the plurality of particles with the biological sample in a sample volume of the plurality of sample volumes, such that one or more sample volume(s) of the plurality of sample volumes are incubated with a distinct particle type of the plurality of particles.

19. The method of claim 1, wherein the contacting the biological samples further comprises contacting the biological sample under multiple conditions that differ by one or more of: incubation time, incubation temperature, or flow of the biological sample in contact with the plurality of particles.

20. The method of claim 1, wherein the assaying comprises determining the conformational state of a protein from the biological sample.

21. The method of claim 1, wherein the assaying comprises measuring an association between two different proteins in the biological sample.

22. The method of claim 1, wherein the biological sample is selected from the group consisting of: blood, plasma, serum, lung lavage, menstrual blood, urine, processed tissue samples, amniotic fluid, cerebrospinal fluid, tears, saliva, sperm, chopped tissue, homogenized tissue, or any lysates or combinations thereof.

23. The method of claim 1, wherein the coronas that form around the plurality of particles further comprise a species of biomolecules selected from the group consisting of polysaccharides, sugars, lipids, lipoproteins, metabolites, oligonucleotides, or any combination thereof.

24. The method of claim 1, wherein at least one particle of the plurality of particles enriches for peptides other than albumin such that a ratio of an amount of albumin to a protein X that binds to the at least one particle is less than a ratio of an amount of albumin to the protein X in the biological sample.

25. The method of claim 1, wherein the different particle types differ from each other by one or more physicochemical properties, wherein the one or more physicochemical properties are selected from the group consisting of: composition, size, surface charge, hydrophobicity, hydrophilicity, surface functionality, surface topography, surface curvature, shape, and any combination thereof.

26. The method of claim 25, wherein the one or more physicochemical properties comprises surface functionality, wherein the surface functionality is selected from the group consisting of aminopropyl functionalization, amine functionalization, boronic acid functionalization, carboxylic acid functionalization, methyl functionalization, N-succinimidyl ester functionalization, polyethylene glycol PEG functionalization, streptavidin functionalization, methyl ether functionalization, triethoxylpropylaminosilane functionalization, thiol functionalization, citrate functionalization, lipoic acid functionalization, polyethylene imine functionalization, carboxyl functionalization, hydroxyl functionalization, and any combination thereof.

27. The method of claim 1, wherein the assaying comprises detecting a signal from a particle from among the plurality of particles, wherein the signal is selected from the group consisting of a fluorescence signal, a luminescence signal, a charge-based signal, and a colorimetric signal.

28. The method of claim 1, wherein the assaying comprises measuring the change in size of a particle of the plurality of particles following corona formation on said particle.

29. The method of claim 1, further comprising centrifuging the biological sample and the plurality of particles prior to (b).

* * * * *

UNITED STATES PATENT AND TRADEMARK OFFICE
CERTIFICATE OF CORRECTION

PATENT NO. : 11,435,360 B2
APPLICATION NO. : 17/215923
DATED : September 6, 2022
INVENTOR(S) : Omid Farokhzad et al.

It is certified that error appears in the above-identified patent and that said Letters Patent is hereby corrected as shown below:

In the Specification

Column 13, Line 41, "90-100 µm" should be --90-100 nm--.

Column 13, Line 49, "90-100 µm" should be --90-100 nm--.

Column 14, Line 2, "Image)" should be --ImageJ--.

Column 15, Line 50, "50,000 µm" should be --50,000 nm--.

Column 15, Line 51, "5 µm" should be --5 nm--.

Column 15, Line 52, "5 µm to about 30000 µm" should be --5 nm to about 30000 nm--.

Column 15, Line 53, "5 µm to about 20,000 µm, alternatively about 5 µm" should be --5 nm to about 20,000 nm, alternatively about 5 nm--.

Column 15, Line 54, "10,000 µm," should be --10,000 nm--.

Column 15, Line 54, "5000 µm" should be --5000 nm--.

Column 15, Line 55, "5 µm to about 1000 µm" should be --5 nm to about 1000 nm--.

Column 15, Line 56, "5 µm to about 500 µm, alternatively about 5 µm" should be --5 nm to about 500 nm, alternatively about 5 nm--.

Column 15, Lines 56-57, "50 µm, alternatively about 10 µm to 100 µm" should be --50 nm, alternatively about 10 nm to 100 nm--.

Signed and Sealed this
Fifteenth Day of November, 2022

Katherine Kelly Vidal
*Director of the United States Patent and Trademark Office*

CERTIFICATE OF CORRECTION (continued)
U.S. Pat. No. 11,435,360 B2

Column 15, Line 58, "20 μm to 200 μm, alternatively about 30 μm to 300 μm," should be --20 nm to 200 nm, alternatively about 30 nm to 300 nm,--.

Column 15, Line 59, "40 μm to 400 μm" should be --40 nm to 400 nm--.

Column 15, Lines 59-60, "50 μm to 500 μm, alternatively about 60 μm to 600 μm," should be --50 nm to 500 nm, alternatively about 60 nm to 600 nm--.

Column 15, Line 61, "70 μm to 700 μm" should be --70 nm to 700 nm--.

Column 15, Lines 61-62, "80 μm to 800 μm, alternatively about 90 μm to 900 μm" should be --80 nm to 800 nm, alternatively about 90 nm to 900 nm--.

Column 15, Line 63, "100 μm to 1000 μm" should be --100 nm to 1000 nm--.

Column 15, line 64, "1000 μm to 10000 μm, alternatively about 10000 μm" should be --1000 nm to 10000 nm, alternatively about 10000 nm--.

Column 15, Line 65, "5000 μm" should be --50000 nm--.

Column 15, Line 66, "10 μm, 15 μm, 20 μm, 25 μm, 30 μm, 35 μm, 40 μm" should be --10 nm, 15 nm, 20 nm, 25 nm, 30 nm, 35 nm, 40 nm--.

Column 15, Line 67, "45 μm, 50 μm, 55 μm, 60 μm, 65 μm, 70 μm, 80 μm, 90 μm" should be --45 nm, 50 nm, 55 nm, 60 nm, 65 nm, 70 nm, 80 nm, 90 nm--.

Column 16, Lines 1-11, "100 μm, 125 μm, 150 μm, 175 μm, 200 μm, 225 μm, 250 μm, 275 μm, 300 μm, 350 μm, 400 μm, 450 μm, 500 μm, 550 μm, 600 μm, 650 μm, 700 μm, 750 μm, 800 μm, 850 μm, 900 μm, 1000 μm, 1200 μm, 1300 μm, 1400 μm, 1500 μm, 1600 μm, 1700 μm, 1800 μm, 1900 nm, 2000 μm, 2500 μm, 3000 μm, 3500 μm, 4000 μm, 4500 μm, 5000 μm, 5500 μm, 6000 nm, 6500 μm, 7000 μm, 7500 μm, 8000 μm, 8500 μm, 9000 μm, 10000 μm, 11000 μm, 12000 μm, 13000 μm, 14000 μm, 15000 μm, 16000 μm, 17000 μm, 18000 μm, 19000 μm, 20000 μm, 25000 μm, 30000 μm, 35000 μm, 40000 μm, 45000 μm, 50000 μm" should be --100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm, 1200 nm, 1300 nm, 1400 nm, 1500 nm, 1600 nm, 1700 nm, 1800 nm, 1900 nm, 2000 nm, 2500 nm, 3000 nm, 3500 nm, 4000 nm, 4500 nm, 5000 nm, 5500 nm, 6000 nm, 6500 nm, 7000 nm, 7500 nm, 8000 nm, 8500 nm, 9000 nm, 10000 nm, 11000 nm, 12000 nm, 13000 nm, 14000 nm, 15000 nm, 16000 nm, 17000 nm, 18000 nm, 19000 nm, 20000 nm, 25000 nm, 30000 nm, 35000 nm, 40000 nm, 45000 nm, 50000 nm--.

Column 16, Line 15-16, "5 μm to about 1000 μm" should be --5 nm to about 1000 nm--.

Column 16, Line 17, "5 μm to about 500 μm" should be --5 nm to about 500 nm--.

Column 16, Lines 17-18, "5 μm to about 400 μm, alternatively about 5 μm" should be --5 nm to about 400 nm, alternatively about 5 nm--.

Column 16, Lines 18-19, "300 μm, alternatively about 5 μm to about 200 μm" should be --300 nm, alternatively about 5 nm to about 200 nm--.

Column 16, Line 20, "5 μm to about 100 μm, alternatively about 5 μm" should be --5 nm to about 100 nm, alternatively about 5 nm--.

Column 16, Line 21, "50 μm, alternatively about 10 μm to about 1000 μm" should be --50 nm, alternatively about 10 nm to about 1000 nm--.

Column 16, Line 22, "10 μm to about 750 μm" should be --10 nm to about 750 nm--.

Column 16, Line 23, "10 μm to about 500 μm, alternatively about 10 μm" should be --10 nm to about 500 nm, alternatively about 10 nm--.

Column 16, Line 24, "250 μm, alternatively about 10 μm to about 200 μm" should be --250 nm, alternatively about 10 nm to about 200 nm--.

Column 16, Line 25, "10 μm to about 100 μm" should be --10 nm to about 100 nm--.

Column 16, Line 26, "50 μm to about 1000 μm, alternatively about 50 μm" should be --50 nm to about 1000 nm, alternatively about 50 nm--.

Column 16, Line 27, "500 μm, alternatively about 50 μm to about 250 μm" should be --500 nm, alternatively about 50 nm to about 250 nm--.

Column 16, Line 28, "50 μm to about 200 μm" should be --50 nm to about 200 nm--.

Column 16, Line 29, "50 μm to about 100 μm" should be --50 nm to about 100 nm--.

Column 16, Lines 30-35, "10 μm, 15 μm, 20 μm, 25 nm, 30 μm, 35 μm, 40 μm, 45 μm, 50 μm, 55 μm, 60 μm, 65 μm, 70 μm, 80 μm, 90 μm, 100 nm, 125 μm, 150 μm, 175 μm, 200 μm, 225 μm, 250 μm, 275 μm, 300 μm, 350 μm, 400 nm, 450 μm, 500 μm, 550 μm, 600 μm, 650 μm, 700 μm, 750 μm, 800 μm, 850 μm, 900 nm, 1000 μm" should be --10 nm, 15 nm, 20 nm, 25 nm, 30 nm, 35 nm, 40 nm, 45 nm, 50 nm, 55 nm, 60 nm, 65 nm, 70 nm, 80 nm, 90 nm, 100 nm, 125 nm, 150 nm, 175 nm, 200 nm, 225 nm, 250 nm, 275 nm, 300 nm, 350 nm, 400 nm, 450 nm, 500 nm, 550 nm, 600 nm, 650 nm, 700 nm, 750 nm, 800 nm, 850 nm, 900 nm, 1000 nm--.

Column 21, Line 7, "100 μm" should be --100 nm--.

Column 48, Line 43, "131GH3" should be --βIGH3--.

Column 48, Line 51, "PRDXS" should be --PRDX5--.

Column 49, Line 32, "FHRS" should be --FHR5--.

Column 50, Line 11, "5100" should be --S100--.

CERTIFICATE OF CORRECTION (continued)
U.S. Pat. No. 11,435,360 B2

Column 58, Line 41, "632.8 μm" should be --632.8 nm--.

Column 58, Line 66, "660 μm" should be --660 nm--.

Column 74, Line 24, "Image)" should be --ImageJ--.

Column 75, Line 34, "20 μm" should be --20 nm--.

Column 78, Line 1, "100 μm" should be --100 nm--.

Column 78, Line 6, "100 μm" should be --100 nm--.

Column 78, Line 24, "100 μm" should be --100 nm--.

Column 79, Line 58, "93 μm up to 120 μm" should be --93 nm up to 120 nm--.

Column 80, Line 13, "≈85 μm" should be --≈85 nm--.

Column 80, Line 14, "40-50 μm" should be --40-50 nm--.

Column 80, Line 16, "≈ 40 μm" should be --≈ 40 nm--.

Column 80, Line 17, "≈30 μm" should be --≈30 nm--.

Column 81, Line 59, "100 μm" should be --100 nm--.

Column 83, Line 2, "100 μm" should be --100 nm--.

Column 83, Line 20, "90-100 μm" should be --90-100 nm--.

Column 83, Line 29, "30 μm" should be --30 nm--.

Column 84, Line 62, "μm" should be --nm--.

Column 85, Line 16, "50 ng/ml" should be --50 μg/ml--.

Column 85, Line 55, "138 mM" should be --138 min--.

Column 86, Line 2, "score 25" should be --score $\geq$ 25--.

Column 86, Line 13, "100 μm" should be --100 nm--.

In the Claims

Column 88, Claim 26, Lines 45-46, "glycol PEG functionalization" should be --glycol functionalization--.